(12) United States Patent
Zion et al.

(10) Patent No.: US 11,707,517 B2
(45) Date of Patent: *Jul. 25, 2023

(54) ANTIGEN SPECIFIC IMMUNOTHERAPY FOR COVID-19 FUSION PROTEINS AND METHODS OF USE

(71) Applicant: Akston Biosciences Corporation, Beverly, MA (US)

(72) Inventors: Todd C. Zion, Marblehead, MA (US); Thomas M. Lancaster, Wenham, MA (US); Thillainayagam Sathiyaseelan, Lexington, MA (US); Kexin Huang, San Mateo, CA (US)

(73) Assignee: Akston Biosciences Corporation, Beverly, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/544,293

(22) Filed: Dec. 7, 2021

(65) Prior Publication Data

US 2022/0088182 A1 Mar. 24, 2022

Related U.S. Application Data

(63) Continuation of application No. 17/226,690, filed on Apr. 9, 2021, now Pat. No. 11,213,581.

(60) Provisional application No. 63/068,775, filed on Aug. 21, 2020, provisional application No. 63/068,894, filed on Aug. 21, 2020, provisional application No. 63/068,805, filed on Aug. 21, 2020, provisional application No. 63/068,911, filed on Aug. 21, 2020, provisional application No. 63/068,843, filed on Aug. 21, 2020, provisional application No. 63/048,939, filed on Jul. 7, 2020, provisional application No. 63/041,579, filed on Jun. 19, 2020, provisional application No. 63/041,574, filed on Jun. 19, 2020, provisional application No. 63/041,584, filed on Jun. 19, 2020, provisional application No. 63/041,582, filed on Jun. 19, 2020, provisional application No. 63/008,509, filed on Apr. 10, 2020, provisional application No. 63/008,497, filed on Apr. 10, 2020, provisional application No. 63/008,515, filed on Apr. 10, 2020, provisional application No. 63/008,503, filed on Apr. 10, 2020.

(51) Int. Cl.
*A61K 39/215* (2006.01)
*A61P 31/14* (2006.01)
*C07K 14/165* (2006.01)
*C12N 7/00* (2006.01)
*A61K 38/00* (2006.01)
*A61K 39/00* (2006.01)

(52) U.S. Cl.
CPC ............ *A61K 39/215* (2013.01); *A61P 31/14* (2018.01); *C07K 14/165* (2013.01); *C12N 7/00* (2013.01); *A61K 38/00* (2013.01); *A61K 2039/54* (2013.01); *A61K 2039/55588* (2013.01)

(58) Field of Classification Search
None
See application file for complete search history.

(56) References Cited

U.S. PATENT DOCUMENTS

| | | |
|---|---|---|
| 8,933,207 B2 | 1/2015 | Chen et al. |
| 9,074,015 B2 | 7/2015 | Lancaster et al. |
| 9,855,318 B2 | 1/2018 | Baldwin et al. |
| 10,597,435 B2 | 3/2020 | Lancaster et al. |
| 10,709,766 B2 | 7/2020 | Baldwin et al. |
| 10,822,386 B2 | 11/2020 | Weiss |
| 10,851,147 B2 | 12/2020 | Lancaster et al. |
| 10,870,686 B2 | 12/2020 | Lancaster et al. |
| 10,894,089 B2 | 1/2021 | Heo et al. |
| 10,947,292 B2 | 3/2021 | Lancaster et al. |

(Continued)

FOREIGN PATENT DOCUMENTS

| | | |
|---|---|---|
| CN | 101891823 | 11/2010 |
| CN | 103509118 | 1/2014 |

(Continued)

OTHER PUBLICATIONS

Alleva, et al., "Immunological characterization and therapeutic activity of an altered-peptide ligand, NBI-6024, based on the immunodominant type 1 diabetes autoantigen insulin B-chain (9-23) peptide", Diabetes, 2002, 51(7) pp. 2126-2134.

(Continued)

*Primary Examiner* — Shanon A. Foley
*Assistant Examiner* — Myron G Hill
(74) *Attorney, Agent, or Firm* — Hovey Williams LLP

(57) ABSTRACT

The present disclosure provides recombinantly manufactured fusion proteins comprising a SARS-CoV-2 Receptor Binding Domain (SARS-CoV-2-RBD) fragment or an analog thereof linked to a human Fc fragment for use in relation to the 2019 Novel Coronavirus (COVID-19). Embodiments include the administration of the fusion proteins to patients that have recovered from COVID-19 as a booster vaccination, to antibody naïve patients to produce antibodies to the SARS-CoV-2 virus to enable the patients to become convalescent plasma donors, to patients who have been infected by the SARS-CoV-2 virus and have contracted COVID-19 in order to limit the scope of the infection and ameliorate the disease, and as a prophylactic COVID-19 vaccine. Exemplary

(56) References Cited

U.S. PATENT DOCUMENTS

| | | | |
|---|---|---|---|
| 10,961,294 | B2 | 3/2021 | Lancaster et al. |
| 11,213,581 | B2* | 1/2022 | Zion .................... C07K 14/005 |
| 2003/0040601 | A1 | 2/2003 | Diers et al. |
| 2012/0093814 | A1 | 4/2012 | Canada et al. |
| 2013/0142795 | A1 | 6/2013 | Bai et al. |
| 2013/0190475 | A1 | 7/2013 | Chen et al. |
| 2013/0190476 | A1 | 7/2013 | Lancaster et al. |
| 2014/0037699 | A1 | 2/2014 | Zion et al. |
| 2014/0302028 | A1 | 10/2014 | Zha |
| 2016/0289290 | A1 | 10/2016 | Meehl et al. |
| 2016/0324932 | A1 | 11/2016 | Baldwin et al. |
| 2016/0376321 | A1 | 12/2016 | Hotez et al. |
| 2018/0009869 | A1 | 1/2018 | Lu et al. |
| 2018/0161448 | A1 | 6/2018 | Heo et al. |
| 2018/0177851 | A1 | 6/2018 | Baldwin et al. |
| 2019/0315828 | A1 | 10/2019 | Lancaster et al. |
| 2019/0382439 | A1 | 12/2019 | Kim et al. |
| 2020/0131243 | A1 | 4/2020 | Lancaster et al. |
| 2020/0140516 | A1 | 5/2020 | Weiss |
| 2020/0140517 | A1 | 5/2020 | Weiss |
| 2020/0157169 | A1 | 5/2020 | Lancaster et al. |
| 2020/0157170 | A1 | 5/2020 | Lancaster et al. |
| 2020/0157171 | A1 | 5/2020 | Lancaster et al. |
| 2020/0231646 | A1 | 7/2020 | Lancaster et al. |
| 2020/0299343 | A1 | 9/2020 | Doerner et al. |
| 2020/0407413 | A1 | 12/2020 | Lancaster et al. |
| 2020/0407414 | A1 | 12/2020 | Lancaster et al. |
| 2021/0000942 | A1* | 1/2021 | Hume .................. A61K 39/215 |
| 2021/0300983 | A1 | 9/2021 | Lancaster et al. |
| 2021/0309709 | A1 | 10/2021 | Lancaster et al. |
| 2021/0324033 | A1 | 10/2021 | Lancaster et al. |
| 2021/0340212 | A1 | 11/2021 | Zion et al. |

FOREIGN PATENT DOCUMENTS

| | | |
|---|---|---|
| CN | 111333704 | 6/2020 |
| CN | 111647077 | 9/2020 |
| CN | 112480268 | 3/2021 |
| EP | 3303380 | 4/2018 |
| EP | 3517544 | 7/2019 |
| EP | 2963056 | 11/2019 |
| EP | 3656792 | 5/2020 |
| WO | 2010117760 | 10/2010 |
| WO | 2016044676 | 3/2016 |
| WO | 2016119023 | 8/2016 |
| WO | 2016177771 | 11/2016 |
| WO | 2016178905 | 11/2016 |
| WO | 2018009921 | 1/2018 |
| WO | 2018073185 | 4/2018 |
| WO | 2018107117 | 6/2018 |
| WO | 2019035010 | 2/2019 |
| WO | 2019204206 | 10/2019 |
| WO | 2020006529 | 1/2020 |
| WO | 2020070276 | 4/2020 |
| WO | 2020106748 | 5/2020 |
| WO | 2020236762 | 11/2020 |
| WO | 2021011827 | 1/2021 |
| WO | 2021022149 | 2/2021 |
| WO | 2021126584 | 6/2021 |

OTHER PUBLICATIONS

Baeshen, et al., "Cell factories for insulin production", Microbial Cell Factories, 2014,13(141).

Brüggemann, et al., "The immunogenicity of chimeric antibodies", Journal of Experimental Medicine, 1989, 170(6) pp. 2153-2157.

Hua, et al., "Design of an Active Ultrastable Single-chain Insulin Analog", Journal of Biological Chemistry, 2008, 283(21) pp. 14703-14716.

Strietzel, et al., "In Vitro functional characterization of feline IgGs", Veterinary Immunology and Immunopathology, 2014, 158(3-4) pp. 214-223 (abstract attached).

Tang, et al., "Cloning and characterization of cDNAs encoding four different canine immunoglobulin γ chains", Veterinary Immunology and Immunopathology, 2001, 80(3-4) pp. 259-270 (abstract attached).

Terada, et al., "A chimeric human-cat Fcγ-Fel d1 fusion protein inhibits systemic, pulmonary, and cutaneous allergic reactivity to intratracheal challenge in mice sensitized to Fel d1, the major cat allergen", Clinical Immunology, 2006, 120(1) pp. 45-56 (abstract attached).

Wang, et al., "Proinsulin-Transferrin Fusion Protein as a Novel Long-Acting Insulin Analog for the Inhibition of Hepatic Glucose Production", Diabetes, 2014, 63 pp. 1779-1788.

yourgenome.org, "What does DNA do?", 2016, https://www.yourgenome.org/facts/what-does-dna-do.

Wang, et al., "IgG Fc engineering to modulate antibody effector functions", Protein Cell, Jan. 2018, 9(1), pp. 63-73.

Kim, et al., "Mammalian cell transfection: the present and the future", Analytical and Bioanalytical Chemistry, 2010, 397(8), pp. 3173-3178.

Fan, et al., "Improving the efficiency of CHO cell line generation using glutamine synthetase gene knockout cells", Biotechnology and Bioengineering, 2012, 109(4), pp. 1007-1015 (abstract attached).

Lodish, et al.,Molecular Cell Biology, Molecular Cell Biology, 4th edition, 2000, www.ncbi.nlm.gov/ books/NBK21654 (abstract attached).

Horvath, et al., "An automated DNA synthesizer employing deoxynucleoside 3'-phosphoramidites", Methods in Enzymology, Academic Press, 1987, 154, pp. 314-326 (abstract attached).

Dumont, et al., "Human cell lines for biopharmaceutical manufacturing: history, status, and future perspectives", Critical Reviews in Biotechnology, 2016, 36(6), pp. 1110-1122.

Singh, et al., "Combined blockade of HER2 and VEGF exerts greater growth inhibition of HER2-overexpressing gastric cancer xenografts than individual blockade", Experimental and Molecular Medicine, 2013, 45, 11 pages.

Huang, et al., "Production of recombinant murine-human chimeric IgM and IgG anti-Jsb for use in the clinical laboratory", Transfusion, 2003,43(6), pp. 758-764 (abstract attached).

International Search Report and Written Opinion in corresponding PCT/US2020/063673, dated Apr. 13, 2021.

Walter, et al., "No effect of the altered peptide ligand NBI-6024 on beta-cell residual function and insulin needs in new-onset type 1 diabetes", Diabetes Care, 2009, 32(11), pp. 2036-2040.

Office Action in corresponding U.S. Appl. No. 17/226,690, dated Sep. 14, 2021.

International Search Report and Written Opinion in corresponding PCT/US2021/026577, dated Jul. 26, 2021.

Du, et al., "Identification of a Receptor-Binding Domain in the S Protein of the Novel Human Coronavirus Middle East Respiratory Syndrome Coronavirus as an Essential Target for Vaccine Development", Journal of Virology, 2013, 87(17), pp. 9939-9942.

Wu, et al., "A new coronavirus associated with human respiratory disease in China", Nature, 2020, 579, pp. 265-284.

Zhao, et al., "A safe and convenient pseudovirus-based inhibition assay to detect neutralizing antibodies and screen for viral entry inhibitors against the novel human coronavirus MERS-CoV", Virology Journal, 2013, 10(266), 8 pages.

He, et al., "Receptor-binding domain of SARS-CoV spike protein induces highly potent neutralizing antibodies: implication for developing subunit vaccine", Biochemical and Biophysical Research Communications, 2004, 324, pp. 773-781.

Sun, et al., "Recombinant vaccine containing an RBD-Fc fusion induced protection against SARS-CoV-2 in nonhuman primates and mice", Cellular & Molecular Immunology, 2021, 18, pp. 1070-1073.

Chan, et al., "Engineering human ACE2 to optimize binding to the spike protein of SARS coronavirus 2", Science, 2020, vol. 369, issue 6508, pp. 1261-1265.

Chan, et al., "Supplementary Materials for: Engineering human ACE2 to optimize binding to the spike protein of SARS coronavirus 2" Science, 2020 pp. 1-28.

Quinlan, et al., "The SARS-CoV-2 receptor-binding domain elicits a potent neutralizing response without antibody-dependent enhancement", 2020, available at: https://www.biorxiv.org/content/10.1101/2020.04.10.036418v1, 24 pages.

(56) References Cited

OTHER PUBLICATIONS

Examination Report in corresponding European Patent Application Serial No. 21720949.3, dated May 6, 2022.
Examination Report in corresponding European Patent Application Serial No. 21720949.3, dated Oct. 5, 2022.

* cited by examiner

```
SEQ ID NO:2    PNITNLCPFGEVFNATRFASVYAWNRKRISNCVADYSVLYNSASFSTFKCYGVSPTKLND    60
SEQ ID NO:9    --QITNLCPFGEVFQATRFASVYAWNRKRISNCVADYSVLYNSASFSTFKCYGVSPTKLND   59
                 :**********:************************************************

SEQ ID NO:2    LCFTNVYADSFVIRGDEVRQIAPGQTGKIADYNYKLPDDFTGCVIAWNSNNLDSKVGGNY    120
SEQ ID NO:9    LMFTNVYADSFVIRGDEVRQIAPGQTGKIADYNYKLPDDFTGCVIAWNSNNLDSKVGGNY    119
               * **********************************************************

SEQ ID NO:2    NYLYRLFRKSNLKPFERDISTEIYQAGSTPCNGVEGFNCYFPLQSYGFQPTNGVGYQPYR    180
SEQ ID NO:9    NYLYRLFRKSNLKPFERDISTEIYQAGSTPCNGVEGFNCYFPLQSYGFQPTNGVGYQPYR    179
               ************************************************************

SEQ ID NO:2    VVVLSFELLHAPATVCGPKKSTNLVKNKCVNFNFNGLTGTGVLTESNKKFLPFQQFGRDI    240
SEQ ID NO:9    VVVLSFELLHAPATV---------------------------------------------    194
               ***************

SEQ ID NO:2    ADTTDAVRDPQTLE        254
SEQ ID NO:9    --------------        194
```

FIG. 13

| | | |
|---|---|---|
| SEQ ID NO:2 | PNITNLCPFGEVFNATRFASVYAWNRKRISNCVADYSVLYNSASFSTFKCYGVSPTKLND | 60 |
| SEQ ID NO:10 | ------------------------------------------------------------ | 0 |

| | | |
|---|---|---|
| SEQ ID NO:2 | LCFTNVYADSFVIRGDEVRQIAPGQTGKIADYNYKLPDDFTGCVIAWNSNNLDSKVGGNY | 120 |
| SEQ ID NO:10 | ------------------------------------------VIAWNSNNLDSKVGGNY | 17 |
| |                                                             *****************  | |

| | | |
|---|---|---|
| SEQ ID NO:2 | NYLYRLFRKSNLKPFERDISTEIYQAGSTPCNGVEGFNCYFPLQSYGFQPTNGVGYQPYR | 180 |
| SEQ ID NO:10 | NYLYRLFRKSNLKPFERDISTEIYQAGSTPCNGVEGFNCYFPLQSYGFQPTNGVGYQPYR | 77 |
| | ************************************************************ | |

| | | |
|---|---|---|
| SEQ ID NO:2 | VVVLSFELLHAPATVCGPKKSTNLVKNKCVNFNFNGLTGTGVLTESNKKFLPFQQFGRDI | 240 |
| SEQ ID NO:10 | VVVLSFELLHAPATV--------------------------------------------- | 92 |
| | ***************  | |

| | | |
|---|---|---|
| SEQ ID NO:2 | ADTTDAVRDPQTLE | 254 |
| SEQ ID NO:10 | -------------- | 92 |

FIG. 14

```
SEQ ID NO:2     ---------------PNITNLCPFGEVFNATRFASVYAWNRKRISNCVADYSVLYNSASFSTFK     49
SEQ ID NO:14    RVQPTESIVRFPNITNLCPFGEVFNATRFASVYAWNRKRISNCVADYSVLYNSASFSTFK     60
                               *********************************************

SEQ ID NO:2     CYGVSPTKLNDLCFTNVYADSFVIRGDEVRQIAPGQTGKIADYNYKLPDDFTGCVIAWNS    109
SEQ ID NO:14    CYGVSPTKLNDLCFTNVYADSFVIRGDEVRQIAPGQTGKIADYNYKLPDDFTGCVIAWNS    120
                ************************************************************

SEQ ID NO:2     NNLDSKVGGNYNYLYRLFRKSNLKPFERDISTEIYQAGSTPCNGVEGFNCYFPLQSYGFQ    169
SEQ ID NO:14    NNLDSKVGGNYNYLYRLFRKSNLKPFERDISTEIYQAGSTPCNGVEGFNCYFPLQSYGFQ    180
                ************************************************************

SEQ ID NO:2     PTNGVGYQPYRVVVLSFELLHAPATVCGPKKSTNLVKNKCVNFNFNGLTGTGVLTESNKK    229
SEQ ID NO:14    PTNGVGYQPYRVVVLSFELLHAPATVCGPKKSTNLVKNKCVNF-----------------    223
                *******************************************

SEQ ID NO:2     FLPFQQFGRDIADTTDAVRDPQTLE    254
SEQ ID NO:14    -------------------------    223
```

FIG. 15

```
SEQ ID NO:2      ---------------PNITNLCPFGEVFNATRFASVYAWNRKRISNCVADYSVLYNSASFSTFK    49
SEQ ID NO:15     RVQPTESIVRFPNITNLCPFGEVFNATRFASVYAWNRKRISNCVADYSVLYNSASFSTFK    60
                                ************************************************

SEQ ID NO:2      CYGVSPTKLNDLCFTNVYADSFVIRGDEVRQIAPGQTGKIADYNYKLPDDFTGCVIAWNS   109
SEQ ID NO:15     CYGVSPTKLNDLCFTNVYADSFVIRGDEVRQIAPGQTGKIADYNYKLPDDFTGCVIAWNS   120
                 ************************************************************

SEQ ID NO:2      NNLDSKVGGNYNYLYRLFRKSNLKPFERDISTEIYQAGSTPCNGVEGFNCYFPLQSYGFQ   169
SEQ ID NO:15     NNLDSKVGGNYNYLYRLFRKSNLKPFERDISTEIYQAGSTPCNGVEGFNCYFPLQSYGFQ   180
                 ************************************************************

SEQ ID NO:2      PTNGVGYQPYRVVVLSFELLHAPATVCGPKKSTNLVKNKCVNFNFNGLTGTGVLTESNKK   229
SEQ ID NO:15     PTNGVGYQPYRVVVLSFELLHAPATVCGPKKSTNLVK-----------------------   217
                 *************************************

SEQ ID NO:2      FLPFQQFGRDIADTTDAVRDPQTLE    254
SEQ ID NO:15     -------------------------    217
```

FIG. 16

```
SEQ ID NO:2        ------------PNITNLCPFGEVFNATRFASVYAWNRKRISNCVADYSVLYNSASFSTFK    49
SEQ ID NO:13       RVQPTESIVRFPNITNLCPFGEVFNATRFASVYAWNRKRISNCVADYSVLYNSASFSTFK    60
                               *************************************************

SEQ ID NO:2        CYGVSPTKLNDLCFTNVYADSFVIRGDEVRQIAPGQTGKIADYNYKLPDDFTGCVIAWNS    109
SEQ ID NO:13       CYGVSPTKLNDLCFTNVYADSFVIRGDEVRQIAPGQTGKIADYNYKLPDDFTGCVIAWNS    120
                   ************************************************************

SEQ ID NO:2        NNLDSKVGGNYNYLYRLFRKSNLKPFERDISTEIYQAGSTPCNGVEGFNCYFPLQSYGFQ    169
SEQ ID NO:13       NNLDSKVGGNYNYLYRLFRKSNLKPFERDISTEIYQAGSTPCNGVEGFNCYFPLQSYGFQ    180
                   ************************************************************

SEQ ID NO:2        PTNGVGYQPYRVVVLSFELLHAPATVCGPKKSTNLVKNKCVNFNFNGLTGTGVLTESNKK    229
SEQ ID NO:13       PTNGVGYQPYRVVVLSFELLHAPATVCGPKKSTNLVKNKCVNFNFNGLTGTGVLTESNKK    240
                   ************************************************************

SEQ ID NO:2        FLPFQQFGRDIADTTDAVRDPQTLE---------    254
SEQ ID NO:13       FLPFQQFGRDIADTTDAVRDPQTLEILDITPCS    273
                   *************************
```

FIG. 17

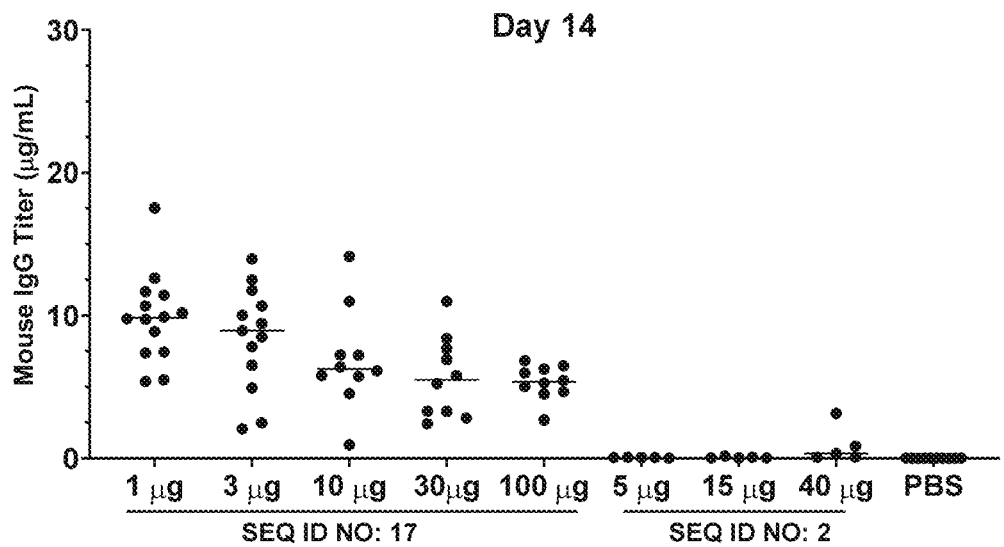
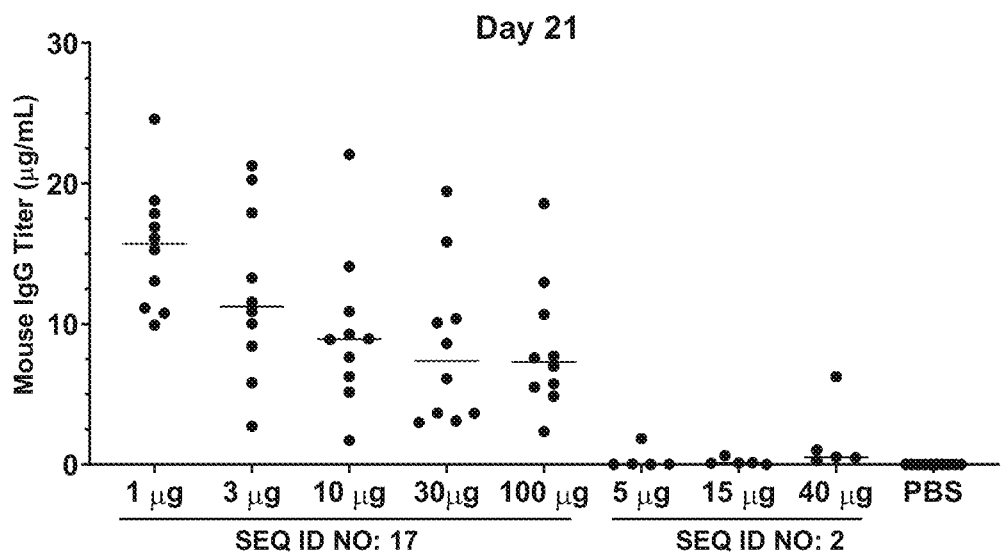
FIG. 28

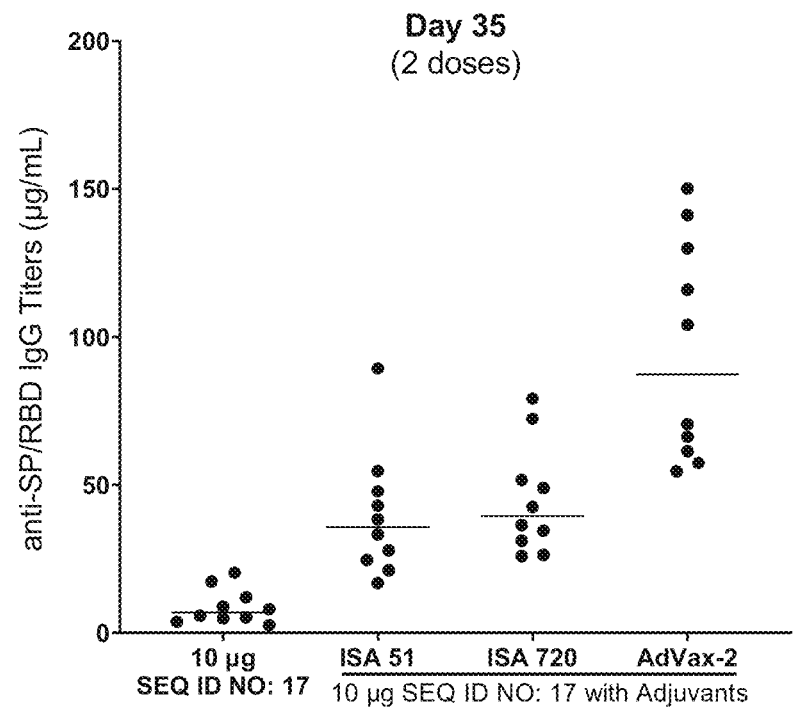
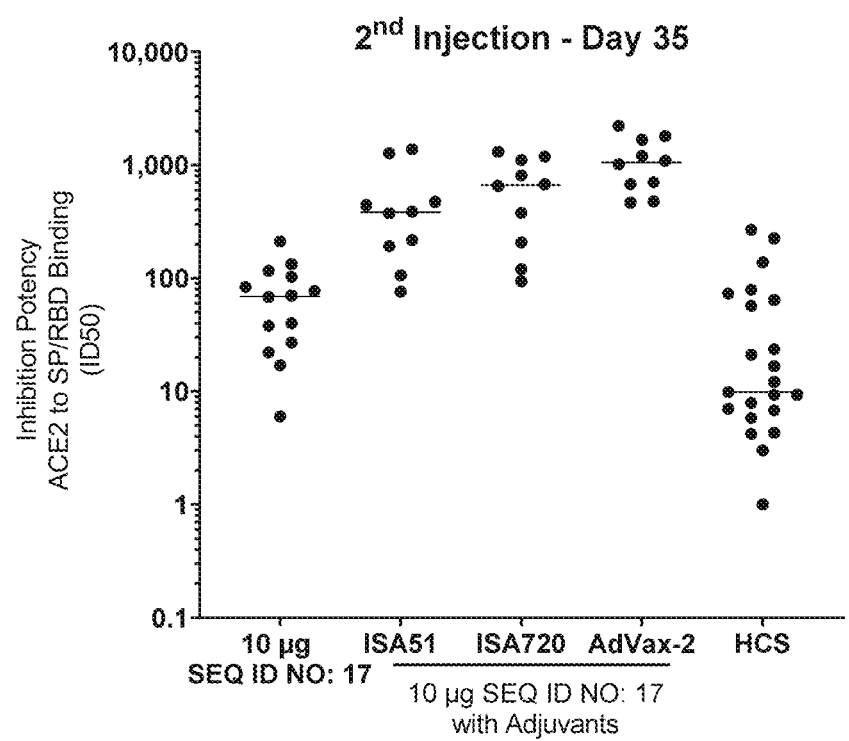
FIG. 38

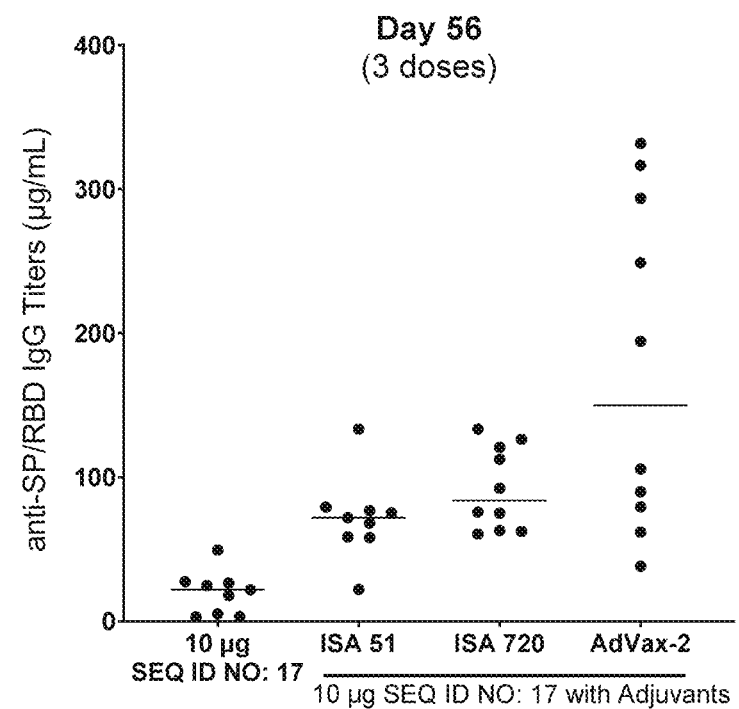
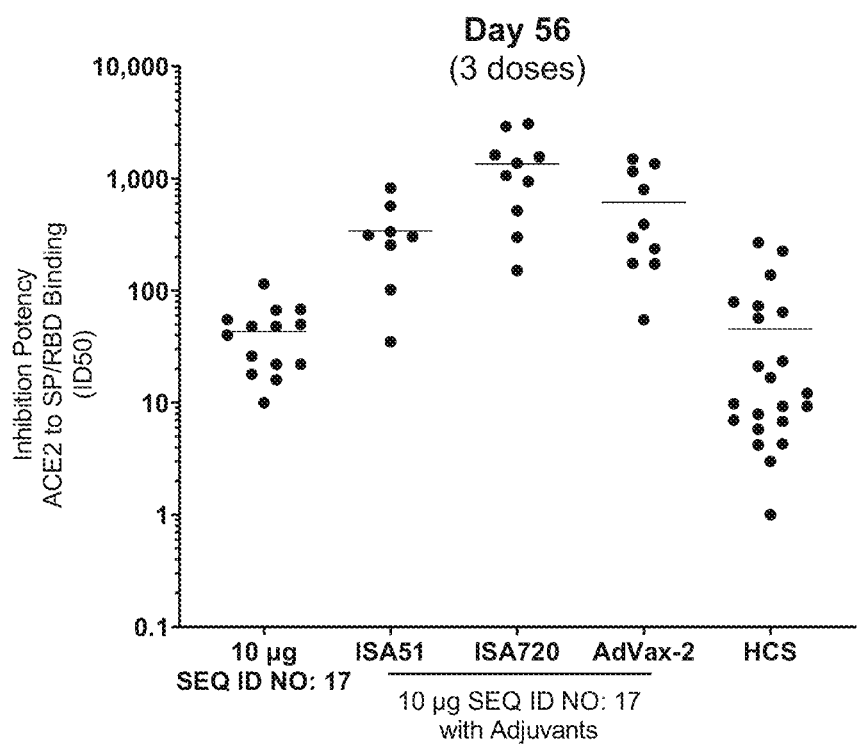
FIG. 39

```
SEQ ID NO:2      PNITNLCPFGEVFNATRFASVYAWNRKRISNCVADYSVLYNSASFSTFKCYGVSPTKLND    60
SEQ ID NO:24     PNITNLCPFGEVFNATRFASVYAWNRKRISNCVADYSVLYNSASFSTFKCYGVSPTKLND    60
SEQ ID NO:25     PNITNLCPFGEVFNATRFASVYAWNRKRISNCVADYSVLYNSASFSTFKCYGVSPTKLND    60
                 ************************************************************

SEQ ID NO:2      LCFTNVYADSFVIRGDEVRQIAPGQTGKIADYNYKLPDDFTGCVIAWNSNNLDSKVGGNY   120
SEQ ID NO:24     LCFTNVYADSFVIRGDEVRQIAPGQTGKIADYNYKLPDDFTGCVIAWNSNNLDSKVGGNY   120
SEQ ID NO:25     LCFTNVYADSFVIRGDEVRQIAPGQTGKIADYNYKLPDDFTGCVIAWNSNNLDSKVGGNY   120
                 ************************************************************

SEQ ID NO:2      NYLYRLFRKSNLKPFERDISTEIYQAGSTPCNGVEGFNCYFPLQSYGFQPTNGVGYQPYR   180
SEQ ID NO:24     NYLYRLFRKSNLKPFERDISTEIYQAGSTPCNGVEGFNCYFPLQSYGFQPTYGVGYQPYR   180
SEQ ID NO:25     NYLYRLFRKSNLKPFERDISTEIYQAGSTPCNGVKGFNCYFPLQSYGFQPTNGVGYQPYR   180
                 **********************************:*****************.******

SEQ ID NO:2      VVVLSFELLHAPATVCGPKKSTNLVKNKCVNFNFNGLTGTGVLTESNKKFLPFQQFGRDI   240
SEQ ID NO:24     VVVLSFELLHAPATVCGPKKSTNLVKNKCVNFNFNGLTGTGVLTESNKKFLPFQQFGRDI   240
SEQ ID NO:25     VVVLSFELLHAPATVCGPKKSTNLVKNKCVNFNFNGLTGTGVLTESNKKFLPFQQFGRDI   240
                 ************************************************************

SEQ ID NO:2      ADTTDAVRDPQTLE    254
SEQ ID NO:24     ADTTDAVRDPQTLE    254
SEQ ID NO:25     ADTTDAVRDPQTLE    254
                 **************
```

FIG. 66

```
SEQ ID NO:8     ---------------NITNLCPFGEVFNATRFASVYAWNRKRISNCVADYSVLYNSASFSTFK    48
SEQ ID NO:9     ---------------QITNLCPFGEVFQATRFASVYAWNRKRISNCVADYSVLYNSASFSTFK    48
SEQ ID NO:10    ----------------------------------------------------------------    0
SEQ ID NO:14    RVQPTESIVRFPNITNLCPFGEVFNATRFASVYAWNRKRISNCVADYSVLYNSASFSTFK    60
SEQ ID NO:15    RVQPTESIVRFPNITNLCPFGEVFNATRFASVYAWNRKRISNCVADYSVLYNSASFSTFK    60

SEQ ID NO:8     CYGVSPTKLNDLCFTNVYADSFVIRGDEVRQIAPGQTGKIADYNYKLPDDFTGCVIAWNS    108
SEQ ID NO:9     CYGVSPTKLNDLMFTNVYADSFVIRGDEVRQIAPGQTGKIADYNYKLPDDFTGCVIAWNS    108
SEQ ID NO:10    -------------------------------------------------------VIAWNS    6
SEQ ID NO:14    CYGVSPTKLNDLCFTNVYADSFVIRGDEVRQIAPGQTGKIADYNYKLPDDFTGCVIAWNS    120
SEQ ID NO:15    CYGVSPTKLNDLCFTNVYADSFVIRGDEVRQIAPGQTGKIADYNYKLPDDFTGCVIAWNS    120
                                                                       ******

SEQ ID NO:8     NNLDSKVGGNYNYLYRLFRKSNLKPFERDISTEIYQAGSTPCNGVEGFNCYFPLQSYGFQ    168
SEQ ID NO:9     NNLDSKVGGNYNYLYRLFRKSNLKPFERDISTEIYQAGSTPCNGVEGFNCYFPLQSYGFQ    168
SEQ ID NO:10    NNLDSKVGGNYNYLYRLFRKSNLKPFERDISTEIYQAGSTPCNGVEGFNCYFPLQSYGFQ    66
SEQ ID NO:14    NNLDSKVGGNYNYLYRLFRKSNLKPFERDISTEIYQAGSTPCNGVEGFNCYFPLQSYGFQ    180
SEQ ID NO:15    NNLDSKVGGNYNYLYRLFRKSNLKPFERDISTEIYQAGSTPCNGVEGFNCYFPLQSYGFQ    180
                ************************************************************

SEQ ID NO:8     PTNGVGYQPYRVVVLSFELLHAPATV-----------------------194
SEQ ID NO:9     PTNGVGYQPYRVVVLSFELLHAPATV-----------------------194
SEQ ID NO:10    PTNGVGYQPYRVVVLSFELLHAPATV-----------------------92
SEQ ID NO:14    PTNGVGYQPYRVVVLSFELLHAPATVCGPKKSTNLVKNKCVNF223
SEQ ID NO:15    PTNGVGYQPYRVVVLSFELLHAPATVCGPKKSTNLVK------217
                *************************
```

FIG. 80

|   | Calibrator IgG Standards | | Sample and Assay Controls Area | | | | | | | | | |
|---|---|---|---|---|---|---|---|---|---|---|---|---|
|   | 1 | 2 | 3 | 4 | 5 | 6 | 7 | 8 | 9 | 10 | 11 | 12 |
| A | Std 1 ○ | ○ | Assay Control 1 ○ | ○ | ID: ○ | ○ | ID: ○ | ○ | ID: ○ | ○ | ID: ○ | ○ |
| B | Std 2 ○ | ○ | Assay Control 2 ○ | ○ | ID: ○ | ○ | ID: ○ | ○ | ID: ○ | ○ | ID: ○ | ○ |
| C | Std 3 ○ | ○ | ID: ○ | ○ | ID: ○ | ○ | ID: ○ | ○ | ID: ○ | ○ | ID: ○ | ○ |
| D | Std 4 ○ | ○ | ID: ○ | ○ | ID: ○ | ○ | ID: ○ | ○ | ID: ○ | ○ | ID: ○ | ○ |
| E | Std 5 ○ | ○ | ID: ○ | ○ | ID: ○ | ○ | ID: ○ | ○ | ID: ○ | ○ | ID: ○ | ○ |
| F | Std 6 ○ | ○ | ID: ○ | ○ | ID: ○ | ○ | ID: ○ | ○ | ID: ○ | ○ | ID: ○ | ○ |
| G | Std 7 ○ | ○ | ID: ○ | ○ | ID: ○ | ○ | ID: ○ | ○ | ID: ○ | ○ | ID: ○ | ○ |
| H | Std 8 ○ | ○ | ID: ○ | ○ | ID: ○ | ○ | ID: ○ | ○ | ID: ○ | ○ | ID: ○ | ○ |

FIG. 81

ANTIGEN SPECIFIC IMMUNOTHERAPY FOR COVID-19 FUSION PROTEINS AND METHODS OF USE

CROSS-REFERENCE TO RELATED APPLICATIONS

The present application is a continuation of U.S. Nonprovisional patent application Ser. No. 17/226,690, filed Apr. 9, 2021, which claims the priority benefit of U.S. Provisional Patent Applications: Ser. No. 63/008,497, filed Apr. 10, 2020, Ser. No. 63/008,503, filed Apr. 10, 2020, Ser. No. 63/008,509, filed Apr. 10, 2020, Ser. No. 63/008,515, filed Apr. 10, 2020, Ser. No. 63/041,574, filed Jun. 19, 2020, Ser. No. 63/041,579, filed Jun. 19, 2020, Ser. No. 63/041,582, filed Jun. 19, 2020, Ser. No. 63/041,584, filed Jun. 19, 2020, Ser. No. 63/048,939, filed Jul. 7, 2020, Ser. No. 63/068,775, filed Aug. 21, 2020, Ser. No. 63/068,805, filed Aug. 21, 2020, Ser. No. 63/068,843, filed Aug. 21, 2020, Ser. No. 63/068,894, filed Aug. 21, 2020, and Ser. No. 63/068,911, filed Aug. 21, 2020, each entitled ANTIGEN SPECIFIC IMMUNOTHERAPY FOR COVID-19 FUSION PROTEINS AND METHODS OF USE, and each of which is incorporated by reference in its entirety herein.

SEQUENCE LISTING

The following application contains a sequence listing in computer readable format (CRF), submitted electronically as a text file in ASCII format entitled "SequenceListing_044," created on Oct. 29, 2021, as 84,572 bytes in size. The content of the CRF is hereby incorporated by reference.

TECHNICAL FIELD

The present technology relates to fusion proteins comprising a truncation of the SARS-CoV-2 surface glycoprotein comprising the SARS-CoV-2 Receptor Binding Domain (SARS-CoV-2-RBD) or an analog thereof linked to human Fc fragments and their use in relation to the 2019 Novel Coronavirus (COVID-19).

BACKGROUND

The following description of the background is provided simply as an aid in understanding the present technology and is not admitted to describe or constitute prior art to the present technology.
Fc Fusion Proteins Fc fusion proteins are comprised of a species-specific immunoglobin Fc domain that is linked to another peptide such as a protein or peptide with therapeutic potential. As used herein, the terms "fusion protein" and "Fc fusion protein" refer to a protein comprising more than one part, for example from different sources (e.g., different proteins, polypeptides, cells, etc.), that are covalently linked through peptide bonds. Fc fusion proteins are preferably covalently linked by (i) connecting the genes that encode for each part into a single nucleic acid molecule and (ii) expressing in a host cell (e.g., HEK cell or CHO cell) the protein for which the nucleic acid molecule encodes. The fully recombinant synthesis approach is preferred over methods in which the therapeutic protein and Fc fragments are synthesized separately and then chemically conjugated. The chemical conjugation step and subsequent purification process increase the manufacturing complexity, reduce product yield, and increase cost.

The terms "Fc fragment," "Fc region," "Fc domain," or "Fc polypeptide," are used herein to define a C-terminal region of an immunoglobulin heavy chain. The Fc fragment, region, domain, or polypeptide may be a native sequence Fc region or a variant/mutant Fc region. Although the boundaries of the Fc region of an immunoglobulin heavy chain may vary, they generally comprise some or all of the hinge region of the heavy chain, the CH2 region of the heavy chain, and the CH3 region of the heavy chain. The hinge region of a Fc fragment (e.g., a canine or human Fc fragment) comprises amino acid sequences that connect the CH1 domain of the heavy chain to the CH2 region of the heavy chain and contains one or more cysteines that form one or more interheavy chain disulfide bridges to form a homodimer of an Fc fusion protein from two identical but separate monomers of the Fc fusion protein. The hinge region may comprise all or part of a naturally occurring amino acid sequence or a non-naturally occurring amino acid sequence.

The presence of the Fc domain increases the plasma half-life due to its interaction with the neonatal Fc-receptor (FcRn) in addition to slower renal clearance of the Fc fusion protein due to the large molecule size, resulting in in vivo recycling of the molecule achieving prolonged activity of the linked peptide and improved solubility and stability of the Fc fusion protein molecule. The Fc domain also enables Fc fusion proteins to interact with Fc receptors on immune cells. In some examples, the therapeutic protein or peptide is linked to the immunoglobin Fc domain via a linker. The therapeutic protein or peptide and linker effectively replace the variable region of an antibody while keeping the Fc region intact.

An Fc receptor (FcR) refers to a receptor that binds to an Fc fragment or to the Fc region of an antibody. In examples, the FcR is a native sequence of the canine or human FcR, and the FcR is one which binds an Fc fragment or the Fc region of an IgG antibody (a gamma receptor) and includes without limitation, receptors of the Fc(gamma) receptor I, Fc(gamma) receptor IIa, Fc(gamma) receptor IIb, and Fc(gamma) receptor III subclasses, including allelic variants and alternatively spliced forms of these receptors. "FcR" also includes the neonatal receptor, FcRn, which is responsible for the transfer of maternal IgG molecules to the fetus and is also responsible for the prolonged in vivo elimination half-lives of antibodies and Fc-fusion proteins in vivo. In examples, FcR of human origin are used in vitro (e.g., in an assay) to measure the binding of Fc fusion proteins comprising Fc fragments of any mammalian origin so as to assess their FcR binding properties. Those skilled in the art will understand that mammalian FcR from one species (e.g., FcR of human origin) are sometimes capable of in vitro binding of Fc fragments from a second species (e.g., FcR of canine origin).

SUMMARY OF THE PRESENT TECHNOLOGY

Described herein are fusion proteins, each comprising a respective viral receptor binding domain and an Fc fragment, wherein the viral receptor binding domain and the Fc fragment are connected by an optional linker, such as a peptide linker. In one or more embodiments, the viral receptor binding domain comprises an RBD fragment of SARS-CoV-2 surface glycoprotein comprising SEQ ID NO: 1, or a functional fragment, analog, or variant/mutant thereof. In one or more embodiments, the viral receptor binding domain comprises a SP/RBD fragment or RBD fragment comprising SEQ ID NO: 2 or SEQ ID NO: 8, or a functional fragment, analog, or variant/mutant thereof. In one or more embodiments, the viral receptor binding domain comprises the following sequences or functional fragment thereof, SEQ ID NO: 9, SEQ ID NO: 10, SEQ ID NO: 13, SEQ ID NO: 14, or SEQ ID NO: 15. In one or more embodiments, the Fc fragment comprises a sequence or functional fragment of SEQ ID NO: 6, SEQ ID NO: 7, or SEQ ID NO: 33. In one or more embodiments, the linker, if present, comprises the following sequence: SEQ ID NO: 3, SEQ ID NO: 4, SEQ ID NO: 5, or SEQ ID NO: 27. In one or more embodiments, the fusion protein comprises (consists essentially or even consists of) a sequence of SEQ ID NO: 11, SEQ ID NO: 12, SEQ ID NO: 16, SEQ ID NO: 17, SEQ ID NO: 18, SEQ ID NO: 19, SEQ ID NO: 20, or SEQ ID NO: 21, or a functional fragment thereof. In one or more embodiments, the fusion protein is a homodimer. In one or more embodiments, the Fc fragment is glycosylated.

Also described herein are immunogenic compositions which comprise or consist essentially of a fusion protein(s) according to any embodiments or combinations of embodiments described herein, and a pharmaceutically-acceptable carrier. In one or more embodiments, the fusion protein is dispersed in the carrier. In one or more embodiments, the compositions further comprise an adjuvant. In one or more embodiments, the adjuvant is Montanide™ ISA-720. In one or more embodiments, the fusion protein is emulsified with the adjuvant. In one or more embodiments, the emulsification is prepared onsite before administration. In one or more embodiments, the prepared emulsification is refrigeration (4° C.) or room temperature stable for at least 8 hours, preferably up to 24 hours. In one or more embodiments, the composition is an injectable formulation. In one or more embodiments, the composition is adapted for subcutaneous administration. In one or more embodiments, the composition is adapted for prophylactic vaccination. In one or more embodiments, the composition is adapted for therapeutic vaccination.

Also described herein are various methods for increasing antibody production in a subject against an antigenic agent. The methods generally comprise administering a therapeutically effective amount of a fusion protein(s) or immunogenic composition(s) according to any embodiments or combinations of embodiments described herein to the subject. In one or more embodiments, the subject has a measurable antibody titer against the antigenic agent prior to administration of the fusion protein or immunogenic composition. In one or more embodiments, the subject is antibody naïve prior to administration of the fusion protein or immunogenic composition. In one or more embodiments, the fusion protein or immunogenic composition is administered via injection. In one or more embodiments, the fusion protein or immunogenic composition is administered subcutaneously or intramuscularly. In one or more embodiments, the fusion protein or immunogenic composition is provided as a unit dosage form. In one or more embodiments, the fusion protein or immunogenic composition is co-administered with an adjuvant. In one or more embodiments, the methods further comprise preparing the fusion protein or immunogenic composition for administration, wherein the preparation comprises pre-mixing the fusion protein or immunogenic composition with an adjuvant before administration. In one or more embodiments, pre-mixing comprises emulsifying the adjuvant and fusion protein to yield an emulsion, and administering the emulsion to the subject. In one or more embodiments, the prepared emulsification is refrigeration (4° C.) or room temperature stable for at least 8 hours, preferably up to 24 hours after preparation.

Also described herein are methods of inducing an immune response in a subject against viral infection, preferably SARS-CoV-2 virus, more preferably COVID-19. The methods generally comprise administering a therapeutically effective amount of a fusion protein(s) or immunogenic composition(s) according to any embodiments or combinations of embodiments described herein to the subject. In one or more embodiments, the subject has a measurable antibody titer against the viral infection prior to administration of the fusion protein or immunogenic composition. In one or more embodiments, the subject is antibody naïve prior to administration of the fusion protein or immunogenic composition. In one or more embodiments, the fusion protein or immunogenic composition is administered via injection. In one or more embodiments, the fusion protein or immunogenic composition is administered subcutaneously or intramuscularly. In one or more embodiments, the fusion protein or immunogenic composition is provided as a unit dosage form. In one or more embodiments, the fusion protein or immunogenic composition is co-administered with an adjuvant. In one or more embodiments, the methods further comprise preparing the fusion protein or immunogenic composition for administration, wherein the preparation comprises pre-mixing the fusion protein or immunogenic composition with an adjuvant before administration. In one or more embodiments, pre-mixing comprises emulsifying the adjuvant and fusion protein to yield an emulsion, and administering the emulsion to the subject. In one or more embodiments, the prepared emulsification is refrigeration (4° C.) or room temperature stable for at least 8 hours, preferably up to 24 hours after preparation.

Also described herein are methods of producing a fusion protein according to any embodiments or combinations of embodiments described herein. The methods generally comprising transiently transfecting a nucleic acid encoding for the fusion protein into a HEK293 or CHO-SE cell, wherein the transfected HEK293 or CHO-SE cell expresses the fusion protein, or stably transfecting a nucleic acid encoding for the fusion protein into a CHO cell, wherein the recombinant CHO cell expresses the fusion protein. In one or more embodiments, the fusion protein is secreted by the cells into cell culture media, further comprising purifying or isolating the fusion protein from the media. Advantageously, the yield of the purified or isolated fusion protein is greater than 20 mg/L in any of the foregoing expression systems.

Also described herein are cells engineered to express a fusion protein a fusion protein according to any embodiments or combinations of embodiments described herein. In one or more embodiments, the cell is transfected with a nucleic acid encoding the fusion protein. In one or more embodiments, the cell is a HEK293 cell or a CHO cell.

Also described herein are cDNA molecules encoding a fusion protein according to any embodiments or combinations of embodiments described herein. The present disclosure also concerns expression vectors and/or DNA expression constructs comprising cDNA encoding a fusion protein according to any embodiments or combinations of embodiments described herein.

As described herein, the fusion protein(s) or immunogenic composition(s) according to any embodiments or combinations of embodiments described herein can be used in therapy and/or as a medicament.

As described herein, the fusion protein(s) or immunogenic composition(s) according to any embodiments or combinations of embodiments described herein can be used in increasing antibody production in a subject.

As described herein, the fusion protein(s) or immunogenic composition(s) according to any embodiments or combinations of embodiments described herein can be used in treatment and/or prophylaxis of a viral infection, preferably SARS-CoV-2 virus, more preferably COVID-19.

As described herein, the fusion protein(s) or immunogenic composition(s) according to any embodiments or combinations of embodiments described herein can be used as a prophylactic, therapeutic and/or booster vaccine.

Particular embodiments concern fusion protein(s) selected from the group consisting of: SEQ ID NO: 16, SEQ ID NO: 18, SEQ ID NO: 19, SEQ ID NO: 20, and SEQ ID NO: 21, or pharmaceutical composition thereof for use in treatment and/or prophylaxis of a viral infection, preferably SARS-CoV-2 virus, more preferably COVID-19.

As described herein, the fusion protein(s) or immunogenic composition(s) according to any embodiments or combinations of embodiments described herein can be used in the manufacture of a medicament for the treatment and/or prophylaxis of a viral infection.

For example, SEQ ID NO: 19 emulsified in ISA 720 adjuvant was initially evaluated in BALB/c mice for immunogenicity and the capacity to induce production of antibodies (Abs) that bind and neutralize the SARS-CoV-2 virus' Spike Protein (SP). Upon binding to the Receptor Binding Domain of the SP (SP/RBD), these vaccine-induced Abs prevent the virus from attaching to the host target protein, ACE2, expressed on a variety of cell types including endothelial cells of the lung, blood vessels, and neurons. Even after a single injection of 1 μg to 100 μg of SEQ ID NO: 19 in the adjuvant Montanide™ ISA 720, substantial neutralizing Abs were induced in mice, NHPs, and rabbits that 1) bound to recombinant SP/RBD, 2) inhibited recombinant ACE2 from binding recombinant SP/RBD, and 3) prevented the SARS-CoV-2 virus from infecting live VERO-E6 cells that naturally express ACE2. Notably, the potency of the SEQ ID NO: 19 vaccine to induce neutralizing Abs in each of the above animal models was usually on par or above the neutralization capacity of human serum obtained from convalescent COVID-19 subjects, setting the expectation that SEQ ID NO: 19 in Montanide™ ISA 720 adjuvant should induce sufficient protection in humans. The assays and animal models described herein were used to demonstrate that the optimal dose level of SEQ ID NO: 19 in Montanide™ ISA 720 adjuvant was in the 30 μg to 100 μg range, that two doses given either subcutaneously (s.c.) or intramuscularly (i.m.) induced maximum immunogenic responses, and that 3 doses of 100 μg of SEQ ID NO: 19 in Montanide™ ISA 720 given 14 days apart showed no toxicities or serious adverse effects in a GLP toxicology study in rabbits. As expected, mild and transient injection site reactions due to the Montanide™ ISA 720 adjuvant were observed.

BRIEF DESCRIPTION OF THE DRAWINGS

FIG. 2 shows a schematic representation of an exemplary SARS-CoV-2-RBD-hIgG-Fc fusion protein homodimer.

FIG. 12 illustrates the promotion of B cell activation and anti-SARS-CoV-2 SP/RBD IgG production.

FIG. 13 illustrates a side-by-side sequence comparison of SEQ ID NO: 2 (extended SP/RBD of SARS-CoV-2) and SEQ ID NO: 9 (novel truncation of the surface glycoprotein of SARS-CoV-2).

FIG. 14 illustrates a side-by-side sequence comparison of SEQ ID NO: 2 (extended SP/RBD of SARS-CoV-2) and SEQ ID NO: 10 (novel truncation of the surface glycoprotein of SARS-CoV-2).

FIG. 15 illustrates a side-by-side sequence comparison of SEQ ID NO: 2 (extended SP/RBD of SARS-CoV-2) and SEQ ID NO: 14 (novel truncation of the surface glycoprotein of SARS-CoV-2).

FIG. 16 illustrates a side-by-side sequence comparison of SEQ ID NO: 2 (extended SP/RBD of SARS-CoV-2) and SEQ ID NO: 15 (novel truncation of the surface glycoprotein of SARS-CoV-2).

FIG. 17 illustrates a side-by-side sequence comparison of SEQ ID NO: 2 (extended SP/RBD of SARS-CoV-2) and SEQ ID NO: 13 (novel truncation of the surface glycoprotein of SARS-CoV-2).

FIG. 28 illustrates the induced anti-SP/RBD IgG Ab titer response after administration of the SP/RBD of SEQ ID NO: 2 or the SARS-CoV-2-RBD-hIgG-Fc fusion protein of SEQ ID NO: 17 to 6- to 8-week old mice without adjuvant at various dose levels as measured on Day 14 and Day 21 after one dose on Day 0.

FIG. 38 illustrates the induced anti-SP/RBD IgG Ab response and the ACE2-SP/RBD binding inhibition potency (ID50) after administration of the SARS-CoV-2-RBD-hIgG-Fc fusion protein of SEQ ID NO: 17 to 8- to 10-month old mice with adjuvant at various dose levels as measured on Day 35 after an injection on Day 0 and Day 21.

FIG. 39 illustrates the induced anti-SP/RBD IgG Ab response and the ACE2-SP/RBD binding inhibition potency (ID50) after administration of the SARS-CoV-2-RBD-hIgG-Fc fusion protein of SEQ ID NO: 17 to 8- to 10-month old mice with adjuvant at various dose levels as measured on Day 56 after an injection on Day 0, Day 21 and Day 42.

FIG. 66 illustrates a side-by-side sequence comparison of the SP/RBD of SEQ ID NO: 2, and the SP/RBD variants of SEQ ID NO: 24, and SEQ ID NO: 25.

FIG. 80 illustrates a side-by-side sequence comparison of SEQ ID NO: 8 (RBD of SARS-CoV-2) with SEQ ID NO: 9, SEQ ID NO: 10, SEQ ID NO: 14 and SEQ ID NO: 15 (all RBD of SARS-CoV-2 with novel mutations).

FIG. 81 illustrates a 96 well microplate such as that which may be used for a general serology assay for evaluating existing SARS-CoV-2 antibody titer in serum.

DETAILED DESCRIPTION

Novel Coronavirus Disease 2019

Figure 1:
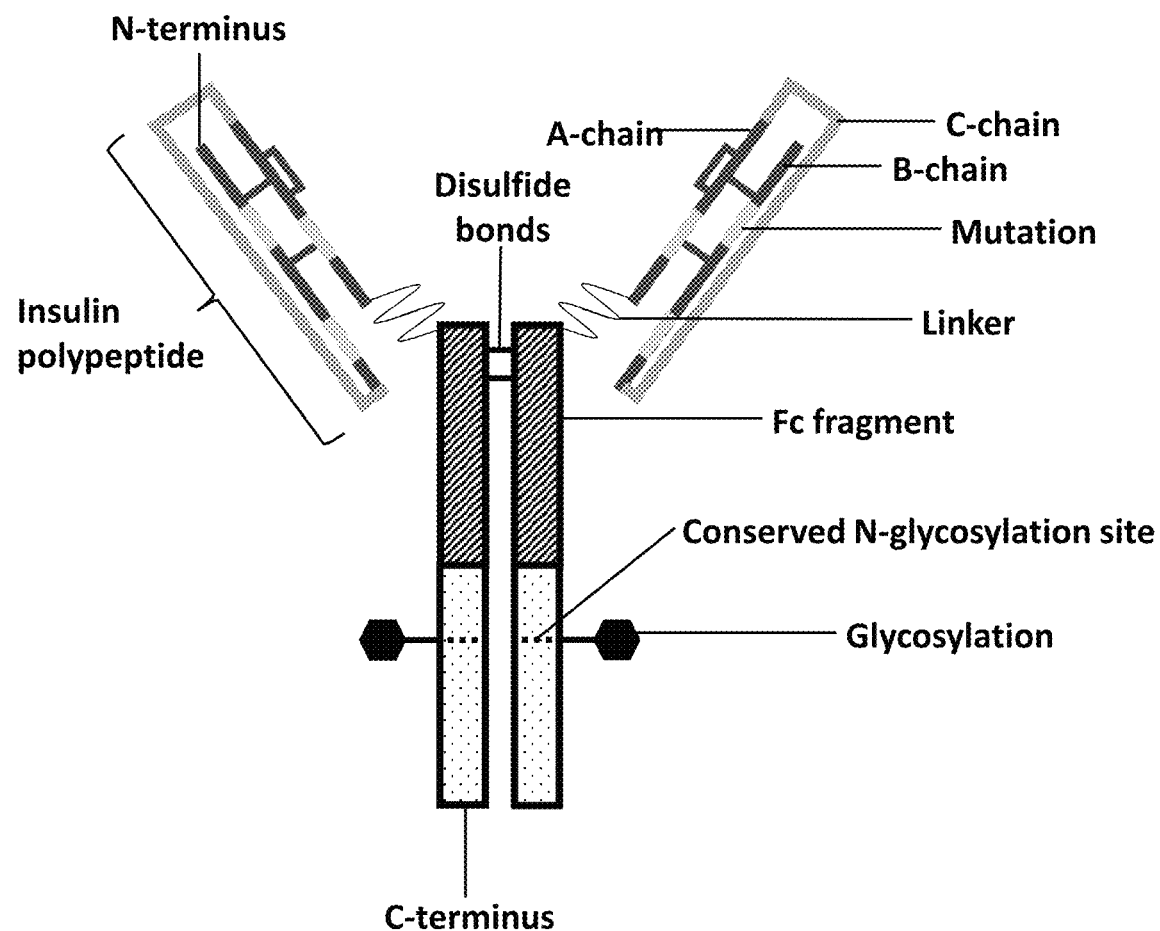
FIG. 1 shows a schematic representation of an insulin-Fc fusion protein homodimer.

Novel Coronavirus Disease 2019 (COVID-19) is a severe and acute respiratory illness caused by the SARS-CoV-2 virus. The first COVID-19 case was reported in Wuhan, China in December 2019 and as of 18 Nov. 2020, there have been approximately 56 million (M) cases worldwide to date (quantified as SARS-CoV-2 virus confirmed and unconfirmed "probable"), in which there are 18.5M active cases, 36M recovered cases, and 1.3M fatal cases attributed to COVID-19 (University, J. H., COVID-19 Dashboard by the Center for Systems Science and Engineering (CSSE) at Johns Hopkins University; www.covidtracker.com/). At the end of 2020, only the Pfizer-BioNTech COVID-19 vaccine BNT162b2 was approved under the World Health Organization's (WHO) Emergency Use Listing (EUL) procedure for emergency use against COVID-19. A second vaccine from Moderna (mRNA-1273) is expected to be approved under the WHO EUL procedure for vaccine emergency use against COVID-19 by the end of February 2021. The consensus among experts is that society cannot return to normal unless and until there is a sufficient level of immunity conferred on the population. Achieving natural herd immunity is estimated to require at least 70% of the population to have been infected which would result in millions of deaths worldwide, an ethically unacceptable outcome.

ACE2 Receptor

Angiotensin-Converting Enzyme 2 (ACE2) is the host cell receptor responsible for mediating infection by SARS-CoV-2 (i.e., to which SARS-CoV-2 binds in order to infect cells). ACE2 is a type 1 transmembrane metallocarboxypeptidase. Polymerase Chain Reaction (PCR) analysis shows that ACE2 is expressed on lung epithelium, blood vessel endothelium, and specific neuronal cells that appears to account for the dominant clinical manifestations of COVID-19, including pulmonary, cardiovascular, and neurological complications, respectively. Based on the sequence similarities of the receptor binding domain between SARS-CoV-2 and SARS-CoV, researchers have shown that SARS-CoV-2 can use ACE2 expressed on the surface of human cells to gain entry into ACE2 expressing HeLa cells.

Convalescent Sera for Treatment of Virus Patients

Clinicians and researchers around the world are working to develop various solutions to mitigate the pandemic caused by SARS-CoV-2. Scientists are working to develop vaccines that can prevent COVID-19 and antiviral treatments to reduce the severity and symptoms of the illness. Development of vaccines, monoclonal antibodies (mAbs), or drugs to treat SARS-CoV-2 is ongoing. Many clinicians believed that human convalescent serum was a viable option for the prevention and treatment of COVID-19.

Convalescent serum is a form of passive antibody therapy, through which sera from infected and recovered individuals containing anti-virus antibodies is transfused to a susceptible or infected individual, providing that individual with some level of immunity to either prevent or reduce the severity of the disease. This treatment is different from a vaccine, which works by inducing an immune response in an individual such that the individual produces their own antibodies against the virus. Experience from the SARS-CoV outbreak in 2002 and the 2009-2010 H1N1 influenza outbreak has shown that sera from patients that have contracted and recovered from the virus (human convalescent sera) contains antibodies capable of neutralizing the virus and is useful as an intervention for individuals with severe disease symptoms or as a prophylactic vaccine.

The use of human convalescent sera has risks and limitations. Firstly, the transfer of blood substances from one person to another comes with it the risk of inadvertent infection of another infectious disease as well as the risk of reactions to other serum constituents. Another challenge in using convalescent sera is that some patients who recover from viral diseases do not have high titers of neutralizing antibody. In one case with respect to another human coronavirus, Middle East respiratory syndrome (MERS-CoV), three patients in South Korea were treated with convalescent serum, but only two of the recipients had neutralizing antibody in their serum. Of those that do have neutralizing antibodies after recovering from viral disease, some may not have sufficiently high titers of neutralizing antibody to be a viable donor. A further survey related to SARS-CoV found that of 99 samples of convalescent sera from patients with SARS, 87 had neutralizing antibody, with a geometric mean titer of 1:61. These and various other studies suggest that few patients made high-titer responses and also that neutralizing antibody titer declines with time. There are a number of companies looking to overcome this challenge by producing recombinant antibodies instead of solely relying on antibodies from recovered patients; however, the scale of production is insufficient, and the medical intervention required to administer effective doses to patients every few weeks to few months, most likely through intravenous injection or infusion, is highly burdensome.

A more significant limitation is that the proposed use of convalescent sera in the COVID-19 epidemic would rely on preparations with high titers of SARS-CoV-2 neutralizing antibodies. This requires a significant population of donors who have recovered from the disease and can donate convalescent serum. Determining who has already had the disease and has developed some immunity presents challenges. COVID-19 presents with a wide variety of severity of symptoms and many individuals with mild cases may not know that they have had the disease. A highly available and low-cost test kit to measure anti-SARS-CoV-2 antibodies is also required.

However, even with the ability to identify recovered patients with high titers of neutralizing antibodies, it is unlikely that a single individual's plasma can treat more than a few patients. Therefore, while current approaches to convalescent sera treatment may be able to prevent or treat COVID-19 in a small number of patients, this solution does not address the greater need of humanity during and after this pandemic.

Overview and Challenges of Current Vaccines

Clinicians and researchers around the world are working to develop various solutions to mitigate the pandemic caused by the SARS-CoV-2 virus. These solutions include vaccines that can prevent COVID-19 and antiviral treatments to reduce the severity and symptoms of the illness. The expectation of the foreseeable future is that natural and vaccine-induced immunity most likely will not be long-lived, and therefore a cost-effective and safe vaccine administered as frequently as every 6 months, if necessary, is required to maintain robust immunity among the population. Thus, the critical design features of an effective prophylactic COVID-19 vaccine are: i) a potent capacity to induce SARS-CoV-2 viral neutralizing IgG titers and a significant T helper type 1 (Th1) cell response, preferably after a single dose; ii) an acceptable safety and tolerability profile, especially with respect to inflammation caused by reactogenicity (systemic effect) and injection site (local effect), a favorable cost-of-goods (COGs) with respect to manufacturability and vaccine potency which dictate dose-frequency and dose-level, and a suitable supply-chain path including a sufficient storage shelf-life and robust test article preparation and administration procedures.

Live-attenuated or inactive whole virus vaccines represent a classic strategy. A major advantage of whole virus vaccines is their inherent immunogenicity and ability to stimulate toll-like receptors (TLRs) including TLR 3, TLR 7/8, and TLR 9. However, live virus vaccines often require extensive additional testing to confirm their safety. This is especially an issue for coronavirus vaccines, given the findings of increased infectivity following immunization with live or killed whole virus SARS coronavirus vaccines. Johnson & Johnson is employing Janssen's AdVac® adenoviral vector manufactured in their PER.C6® cell line technology to generate their lead vaccine, JNJ-78436735, which recently completed Phase 3 trials and has been authorized for emergency use in the United States. This technology is an attempt to produce a viral vector to replace the whole virus with a purportedly benign adenoviral vector that carries a portion of the SARS-CoV-2 virus DNA. However, use of JNJ-78436735 encountered significant serious adverse events (SAEs) that caused clinical trial pauses.

Two additional hurdles in the early development of SARS coronavirus vaccines have been the finding of 1) undesired immunopotentiation in the form of Th2-mediated eosinophilic infiltration and 2) increased viral infectivity driven by ADE, which is noted to occur following challenge infections after immunizations with whole virus vaccines and complete SP vaccines. The risk of Th2-mediated eosinophilic infiltration and lung pathology is still under investigation in SARS-CoV-2 infection but it has been found in infants and animals challenged with respiratory syncytial virus (RSV) or with immunization with whole RSV vaccines.

ADE is an adverse characteristic of other viral vaccines, including those for the original SARS-CoV, dengue virus, and Zika viral infections, in which vaccine-induced Ab concentrations or affinities are too low to neutralize virus infection, but rather form immune complexes with virus that tend to interact with Fcγ receptors on myeloid cell surface through Fc domains of Abs. Such Abs do not neutralize viral infection or induce Fcγ-mediated viral clearance (Li), but aid virus infection by directly increasing virus uptake through Fcγ receptor or boosting virus replication intracellularly via activating downstream pathways to antagonize the innate immunity (reviewed in Sun). In both ADE and Th2-immunopotentiation, there is evidence that feline IgG2a mAbs (possibly of the Th2 isotype) can mediate both adverse conditions while IgG1 mAbs (known to have strong effector function, i.e., Th1 isotype) avoid such effects.

In addition to their risk of causing ADE and/or Th2-immunopotentiation, another challenge with viral vector vaccines is the relatively low manufacturability throughput and therefore high cost of goods (COGs) due to either chicken egg-based production or cell expression systems (Ewer).

As an alternative, nucleic acid expression vector vaccine platforms for COVID-19 encode the major coronavirus target antigen (Ag), the Spike Protein (SP), that mediates the virus' infective mechanism via its binding the host receptor, ACE2. Two examples of such vaccines that have advanced through Phase 3 trials are the mRNA vaccines encoding the full-length SP developed by BioNTech/Pfizer, BNT162b2 and Moderna, mRNA-1273. Both vaccines have reported very positive Phase 3 results with efficacy in protecting from symptomatic SARS-CoV-2 viral infection of greater than 90% leading to recent emergency use authorizations (EUAs) by the United States FDA. The concept of immunizing with RNA or DNA began with promising results in mice in 1993 showing protective immunity against influenza, but for decades these findings have not translated to similar findings in humans. Moreover, while non-replicative, many of these RNA and DNA expression vector vaccines continue to endogenously produce the target viral Ag well after induction of the intended immune response, an aspect that could ultimately create immune tolerance to the virus which is a growing concern and may become a practical risk with such current COVID-19 mRNA vaccines. Other challenges of these nucleic acid vaccines are the low durability of the response that may require too frequent dosing, and an unfavorable COGs due to cumbersome manufacturability via chemical synthesis. Furthermore, due to the inherent instability of RNA, the products must be kept and transported under frozen conditions, making them very difficult for most of the world to access.

As an additional alternative, recombinant subunit vaccines rely on eliciting an immune response against the SP to prevent its docking with the host target protein, ACE2. Such vaccines comprise all or a portion of the SP, rather than the DNA or RNA encoding for the protein, which is then mixed with an adjuvant to enhance the immune response. Due to the inherent stability of proteins relative to RNA and DNA, the storage and transportation requirements are less strict for subunit vaccines. Companies developing recombinant subunit vaccines include Novavax who has developed and produced immunogenic virus-like nanoparticles based on recombinant expression of SP, NVX-Cov2373, that are formulated with a saponin-based adjuvant system, Matrix-M™, and Clover Biopharmaceuticals who is developing a subunit vaccine consisting of a trimerized SARS-CoV-2 SP using their patented Trimer-Tag® technology. However, the full-length SP target Ag is known to have low expression yields in cell-expression systems and when used in SARS vaccines is known to induce anti-SP IgG titers against non-neutralizing epitopes of SP that again could mediate increased viral infectivity (i.e., ADE) and inflammation caused by lung eosinophilia (i.e., Th2-mediated immunopotentiation, discussed below). A subunit vaccine comprised of only the receptor-binding domain (RBD) of the SARS SP has the potential to mitigate against these safety challenges.

A consortium led by Texas Children's Hospital Center for Vaccine Development at Baylor College of Medicine has developed and tested a subunit vaccine comprised of only the receptor-binding domain (RBD) of the SARS SP, and when formulated with alum, this RBD-based vaccine can elicit high levels of protective immunity upon homologous virus challenge, in addition to avoiding ADE and immunopotentiation. Initial findings that the SARS and SARS-CoV-2 RBDs exhibit more than 80% amino acid similarity and bind the same ACE2 target offer an opportunity to develop either protein Ag as a subunit vaccine. Indeed, such a subunit vaccine proof-of-concept has been successfully demonstrated with coronavirus SP/RBD Ag's of MERS and SARS infections.

Some, but not all, of these features are being implemented in over 170 SARS-CoV-2 vaccine candidates currently in development, including live viruses, nucleic acids, and recombinant protein subunits that may ultimately offer promise as preventive vaccines against COVID-19. However, each vaccine strategy has unique advantages and challenges with respect to manufacturing, safety, and efficacy that must be simultaneously managed in an optimal manner.

The present disclosure is directed to methods for making and using novel fusion proteins which allow for the cost-effective production of large quantities of a recombinant subunit vaccine against the SARS-CoV-2 virus which can be transported and stored at mild temperatures. The present disclosure is specifically directed to methods for making and using fusion proteins for use in a prophylactic, therapeutic or booster vaccine which is efficacious for causing patients to create anti-virus antibodies to the SARS-CoV-2 virus. Using a SARS-CoV-2-RBD-hIgG-Fc fusion protein to cause a patient to create endogenous antibodies targeted to the receptor binding domain (RBD) portion of the SARS-CoV-2 virus is expected to be significantly more cost effective than recombinantly generating anti-SARS-CoV-2 therapeutic antibodies to later be injected into a patient.

In examples, a booster vaccine comprising a SARS-CoV-2-RBD-hIgG-Fc fusion protein may be administered to patients that have recovered from COVID-19 as an antibody amplification treatment (AAT), to increase their anti-SARS-CoV-2 antibody titers so that the serum they donate for use as a convalescent serum treatment can be used to treat more people. Recovered patients can be administered this AAT a few weeks before every new serum donation, significantly increasing the anti-SARS-CoV-2 antibody titer of the extracted sera and consequently significantly increasing the number of viral patients that can be treated with each donation.

In examples, a SARS-CoV-2-RBD-hIgG-Fc fusion protein may be used for detecting anti-SARS-CoV-2 antibodies in serum that is extracted from individuals. The ability to create a test kit using a SARS-CoV-2-RBD-hIgG-Fc fusion protein as a key reagent to reliably determine the presence and concentration of anti-SARS-CoV-2 antibodies in serum, permits clinicians to determine which individuals have had and recovered from the virus, which is particularly important in the case where patients may have experienced few or no symptoms. In examples, such a test kit could be used to evaluate performance of emerging vaccine candidates for SARS-CoV-2, by enabling the rapid and cost-effective ability to determine the presence and concentration of host-produced anti-SARS-CoV-2 antibodies in extracted serum post-vaccination. Broad deployment of such a test kit is expected to dramatically increase the number of potential donors of convalescent serum.

In an example, a pharmaceutical composition of a SARS-CoV-2-RBD-hIgG-Fc fusion protein is administered to patients who have been infected by the SARS-CoV-2 virus and have contracted COVID-19 to limit the scope of the infection and to ameliorate the disease. In examples, the SARS-CoV-2-RBD-hIgG-Fc fusion protein binds the ACE2 receptor, blocking the further uptake of the receptor binding domain (RBD) of the SARS-CoV-2 virus while also generating antibodies to neutralize the SARS-CoV-2 virus, leaving fewer RBD exposed to host cells.

In an example, a pharmaceutical composition of a SARS-CoV-2-RBD-hIgG-Fc fusion protein is administered as a prophylactic COVID-19 vaccine for individuals that have not been infected by the SARS-CoV-2 virus, resulting in the individual producing their own pool of anti-SARS-CoV-2 antibodies and immunity.

Equivalents and Definitions

As used herein, the articles "a" and "an" refer to one or more than one, e.g., to at least one, of the grammatical object of the article. The use of the words "a" or "an" when used in conjunction with the term "comprising" herein may mean "one," but it is also consistent with the meaning of "one or more," "at least one," and "one or more than one." As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

As used herein, "about" and "approximately" generally mean an acceptable degree of error for the quantity measured given the nature or precision of the measurements.

As used herein, an amount of a molecule, compound, conjugate, or substance effective to treat a disorder (e.g., a disorder described herein), "therapeutically effective amount," or "effective amount" refers to an amount of the molecule, compound, conjugate, or substance which is effective, upon single or multiple dose administration(s) to a subject, in treating a subject, or in curing, alleviating, relieving or improving a subject with a disorder (e.g., a disorder described herein) beyond that expected in the absence of such treatment.

As used herein, the term "analog" refers to a compound or conjugate (e.g., a compound or conjugate as described herein, e.g., RBD) having a chemical structure similar to that of another compound or conjugate but differing from it in at least one aspect.

As used herein, the term "antigen" refers to any substance that causes a patient's immune system to produce antibodies against it. An antigen may be a substance from the environment, such as chemicals, bacteria, viruses, or pollen, or an antigen may also form inside the body. An example of an antigen is the SARS-CoV-2 virus.

As used herein, the term "antibody" or "antibody molecule" refers to an immunoglobulin molecule (Ig), or immunologically active portions of an immunoglobulin (Ig) molecule, i.e., a molecule that contains an antigen binding site that specifically binds, e.g., immunoreacts with, an antigen. As used herein, the term "antibody domain" refers to a variable or constant region of an immunoglobulin. It is documented in the art that human antibodies comprise several classes, for example IgA, IgM, or IgG in the case of mammals (e.g., humans and dogs). Classes of mammalian IgG immunoglobulins can be further classified into different isotypes, such as IgGA, IgGB, IgGC and IgGD for dogs and IgG1, IgG2, IgG3, and IgG4 for humans. Those skilled in the art will recognize that immunoglobulin isotypes of a given immunoglobulin class will comprise different amino acid sequences, structures, and functional properties from one another (e.g., different binding affinities to Fc(gamma) receptors or ACE2 receptor). "Specifically binds" or "immunoreacts with" means that the antibody reacts with one or more antigenic determinants of the desired antigen and has a lower affinity for other polypeptides, e.g., does not react with other polypeptides.

Figure 2:
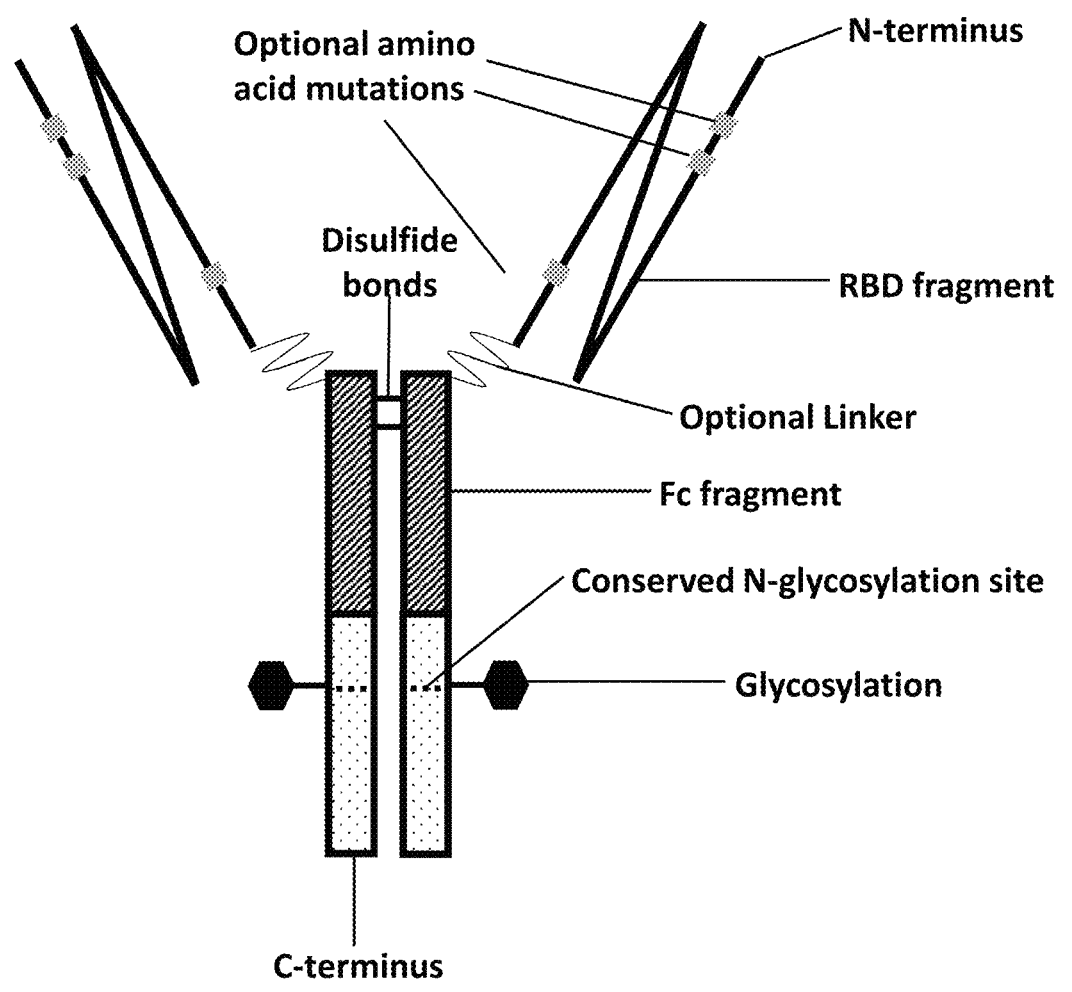

As used herein, the term "dimer" refers to a protein or a fusion protein comprising two polypeptides linked covalently. In embodiments, two identical polypeptides are linked covalently (e.g., via disulfide bonds) forming a "homodimer" (diagrammatically represented in FIG. 1, which is an illustration of an insulin-Fc fusion protein for reference, and FIG. 2, which is an illustration of a SARS-CoV-2-RBD-hIgG-Fc fusion protein). Referring to FIG. 1 in more detail, the insulin polypeptide (comprising an insulin B-chain analog connected via a C-chain peptide to an insulin A-chain analog) may have one or more amino acid mutations from native insulin. The insulin peptide is connected via a linker to an Fc fragment. Disulfide bonds (the total number of disulfide bonds in actuality may be greater or less than the number shown in FIG. 1) create a homodimer from two identical Fc fusion proteins. Referring to FIG. 2 in more detail, a SARS-CoV-2 RBD fragment may comprise a portion of the full SARS-CoV-2 surface glycoprotein. The RBD fragment may have one or more amino acid mutations from the native SARS-CoV-2 surface glycoprotein. The RBD fragment is connected to an Fc fragment using an optional linker (in some examples, the RBD fragment is covalently linked to an Fc fragment directly with no linker). Disulfide bonds create a homodimer from two identical SARS-CoV-2-RBD-hIgG-Fc fusion proteins (the total number of disulfide bonds in actuality may be greater or less than the number shown in FIG. 2). The Fc fusion protein homodimer may be encoded by a single nucleic acid molecule, wherein the homodimer is made recombinantly inside a cell by first forming Fc fusion protein monomers and by then assembling two identical Fc fusion protein monomers into the homodimer upon further processing inside the cell.

As used herein, the terms "multimer," "multimeric," or "multimeric state" refer to non-covalent, associated forms of Fc fusion protein dimers that may be in equilibrium with Fc fusion protein dimers or may act as permanently aggregated versions of Fc fusion protein dimers (e.g., dimers of Fc fusion protein homodimers, trimers of Fc fusion protein homodimers, tetramers of Fc fusion protein homodimers, or higher order aggregates containing five or more Fc fusion protein homodimers). It may be expected that multimeric forms of Fc fusion proteins may have different physical, stability, or pharmacologic activities from that of fusion protein homodimers.

As used herein, RBD-Fc fusion protein and SARS-CoV-2-RBD-hIgG-Fc fusion protein (which terms may be interchangeably used) refers to a human immunoglobin Fc domain that is linked to a SARS-CoV-2 spike protein (SP) receptor binding domain (SP/RBD or RBD) or an analog thereof, which is useful in generating antibodies that specifically bind the SARS-CoV-2 antigen. For ease of reference, the terms "RBD" and/or "SP/RBD" may be used interchangeably herein, and unless otherwise dictated by the context, encompass protein residues consisting of the receptor binding domain per se, smaller fragments of the receptor binding domain, or larger variants comprising the receptor binding domain and adjacent residues from the spike protein segment, provided that the fragments and/or larger variants retain the activity of the RBD (e.g., retain the ability to bind the spike protein receptor). As used herein, the general terms "fusion protein" and "Fc fusion protein" refer to a protein comprising more than one part, for example from different sources (e.g., different proteins, polypeptides, cells, etc.), that are covalently linked through peptide bonds. Fc fusion proteins are covalently linked by (i) connecting the genes that encode for each part into a single nucleic acid molecule and (ii) expressing in a host cell (e.g., HEK cell or CHO cell) the protein for which the nucleic acid molecule encodes. The fully recombinant synthesis approach is preferred over methods in which the therapeutic protein and Fc fragments are synthesized separately and then chemically conjugated. The chemical conjugation step and subsequent purification process increase the manufacturing complexity, reduce product yield, and increase cost.

As used herein, the term "bioactivity," "activity," "biological activity," "potency," "bioactive potency," or "biological potency" refers to the extent to which an Fc fusion protein binds to or activates a cell receptor and/or exerts the production or reduction of native or foreign substances. As used herein, "in vitro activity" or "receptor activity" refers to the affinity with which an Fc fusion protein binds to the cell receptor and is typically measured by the concentration of an Fc fusion protein that causes the Fc fusion protein to reach half of its maximum binding (i.e., EC50 value). For example, the "bioactivity" of a SARS-CoV-2-RBD-hIgG-Fc fusion protein refers to the extent to which the SARS-CoV-2-RBD-hIgG-Fc fusion protein induces the production of anti-SARS-CoV-2 antibodies in a cellular assay or in a target subject.

As used herein, the term "biosynthesis," "recombinant synthesis," or "recombinantly made" refers to the process by which an Fc fusion protein is expressed within a host cell by transfecting the cell with a nucleic acid molecule (e.g., vector) encoding the Fc fusion protein (e.g., where the entire Fc fusion protein is encoded by a single nucleic acid molecule). Exemplary host cells include mammalian cells, e.g., HEK293 cells or CHO cells. The cells can be cultured using standard methods in the art and the expressed Fc fusion protein may be harvested and purified from the cell culture using standard methods in the art.

As used herein, the term "cell surface receptor" refers to a molecule such as a protein, generally found on the external surface of the membrane of a cell and which interacts with soluble molecules, e.g., molecules that circulate in the blood supply. In some embodiments, a cell surface receptor may include a host cell receptor (e.g., an ACE2 receptor) or an Fc receptor which binds to an Fc fragment or the Fc region of an antibody (e.g., an Fc(gamma) receptor, for example Fc(gamma) receptor I, or an Fc neonatal receptor, for example FcRn). As used herein, "in vitro activity" or "Fc (gamma) receptor activity" or "Fc(gamma) receptor binding" or "FcRn receptor activity" or "FcRn binding" refers to the affinity with which an Fc fusion protein binds to the Fc receptor (e.g. Fc(gamma) receptor or FcRn receptor) and is typically measured by the concentration of an Fc fusion protein that causes the Fc fusion protein to reach half of its maximum binding (i.e., EC50 value) as measured on an assay (e.g., an enzyme-linked immunosorbent assay (ELISA) assay) using OD 450 nm values as measured on a microplate reader.

As used herein, the term "immunogenic" or "immunogenicity" refers to the capacity for a given molecule (e.g., an Fc fusion protein of the present invention) to provoke the immune system of a target subject such that after administration of the molecule, the subject develops antibodies capable of binding all or specific portions of the molecule (i.e., anti-drug antibodies or ADA). As used herein, the terms "neutralizing," "neutralizing antibodies", or "neutralizing anti-drug antibodies" refer to the capacity for antibodies to interfere with all or a portion of the Fc fusion protein's biological activity in the target subject. For example, in the case of a SARS-CoV-2-RBD-hIgG-Fc fusion molecule administered to humans, the immunogenicity refers to antibodies that bind to the SARS-CoV-2 RBD portion of the molecule since the hIgG-Fc portion of the molecule is endogenous to humans and therefore unlikely to elicit anti-hIgG-Fc antibodies. Likewise, antibodies generated by the administration of a SARS-CoV-2-RBD-hIgG-Fc fusion molecule are neutralizing when those anti-SARS-CoV-2 RBD antibodies inhibit the binding between SARS-CoV-2 RBD and the ACE2 receptor, which is directly related to the bioactivity of the SARS-CoV-2 RBD in the subject.

As used herein, the term "monomer" refers to a protein or a fusion protein comprising a single polypeptide. In embodiments, the "monomer" is a protein or a fusion protein, e.g., a single polypeptide, comprising an RBD polypeptide and an Fc fragment polypeptide, wherein the RBD and Fc fragment polypeptides are joined by peptide bonds to form the single polypeptide. In embodiments, the monomer is encoded by a single nucleic acid molecule.

As used herein and as illustrated in FIG. 1 and FIG. 2, "N-terminus" refers to the start of a protein or polypeptide that is initiated by an amino acid containing a free amine group that is the alpha-amino group of the amino acid (e.g., the free amino that is covalently linked to one carbon atom that is located adjacent to a second carbon atom, wherein the second carbon atom is part of the carbonyl group of the amino acid). As used herein and as illustrated in FIG. 1 and FIG. 2, "C-terminus" refers to the end of a protein or polypeptide that is terminated by an amino acid containing a carboxylic acid group, wherein the carbon atom of the carboxylic acid group is located adjacent to the alpha-amino group of the amino acid.

As used herein, the term "carrier" is used herein to refer to diluents, excipients, vehicles, and the like, in which the Fc fusion protein(s) may be dispersed, emulsified, or encapsulated for administration. Suitable carriers will be pharmaceutically acceptable. As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained. A pharmaceutically-acceptable carrier would naturally be selected to minimize any degradation of the compound or other agents and to minimize any adverse side effects in the subject, as would be well known to one of skill in the art. Pharmaceutically-acceptable ingredients include those acceptable for veterinary use as well as human pharmaceutical use and will depend on the route of administration. Any carrier compatible with the excipient(s) and the Fc fusion protein(s) can be used.

As used herein, "pharmacodynamics" or "PD" generally refers to the biological effects of an Fc fusion protein in a subject. As an example, herein, the PD of a SARS-CoV-2-RBD-hIgG-Fc fusion protein refers to the measure of the anti-SARS-CoV-2 antibody titers over time in a subject after the administration of the SARS-CoV-2-RBD-hIgG-Fc fusion protein.

As used herein, "pharmacokinetics" or "PK" generally refers to the characteristic interactions of an Fc fusion protein and the body of the subject in terms of its absorption, distribution, metabolism, and excretion. As an example, herein, the PK refers to the concentration of a SARS-CoV-2-RBD-hIgG-Fc fusion protein in the blood or serum of a subject at a given time after the administration of the SARS-CoV-2-RBD-hIgG-Fc fusion protein. As used herein, "half-life" refers to the time taken for the concentration of Fc fusion protein in the blood or serum of a subject to reach half of its original value as calculated from a first order exponential decay model for drug elimination. Fc fusion proteins with greater "half-life" values demonstrate greater duration of action in the target subject.

The terms "sequence identity," "sequence homology," "homology," or "identical" in amino acid or nucleotide sequences as used herein describes that the same nucleotides or amino acid residues are found within the variant and reference sequences when a specified, contiguous segment of the nucleotide sequence or amino acid sequence of the variant is aligned and compared to the nucleotide sequence or amino acid sequence of the reference sequence.

Methods for sequence alignment and for determining identity between sequences are known in the art, including the use of Clustal Omega, which organizes, aligns, and compares sequences for similarity, wherein the software highlights each sequence position and compares across all sequences at that position and assigns one of the following scores: an "*" (asterisk) for sequence positions which have a single, fully conserved residue, a ":" (colon) indicates conservation between groups of strongly similar properties with scoring greater than 0.5 in the Gonnet PAM 250 matrix, and a "." (period) indicates conservation between groups of weakly similar properties with scoring less than or equal to 0.5 in the Gonnet PAM 250 matrix, a "-" (dash) indicates a sequence gap, meaning that no local homology exists within a particular set of comparisons within a certain range of the sequences, and an empty space " " indicates little or no sequence homology for that particular position across the compared sequences.

With respect to optimal alignment of two nucleotide sequences, the contiguous segment of the variant nucleotide sequence may have additional nucleotides or deleted nucleotides with respect to the reference nucleotide sequence. Likewise, for purposes of optimal alignment of two amino acid sequences, the contiguous segment of the variant amino acid sequence may have additional amino acid residues or deleted amino acid residues with respect to the reference amino acid sequence. In some embodiments, the contiguous segment used for comparison to the reference nucleotide sequence or reference amino acid sequence will comprise at least 6, 10, 15, or 20 contiguous nucleotides, or amino acid residues, and may be 30, 40, 50, 100, or more nucleotides or amino acid residues. Corrections for increased sequence identity associated with inclusion of gaps in the variant's nucleotide sequence or amino acid sequence can be made by assigning gap penalties. Methods of sequence alignment are known in the art.

In embodiments, the determination of percent identity or "homology" between two sequences is accomplished using a mathematical algorithm. For example, the percent identity of an amino acid sequence is determined using the Smith-Waterman homology search algorithm using an affine 6 gap search with a gap open penalty of 12 and a gap extension penalty of 2, BLOSUM matrix 62. In embodiments, the percent identity of a nucleotide sequence is determined using the Smith-Waterman homology search algorithm using a gap open penalty of 25 and a gap extension penalty of 5. Such a determination of sequence identity can be performed using, for example, the DeCypher Hardware Accelerator from TimeLogic.

As used herein, the term "homology" is used to compare two or more proteins by locating common structural characteristics and common spatial distribution of, for instance, beta strands, helices, and folds. Accordingly, homologous protein structures are defined by spatial analyses. Measuring structural homology involves computing the geometric-topological features of a space. One approach used to generate and analyze three-dimensional (3D) protein structures is homology modeling (also called comparative modeling or knowledge-based modeling) which works by finding similar sequences on the basis of the fact that 3D similarity reflects 2D similarity. Homologous structures do not imply sequence similarity as a necessary condition.

As used herein, the terms "subject" and "patient" are intended to include mice, non-human primates (NHP), rabbits, canines, and humans. Exemplary canine subjects include dogs having a disease or a disorder, e.g., diabetes or another disease or disorder described herein, or normal subjects. Exemplary human subjects include individuals that have a disease, e.g., COVID-19, including variants of COVID-19 or SARS-Co-V-2 infection, or another virus, have previously had a disease or disorder described herein, or normal subjects.

As used herein, the term "titer" or "yield" refers to the amount of a fusion protein product (e.g., an Fc fusion protein described herein) resulting from the biosynthesis (e.g., in a mammalian cell, e.g., in a HEK293 cell or CHO cell) per volume of the cell culture. The amount of product may be determined at any step of the production process (e.g., before or after purification), but the yield or titer is always stated per volume of the original cell culture. As used herein, the term "product yield" or "total protein yield" refers to the total amount of Fc fusion protein expressed by cells and purified via at least one affinity chromatography step (e.g., Protein A or Protein G) and includes monomers of Fc fusion protein, homodimers of Fc fusion protein, and higher-order molecular aggregates of homodimers of Fc fusion protein. As used herein, the term "percent homodimer" or "% homodimer" refers to the proportion of a fusion protein product (e.g., an Fc fusion protein described herein) that is the desired homodimer. As used herein, the term "homodimer titer" refers to the product of the % homodimer and the total protein yield after Protein A purification step reported per volume of the cell culture.

As used herein, the terms "treat" or "treating" or "treatment" of a subject having a disease or a disorder refers to an intervention performed with the intention of preventing the development or altering the pathology of infection. Accordingly, "treatment" refers to both therapeutic treatment and prophylactic or preventative measures. A therapeutic agent may directly decrease the pathology of infection or render the infection more susceptible to treatment by other therapeutic agents or, for example the host's immune system. Improvement after treatment may be manifested as a decrease or elimination of such symptoms. Thus, the compositions are useful in treating an infection by preventing the development of observable clinical symptoms from infection, and/or reducing the incidence or severity of clinical symptoms and/or effects of the infection, and/or reducing the duration of the infection/symptoms/effect. Treating a subject having a disease or disorder may refer to a subject having a disease or a disorder refer to subjecting the subject to a regimen, for example the administration of a fusion protein such as an Fc fusion protein described herein, or a pharmaceutical composition of a fusion protein such as an Fc fusion protein described herein, such that at least one symptom of the disease or disorder is cured, healed, alleviated, relieved, altered, remedied, ameliorated, or improved. Treating includes administering an amount effective to alleviate, relieve, alter, remedy, ameliorate, improve, or affect the disease or disorder, or the symptoms of the disease or disorder. Treating includes administering an amount effective to generate antibodies to a disease or disorder in a normal subject or a subject that has previously had the disease or disorder. The treatment may inhibit deterioration or worsening of a symptom of a disease or disorder.

As used herein, "prophylactic vaccine" refers to a treatment that introduces an antigen into a patient with the goal that the patient's immune system will create antibodies for the antigen and increase or improve the subject's immune response to the associated illness or virus. In other words, a vaccinated subject will have a higher degree of resistance to illness or disease from the associated virus as compared to a non-vaccinated subject. This resistance may be evident by a decrease in severity or duration of symptoms of illness, decrease or elimination of viral shedding, and in some case the prevention of observable symptoms of infection in the vaccinated subject. In embodiments, a patient treated with a prophylactic vaccine does not have antibodies for the antigen prior to the treatment with the prophylactic vaccine (otherwise stated, the patient is "antibody naïve").

As used herein, "therapeutic vaccine" refers to a treatment that introduces an antigen into a patient that already has the associated illness or virus, with the goal that the patient's immune system will create antibodies for the antigen enabling the patient's body to fight harder against the illness or virus that it already has.

As used herein, "booster vaccine" refers to an extra administration of a vaccine after the patient has previously received an initial administration of a vaccine, or after a patient has acquired antibodies through having had and recovered from the associated illness or virus. In some examples, an additional dose of a vaccine is needed periodically to "boost" the immunity of a patient to an illness or virus causing antigen by increasing the patient's antigen antibody titer.

As used herein, when referring to an amino acid in some portion of the SARS-CoV-2 surface glycoprotein, including a receptor binding domain (RBD) of the SARS-CoV-2 surface glycoprotein, a cited amino acid position is referenced as the position of the amino acid in the SARS-CoV-2 surface glycoprotein of SEQ ID NO: 1. As an example, a reference to a mutation of an amino acid at position 331 of a SARS-CoV-2 RBD refers to the amino acid at the 331' position in SEQ ID NO: 1, even when the SARS-CoV-2 RBD comprises only a portion of SEQ ID NO: 1.

As used herein, "RBD fragment" refers to a portion of a SARS-CoV-2-hIgG-Fc fusion protein that comprises some portion of the receptor binding domain (RBD) of the SARS-CoV-2 surface glycoprotein of SEQ ID NO: 1, and which may also include adjacent residues of the spike protein (SP) unless otherwise indicated by context. In examples, the RBD fragment portion of the SARS-CoV-2 surface glycoprotein is linked to an Fc fragment as illustrated in FIG. 2.

Rationale for Fc Fusion Protein Vaccines

As discussed above, the recombinant protein-based subunit vaccine approach has an advantage of safety and multiple-booster dosing relative to inactivated or live-attenuated virus and nucleic acid vector-based vaccine formats, in addition to allowing for the selective use of the most dominant epitopes to generate potent neutralizing Ab titers. Furthermore, such a protein-based vaccine is more cost-effectively manufactured in large quantities and is stable at mild temperatures, allowing for easier transportation and storage. However, given the challenges of a recombinant SARS-CoV-2 SP subunit vaccine to induce a strong protective immune response in an immunologically naïve human population, the SP antigen must be modified and/or formulated with additional immune-enhancing features to overcome the activation thresholds of naïve T and B cells.

Experimental Experience with Insulin-Fc Fusion Proteins in Canines

One example of a fusion protein formed by linking a therapeutic protein to an immunoglobin Fc domain is an insulin-Fc fusion protein. This construct has been used to provide ultra-long acting basal insulin therapy for diabetic subjects. The combination of an insulin analog as the therapeutic protein with an Fc domain via a peptide linker has been shown to achieve significantly longer activity in vivo, in the order of days. An example of ultra-long acting insulin-Fc fusion proteins for use in treating diabetes in cats and dogs is described in WO2020006529A1. In an example from WO2020006529A1, an exemplary insulin analog is:

(SEQ ID NO: 28)
FVNQHLCGSHLVEALELVCGERGFHYGGGGGGSGGGGGIVEQCCTSTCSL

DQLENYC and an exemplary linker, used to link the therapeutic protein (i.e., the insulin analog) to the Fc domain is:

(SEQ ID NO: 27)
GGGGGQGGGGQGGGGQGGGGG.

Insulin-Fc fusion protein molecules for a given species (e.g., dog, cat, or human) suitable for ultra-long acting treatment for diabetes should be manufacturable in mammalian cells, for example human embryonic kidney (HEK, e.g. HEK293) cells, with an acceptable titer of the desired homodimer product (e.g., greater than 50 mg/L homodimer titer from transiently transfected HEK cells, greater than 75 mg/L from transiently transfected HEK cells, greater than 100 mg/L from transiently transfected HEK cells, etc.). Experience has demonstrated that homodimer titers less than 50 mg/L will not likely result in commercial production homodimer titers in Chinese hamster ovary (CHO) cells that meet the stringently low manufacturing cost requirements for veterinary products.

The insulin-Fc fusion proteins for dogs described in WO2020006529A1 (incorporated by reference herein) and herein were manufactured in HEK cells according to Example 45 or in CHO cells according to Example 46. The insulin-Fc fusion proteins were purified according to Example 47. Using the conventional purification method, only the compounds comprising the canine IgGA and the canine IgGB immunoglobin Fc fragment showed any appreciable protein yields. The structure of the insulin-Fc fusion proteins was confirmed by non-reducing and reducing CE-SDS according to Example 48 and the sequence was confirmed by LC-MS with glycan removal according to Example 49. The purity (as assessed by the percent homodimer of the fusion protein yield) was measured according to Example 50. The canine IgGA version of the insulin-Fc fusion protein was highly aggregated with low levels of bioactivity, whereas the canine IgGB version of the insulin-Fc fusion protein exhibited a low degree of aggregation (i.e., high % homodimer), a high titer of the desired homodimer (i.e., a homodimer titer greater than 50 mg/L), and appreciable levels of long-duration glucose lowering bioactivity in dogs. Therefore, the canine IgGB (SEQ ID NO: 26) immunoglobin Fc fragment is the preferred Fc fragment for insulin-Fc fusion proteins used in dogs.

(SEQ ID NO: 26)
DCPKCPAPEMLGGPSVFIFPPKPKDTLLIARTPEVTCVVVDLDPEDPEVQ

ISWFVDGKQMQTAKTQPREEQFNGTYRVVSVLPIGHQDWLKGKQFTCKVN

NKALPSPIERTISKARGQAHQPSVYVLPPSREELSKNTVSLTCLIKDFFP

PDIDVEWQSNGQQEPESKYRTTPPQLDEDGSYFLYSKLSVDKSRWQRGDT

FICAVMHEALHNHYTQESLSHSPG

An exemplary canine ultra-long acting insulin-Fc fusion protein comprising the insulin analog of SEQ ID NO: 28 with the canine native IgGB fragment of SEQ ID NO: 26 via the peptide linker of SEQ ID NO: 27 is:

(SEQ ID NO: 29)
FVNQHLCGSHLVEALELVCGERGFHYGGGGGGSGGGGGIVEQCCTSTCSL

DQLENYCGGGGGQGGGGQGGGGQGGGGGDCPKCPAPEMLGGPSVFIFPPK

PKDTLLIARTPEVTCVVVDLDPEDPEVQISWFVDGKQMQTAKTQPREEQF

-continued

NGTYRVVSVLPIGHQDWLKGKQFTCKVNNKALPSPIERTISKARGQAHQP

SVYVLPPSREELSKNTVSLTCLIKDFFPPDIDVEWQSNGQQEPESKYRTT

PPQLDEDGSYFLYSKLSVDKSRWQRGDTFICAVMHEALHNHYTQESLSHS

PG

Figure 3:
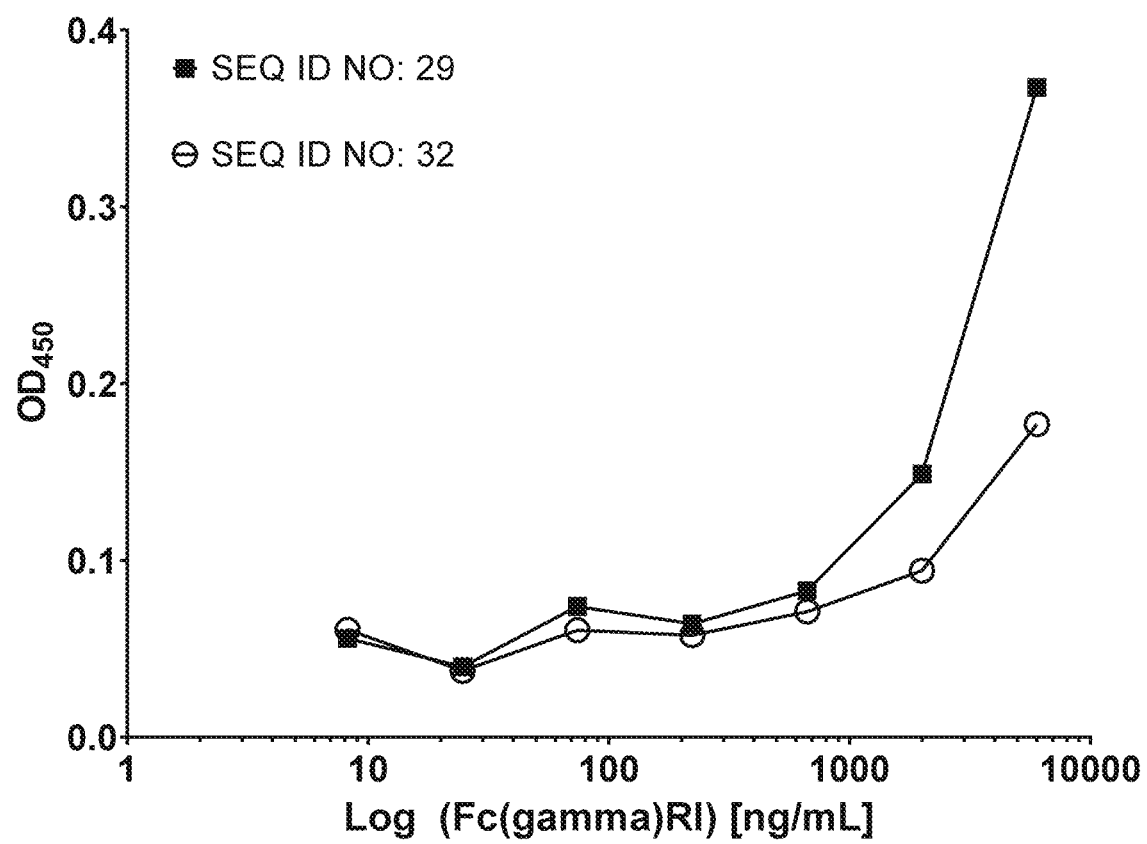
FIG. 3 shows Fc(gamma) receptor I binding for the insulin-Fc fusion proteins of SEQ ID NO: 29 and SEQ ID NO: 32.

The binding of the insulin-Fc fusion protein of SEQ ID NO: 29 to the Fc(gamma) Receptor I (RI) was assessed according to Example 51. Since canine receptor I was not commercially available, human Fc(gamma) receptor I (i.e., rhFc(gamma) receptor I) was used as a surrogate mammalian receptor. The OD values proportional to the binding of rhFc(gamma) receptor I to SEQ ID NO: 29 were plotted against log concentrations of rhFc (gamma) receptor I added to each, to generate binding curves using GraphPad Prism software. The results shown in FIG. 3 illustrate that the OD450 values increase with increased doses of the insulin-Fc fusion protein of SEQ ID NO: 29 for all Fc(gamma) receptors.

Figure 4:
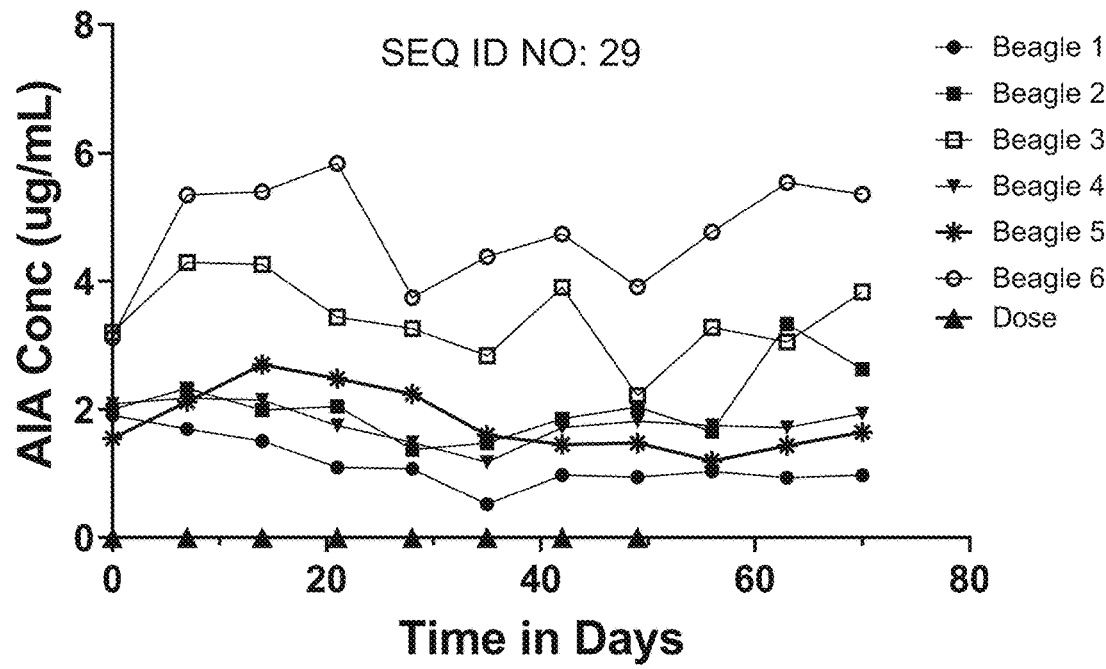
FIG. 4 shows titers of anti-insulin-antibodies (AIA) against RHI averaged over 200-fold dilutions for 6 beagles with chemically induced diabetes over a series of 8 doses of the insulin-Fc fusion protein of SEQ ID NO: 29.
Figure 5:
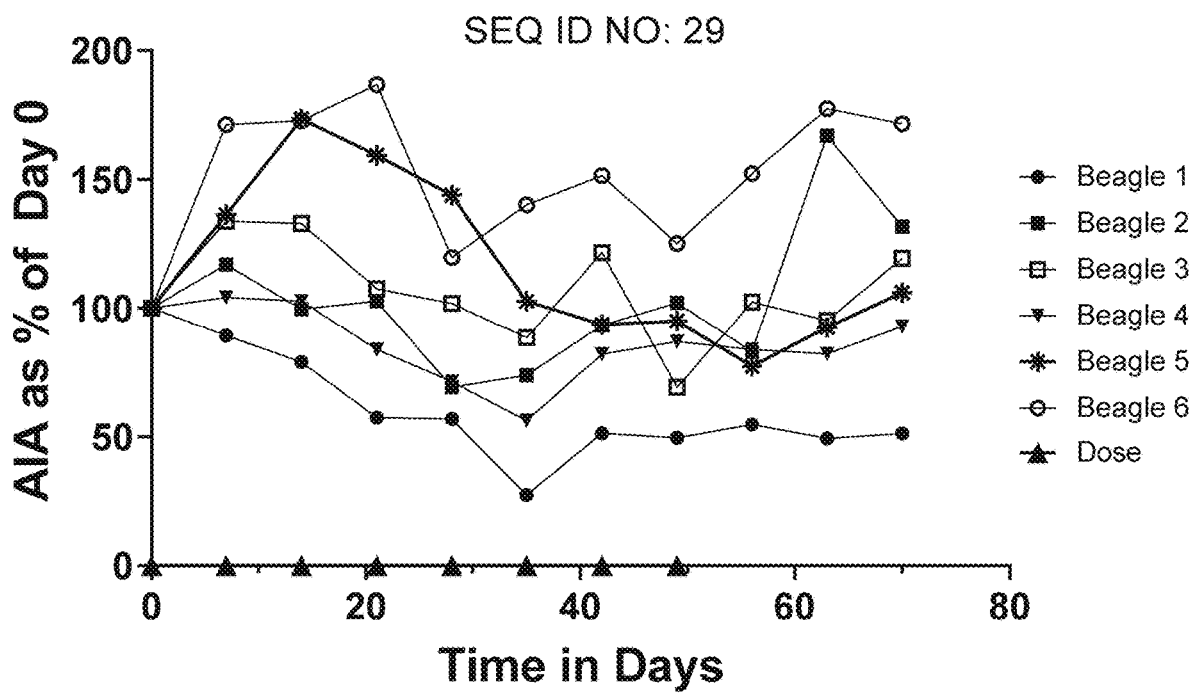
FIG. 5 shows percentage change in the titers of anti-insulin antibodies (AIA) against RHI from Day 0 of the trial for 6 beagles with chemically induced diabetes over a series of 8 weekly doses of the insulin-Fc fusion protein of SEQ ID NO: 29.

The in vivo pharmacodynamics (PD) after periodic administrations of the insulin-Fc fusion protein of SEQ ID NO: 29 manufactured in HEK cells according to Example 45 was evaluated according to Example 52. The test population consisted of six beagle dogs with diabetes that was chemically induced using alloxan-streptozotocin, each weighing approximately 10 kg. The anti-insulin antibody (AIA) titers were measured weekly over 8 weeks for the six beagle dogs with chemically induced diabetes that were subjects in the lab test for SEQ ID NO: 29 according to Example 53. FIG. 4 shows titers of AIA for the six beagles with chemically induced diabetes over a series of eight weekly doses of the insulin-Fc fusion protein of SEQ ID NO: 29. FIG. 5 shows percentage change in the titers of AIA from Day 0 of the trial for the six beagles with chemically induced diabetes over a series of eight weekly doses of the insulin-Fc fusion protein of SEQ ID NO: 29. The data demonstrates that the beagles' AIA titers did not substantially increase over the eight administered doses of the insulin-Fc fusion protein of SEQ ID NO: 29.

Based on these positive lab test results with the chemically induced diabetic beagles, field trials with actual client-owned, naturally occurring diabetic dogs of varying ages, breeds, and extent of diabetes disease were initiated according to Example 52. The client dogs in the field trial had all been receiving insulin treatment with a known veterinary or human insulin product up to the point of the trial initiation and were given SEQ ID NO: 29 according to Protocol 1 or Protocol 2 as described in Example 52.

Figure 6:
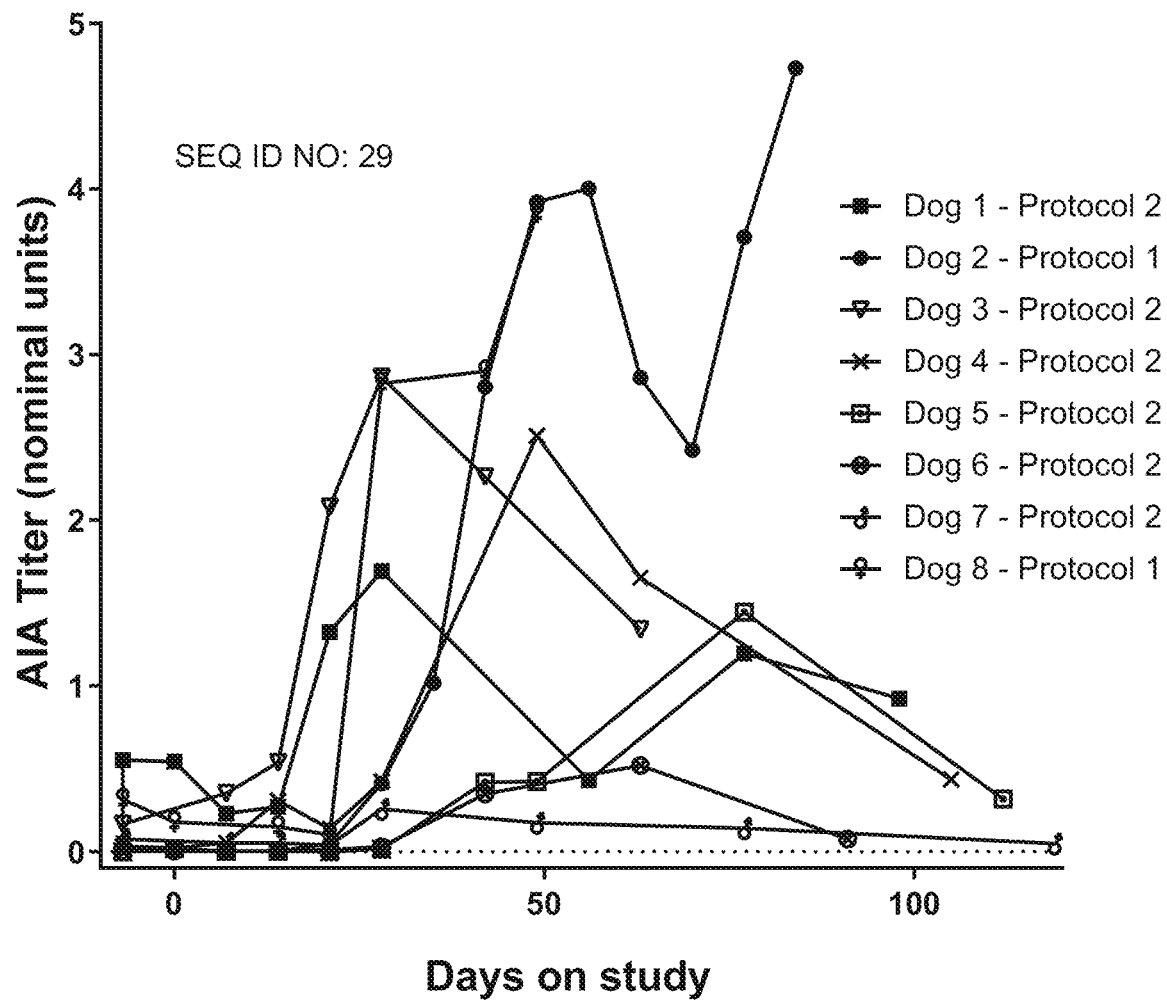
FIG. 6 shows the normalized AIA titers for 8 client dogs treated for diabetes with the insulin-Fc fusion protein of SEQ ID NO: 29 according to Protocol 1 or Protocol 2 of Example 52.

The MA titer was again measured weekly over the course of the treatment according to Example 54. Unexpectedly, in contrast to the results obtained in the chemically induced diabetic beagles, several (8/20) client dogs in this "wild" patient population demonstrated a marked increase in anti-insulin antibodies. A normalized AIA titer of 0.15 was considered the minimum measurement for the client dog to be considered immunogenic to SEQ ID NO: 29. For client dogs that had a non-zero AIA titer at the start of the treatment, if the AIA more than doubled after being treated with the insulin-Fc fusion protein of SEQ ID NO: 29, the insulin-Fc fusion protein of SEQ ID NO: 29 was considered to be immunogenic in that particular client dog. FIG. 6 is a plot of normalized AIA titer for each of the client dogs in which the insulin-Fc fusion protein of SEQ ID NO: 29 was considered immunogenic as measured weekly during the duration of their treatment (the specific protocol of Example 52 followed for the treatment is indicated for each dog). In each of the dogs shown in FIG. 6, the AIAs neutralized the therapeutic effect of the insulin-Fc fusion protein of SEQ ID NO: 29, rendering it no longer capable of controlling blood glucose levels in the client-owned diabetic dogs. The observed immunogenicity was additionally unexpected because the insulin analog portion of the insulin-Fc fusion protein is a near-native peptide for the dogs. Furthermore, the IgGB Fc fragment portion of the insulin-Fc fusion protein is a native canine Fc fragment. The results indicate that the specific activity of the dog IgGB Fc fragment was capable of inducing a pronounced and lasting increase in antibody titers specific to the therapeutic protein region of the fusion protein (i.e., the insulin). Other than demonstrating a significant increase in neutralizing AIA titers, the dogs otherwise remained healthy through repeated dosing and did not experience any signs of anaphylaxis or cytokine storms associated with the treatment.

Figure 7:
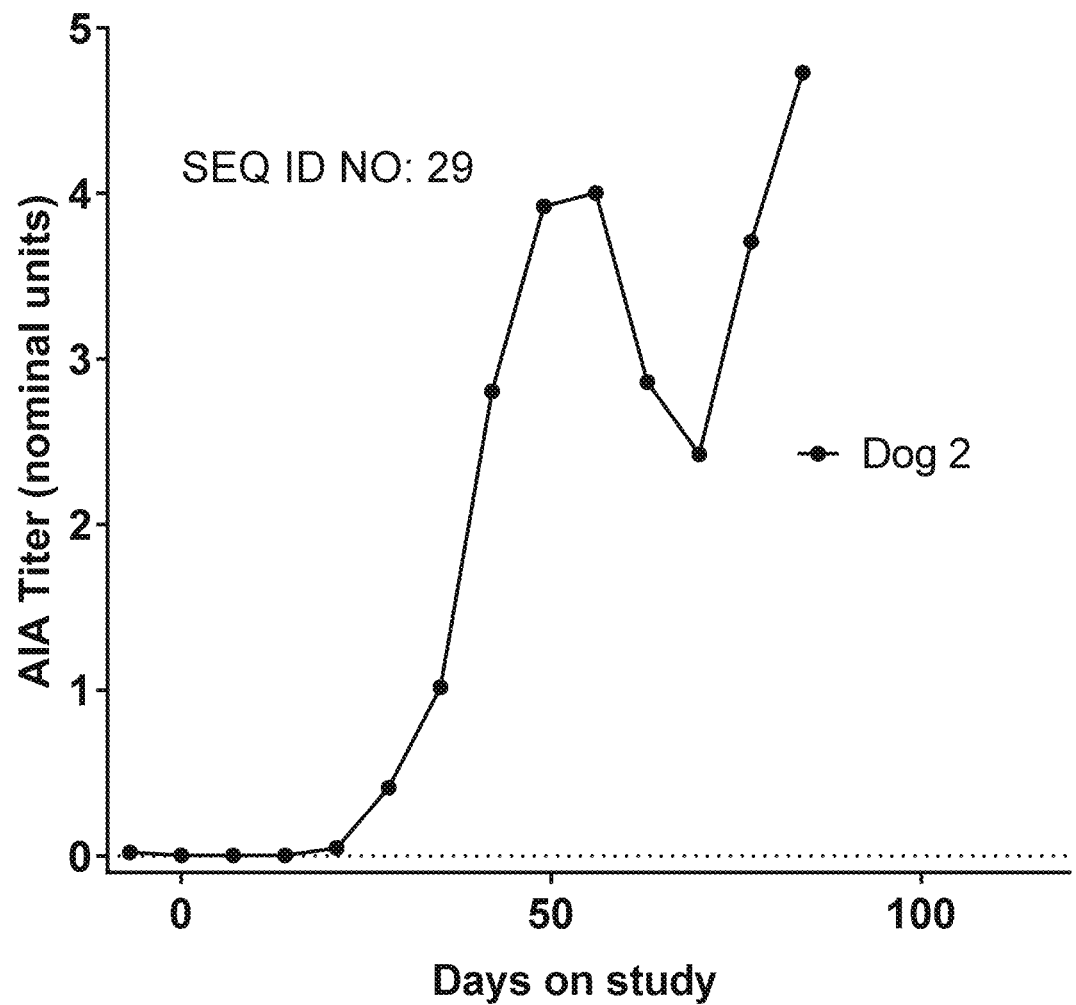
FIG. 7 shows the normalized AIA titer for a single dog treated for diabetes with the insulin-Fc fusion protein of SEQ ID NO: 29 with an interruption in treatment.

In some cases, when the client dog began to show high levels of AIAs, the dosing of the insulin-Fc fusion protein of SEQ ID NO: 29 was discontinued, at which point the AIA titer began to decrease (see for example Dog 2 on FIG. 4). FIG. 7 is a plot of normalized AIA titer for example Dog 2 over a period of 12 weeks of once-weekly dosing. It can be seen that the AIA titer began to measurably increase after the $4^{th}$ dose (Day 21) and the AIA titer began to steeply increase after the $6^{th}$ dose (Day 35). The dosing was stopped after the $8^{th}$ dose (Day 49), and no drug was administered on Day 56 or Day 63. FIG. 7 illustrates that the AIA titer growth immediately slowed and then the MA titer began to fall after Day 56. The dosing regime was resumed on Day 70, with doses on Day 70 and again on Day 77. The AIA titer growth after the resumption of dosing on Day 70 matched or exceeded the maximum AIA titer growth in the 7 weeks up to when the dosing was stopped, illustrating that the titer of anti-drug antibodies was unexpectedly restored in an appreciably shorter time than the build-up over the initial series of doses. This robust recall response may be indicative of a responsive memory immune cell population.

Figure 8:
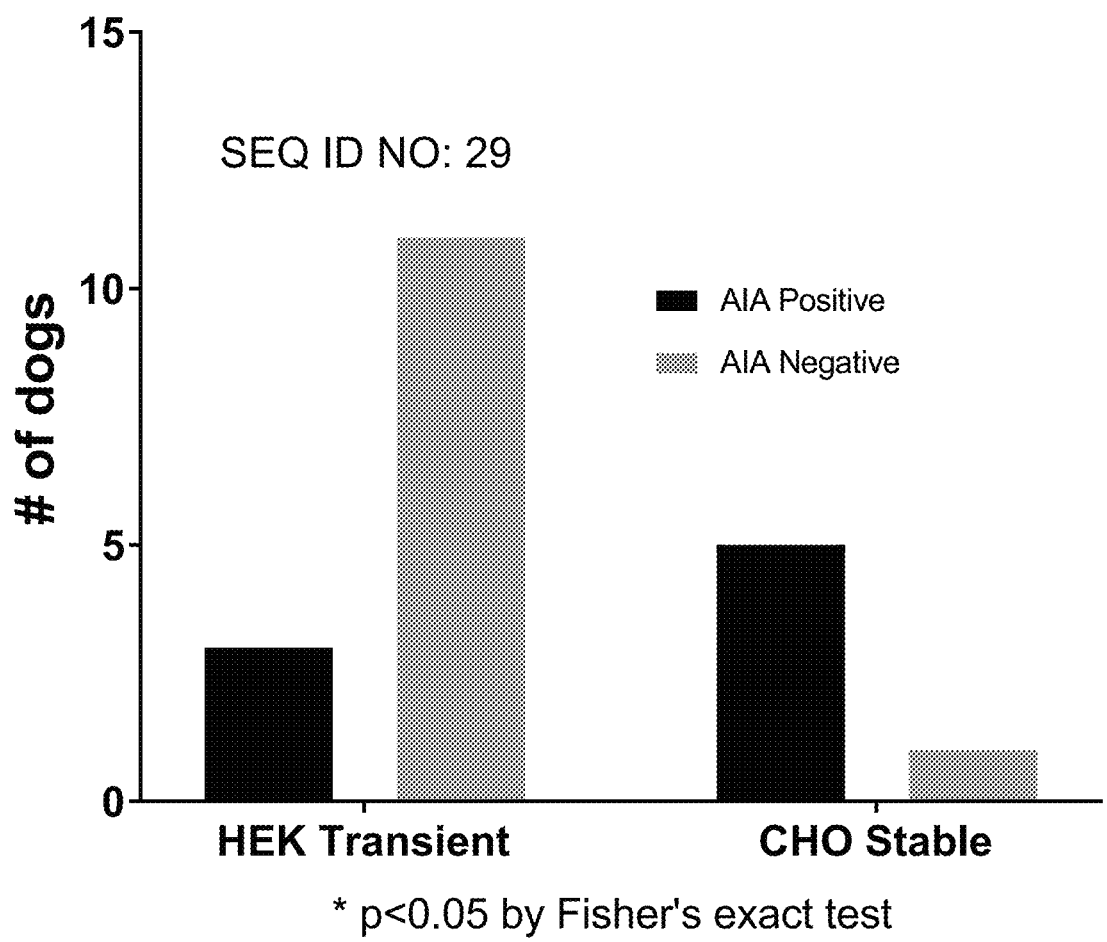
FIG. 8 shows a graphical representation of the number of dogs that showed AIA after being treated for diabetes with the insulin-Fc fusion protein of SEQ ID NO: 29 manufactured in either an HEK transient cell pool or a CHO stable cell pool.

Another observation from the field trial of client owned diabetic dogs was that there was an apparent difference in the dogs treated with the insulin-Fc fusion protein of SEQ ID NO: 29 made in CHO cells according to Example 46, and the insulin-Fc fusion protein of SEQ ID NO: 29 made in HEK cells according to Example 45, with the CHO-made insulin-Fc fusion protein of SEQ ID NO: 29 showing a markedly higher prevalence of anti-drug antibodies, as shown in FIG. 8.

Each IgG fragment contains a conserved asparagine (N)-glycosylation site in the CH2 domain of each heavy chain of the Fc region. Herein, the notation used to refer to the conserved N-glycosylation site is "cNg" (shown in FIG. 1 and in FIG. 2). In therapeutic monoclonal antibodies, the glycosylation is at the conserved amino acid N297 in the CH2 region (shown in FIG. 1 and FIG. 2). For an insulin-Fc fusion protein, the absolute position of the cNg site from the N-terminus of the B-chain of the insulin-Fc fusion protein varies depending on the length of the insulin polypeptide, the length of the linker, and any omitted amino acids in the Fc fragment prior to the cNg site. Herein, the notation used to refer to the absolute position of the cNg site in a given insulin-Fc fusion protein sequence (as measured counting from the N-terminus of the B-chain of the insulin-Fc fusion protein) is "NB(number)". For example, if the cNg site is found at the $151^{st}$ amino acid position as counted from the N-terminus of the B-chain, the absolute position of this site is referred to as cNg-NB151. As a further example, if the cNg site is found at the 151$^{st}$ amino acid position as counted from the N-terminus of the B-chain, and the asparagine at this site is mutated to serine, this mutation is noted as "cNg-NB151-S".

One possible difference between fusion proteins recombinantly manufactured in HEK cells according to Example 45 and fusion proteins recombinantly manufactured in CHO cells according to Example 46 is the composition of the oligosaccharides that attach at the cNg site. Given that the canine IgGB isotypes interact with Fc(gamma) receptors, there may be a risk of unwanted immunogenicity after repeated injections. One method for reducing the Fc(gamma) interaction involves deglycosylating or preventing the glycosylation of the Fc fragment during synthesis in the host cell. Creation of antibodies is clearly undesirable for treatment of a chronic disease such as diabetes as the antibodies neutralize the therapeutic value of the drug. Accordingly, this led to attempting to create a non-glycosylated canine insulin-Fc fusion protein. One way to remove the attached glycan from a synthesized insulin-Fc fusion protein is to mutate the cNg site to prevent the attachment of glycans altogether during production in the host cell. Herein, the notation used to describe a cNg mutation is cNg-(substituted amino acid). For example, if the asparagine at the cNg site is mutated to serine, this mutation is notated as "cNg-S". A general representation of a canine IgGB Fc fragment with a cNg mutation is shown in SEQ ID NO: 30:

```
DCPKCPAPEMLGGPSVFIFPPKPKDTLLIARTPEVTCVVVDLDPEDPEVQ

ISWFVDGKQMQTAKTQPREEQFX₁GTYRVVSVLPIGHQDWLKGKQFTCKV

NNKALPSPIERTISKARGQAHQPSVYVLPPSREELSKNTVSLTCLIKDFF

PPDIDVEWQSNGQQEPESKYRTTPPQLDEDGSYFLYSKLSVDKSRWQRGD

TFICAVMHEALHNHYTQESLSHSPG
``` wherein $X_1$=S, D, K, Q, or A (SEQ ID NO: 30).

A canine insulin-Fc fusion protein was designed, comprising the IgGB Fc fragment of SEQ ID NO: 30 with X1=S (bold residue below), the linker of SEQ ID NO: 27, and the following insulin analog:

```
                                        (SEQ ID NO: 31)
FVNQHLCGSHLVEALALVCGERGFHYGGGGGSGGGGIVEQCCTSTCSL

DQLENYC
```

The resulting insulin-Fc fusion protein is shown below:

```
                                        (SEQ ID NO: 32)
FVNQHLCGSHLVEALALVCGERGFHYGGGGGSGGGGIVEQCCTSTCSL

DQLENYCGGGGGQGGGGQGGGGQGGGGDCPKCPAPEMLGGPSVFIFPPK

PKDTLLIARTPEVTCVVVDLDPEDPEVQISWFVDGKQMQTAKTQPREEQF

SGTYRVVSVLPIGHQDWLKGKQFTCKVNNKALPSPIERTISKARGQAHQP

SVYVLPPSREELSKNTVSLTCLIKDFFPPDIDVEWQSNGQQEPESKYRTT

PPQLDEDGSYFLYSKLSVDKSRWQRGDTFICAVMHEALHNHYTQESLSHS

PG
```

The insulin-Fc fusion protein of SEQ ID NO: 32 was manufactured in HEK cells according to Example 45 or in CHO cells according to Example 46. The insulin-Fc fusion protein was purified according to Example 47. The structure of the insulin-Fc fusion protein was confirmed by non-reducing and reducing CE-SDS according to Example 48 and the sequence was confirmed by LC-MS with glycan removal according to Example 49. The purity (as assessed by the percent homodimer of the fusion protein yield) was measured according to Example 50.

This fusion protein demonstrated desirable in vitro and in vivo properties similar to SEQ ID NO: 29. As illustrated in FIG. 3, the only difference is that the Fc(gamma) RI binding affinity for the insulin-Fc fusion protein of SEQ ID NO: 32 was significantly reduced compared to that of the insulin-Fc fusion protein of SEQ ID NO: 29. A field trial in five diabetic client dogs of varying ages, breeds, and extent of diabetes disease was initiated. The five client dogs in the field trial had all been receiving insulin treatment with a known veterinary or human insulin product to the point of the trial initiation and were given the insulin-Fc fusion protein of SEQ ID NO: 32 on a once-a-week basis.

Figure 9:
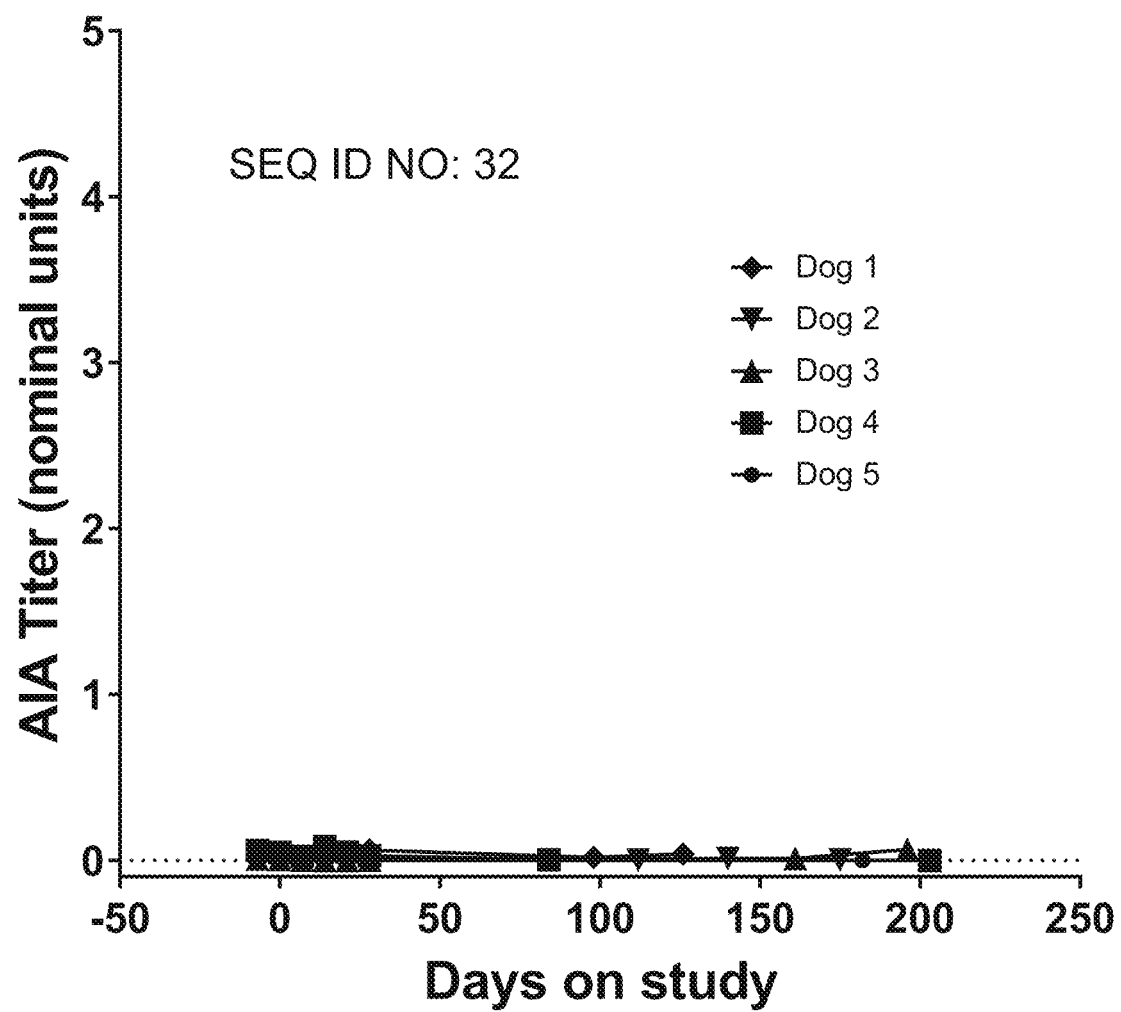
FIG. 9 shows the normalized AIA titers for 8 dogs treated for diabetes with the insulin-Fc fusion protein of SEQ ID NO: 32.
Figure 10:
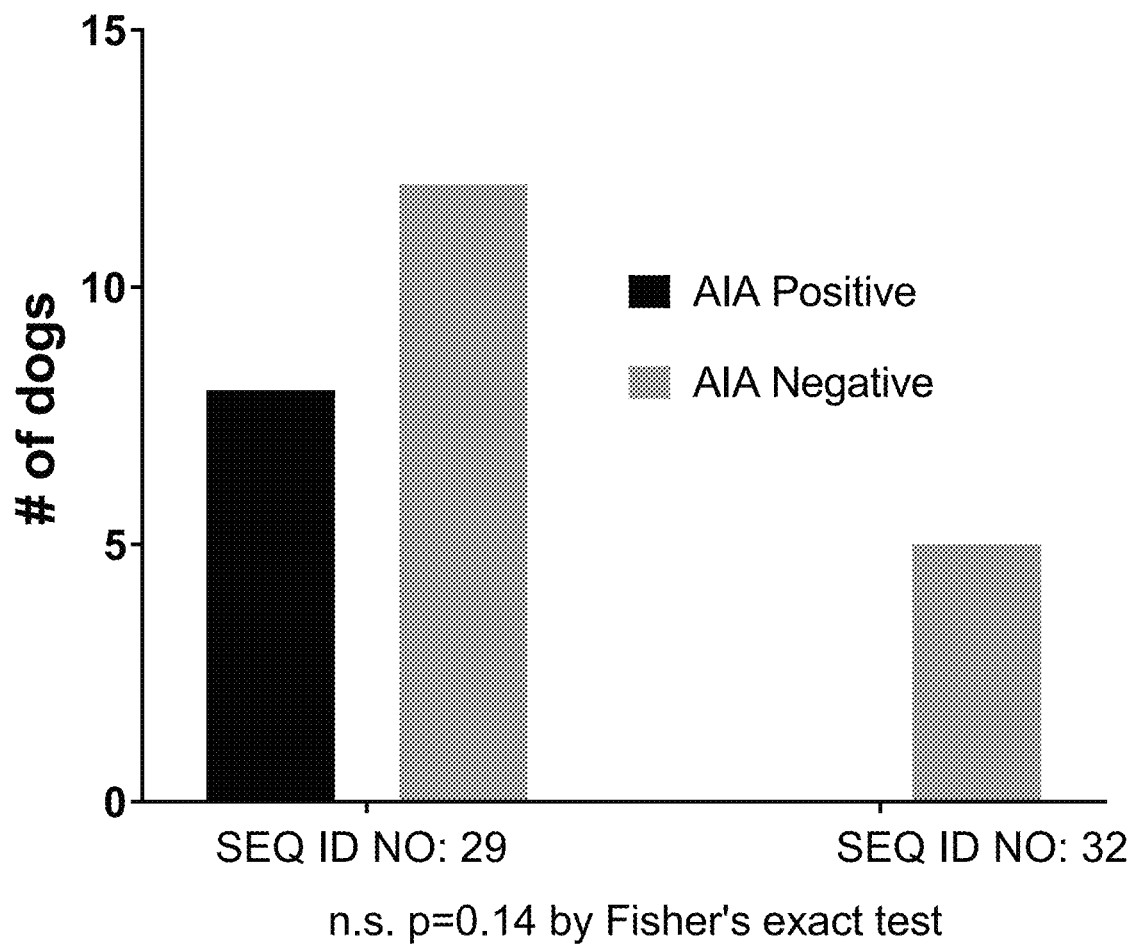
FIG. 10 shows a graphical representation of the number of dogs that showed AIA after being treated for diabetes with the insulin-Fc fusion protein of SEQ ID NO: 29 or SEQ ID NO: 32.
Figure 11:
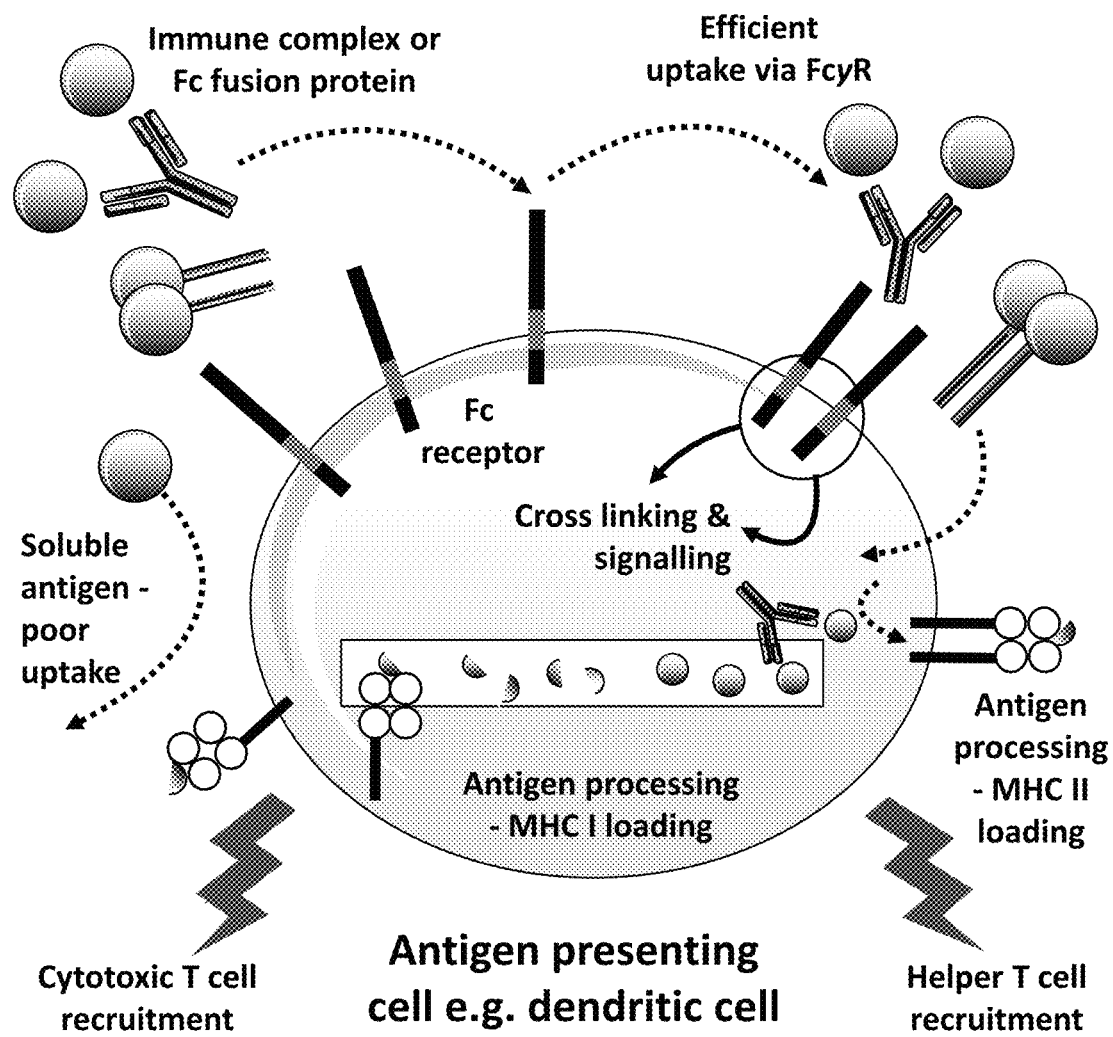
FIG. 11 illustrates APC processing of Fc-fusion proteins via the Fc(gamma) receptors.

The AIA titer was again measured weekly or as frequently as possible over the course of the treatment according to Example 54. As compared to the dogs receiving the insulin-Fc fusion protein of SEQ ID NO: 29, none of the client dogs in this "wild" patient population demonstrated insulin anti-drug antibodies when dosed with the non-glycosylated insulin-Fc fusion protein of SEQ ID NO: 32. A normalized AIA titer of 0.15 was considered the minimum measurement for the client dog to be considered immunogenic to SEQ ID NO: 32. For client dogs that had a non-zero AIA titer at the start of the treatment, if the AIA more than doubled after being treated with the insulin-Fc fusion protein of SEQ ID NO: 32, the client dog was considered to be immunogenic. FIG. 9 is a plot of the normalized AIA titers for each of the client dogs as measured over the duration of their treatment, demonstrating that none of the five client dogs in this "wild" patient population demonstrated insulin anti-drug antibodies when dosed with the non-glycosylated insulin-Fc fusion protein of SEQ ID NO: 32. As shown in FIG. 10, this is in contrast to the dogs receiving the insulin-Fc fusion protein of SEQ ID NO: 29, where twelve dogs total demonstrated insulin anti-drug antibodies compared to none of the dogs receiving the non-glycosylated insulin-Fc fusion protein of SEQ ID NO: 32.

Taken together, the results demonstrate that, unexpectedly, outside a laboratory animal population, certain Fc fusion proteins have the potential of inducing high titers of antibodies against the therapeutic peptide or protein component, and that this response may be re-induced rapidly and robustly upon subsequent presentation of the therapeutic peptide or protein component. Furthermore, these preliminary data indicate that the induction of anti-therapeutic protein or peptide antibodies is more likely in individuals who have already developed an immune response to that particular therapeutic protein or peptide. These results are in contrast to numerous published results that show the potential for Fc fusion proteins to induce immune tolerance against the fused therapeutic peptide or protein, and that haptens like DNP, nucleosides or peniciloyl groups, when chemically coupled to IgG carriers, were highly tolerogenic hapten-carrier conjugates.

For a therapeutic protein such as insulin which is used to treat a chronic disease (i.e., diabetes), anti-insulin antibodies render the therapy useless. Nevertheless, the aforementioned results led to the unique insight of how one might effectively design an Fc fusion protein to induce antibodies against, for example, a viral antigen to neutralize its activity. Based on the field experiments, the desired Fc fusion protein should be, at a minimum, native to the target subject (e.g., a human Fc or hFc for a human subject, a dog Fc or dFc for a dog subject), properly glycosylated at the Fc-cNg site, and capable of binding the Fc(gamma) I receptor. These findings present an opportunity to develop a novel therapeutic Fc-fusion protein against, for example, the novel coronavirus SARS-CoV-2.

SARS-CoV-2-RBD-hIgG-Fc Fusion Proteins

The outbreak of COVID-19 represents a serious threat to public health. There is an urgent need for safe and effective solutions to prevent against infection by its causative agent, the SARS-CoV-2 virus. The surface glycoprotein including the receptor-binding domain (RBD) of the SARS-CoV-2 spike protein (SP) has been identified, and it has been found that the SARS-CoV-2 SP/RBD binds strongly to human and bat angiotensin-converting enzyme 2 (ACE2) receptors. The SARS-CoV-2 SP/RBD being a foreign antigen, a fusion protein comprising this antigen and a glycosylated human immunoglobin Fc fragment (herein referred to as a SARS-CoV-2-RBD-hIgG-Fc fusion protein or SP/RBD-Fc fusion protein) is a promising approach to create a fusion protein that can amplify existing antibody titers in a patient or induce new antibody titers in patients with no or low immune response against SARS-CoV-2. Specifically, methods for making and using fusion proteins for use in a prophylactic or booster vaccine which is efficacious for causing patients to create anti-virus antibodies to the SARS-CoV-2 virus meets this urgent need and would have significant public health value.

The goal therefore is to create an Fc fusion protein comprising some portion of the SARS-CoV-2 surface glycoprotein (or an analog thereof) and a human Fc fragment (e.g., human IgG1 or hIgG1) containing a site or residue with a tendency towards glycosylation in order to create a manufacturable conjugate that presents the antigen (SARS-CoV-2-SP/RBD) in a novel manner to cause a patient to produce anti-SARS-CoV-2 antibodies rapidly at high titers.

Figure 12:
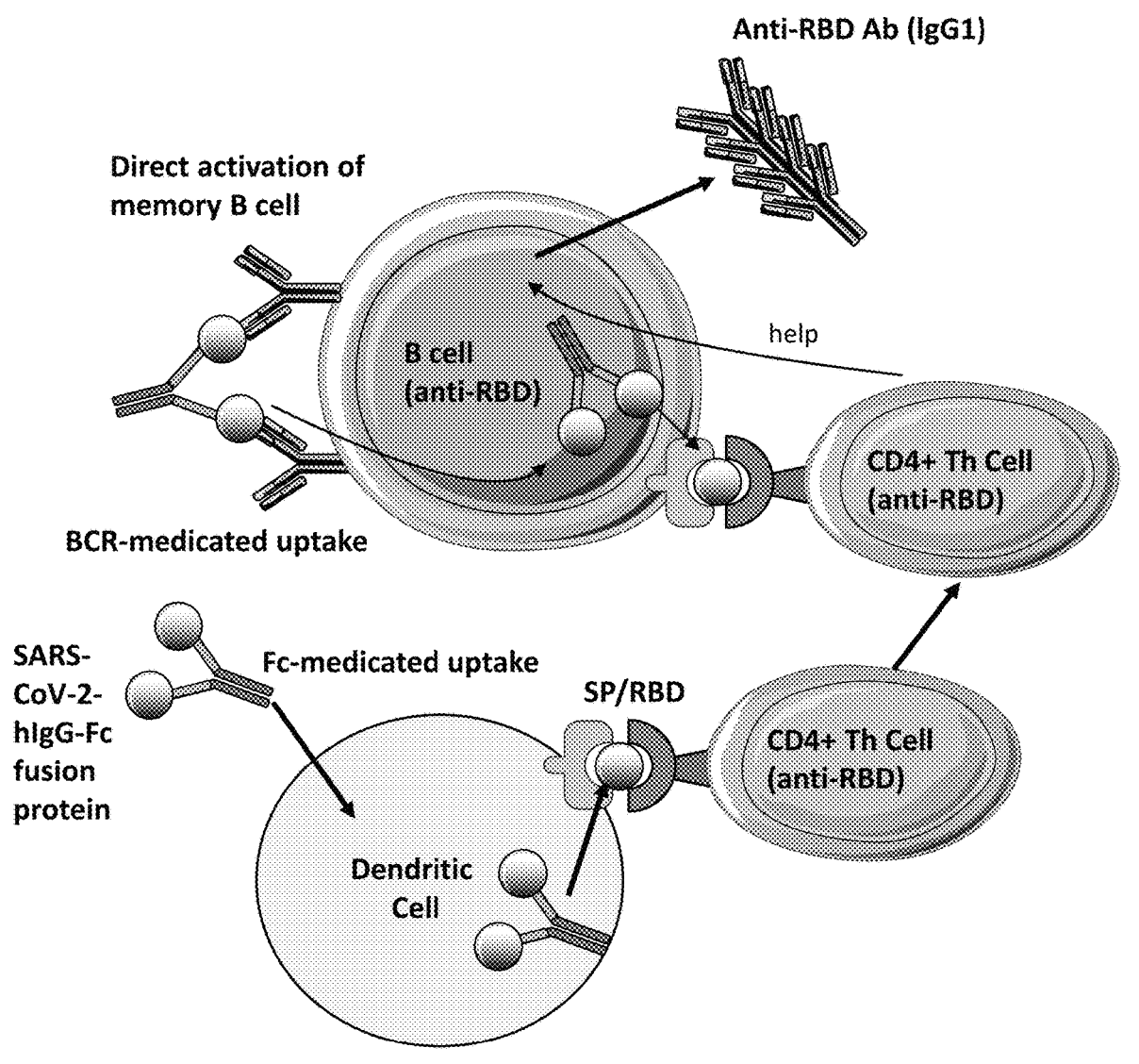

An SP/RBD-Fc fusion protein comprising a bivalent analog of SP/RBD recombinantly fused to a human IgG1 Fc moiety as shown in FIG. 2 would (i) facilitate the focused delivery of the SP/RBD Ag to local APCs that internalize SP/RBD-Fc via Fc(gamma) receptors, and then process and present SP/RBD fragments as illustrated in FIG. 12 to CD4+Th cells that in turn promote ("help") B cell activation and anti-SARS-CoV-2 SP/RBD IgG (i.e., Ab) production as illustrated in FIG. 12. In addition, a more direct and unique mechanism might be the direct binding of the SP/RBD-Fc fusion protein to existing SARS-CoV-2-specific memory B cells through their Ag-specific B cell receptors (BCRs). Such binding triggers activation signals upon BCR cross-linking via the SP/RBD bivalency feature of SEQ ID NO: 19 that leads to enhanced proliferation and anti-SARS-CoV-2 IgG production in the absence of CD4+Th cells as illustrated in FIG. 12. Furthermore, the Fc fragment of the SP/RBD-Fc fusion protein should enhance the half-life and bio-exposure of SP/RBD to more APCs due to binding of the neonatal FcR (FcRn) receptor expressed on cells that enables long serum half-lives of most monoclonal Ab (mAb) therapeutics.

The complete surface glycoprotein protein for SARS-CoV-2 is shown below (GenBank: QHD43416.1):

(SEQ ID NO: 1)
MFVFLVLLPLVSSQCVNLTTRTQLPPAYTNSFTRGVYYPDKVFRSSVLHS

TQDLFLPFFSNVTWFHAIHVSGTNGTKRFDNPVLPFNDGVYFASTEKSNI

IRGWIFGTTLDSKTQSLLIVNNATNVVIKVCEFQFCNDPFLGVYYHKNNK

SWMESEFRVYSSANNCTFEYVSQPFLMDLEGKQGNFKNLREFVFKNIDGY

FKIYSKHTPINLVRDLPQGFSALEPLVDLPIGINITRFQTLLALHRSYLT

PGDSSSGWTAGAAAYYVGYLQPRTFLLKYNENGTITDAVDCALDPLSETK

CTLKSFTVEKGIYQTSNFRVQPTESIVRFPNITNLCPFGEVFNATRFASV

YAWNRKRISNCVADYSVLYNSASFSTFKCYGVSPTKLNDLCFTNVYADSF

VIRGDEVRQIAPGQTGKIADYNYKLPDDFTGCVIAWNSNNLDSKVGGNYN

YLYRLFRKSNLKPFERDISTEIYQAGSTPCNGVEGFNCYFPLQSYGFQPT

NGVGYQPYRVVVLSFELLHAPATVCGPKKSTNLVKNKCVNFNFNGLTGTG

VLTESNKKFLPFQQFGRDIADTTDAVRDPQTLEILDITPCSFGGVSVITP

GTNTSNQVAVLYQDVNCTEVPVAIHADQLTPTWRVYSTGSNVFQTRAGCL

IGAEHVNNSYECDIPIGAGICASYQTQTNSPRRARSVASQSHAYTMSLGA

ENSVAYSNNSIAIPTNFTISVTTEILPVSMTKTSVDCTMYICGDSTECSN

LLLQYGSFCTQLNRALTGIAVEQDKNTQEVFAQVKQIYKTPPIKDFGGFN

FSQILPDPSKPSKRSFIEDLLFNKVTLADAGFIKQYGDCLGDIAARDLIC

AQKFNGLTVLPPLLTDEMIAQYTSALLAGTITSGWTFGAGAALQIPFAMQ

MAYRFNGIGVTQNVLYENQKLIANQFNSAIGKIQDSLSSTASALGKLQDV

VNQNAQALNTLVKQLSSNFGAISSVLNDILSRLDKVEAEVQIDRLITGRL

QSLQTYVTQQLIRAAEIRASANLAATKMSECVLGQSKRVDFCGKGYHLMS

FPQSAPHGVVFLHVTYVPAQEKNFTTAPAICHDGKAHFPREGVFVSNGTH

WFVTQRNFYEPQIITTDNTFVSGNCDVVIGIVNNTVYDPLQPELDSFKEE

LDKYFKNHTSPDVDLGDISGINASVVNIQKEIDRLNEVAKNLNESLIDLQ

ELGKYEQYIKWPWYIWLGFIAGLIAIVMVTIMLCCMTSCCSCLKGCCSCG

SCCKFDEDDSEPVLKGVKLHYT

The spike protein receptor binding domain (SP/RBD) of the surface glycoprotein of SARS-CoV-2 according to Gen-Bank QHD43416.1 comprises the portion of the surface glycoprotein from amino acid 330 to amino acid 583 as is shown below:

(SEQ ID NO: 2)
PNITNLCPFGEVFNATRFASVYAWNRKRISNCVADYSVLYNSASFSTFKC

YGVSPTKLNDLCFTNVYADSFVIRGDEVRQIAPGQTGKIADYNYKLPDDF

TGCVIAWNSNNLDSKVGGNYNYLYRLFRKSNLKPFERDISTEIYQAGSTP

CNGVEGFNCYFPLQSYGFQPTNGVGYQPYRVVVLSFELLHAPATVCGPKK

STNLVKNKCVNFNFNGLTGTGVLTESNKKFLPFQQFGRDIADTTDAVRDP

QTLE.

The RBD of the spike protein comprises amino acid 331 through 524 of the SARS-CoV-2 surface glycoprotein as shown below:

(SEQ ID NO: 8)
NITNLCPFGEVFNATRFASVYAWNRKRISNCVADYSVLYNSASFSTFKCY

GVSPTKLNDLCFTNVYADSFVIRGDEVRQIAPGQTGKIADYNYKLPDDFT

GCVIAWNSNNLDSKVGGNYNYLYRLFRKSNLKPFERDISTEIYQAGSTPC

NGVEGFNCYFPLQSYGFQPTNGVGYQPYRVVVLSFELLHAPATV

Previous work with insulin-Fc fusion proteins, such as is described in WO2018107117A1 and WO2020006529A1 has demonstrated that the choices of the protein sequence, the linker sequence, and the composition of the Fc domain can all potentially influence protein yields, purity, and bioactivity.

In choosing the viral protein for the SARS-CoV-2-RBD-hIgG-Fc fusion protein it is conceivable that one could choose a subset of the surface glycoprotein that includes some portion of the SP/RBD. The viral protein for the SARS-CoV-2-RBD-hIgG-Fc fusion protein may comprise all or a portion of the SP/RBD of the SARS-CoV-2 surface glycoprotein. The viral protein for the SARS-CoV-2-RBD-hIgG-Fc fusion protein may comprise all or a portion of the non-SP/RBD portions of the SARS-CoV-2 surface glycoprotein. In examples, the viral protein for the SARS-CoV-2-RBD-hIgG-Fc fusion protein comprises all or a portion of the RBD of the SARS-CoV-2 surface glycoprotein and all or a portion of the non-SP/RBD portions of the SARS-CoV-2 surface glycoprotein. Some amino acids in the SP/RBD fragment of the SARS-CoV-2-RBD-hIgG-Fc fusion protein are mutated from their native state.

Based on experience manufacturing insulin-Fc fusion proteins, different viral protein designs will result in different protein yields of the SARS-CoV-2-RBD-hIgG-Fc fusion protein. For example, one could choose larger or shorter portions of the SP/RBD sequence of SEQ ID NO: 8, and optionally mutate certain amino acids, to produce the desired viral portion for the Fc fusion protein. The resulting protein yield when the selected viral protein is attached to an Fc fragment can be experimentally determined. Furthermore, the length and composition of the linker connecting the selected viral protein to the Fc fragment will similarly have an impact on the protein yield, as will the choice of the Fc fragment and the portion of the Fc fragment hinge region that is linked to the viral protein.

FIG. 2 shows an illustration of an exemplary SARS-CoV-2-RBD-hIgG-Fc fusion protein according to the present disclosure. The SARS-CoV-2-RBD-hIgG-Fc fusion protein may comprise a linker, for example a peptide linker. The SP/RBD fragment of the SARS-CoV-2-RBD-hIgG-Fc fusion protein may be directly connected to the Fc fragment, i.e., no linker is present. In examples, some amino acids in the SP/RBD fragment of the SARS-CoV-2-RBD-hIgG-Fc fusion protein are mutated from their native state. The therapeutic protein comprising a portion of the SARS-CoV-2 surface glycoprotein is located on the N-terminal side of the Fc fragment. The fusion protein comprises domains in the following orientation from N- to C-termini: (N-terminus)-therapeutic protein-linker-Fc fragment-(C-terminus) (e.g., (N-terminus)-SARS-CoV-2 peptide-linker-Fc fragment-(C-terminus)). The linker may be omitted, such that the fusion protein comprises domains in the following orientation from N- to C-termini: (N-terminus)-therapeutic protein-Fc fragment-(C-terminus) (e.g., (N-terminus)-SARS-CoV-2 peptide-Fc fragment-(C-terminus)). The SP/RBD fragment of the fusion protein shown in FIG. 2 may or may not express well as part of a fusion protein recombinantly manufactured in host cells (i.e., manufactured in HEK cells according to Example 1, in CHO cells transiently according to Example 2, or in stable CHO cells according to Example 3).

In all descriptions that follow, a cited amino acid position is referenced to the position of the amino acid in the SARS-CoV-2 surface glycoprotein of SEQ ID NO: 1. As a first attempt in creating a SARS-CoV-2-RBD-hIgG-Fc fusion protein, the main viral SARS-CoV-2 RBD of SEQ ID NO: 2 was shortened, eliminating the first amino acid (position 330). The resulting SP/RBD fragment of the SARS-CoV-2 RBD of SEQ ID NO: 8 comprised amino acids 331 to 524. Novel mutations were then made in the SP/RBD fragment. First, the asparagine at positions 331 and 343 were mutated to glutamine (general mutations are diagrammatically illustrated in FIG. 2). These mutations were made to reduce the number of glycosylation sites in the SP/RBD fragment, as having too many glycosylation sites was believed likely to lead to lower manufacturing yields when the Fc fusion protein is recombinantly manufactured according to Example 1 (HEK cells), Example 2 (transient CHO-SE™ cells) or Example 3 (CHO cells). That glycan on the SP/RBD fragment of the molecule may shield key epitopes that may be required to develop antibodies. In embodiments, the SP/RBD fragment was located on the N-terminal side of the Fc fragment as illustrated in FIG. 2.

A further novel mutation was made at position 391 in the SP/RBD fragment, from cysteine to methionine. This mutation was made to eliminate the unpaired cysteine to prevent undesirable protein folding and undesirable artifacts during recombinant manufacturing in HEK or CHO cells. The resulting analog SP/RBD fragment of the SARS-CoV-2 surface glycoprotein of SEQ ID NO: 1 is shown below:

```
                                               (SEQ ID NO: 9)
QITNLCPFGEVFQATRFASVYAWNRKRISNCVADYSVLYNSASFSTFKCY

GVSPTKLNDLMFTNVYADSFVIRGDEVRQIAPGQTGKIADYNYKLPDDFT

GCVIAWNSNNLDSKVGGNYNYLYRLFRKSNLKPFERDISTEIYQAGSTPC

NGVEGFNCYFPLQSYGFQPTNGVGYQPYRVVVLSFELLHAPATV.
```

A side-by-side comparison of the SARS-CoV-2 native SP/RBD of SEQ ID NO: 2 and the analog SP/RBD fragment (SEQ ID NO: 9) was performed using Clustal Omega and is shown in FIG. 13. "*" represents complete homology across all sequences at a given sequence position. A ":" (colon) indicates conservation between groups of strongly similar properties with scoring greater than 0.5 in the Gonnet PAM 250 matrix. A "-" (dash) indicates a sequence gap, meaning that no local homology exists within a particular set of comparisons within a certain range of the sequences.

The analog SP/RBD fragment (SEQ ID NO: 9) was linked using the linker GGGGGQGGGGQGGGGQGGGGG (SEQ ID NO: 4) to a native human IgG1 Fc fragment comprising the following sequence:

```
                                               (SEQ ID NO: 6)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPG
```

The N-terminal lysine on the human IgG1 fragment was eliminated as shown above in SEQ ID NO: 6 in an attempt to improve manufacturing yield and purity. In addition, the asparagine at the cNg site on the human IgG1 fragment was conserved to preserve the glycan attachment during fusion protein production in host cells. The resultant SARS-CoV-2-RBD-hIgG-Fc fusion protein is given below:

(SEQ ID NO: 11)
QITNLCPFGEVFQATRFASVYAWNRKRISNCVADYSVLYNSASFSTFKCY

GVSPTKLNDLMFTNVYADSFVIRGDEVRQIAPGQTGKIADYNYKLPDDFT

GCVIAWNSNNLDSKVGGNYNYLYRLFRKSNLKPFERDISTEIYQAGSTPC

NGVEGFNCYFPLQSYGFQPTNGVGYQPYRVVVLSFELLHAPATVGGGGGQ

GGGGQGGGGQGGGGGDKTHTCPPCPAPELLGGPSVFLFPPKPKDTLMISR

TPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSFF

LYSKLTVDKSRWQQGNVFSCSVMHEALHNHYTQKSLSLSPG

The SARS-CoV-2-RBD-hIgG-Fc fusion protein of SEQ ID NO: 11 was manufactured in HEK293 cells according to Example 1 and purified according to Example 4. Unexpectedly, this gave rise to a highly aggregated SARS-CoV-2-RBD-hIgG-Fc fusion protein with extremely low homodimer titers of less than 5 mg/L.

In a second attempt to create a SARS-CoV-2-RBD-hIgG-Fc fusion protein, the main SARS-CoV-2 RBD (SEQ ID NO: 2) sequence was shortened and the first 103 amino acids (amino acids at positions 330-432 of SEQ ID NO: 1) were eliminated. The resulting RBD fragment of SEQ ID NO: 1 comprised amino acids 433 to 524 and was deemed to be structurally continuous as per a 3D model.

The resulting analog SP/RBD fragment is shown below:

(SEQ ID NO: 10)
VIAWNSNNLDSKVGGNYNYLYRLFRKSNLKPFERDISTEIYQAGSTPCNG

VEGFNCYFPLQSYGFQPTNGVGYQPYRVVVLSFELLHAPATV

A side-by-side comparison of the SARS-CoV-2 native SP/RBD (SEQ ID NO: 2) and the analog SP/RBD fragment (SEQ ID NO: 10) was performed using Clustal Omega and is shown in FIG. 14. "*" represents complete homology across all sequences at a given sequence position. A ":" (colon) indicates conservation between groups of strongly similar properties with scoring greater than 0.5 in the Gonnet PAM 250 matrix. A "-" (dash) indicates a sequence gap, meaning that no local homology exists within a particular set of comparisons within a certain range of the sequences.

The analog SP/RBD fragment of SEQ ID NO: 10 was linked via the same linker that was used in the SARS-CoV-2-RBD-hIgG-Fc fusion protein of SEQ ID NO: 11—GGGGGQGGGGQGGGGQGGGGG (SEQ ID NO: 4)—to a native human IgG1 Fc fragment comprising the following sequence:

(SEQ ID NO: 6)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPG

The N-terminal lysine on the human IgG1 fragment was eliminated as shown above in SEQ ID NO: 6 in an attempt to improve manufacturing yield and purity. In addition, the asparagine at the cNg site on the human IgG1 fragment was conserved to preserve the glycan attachment during fusion protein production in host cells. The resultant SARS-CoV-2-RBD-hIgG-Fc fusion protein is given below:

(SEQ ID NO: 12)
VIAWNSNNLDSKVGGNYNYLYRLFRKSNLKPFERDISTEIYQAGSTPCNG

VEGFNCYFPLQSYGFQPTNGVGYQPYRVVVLSFELLHAPATVGGGGQGG

GGQGGGGQGGGGGDKTHTCPPCPAPELLGGPSVFLFPPKPKDTLMISRTP

EVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLY

SKLTVDKSRWQQGNVFSCSVMHEALHNHYTQKSLSLSPG

The SARS-CoV-2-RBD-hIgG-Fc fusion protein of SEQ ID NO: 12 was manufactured in HEK293 cells according to Example 1 and purified according to Example 4. Unexpectedly, this gave rise to a highly aggregated SARS-CoV-2-RBD-hIgG-Fc fusion protein with extremely low homodimer titers of less than 1 mg/L.

In a further attempt to produce a SARS-CoV-2-RBD-hIgG-Fc fusion protein, instead of further shortening the SARS-CoV-2 RBD, the SP/RBD fragment of the SARS-CoV-2-RBD-hIgG-Fc fusion protein was selected by extending the N- and C-termini of the SP/RBD sequence to comprise amino acids 319 through 541 of SEQ ID NO: 1 to create a sequence which might express better, fold better, and better enable pairing up of cysteines. The resulting analog SP/RBD fragment of SEQ ID NO: 14 is shown below:

(SEQ ID NO: 14)
RVQPTESIVRFPNITNLCPFGEVFNATRFASVYAWNRKRISNCVADYSVL

YNSASFSTFKCYGVSPTKLNDLCFTNVYADSFVIRGDEVRQIAPGQTGKI

ADYNYKLPDDFTGCVIAWNSNNLDSKVGGNYNYLYRLFRKSNLKPFERDI

STEIYQAGSTPCNGVEGFNCYFPLQSYGFQPTNGVGYQPYRVVVLSFELL

HAPATVCGPKKSTNLVKNKCVNF.

A side-by-side comparison of the SARS-CoV-2 native SP/RBD (SEQ ID NO: 2) and the SP/RBD fragment (SEQ ID NO: 14) was performed using Clustal Omega and is shown in FIG. 15. "*" represents complete homology across all sequences at a given sequence position. A ":" (colon) indicates conservation between groups of strongly similar properties with scoring greater than 0.5 in the Gonnet PAM 250 matrix. A "-" (dash) indicates a sequence gap, meaning that no local homology exists within a particular set of comparisons within a certain range of the sequences, while ":", "." or spaces refer to conservative, moderate, or very different amino acid mutations across the sequences at a given sequence position respectively.

In one attempt, the linker was also shortened and changed in composition to GGGSGGG (SEQ ID NO: 3), and the hinge region and the C-terminal lysine on the human IgG1 Fc fragment was restored, producing the Fc fragment of SEQ ID NO: 7.

(SEQ ID NO: 7)
SPKSSDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK

The asparagine at the cNg site on the human IgG1 fragment was conserved to preserve the glycan attachment during fusion protein production in host cells. The resulting SARS-CoV-2-RBD-hIgG-Fc fusion protein (SEQ ID NO: 17) is shown below.

(SEQ ID NO: 17)
RVQPTESIVRFPNITNLCPFGEVFNATRFASVYAWNRKRISNCVADYSVLY

NSASFSTFKCYGVSPTKLNDLCFTNVYADSFVIRGDEVRQIAPGQTGKIAD

YNYKLPDDFTGCVIAWNSNNLDSKVGGNYNYLYRLFRKSNLKPFERDISTE

IYQAGSTPCNGVEGFNCYFPLQSYGFQPTNGVGYQPYRVVVLSFELLHAPA

TVCGPKKSTNLVKNKCVNFGGGSGGGSPKSSDKTHTCPPCPAPELLGGPSV

FLFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLS

PGK

The Fc(gamma) Receptor I binding of the SARS-CoV-2-RBD-hIgG-Fc fusion protein of SEQ ID NO: 17 manufactured in HEK293 cells according to Example 1 is measured according to Example 9. It is expected that the OD450 measurements for Fc(gamma) Receptor I, Fc(gamma) Receptor IIA, Fc(gamma) Receptor IIB, Fc(gamma) Receptor III, FcRn, and ACE2 receptor binding will increase as a function of the concentration of the SARS-CoV-2-RBD-hIgG-Fc fusion protein.

In a further attempt, the SARS-CoV-2 RBD fragment of SEQ ID NO: 14 and the linker of SEQ ID NO: 3 were retained, and the C-terminal lysine on the human IgG1 Fc fragment was removed again, producing the Fc fragment of SEQ ID NO: 33.

(SEQ ID NO: 33)
SPKSSDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQ

GNVFSCSVMHEALHNHYTQKSLSLSPG

The asparagine at the cNg site on the human IgG1 fragment was conserved to preserve the glycan attachment during fusion protein production in host cells. The resulting SARS-CoV-2-RBD-hIgG-Fc fusion protein is shown below.

(SEQ ID NO: 16)
RVQPTESIVRFPNITNLCPFGEVFNATRFASVYAWNRKRISNCVADYSVLY

NSASFSTFKCYGVSPTKLNDLCFTNVYADSFVIRGDEVRQIAPGQTGKIAD

YNYKLPDDFTGCVIAWNSNNLDSKVGGNYNYLYRLFRKSNLKPFERDISTE

IYQAGSTPCNGVEGFNCYFPLQSYGFQPTNGVGYQPYRVVVLSFELLHAPA

TVCGPKKSTNLVKNKCVNFGGGSGGGSPKSSDKTHTCPPCPAPELLGGPSV

FLFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLS

PG

The Fc fusion protein of SEQ ID NO: 16 was recombinantly manufactured in transiently transfected CHO cells according to Example 2. The Fc fusion protein of SEQ ID NO: 16 was purified according to Example 5. The fusion protein structure of SEQ ID NO: 16 was confirmed according to Example 6, and the sequence identification was performed according to Example 7. To obtain the homodimer titer of the manufactured SARS-CoV-2-RBD-hIgG-Fc fusion protein, the % homodimer was measured according to Example 8 and the homodimer titer was calculated by multiplying the % homodimer by the protein titer of the recombinantly manufactured fusion protein. The homodimer titer of the SARS-CoV-2-RBD-hIgG-Fc fusion protein of SEQ ID NO: 16 was calculated to be 139 mg/L.

The Fc(gamma) Receptor I binding of the SARS-CoV-2-RBD-hIgG-Fc fusion protein of SEQ ID NO: 16 manufactured in transiently transfected CHO cells according to Example 2, or in CHO cells according to Example 3 is measured according to Example 9. It is expected that the OD450 measurements for Fc(gamma) Receptor I, Fc(gamma) Receptor IIA, Fc(gamma) Receptor IIB, Fc(gamma) Receptor III, FcRn, and ACE2 receptor binding will increase as a function of the concentration of the SARS-CoV-2-RBD-hIgG-Fc fusion protein.

In a further attempt to produce a SARS-CoV-2-RBD-hIgG-Fc fusion protein, the SARS-CoV-2 SP/RBD fragment of SEQ ID NO: 14 was linked via the same linker that was used in the SARS-CoV-2-RBD-hIgG-Fc fusion protein of SEQ ID NO: 11—GGGGGQGGGGQGGGGQGGGGG (SEQ ID NO: 4)—to a human IgG1 Fc fragment comprising SEQ ID NO: 6. The resulting SARS-CoV-2-RBD-hIgG-Fc fusion protein is shown below.

(SEQ ID NO: 18)
RVQPTESIVRFPNITNLCPFGEVFNATRFASVYAWNRKRISNCVADYSVLY

NSASFSTFKCYGVSPTKLNDLCFTNVYADSFVIRGDEVRQIAPGQTGKIAD

YNYKLPDDFTGCVIAWNSNNLDSKVGGNYNYLYRLFRKSNLKPFERDISTE

IYQAGSTPCNGVEGFNCYFPLQSYGFQPTNGVGYQPYRVVVLSFELLHAPA

TVCGPKKSTNLVKNKCVNFGGGGQGGGGQGGGGQGGGGGDKTHTCPPCPA

PELLGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESN

-continued
GQPENNYKTTPPVLDSDGSFFLYSKLTVDKSRWQQGNVFSCSVMHEALHNH

YTQKSLSLSPG

The Fc fusion protein of SEQ ID NO: 18 was recombinantly manufactured in transiently transfected CHO cells according to Example 2 and was purified according to Example 5. In examples, the fusion protein structure of SEQ ID NO: 18 was confirmed according to Example 6, and the sequence identification was performed according to Example 7. To obtain the homodimer titer of the manufactured SARS-CoV-2-RBD-hIgG-Fc fusion protein of SEQ ID NO: 18, the % homodimer was measured according to Example 8 and the homodimer titer was calculated by multiplying the % homodimer by the protein titer of the recombinantly manufactured fusion protein. The homodimer titer of the SARS-CoV-2-RBD-hIgG-Fc fusion protein of SEQ ID NO: 18 was calculated to be 124 mg/L.

The Fc(gamma) Receptor I binding of the SARS-CoV-2 Fc Hu fusion protein of SEQ ID NO: 18 manufactured in transiently transfected CHO cells according to Example 2, or in CHO cells according to Example 3 is measured according to Example 9. It is expected that the OD450 measurements for Fc(gamma) Receptor I, Fc(gamma) Receptor IIA, Fc(gamma) Receptor IIB, Fc(gamma) Receptor III, FcRn, and ACE2 receptor binding will increase as a function of the concentration of the SARS-CoV-2-RBD-hIgG-Fc fusion protein and at a given concentration the OD450 measurements is greater than a reference standard.

In a further attempt to produce a SARS-CoV-2-RBD-hIgG-Fc fusion protein, instead of further shortening the SARS-CoV-2 SP/RBD, the SP/RBD fragment of the SARS-CoV-2-RBD-hIgG-Fc fusion protein was selected by extending the N- and C-termini of the SP/RBD sequence to comprise amino acids 319 through 541 of SEQ ID NO: 1 as shown below in SEQ ID NO: 15, to create a sequence which might express better, fold better, and better enable pairing up of cysteines.

(SEQ ID NO: 15)
RVQPTESIVRFPNITNLCPFGEVFNATRFASVYAWNRKRISNCVADYSVLY

NSASFSTFKCYGVSPTKLNDLCFTNVYADSFVIRGDEVRQIAPGQTGKIAD

YNYKLPDDFTGCVIAWNSNNLDSKVGGNYNYLYRLFRKSNLKPFERDISTE

IYQAGSTPCNGVEGFNCYFPLQSYGFQPTNGVGYQPYRVVVLSFELLHAPA

TVCGPKKSTNLVK

A side-by-side comparison of the SARS-CoV-2 native SP/RBD (SEQ ID NO: 2) and the SP/RBD fragment of SEQ ID NO: 15 was performed using Clustal Omega and is shown in FIG. 16. "*" represents complete homology across all sequences at a given sequence position. A ":" (colon) indicates conservation between groups of strongly similar properties with scoring greater than 0.5 in the Gonnet PAM 250 matrix. A "-" (dash) indicates a sequence gap, meaning that no local homology exists within a particular set of comparisons within a certain range of the sequences, while ":", "." or spaces refer to conservative, moderate, or very different amino acid mutations across the sequences at a given sequence position respectively.

The linker was also shortened and changed in composition to GGGSGGGS (SEQ ID NO: 5) and was used to link the SP/RBD fragment to the human IgG1 Fc fragment comprising SEQ ID NO: 6. The resulting SARS-CoV-2-RBD-hIgG-Fc fusion protein is shown below.

(SEQ ID NO: 20)
RVQPTESIVRFPNITNLCPFGEVFNATRFASVYAWNRKRISNCVADYSVLY

NSASFSTFKCYGVSPTKLNDLCFTNVYADSFVIRGDEVRQIAPGQTGKIAD

YNYKLPDDFTGCVIAWNSNNLDSKVGGNYNYLYRLFRKSNLKPFERDISTE

IYQAGSTPCNGVEGFNCYFPLQSYGFQPTNGVGYQPYRVVVLSFELLHAPA

TVCGPKKSTNLVKGGGSGGGSDKTHTCPPCPAPELLGGPSVFLFPPKPKDT

LMISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDGS

FFLYSKLTVDKSRWQQGNVFSCSVMHEALHNHYTQKSLSLSPG

The Fc fusion protein of SEQ ID NO: 20 was recombinantly manufactured in transiently transfected CHO cells according to Example 2 and was purified according to Example 4. In examples, the fusion protein structure of SEQ ID NO: 20 was confirmed according to Example 6, and the sequence identification was performed according to Example 7. To obtain the homodimer titer of the manufactured SARS-CoV-2-RBD-hIgG-Fc fusion protein, the % homodimer of SEQ ID NO: 20 was measured according to Example 8 and the homodimer titer was calculated by multiplying the % homodimer by the protein titer of the recombinantly manufactured fusion protein. The homodimer titer of the SARS-CoV-2-RBD-hIgG-Fc fusion protein of SEQ ID NO: 20 was calculated to be 134 mg/L.

The Fc(gamma) Receptor I binding of the SARS-CoV-2-RBD-hIgG-Fc fusion protein of SEQ ID NO: 20 manufactured in transiently transfected CHO cells according to Example 2, or in CHO cells according to Example 3 is measured according to Example 9. It is expected that the OD450 measurements for Fc(gamma) Receptor I, Fc(gamma) Receptor IIA, Fc(gamma) Receptor IIB, Fc(gamma) Receptor III, FcRn, and ACE2 receptor binding will increase as a function of the concentration of the SARS-CoV-2-RBD-hIgG-Fc fusion protein and at a given concentration the OD450 measurements is greater than a reference standard.

In a further attempt to produce a SARS-CoV-2-RBD-hIgG-Fc fusion protein, instead of further shortening the SARS-CoV-2 SP/RBD, the SP/RBD fragment of SEQ ID NO: 15 was retained. The linker was eliminated and the SP/RBD fragment of SEQ ID NO: 15 was connected directly to the human IgG1 Fc fragment of SEQ ID NO: 6. The resulting SARS-CoV-2-RBD-hIgG-Fc fusion protein is shown below.

(SEQ ID NO: 21)
RVQPTESIVRFPNITNLCPFGEVFNATRFASVYAWNRKRISNCVADYSVLY

NSASFSTFKCYGVSPTKLNDLCFTNVYADSFVIRGDEVRQIAPGQTGKIAD

YNYKLPDDFTGCVIAWNSNNLDSKVGGNYNYLYRLFRKSNLKPFERDISTE

IYQAGSTPCNGVEGFNCYFPLQSYGFQPTNGVGYQPYRVVVLSFELLHAPA

TVCGPKKSTNLVKDKTHTCPPCPAPELLGGPSVFLFPPKPKDTLMISRTPE

VTCVVVDVSHEDPEVKFNWYVDGVEVHNAKTKPREEQYNSTYRVVSVLTVL

-continued

HQDWLNGKEYKCKVSNKALPAPIEKTISKAKGQPREPQVYTLPPSRDELTK

NQVSLTCLVKGFYPSDIAVEWESNGQPENNYKTTPPVLDSDGSFFLYSKLT

VDKSRWQQGNVFSCSVMHEALHNHYTQKSLSLSPG

The Fc fusion protein of SEQ ID NO: 21 was recombinantly manufactured in transiently transfected CHO cells according to Example 2 and was purified according to Example 4. In examples, the fusion protein structure of SEQ ID NO: 21 was confirmed according to Example 6, and the sequence identification was performed according to Example 7. To obtain the homodimer titer of the manufactured SARS-CoV-2-RBD-hIgG-Fc fusion protein of SEQ ID NO: 21, the % homodimer was measured according to Example 8 and the homodimer titer was calculated by multiplying the % homodimer by the protein titer of the recombinantly manufactured fusion protein. The protein titer was 156 mg/L and the % homodimer was 98.7%, resulting in a homodimer titer of the SARS-CoV-2-RBD-hIgG-Fc fusion protein of SEQ ID NO: 21 of 154 mg/L.

The Fc(gamma) Receptor I binding of the SARS-CoV-2 Fc Hu fusion protein of SEQ ID NO: 21 manufactured in transiently transfected CHO cells according to Example 2, or in CHO cells according to Example 3 is measured according to Example 9. It is expected that the OD450 measurements for Fc(gamma) Receptor I, Fc(gamma) Receptor IIA, Fc(gamma) Receptor IIB, Fc(gamma) Receptor III, FcRn, and ACE2 receptor binding will increase as a function of the concentration of the SARS-CoV-2-RBD-hIgG-Fc fusion protein and at a given concentration the OD450 measurements is greater than a reference standard.

In a further attempt to produce a SARS-CoV-2-RBD-hIgG-Fc fusion protein, the SP/RBD fragment of the SARS-CoV-2-RBD-hIgG-Fc fusion protein was selected by extending the C-termini of the SP/RBD sequence such that the SP/RBD comprises amino acids 319 through 591 of SEQ ID NO: 1 as shown below in SEQ ID NO: 13.

(SEQ ID NO: 13)
RVQPTESIVRFPNITNLCPFGEVFNATRFASVYAWNRKRISNCVADYSVLY

NSASFSTFKCYGVSPTKLNDLCFTNVYADSFVIRGDEVRQIAPGQTGKIAD

YNYKLPDDFTGCVIAWNSNNLDSKVGGNYNYLYRLFRKSNLKPFERDISTE

IYQAGSTPCNGVEGFNCYFPLQSYGFQPTNGVGYQPYRVVVLSFELLHAPA

TVCGPKKSTNLVKNKCVNFNFNGLTGTGVLTESNKKFLPFQQFGRDIADTT

DAVRDPQTLEILDITPCS

The side-by-side comparison of the SARS-CoV-2 native SP/RBD (SEQ ID NO: 2) and the SP/RBD fragment (SEQ ID NO: 13) was performed using Clustal Omega and is shown in FIG. 17. "*" represents complete homology across all sequences at a given sequence position. A ":" (colon) indicates conservation between groups of strongly similar properties with scoring greater than 0.5 in the Gonnet PAM 250 matrix. A "-" (dash) indicates a sequence gap, meaning that no local homology exists within a particular set of comparisons within a certain range of the sequences, while ":", "." or spaces refer to conservative, moderate, or very different amino acid mutations across the sequences at a given sequence position respectively.

The shortened linker of GGGSGGGS (SEQ ID NO: 5) was used to link the SP/RBD fragment of SEQ ID NO: 13 to the human IgG1 Fc fragment of SEQ ID NO: 6. The resulting SARS-CoV-2-RBD-hIgG-Fc fusion protein is shown below.

(SEQ ID NO: 19)
RVQPTESIVRFPNITNLCPFGEVFNATRFASVYAWNRKRISNCVADYSVLY

NSASFSTFKCYGVSPTKLNDLCFTNVYADSFVIRGDEVRQIAPGQTGKIAD

YNYKLPDDFTGCVIAWNSNNLDSKVGGNYNYLYRLFRKSNLKPFERDISTE

IYQAGSTPCNGVEGFNCYFPLQSYGFQPTNGVGYQPYRVVVLSFELLHAPA

TVCGPKKSTNLVKNKCVNFNFNGLTGTGVLTESNKKFLPFQQFGRDIADTT

DAVRDPQTLEILDITPCSGGGSGGGSDKTHTCPPCPAPELLGGPSVFLFPP

KPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG

The Fc fusion protein of SEQ ID NO: 19 was recombinantly manufactured in transiently transfected CHO cells according to Example 2 and was purified according to Example 5. In examples, the fusion protein structure of SEQ ID NO: 19 was confirmed according to Example 6, and the sequence identification was performed according to Example 7. To obtain the homodimer titer of the manufactured SARS-CoV-2-RBD-hIgG-Fc fusion protein, the % homodimer was measured according to Example 8 and the homodimer titer was calculated by multiplying the % homodimer by the protein titer of the recombinantly manufactured fusion protein. The homodimer titer of the SARS-CoV-2-RBD-hIgG-Fc fusion protein of SEQ ID NO: 19 was calculated to be 204 mg/L.

In an embodiment, the Fc fusion protein of SEQ ID NO: 19 was recombinantly manufactured in stably transfected CHO cells according to Example 3. The Fc fusion protein of SEQ ID NO: 19 was purified according to Example 5. In examples, the fusion protein structure of SEQ ID NO: 19 was confirmed according to Example 6, and the sequence identification was performed according to Example 7. To obtain the homodimer titer of the manufactured SARS-CoV-2-RBD-hIgG-Fc fusion protein, the % homodimer was measured according to Example 8 and the homodimer titer was calculated by multiplying the % homodimer by the protein titer of the recombinantly manufactured fusion protein. The homodimer titer of the SARS-CoV-2-RBD-hIgG-Fc fusion protein of SEQ ID NO: 19 was calculated to be greater than 750 mg/L.

The Fc(gamma) Receptor I binding of the SARS-CoV-2-RBD-hIgG-Fc fusion protein of SEQ ID NO: 19 manufactured in CHO cells according to Example 3 is measured according to Example 9. As described in Example 16 and shown in FIG. 19, FIG. 20, FIG. 21, FIG. 22, and FIG. 23, the OD450 measurements for Human Fc(gamma) Receptor I, Fc(gamma) Receptor IIA, Fc(gamma) Receptor IIB, Fc(gamma) Receptor III, FcRn, and ACE2 receptor binding increase as a function of the concentration of the SARS-CoV-2-RBD-hIgG-Fc fusion protein.

A side-by-side comparison of the SP/RBD domains of SEQ ID NO: 8, SEQ ID NO: 9, SEQ ID NO: 10, SEQ ID NO: 14 and SEQ ID NO: 15 was performed using Clustal Omega and is shown in FIG. 80. "*" represents complete homology across all sequences at a given sequence position. A ":" (colon) indicates conservation between groups of strongly similar properties with scoring greater than 0.5 in the Gonnet PAM 250 matrix. A "-" (dash) indicates a sequence gap, meaning that no local homology exists within a particular set of comparisons within a certain range of the sequences, while ":", "." or spaces refer to conservative, moderate, or very different amino acid mutations across the sequences at a given sequence position respectively.

SARS-CoV-2-RBD-hIgG-Fc Fusion Proteins for Use as a Primary Vaccine

A SARS-CoV-2-RBD-hIgG-Fc fusion protein may be used as a primary vaccine. In one or more embodiments, the SARS-CoV-2-RBD-hIgG-Fc fusion protein is provided in a pharmaceutical composition. Injection of any protein can induce an immune response, the magnitude and type of which is highly dependent on the "status" of the respective immune system. For example, injection of a foreign antigen (Ag) relative to a self Ag will induce a greater immune response in an immune system that maintains central and peripheral tolerance mechanisms. Moreover, foreign Ag administration to an immune system that has been primed to previous exposure to the respective Ag (e.g., a viral infection) will lodge a more rapid and elevated immune response relative to that of an Ag-naïve system. The immunological basis of this priming is two-fold: 1) an Ag-naïve immune system has naïve B and T lymphocytes that have a much higher threshold of activation than do the Ag-primed "memory" cells of a Ag-primed immune system, such that the antigen-presenting cells (APCs) that present Ag require much less Ag to activate primed memory T cells, and 2) due to expansion of memory T cells during the Ag priming exposure, there are inherently greater numbers of such cells upon re-exposure to an injected Ag. Note that dominant APCs are dendritic cells (DCs) and macrophages that present Ag in complex with Major Histocompatibility Complex (MHC) molecules on their surface to T cell Ag receptors.

APCs can influence both the "magnitude" and "type" of response to Ag. B cells participate in the immune response directly by humoral immunity (antibody production) and also participate in the T-cell immune response as specific APCs that selectively capture and present antigens to T cells. Both these functions are achieved through activation of the surface B cell receptor (BCR), which is essentially a membrane bound antibody that binds specifically to a particular antigen. Multivalent soluble antigens such as the Fc-fusion homodimer containing the specific antigen can be recognized by BCRs and activate them. Thus, the SARS-CoV-2-RBD-hIgG-Fc protein homodimers can activate B cells through antigen-specific BCR activation leading to an increase in antibody production, as well as an increase in T cell activity directed specifically against the RBD. Thus, these fusion proteins activate both humoral and cellular immunity after administration. More particularly, the induced Th1-type (cellular) immunity activates the body's cell-killing machinery like cytotoxic T cells, NK cells, and macrophages which target cells that are already infected with the virus. Concurrently, in Th2-type immunity, the T helper cells stimulate B cells to proliferate and differentiate into plasma cells that secrete antigen-specific antibodies. These antibodies help control infection by antibody directed cellular toxicity (ADC) which occurs when the antibodies bind antigen presented on the surface of infected cells and direct NK cells to destroy them. The antibodies also help by binding to and neutralizing the virus by preventing its interaction with cells and ultimately clearing the virus via Fc-directed phagocytosis.

Adjuvants

Figure 18:
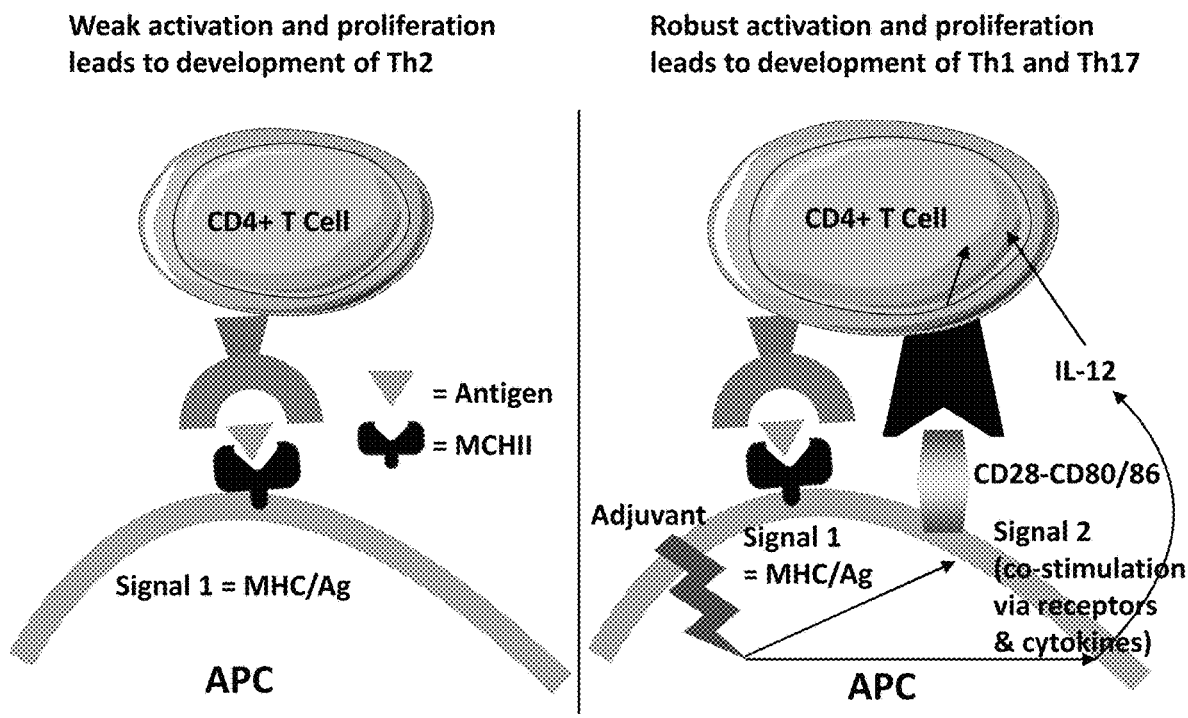
FIG. 18 illustrates a general mechanism of action of a vaccine adjuvant.

In some examples, the Th1 cell response is required to clear most viral and bacterial infections, in which virus-like or bacterial-like substances (non-Ag in nature) condition APCs to express key cytokines and surface co-stimulatory molecules that, during Ag presentation, drive T cells to become the Th1 type. In fact, this APC activation is the conceptual basis of many immune enhancing substances called adjuvants. The general mechanism of a vaccine adjuvant is illustrated in FIG. 18. Note that dominant APCs are dendritic cells (DCs) and macrophages that present Ag in complex with Major Histocompatibility Complex (MHC) molecules on their surface to T cell Ag receptors (FIG. 1). These APCs can influence both the "magnitude" and "type" of response to Ag. Some adjuvants are designed to trick the immune system into reacting to the injected vaccine Ag as if it were part of an on-going infection (i.e., infectious agents provide such natural viral or bacterial adjuvant substances). Therefore, adjuvants activate APCs for greater Ag-presentation capabilities necessary to overcome the high activation threshold of naïve T cells, in addition to shaping their development into the Th1 response to effectively clear the respective infection. Note that such T cells provide critical help to B cells that specifically bind the respective Ag to produce Ag-specific antibody (Ab) titers (FIG. 12).

The Fc fusion protein used as a primary vaccine may be co-administered with an adjuvant to enhance or otherwise alter the immune response in the target subject. Adjuvants activate APCs for greater Ag-presentation capabilities which are necessary to overcome the high activation threshold of naïve T cells, in addition to shaping their development into the Th1 response to effectively clear the respective infection. In examples, known adjuvants may be used in a pharmaceutical composition of the SARS-CoV-2-RBD-hIgG-Fc fusion protein to enhance the induction of anti-SARS-CoV-2 antibodies. Known adjuvants include adjuvants used for respiratory virus infections including trivalent or monovalent influenza vaccines, pandemic H1N1, H5N1, and SARS-CoV vaccines during the last decade in human clinical studies.

Examples of adjuvants that may be employed in the pharmaceutical compositions disclosed herein include but are not limited to oil-in-water, amorphous aluminum hydroxyphosphate sulfate (AAHS), aluminum hydroxide, aluminum phosphate, potassium aluminum sulfate (Alum), Freund's adjuvant (complete and/or incomplete), squalene, AS02, AS03, AS04, MF59, ASO1B, QS-21, CpG 1018, ISCOMS, Montanide™ ISA-51, Montanide™ ISA-720, polylactide co-glycolide (PLG), monophosphoryl lipid A (MPL), Detox, AGP [RC-529], DC_Chol, OM-174 (lipid A derivative), CpG motifs (synthetic oligonucleotides containing immunostimulatory CpG motifs), modified LT and CT, hGM-CSF, hIL-12, Immudaptin, Inert vehicles, such as gold particles as well as various experimental adjuvants from sources such as Advax (Australia) such as AddaVax (Invivogen) or other Advax-based vaccine adjuvants.

In some examples, the selected adjuvant may be MF59 (Novartis) and AS-03 (GlaxoSmithKline). A custom formulation of MF59 (Novartis) or an equivalent such as AddaVax (Invivogen) or other Advax-based vaccine adjuvants from Vaxine Pvt Ltd. (Australia) may be used in a pharmaceutical composition of the SARS-CoV-2-RBD-hIgG-Fc fusion protein. In preferred embodiments, the SARS-CoV-2-RBD-hIgG-Fc fusion protein is co-administered with the Montanide™ ISA-720 adjuvant to enhance or otherwise alter the immune response in the target subject. Many different adjuvants used for respiratory virus infections are tested extensively in seasonal trivalent flu vaccines and with pandemic H1N1 and H5N1 vaccines (Protein Sciences) in Australia and recently in NIH supported human influenza vaccine trials conducted by Sanofi Pasteur in the United States and may be used in a pharmaceutical composition of the SARS-CoV-2-RBD-hIgG-Fc fusion protein.

In one or more embodiments, the SARS-CoV-2-RBD-hIgG-Fc fusion protein formulation is prepared onsite for administration. In one aspect, the SARS-CoV-2-RBD-hIgG-Fc fusion protein is mixed with an adjuvant onsite under sterile mixing conditions. In one aspect, the SARS-CoV-2-RBD-hIgG-Fc fusion protein and adjuvant are thoroughly mixed and/or emulsified to prepare a homogenous emulsion for administration to the subject. The adjuvanted formulation of the Fc fusion protein or a pharmaceutical composition thereof is administered to a patient by subcutaneous (s.c.) injection or intramuscular (i.m.) injection, as the s.c. or i.m. injection sites are more likely to induce a strong antibody response due to there being more dendritic cells (DCs) in the subcutaneous and intramuscular spaces.

After administering one or more than one treatment of an exemplary SARS-CoV-2-RBD-hIgG-Fc fusion protein of this disclosure or a pharmaceutical composition thereof to an antibody naïve patient, anti-SARS-CoV-2 antibodies are measured according to Example 11 and their neutralizing capacity assessed according to Example 13. It is expected that one or more than one treatment with an exemplary SARS-CoV-2-RBD-hIgG-Fc fusion protein of this disclosure or a pharmaceutical composition thereof to previously antibody naïve patients will induce measurable anti-SARS-CoV-2 antibody titers in extracted serum post-treatment.

As described above, in some cases, it may be advantageous to use an adjuvant in the pharmaceutical composition in order to increase the quantity of anti-SARS-CoV-2 antibody titers as measured according to Example 11 and/or the virus-neutralizing capacity of the anti-SARS-CoV-2 antibody titers as measured according to Example 13. The use of an adjuvant may be especially advantageous in antibody naïve patients who do not possess an underlying immune response to the virus or the SP/RBD. Furthermore, an adjuvant may be advantageous in older subjects who experience altered immune competence with increasing age, so-called immunosenescence, which is the result of changes at multiple levels of the immune system over time. Once a patient has measurable antibodies, upon re-challenge with the SARS-CoV-2 virus, the patient will exhibit very rapid development of anti-SARS-CoV-2 antibodies to mount their own defense against COVID-19.

Primary SARS-CoV-2-RBD-hIgG-Fc Fusion Vaccines Evaluated in Mice

The efficacy of an exemplary SARS-CoV-2-RBD-hIgG-Fc fusion proteins of this disclosure or a pharmaceutical composition thereof have been initially evaluated in mice immunization studies for their capacity to induce high-titer neutralizing AB responses using different dosing strategies according to the procedure in Example 12. BALB/c mice are a relevant animal model that has been extensively used for preclinical immunogenicity assessment of vaccines. This strain generates robust Ab responses when immunized with adjuvanted and non-adjuvanted vaccine candidates. Moreover, mouse-specific reagents are widely available for evaluating the kinetics and characteristics of a variety of immune responses to vaccination, including relevant Ab isotypes and T cell responses (e.g., Th1 vs. Th2 responses). Therefore, the BALB/c mouse model was selected to evaluate the immunogenicity of SP/RBD-Fc vaccines with respect to Ag dose, potentiation by adjuvants, routes of administration, and dosing frequency required to achieve optimal Ab responses.

Briefly, target mice (e.g., BALB/c mice) were injected up to three times at predetermined intervals (e.g., every three weeks) with SARS-CoV-2-RBD-hIgG-Fc fusion proteins (with or without adjuvant) or pharmaceutical compositions thereof, and serum was collected at regular intervals. The serum anti-SARS-CoV-2 antibody titers were measured according to the procedure in Example 10 or the procedure in Example 11 and their potency to inhibit ACE2-SP/RBD binding was assessed according to Example 13. Experimental variables included the SARS-CoV-2-RBD-hIgG-Fc fusion protein composition and dose level, number of injections, and type of adjuvant.

Figure 25:
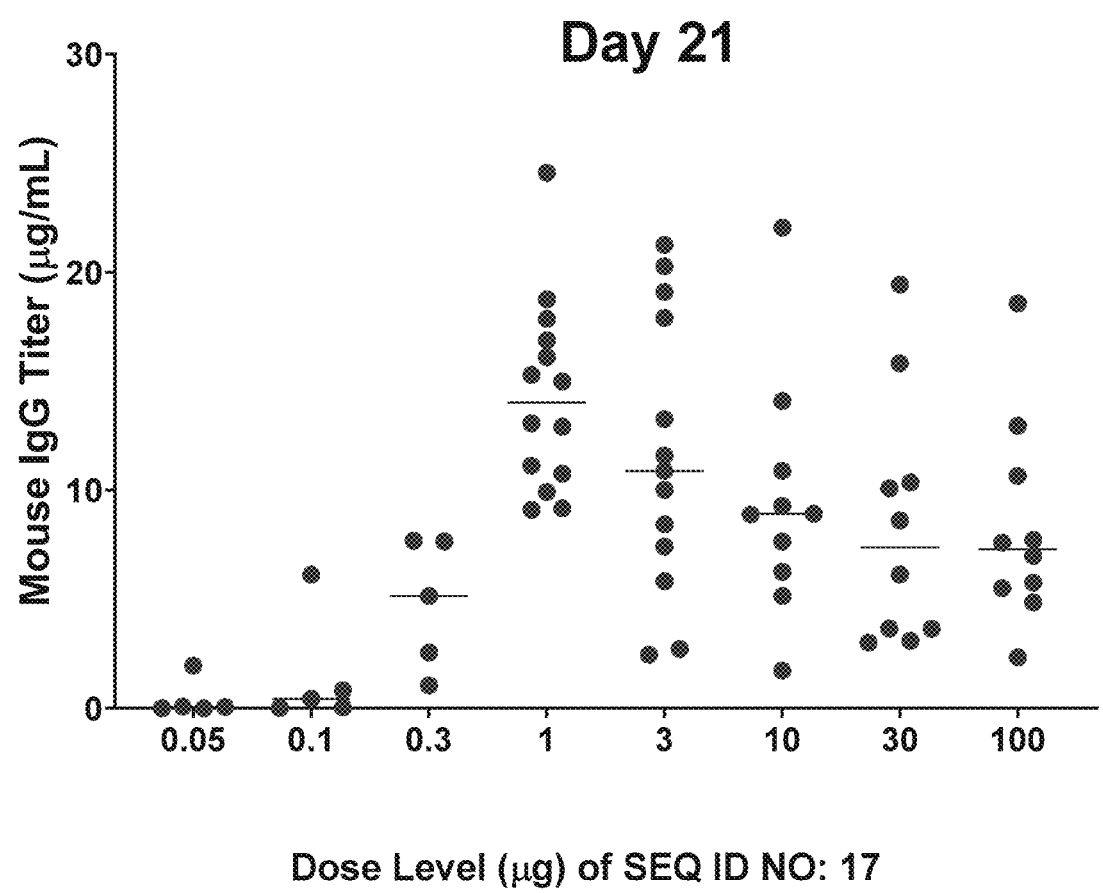
FIG. 25 illustrates the anti-SP/RBD IgG Ab titer response in 6- to 8-week old female BALB/c mice 21 days after a single dose of the SARS-CoV-2 RBD-hIgG-Fc fusion protein of SEQ ID NO: 17 across various dose levels.
Figure 26:
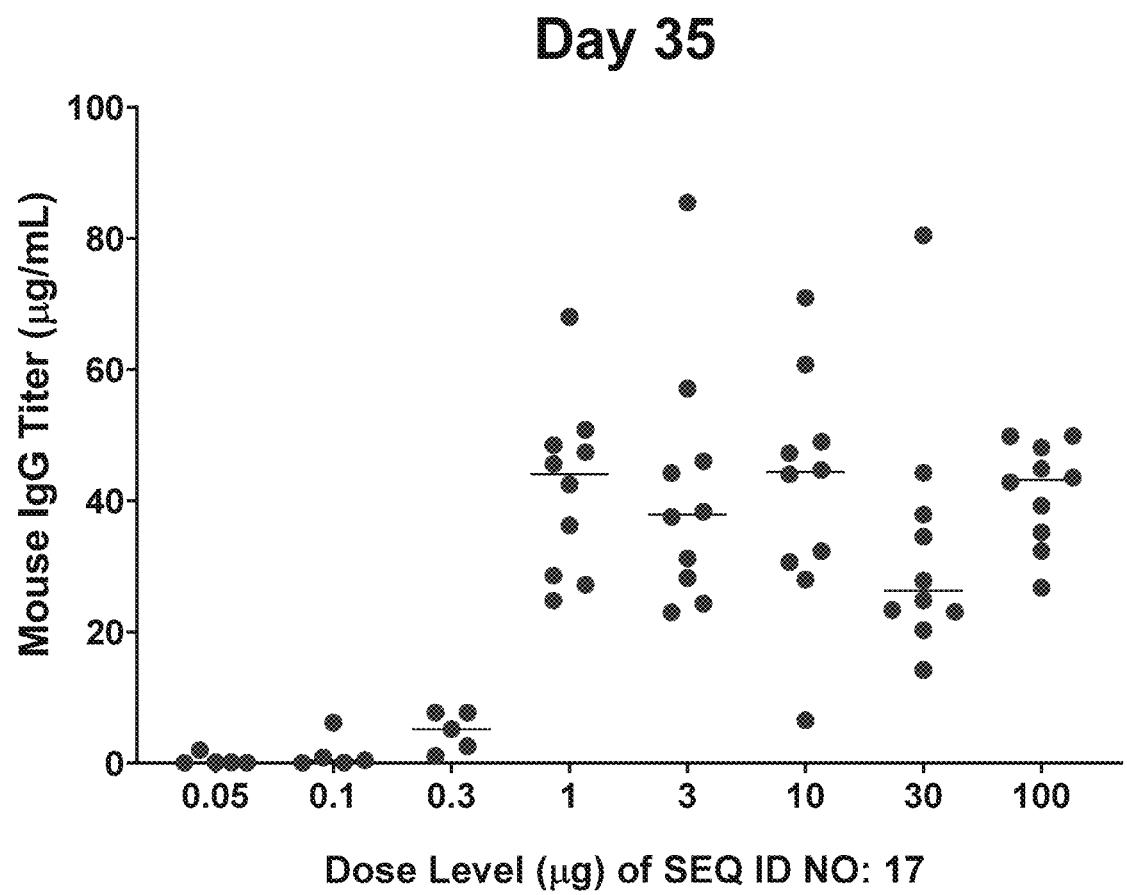
FIG. 26 illustrates the anti-SP/RBD IgG Ab titer response in 6- to 8-week old female BALB/c mice on Day 35 after an injection on Day 0 and on Day 21 of the SARS-CoV-2 RBD-hIgG-Fc fusion protein of SEQ ID NO: 17 across various dose levels.
Figure 27:
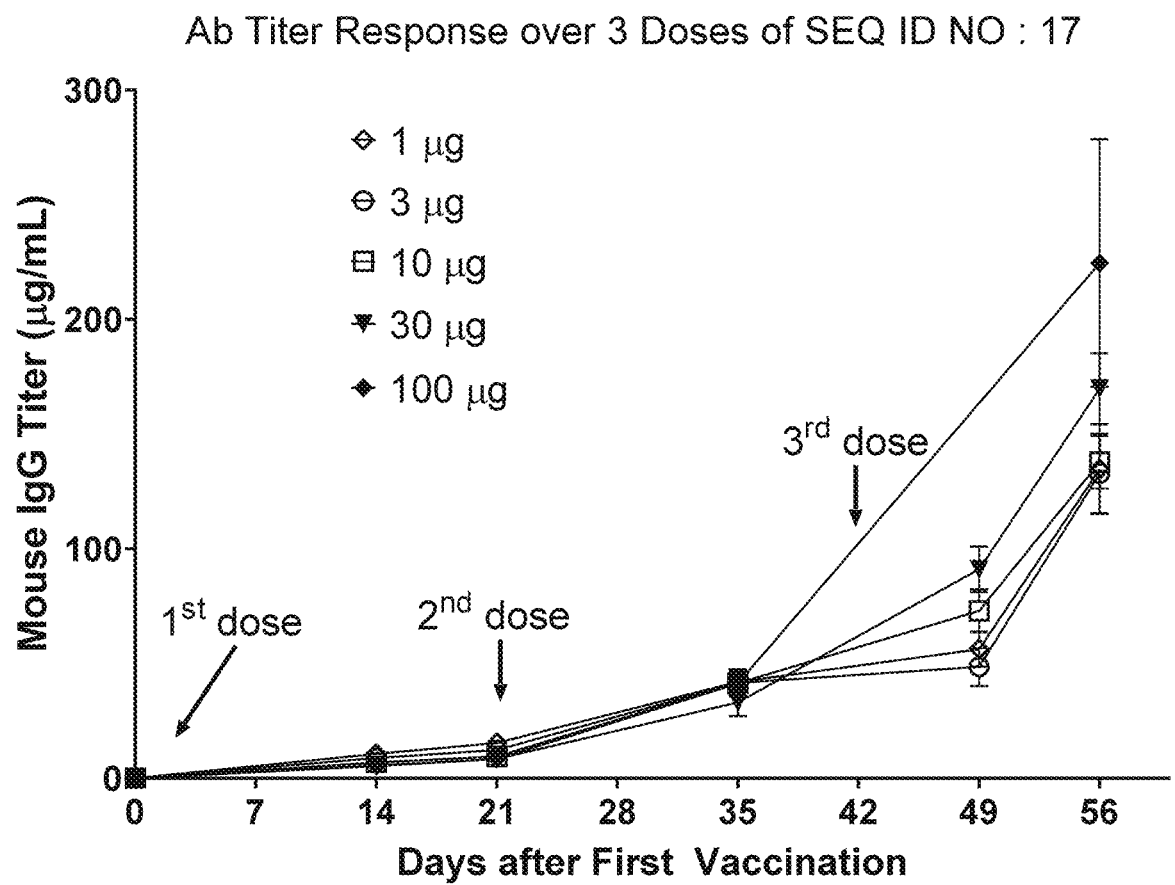
FIG. 27 illustrates the kinetic response to dose levels of 1 μg, 3 μg, 10 μg, 30 μg and 100 μg after an injection on Day 0, Day 21 and Day 42 of the SARS-CoV-2 RBD-hIgG-Fc fusion protein of SEQ ID NO: 17.

As described in detail in Example 17 it was shown that dose levels between 1 and 100 µg of the SARS-CoV-2-RBD-hIgG-Fc fusion protein of SEQ ID NO: 17 induced significant anti-SP/RBD Ab titers 21 days after a single injection, and 14 days after a second injection, as shown in FIG. 25 and FIG. 26 respectively. The kinetic response, that is the duration of response, to dose levels varying from 1 µg to 100 µg after 1, 2, and 3 doses demonstrated increasing anti-SP/RBD Ab titers at all dose levels up to at least 56 days post vaccination, as shown in FIG. 27. The results highlight that a measurable increase in anti-SP/RBD IgG Ab titer response can be seen 14 days after each dose, and that the SP/RBD IgG Ab titer response continued to increase with each additional dose for all dose levels.

In Example 18 it was importantly shown that the Fc fragment of the non-adjuvanted SARS-CoV-2-RBD-hIgG-Fc fusion protein of SEQ ID NO: 17 was necessary to induce significant anti-SP/RBD IgG Ab titers, as demonstrated by the fact that the SP/RBD monomeric Ag of SEQ ID NO: 2 (that lacks Fc) was not effective with respect to measured immunogenicity response at Day 21. The induced anti-SP/RBD IgG Ab titer response of SEQ ID NO: 17 including the Fc fragment reached near maximum titers even at 14 days after the initial dose as shown in FIG. 28, whereas the SP/RBD monomeric Ag of SEQ ID NO: 2 with no Fc fragment induced virtually no anti-SP/RBD IgG Ab titer response even after 21 days. This Day 21 effect of the Fc moiety is very robust in that it was maintained at several dose levels. This difference in immunogenicity between these two non-adjuvanted materials demonstrates the significant "built-in adjuvant" capability of the Fc moiety of the fusion protein Ag.

Figure 29:
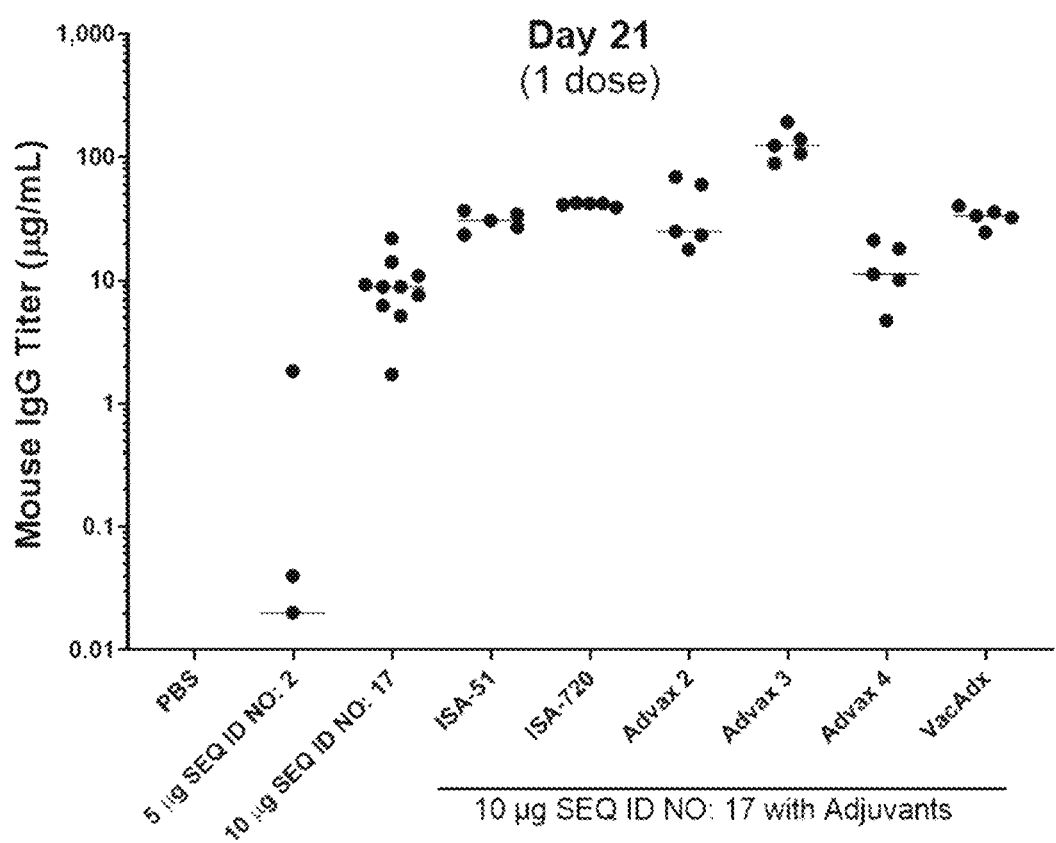
FIG. 29 illustrates the anti-SP/RBD IgG Ab titer response in 6- to 8-week old female BALB/c mice in various adjuvanted formulations containing a 10 μg dose level of the SARS-CoV-2-RBD-hIgG-Fc fusion protein of SEQ ID NO: 17 on Day 21 after one dose on Day 0.
Figure 30:
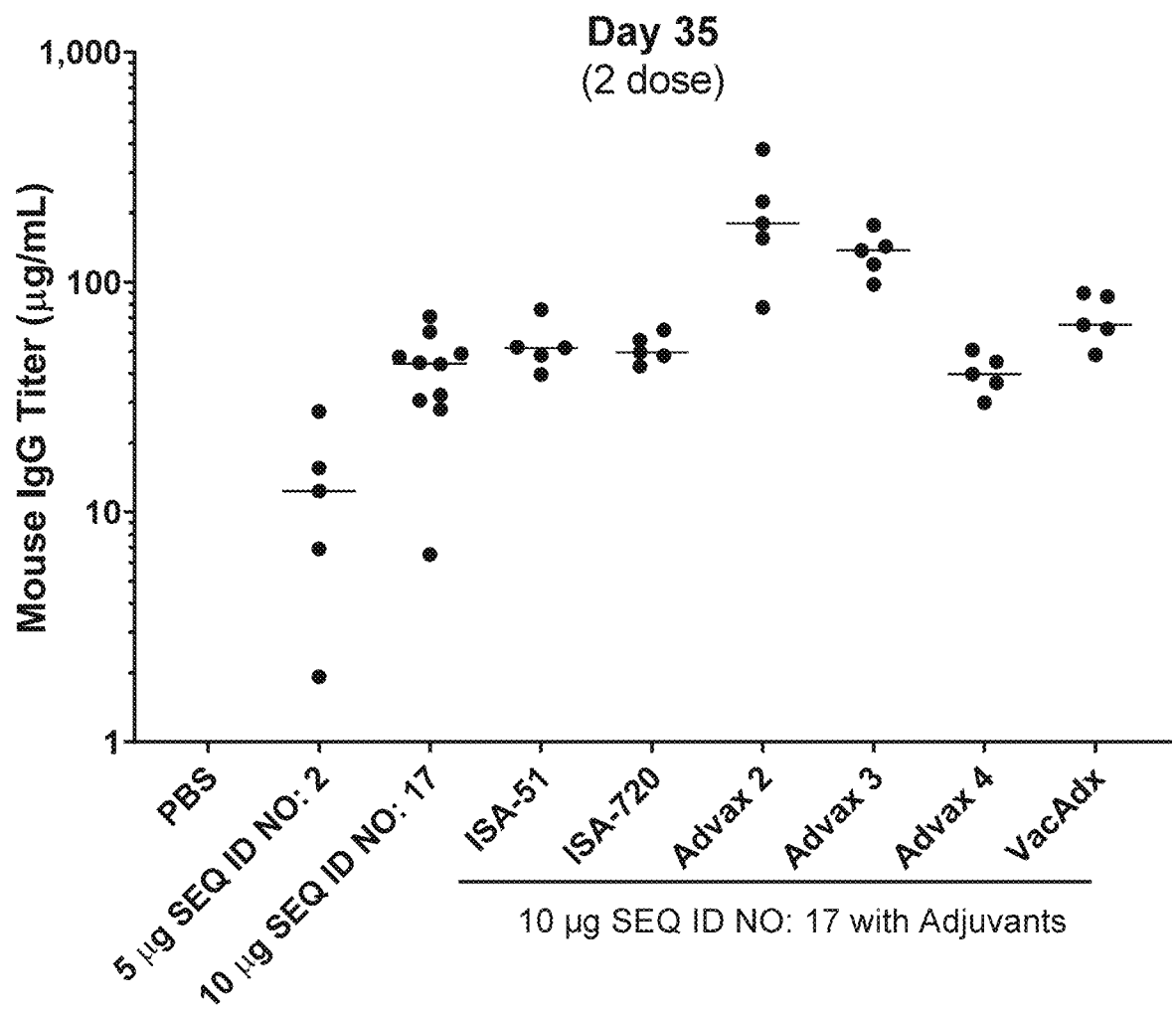
FIG. 30 illustrates the anti-SP/RBD IgG Ab titer response in 6- to 8-week old female BALB/c mice in various adjuvanted formulations containing a 10 μg dose level of the SARS-CoV-2-RBD-hIgG-Fc fusion protein of SEQ ID NO: 17 on Day 35 after an injection on Day 0 and on Day 21.
Figure 31:
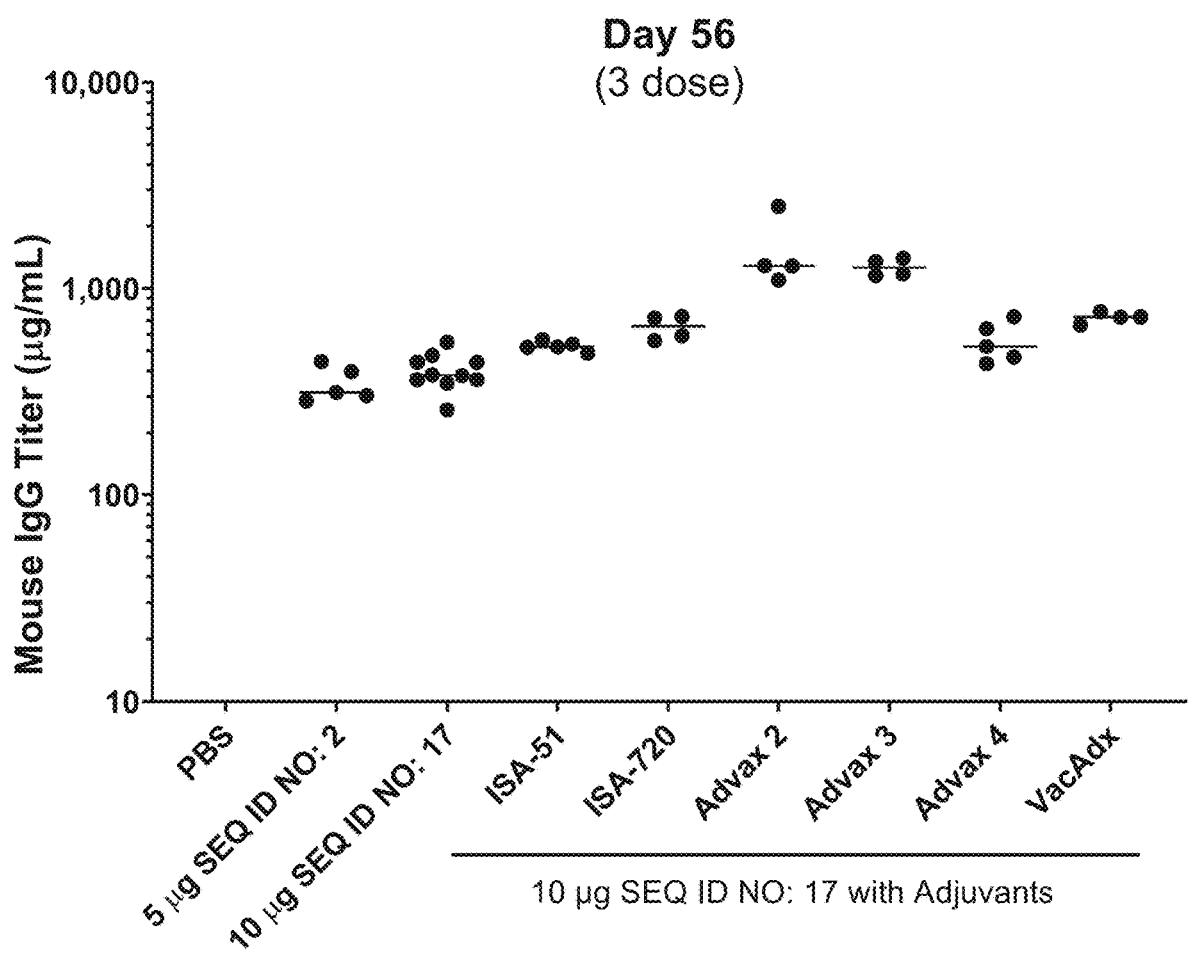
FIG. 31 illustrates the anti-SP/RBD IgG Ab titer response in 6- to 8-week old female BALB/c mice in various adjuvanted formulations containing a 10 μg dose level of the SARS-CoV-2-RBD-hIgG-Fc fusion protein of SEQ ID NO: 17 on Day 56 after an injection on Day 0, Day 21 and Day 42.

As previously discussed, adjuvants activate APCs for greater Ag-presentation capabilities which are necessary to overcome the high activation threshold of naïve T cells, in addition to shaping their development into the Th1 response to effectively clear the respective infection. In Example 19 it was shown that some, but not all, adjuvanted formulations containing a 10 µg dose level of the SARS-CoV-2-RBD-hIgG-Fc fusion protein of SEQ ID NO: 17 enhanced immunogenicity after one (measured on Day 21—as shown on FIG. 29), two (measured on Day 35—as shown on FIG. 30), and three (measured on Day 56—as shown on FIG. 31) doses by approximately 3- to 5-fold, demonstrating a range of effectiveness among the adjuvants. Notably, 32 days after the third dose (i.e., measured on Day 88 as shown on FIG. 32), titers induced by all formulations remained significantly elevated, demonstrating the durability of immunogenicity responses to the SARS-CoV-2-RBD-hIgG-Fc fusion protein of SEQ ID NO: 17 even at three months after the first injection.

Figure 36:
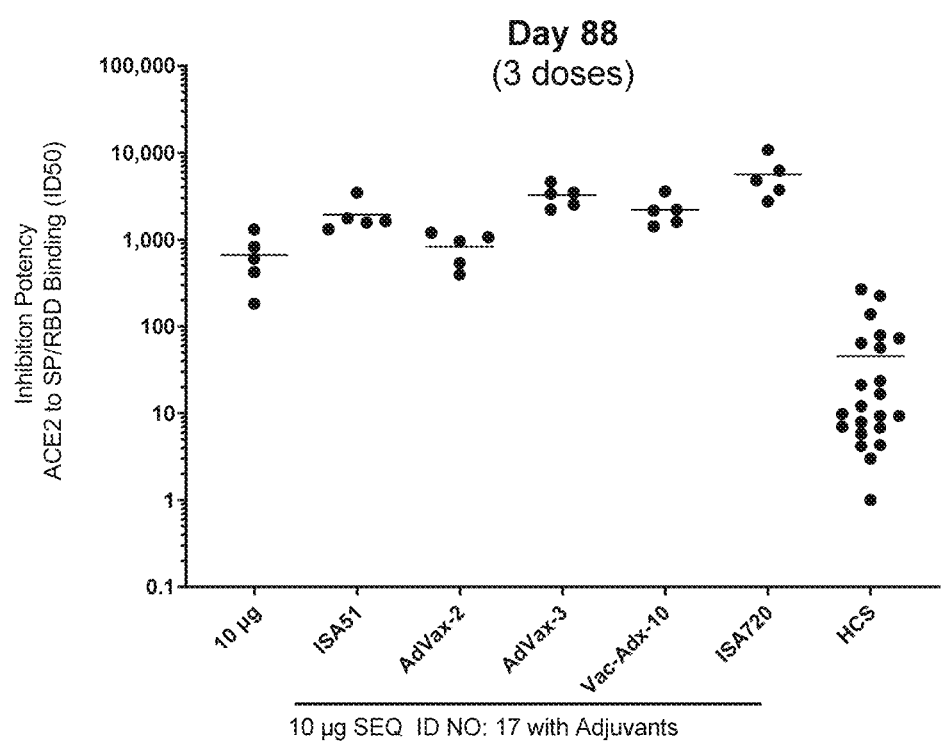
FIG. 36 illustrates the ACE2-SP/RBD binding inhibition potency (ID50) calculated at Day 88 after injections on Day 0, Day 21 and Day 42 of the SARS-CoV-2-RBD-hIgG-Fc fusion protein of SEQ ID NO: 17 with and without adjuvants in 6- to 8-week old mice compared to human convalescent serum.

The inhibition potency of ACE2-SP/RBD binding is calculated as the ID50 value which represents the reciprocal of the dilution at which 50% of the ACE2 binding was achieved by a serum sample. As described in Example 20, the induced inhibition potency of ACE2-SP/RBD binding was calculated at Day 21 after a single injection on Day 0, on Day 42 after injections at Day 0 and Day 21, and on Day 56 and Day 88 after injections on Day 0, Day 21 and Day 42. The calculated ID50 values of immune serum from mice immunized with 3 doses of SEQ ID NO: 17 showed a response in which the inhibition potency was maintained to 32 days after the last injection (FIG. 36). Moreover, the Montanide™ ISA 720 adjuvant consistently induced the top potency at each timepoint. The Montanide™ ISA 720 result was particularly interesting and surprising given that the total IgG titers obtained with this adjuvant were not exceptionally potent relative to the other adjuvanted formulations, thus suggesting induction of greater intrinsic potency per IgG molecule with Montanide™ ISA 720. These data strongly supported the selection of Montanide™ ISA 720 as the lead adjuvant candidate for this vaccine development program.

Individuals greater than 60 years of age found to have a greater susceptibility to severe illness with a higher mortality due to COVID-19. Therefore, it was important to evaluate the capacity of SARS-CoV-2-RBD-hIgG-Fc fusion protein formulations to induce immune responses in older mice whose immune systems are a reliable model for the senescent immune systems of aging human adults.

Following the procedure of Example 21, BALB/c mice 8- to 10-months of age were immunized with the SARS-CoV-2-RBD-hIgG-Fc fusion protein of SEQ ID NO: 17. Because of the higher natural mortality in mice after 8-months of age, approximately 15 mice were allocated for each study group. While 10, 30, and 100 μg dose levels of the SARS-CoV-2-RBD-hIgG-Fc fusion protein of SEQ ID NO: 17 induced significant IgG titers after 1 dose (measured on Day 21), 2 doses (measured on Day 35) and 3 doses (measured on Day 56) without adjuvant, the adjuvants strongly potentiated this immunogenicity in formulations with 10 μg of the SARS-CoV-2-RBD-hIgG-Fc fusion protein of SEQ ID NO: 17, as illustrated in FIG. 37, FIG. 38 and FIG. 39. Similar to the immunogenic profile in younger mice, use of the adjuvant Montanide™ ISA 720 dramatically and unexpectedly enhanced the inhibition potency (ID50) of the SARS-CoV-2-RBD-hIgG-Fc fusion protein of SEQ ID NO: 17 by 17-fold relative to the level obtained without adjuvant measured at Day 56. Moreover, the inhibition potency (ID50) obtained with Montanide™ ISA 720 was again superior to the other adjuvants. Importantly, this inhibition potency induced by the SARS-CoV-2-RBD-hIgG-Fc fusion protein of SEQ ID NO: 17 with and without adjuvant was above that of human convalescent serum (see FIG. 33, FIG. 34, FIG. 35 and FIG. 36), demonstrating the promising effectiveness of such a SARS-CoV-2-RBD-hIgG-Fc fusion protein vaccine.

Collectively, the results in BALB/c mice described above demonstrated that the SARS-CoV-2-RBD-hIgG-Fc fusion protein of SEQ ID NO: 17 substantially induces IgG titers that have a significant potential to inhibit SARS-CoV-2 viral SP/RBD binding to ACE2. In addition, because immunization with Montanide™ ISA 720 showed the greatest inhibitory potency, and because it is formulated for reduced reactogenicity in humans, it was selected as a lead development candidate adjuvant for further evaluation.

Similar studies were performed using the higher yielding SARS-CoV-2-RBD-hIgG-Fc fusion protein of SEQ ID NO: 19. As described in more detail in Example 22, the SARS-CoV-2-RBD-hIgG-Fc fusion protein of SEQ ID NO: 19 induced substantial IgG titers in mice at 1 μg and 10 μg dose levels in the absence of adjuvant as measured according to the improved ELISA format of Example 11, consistent with the immunogenicity profile of the SARS-CoV-2-RBD-hIgG-Fc fusion protein of SEQ ID NO: 17 described above, showing a pronounced dose-response between the two dose levels after the 1st (Day 14) and 2nd (Day 35) doses (FIG. 40, FIG. 41, and FIG. 42). As expected, the SARS-CoV-2-RBD-hIgG-Fc fusion protein of SEQ ID NO: 19 formulated with different adjuvants induced substantially higher titers as measured according to Example 22 relative to those in the absence of adjuvant after each dose (~3- to 10-fold after the 1st and 2nd doses), and that Montanide™ ISA 720 was similar in effectiveness to that of Ad-Vax-2 after each dose whereas Montanide™ ISA 51 was less effective. In addition, the SARS-CoV-2-RBD-hIgG-Fc fusion protein of SEQ ID NO: 19 induced strong ACE2-SP/RBD inhibitory potencies (ID50 values) as measured according to Example 23 that were significantly above those of human convalescent serum at after each dose (FIG. 43, FIG. 44 and FIG. 45). Note that Montanide™ ISA 720 achieved the highest potencies after the third dose.

Example 24 verified that the SARS-CoV-2-RBD-hIgG-Fc fusion protein of SEQ ID NO: 19 with all adjuvants induced significant Th1-promoted IgG2a, IgG2b and IgG3 isotype titers in which Montanide™ ISA 720 consistently showed a strong enhancement at all timepoints (FIG. 48, FIG. 49 and FIG. 50). In addition, Th2-promoted isotype, IgG1 titers were approximately 10-fold less than those of the Th1-associated isotype (FIG. 47). These results demonstrate that the Montanide™ ISA 720 adjuvant maintained a strong enhancing effect when delivered with SEQ ID NO: 19, especially by promoting the desired shift towards a Th1 response, supporting its dose-sparing characteristics and selection as the clinical lead adjuvant.

The role of the Fc fragment in its contribution to the immunogenicity of the SP/RBD-Fc fusion protein vaccine was further investigated in mice by attempting to understand how the use of a human IgG Fc construct in mice may affect the efficacy. Mouse IgG2a is the functional analog to human IgG1. The experiments described in Example 25 were aimed at determining i) whether the Fc species mismatch might be the cause of the underlying immunogenicity of the SP/RBD-Fc fusion protein and ii) whether results from human IgG Fc constructs in animal models are appropriate for predicting performance in humans.

Immunizations with SEQ ID NO: 19 (human Fc) and SEQ ID NO: 23 containing the murine Fc comprising mouse IgG2a without adjuvant showed no significant differences in induction of anti-SP/RBD IgG Ab titers 14 days after the first or second doses (i.e., Day 14 as shown in FIG. 51 and Day 35 as shown in FIG. 52), demonstrating that human Fc antigenic sequences do not perform any differently than native mouse Fc sequences in the BALB/c mouse immunogenicity model. Furthermore, immunizations with SEQ ID NO: 19 and SEQ ID NO: 23 without adjuvant showed no significant differences in ACE2-SP/RBD binding inhibition potency 14 days after the first or second doses (i.e., Day 14 as shown in FIG. 53 and Day 35 as shown in FIG. 54), demonstrating that human Fc antigenic sequences do not perform any differently than native mouse Fc sequences in the BALB/c mouse immunogenicity model. Both SEQ ID NO: 19 and SEQ ID NO: 23 exhibited ACE2-SP/RBD binding inhibition potency greater than human convalescent serum (HCS) even after just one dose. Given that the mouse version of the SARS-CoV-2-RBD-hIgG-Fc fusion protein (SEQ ID NO: 23) demonstrates enhanced immunogenicity in mice relative to the naked SP/RBD protein (SEQ ID NO:

2), it is highly likely that the human version will demonstrate enhanced immunogenicity in humans.

Figure 46:
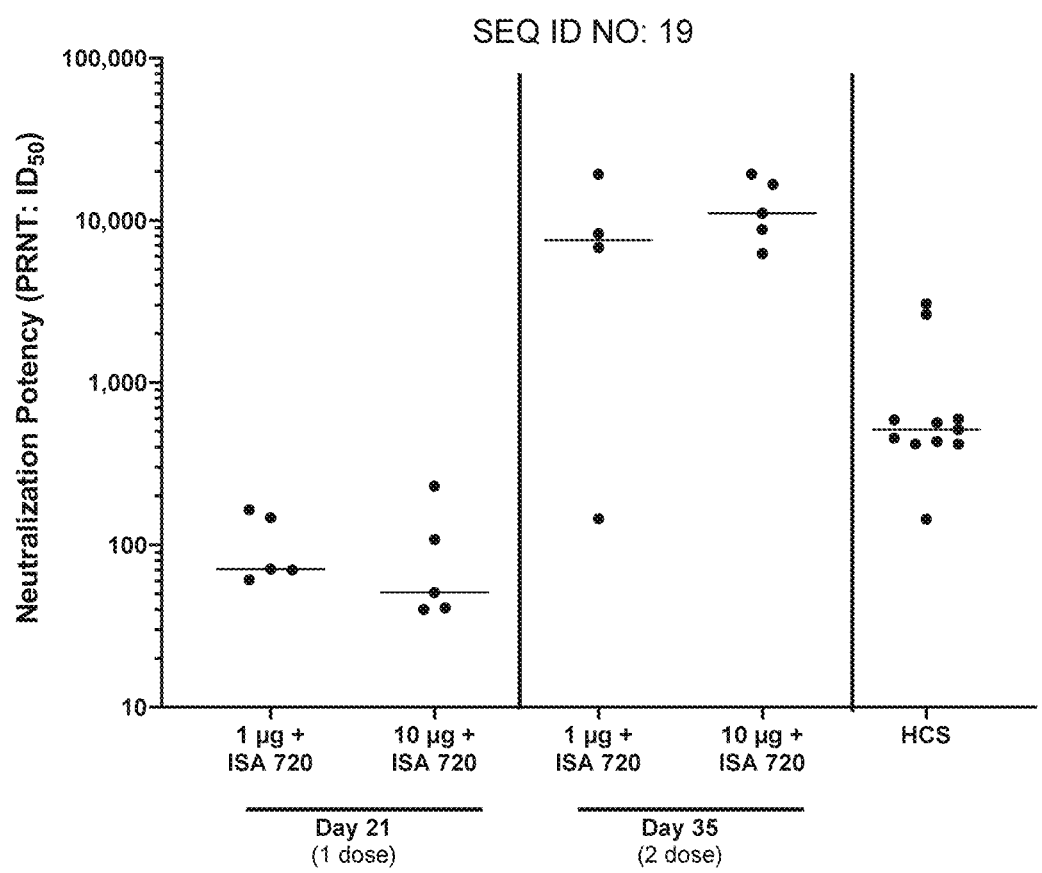
FIG. 46 illustrates the induction of anti-SP/RBD PRNT neutralization potency in serum samples from 6- to 8-week old female BALB/c mice administered either a 1 μg or 10 μg dose level of SEQ ID NO: 19 on Day 0 and Day 21, as measured on Day 21 and Day 35.

In furthering such translational research, this inhibitory potency of disrupting the biochemical interaction of recombinant ACE2 and SP/RBD was confirmed with the neutralization of live SARS-CoV-2 virus from infecting live VERO-E6 cells in the Plaque Reduction Neutralization Test (PRNT) according to the procedure of Example 15 and shown in FIG. 46.

The ability to store and/or transport a vaccine at refrigerated temperature or room temperature is very important to the effective distribution of the vaccine, in particular in countries that lack sophisticated cold chain transportation and storage infrastructure. Example 26 describes in vivo studies that compared the effectiveness of generating SP/RBD IgG Ab titer responses of freshly made SARS-CoV-2-RBD-hIgG-Fc fusion protein of SEQ ID NO: 19/ISA 720 emulsion with the same emulsion stored at 4° C. and 25° C. for one day and seven days after preparation.

Figure 55:
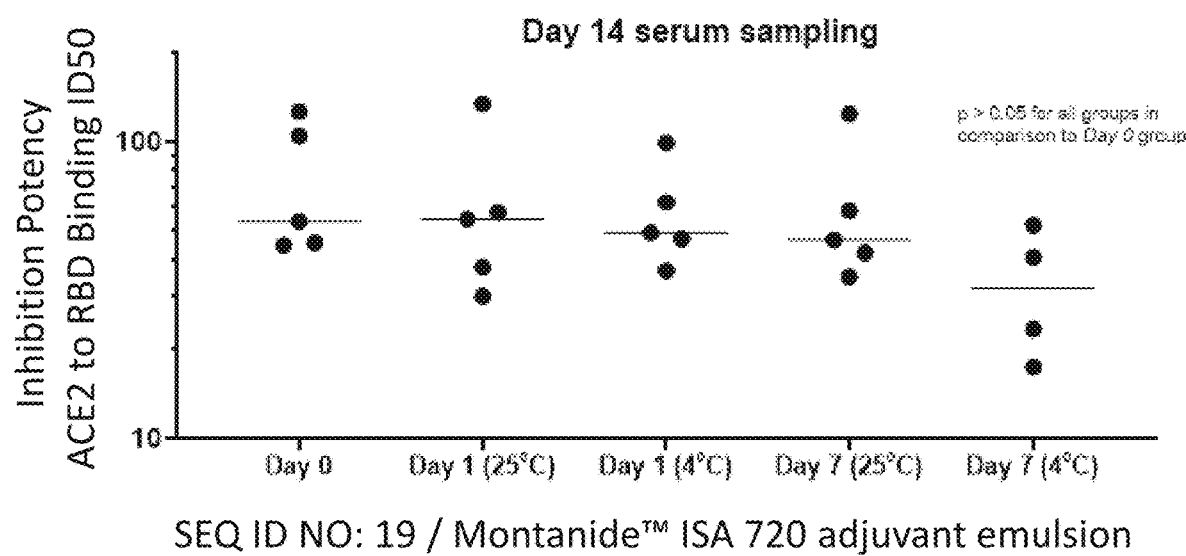
FIG. 55 illustrates the induced ACE2-SP/RBD binding inhibition of the SARS-CoV-2-RBD-hIgG-Fc fusion protein of SEQ ID NO: 19 in mice as measured on Day 14 after injection of freshly made emulsion versus the emulsion stored for 1 day and 7 days at 4° C. and 25° C.
Figure 56:
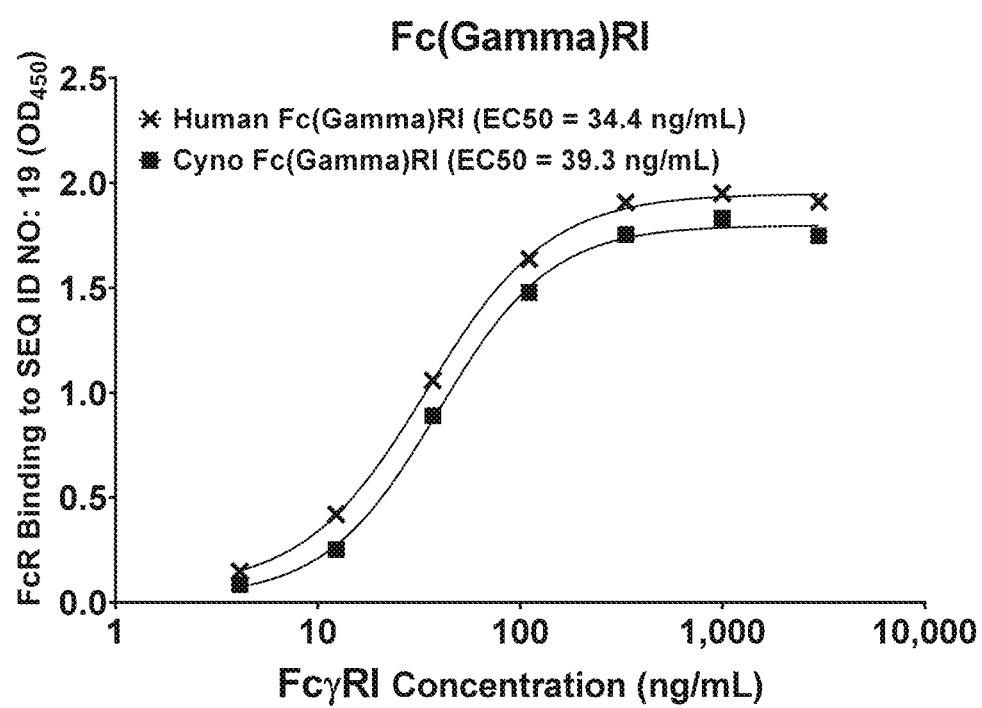
FIG. 56 illustrates binding of the SARS-CoV-2-RBD-hIgG-Fc fusion protein of SEQ ID NO: 19 to human Fc(gamma)RI receptor as compared to the Fc(gamma)RI receptor of Cynomolgus monkeys.
Figure 57:
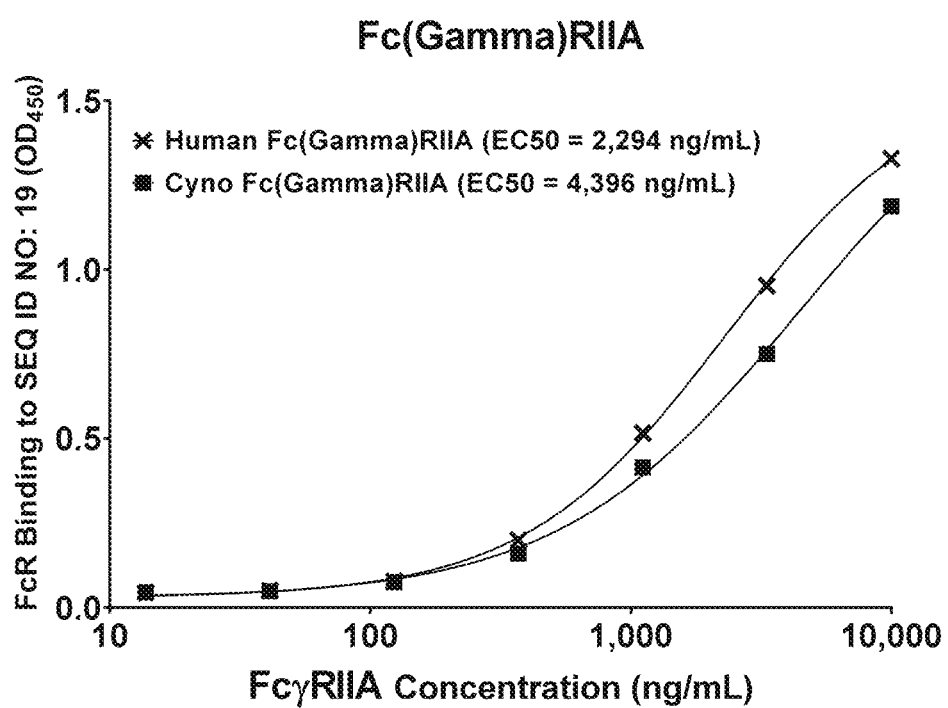
FIG. 57 illustrates binding of the SARS-CoV-2-RBD-hIgG-Fc fusion protein of SEQ ID NO: 19 to human Fc(gamma)RIIa receptor as compared to the Fc(gamma)RIIa receptor of Cynomolgus monkeys.
Figure 58:
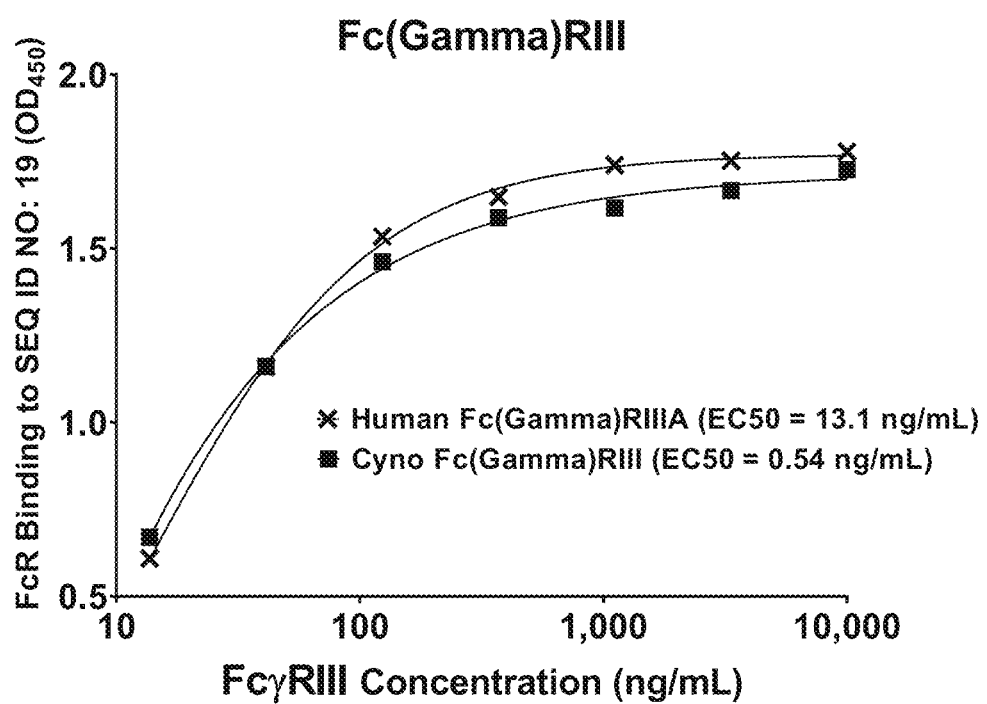
FIG. 58 illustrates binding of the SARS-CoV-2-RBD-hIgG-Fc fusion protein of SEQ ID NO: 19 to human Fc(gamma)RIII receptor as compared to the Fc(gamma)RIII receptor of Cynomolgus monkeys.
Figure 59:
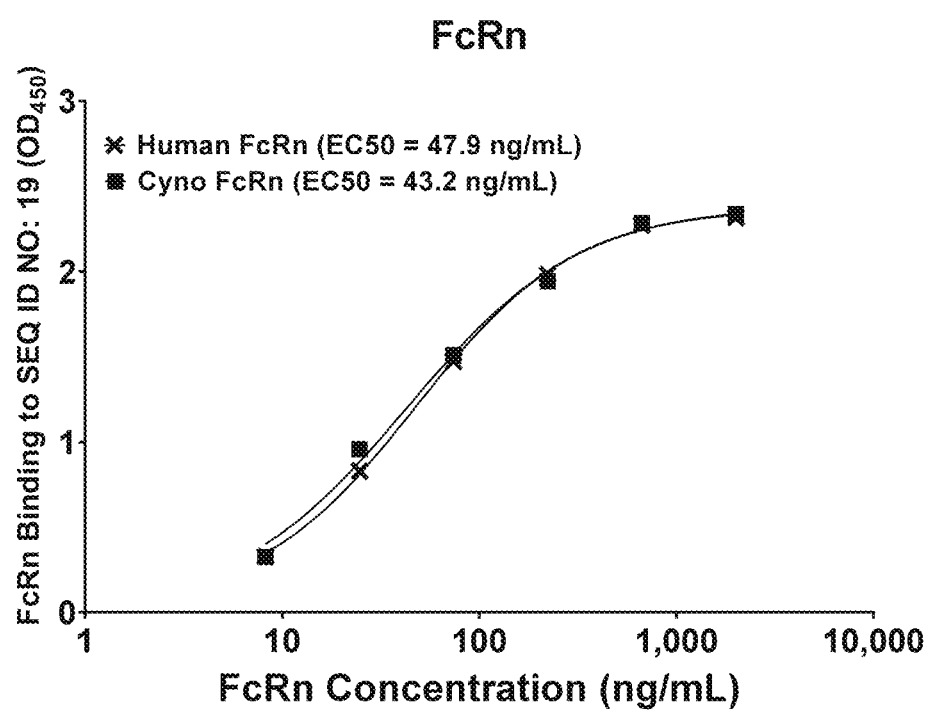
FIG. 59 illustrates binding of the SARS-CoV-2-RBD-hIgG-Fc fusion protein of SEQ ID NO: 19 to human FcRn receptor as compared to the FcRn receptor of Cynomolgus monkeys.

The results from the ACE2 binding inhibition assay described in Example 13 demonstrated that the SARS-CoV-2-RBD-hIgG-Fc fusion protein of SEQ ID NO: 19 induced similar inhibitory potency in serum (ID50 values) in mice after injection of freshly made emulsion versus the emulsion stored for 1 day and 7 days at 4° C. and 25° C. As shown in FIG. 55, there is no significant difference (p>0.05) in ID50 values between the animals injected with freshly made emulsion versus any of the aged emulsions.

In an attempt to understand whether the SARS-CoV-2-RBD-hIgG-Fc Fusion Protein Vaccine of SEQ ID NO: 19 with the adjuvant, Montanide™ ISA 720 was effective against variants of the SARS-CoV-2 virus, the analog RBD fragment of the UK N501Y viral variant (SEQ ID NO: 24) and the South African E484K viral variant (SEQ ID NO: 25) were analyzed using Day 56 serum samples from mice immunized according to Example 22 with 2 doses of the SARS-CoV-2-RBD-hIgG-Fc Fusion Protein Vaccine of SEQ ID NO: 19 with the adjuvant, Montanide™ ISA 720. FIG. 66 illustrates a side by side comparison of the SARS-CoV-2 native RBD of SEQ ID NO: 2 and the analog RBD fragment of the UK N501Y viral variant (SEQ ID NO: 24) and the South African E484K viral variant (SEQ ID NO: 25) performed using Clustal Omega where "*" represents complete homology across all sequences at a given sequence position. A ":" (colon) indicates conservation between groups of strongly similar properties with scoring greater than 0.5 in the Gonnet PAM 250 matrix. A "-" (dash) indicates a sequence gap, meaning that no local homology exists within a particular set of comparisons within a certain range of the sequences.

Figure 65:
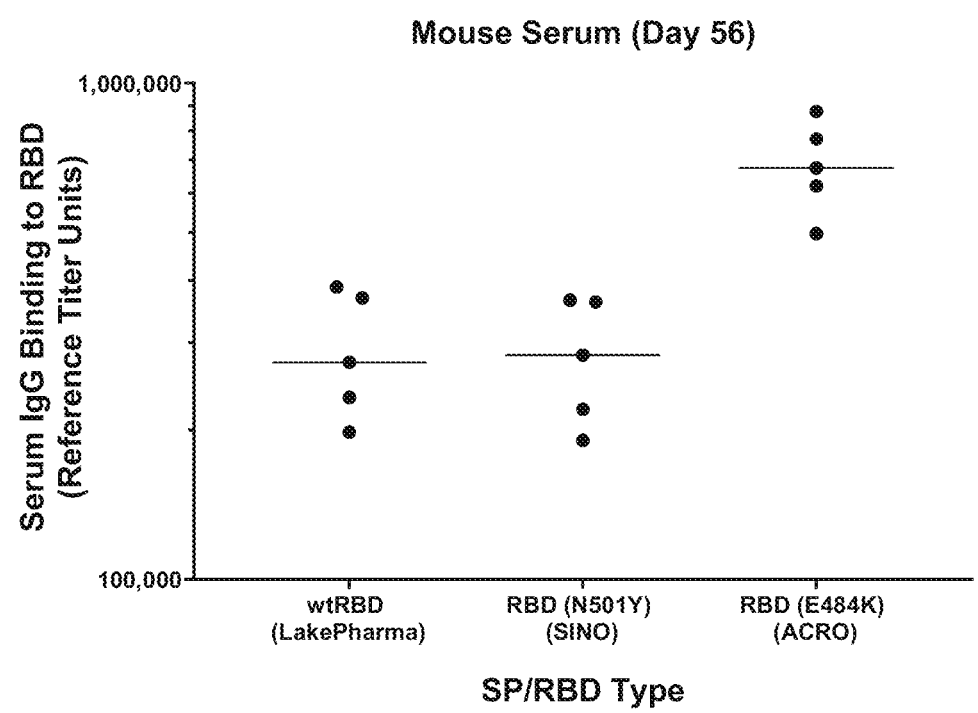
FIG. 65 illustrates that immune sera from mice treated with SEQ ID NO: 19 bound the recombinant, N501Y and E484K RBD mutants as well as, or greater than, the wild-type RBD.
Figure 67:
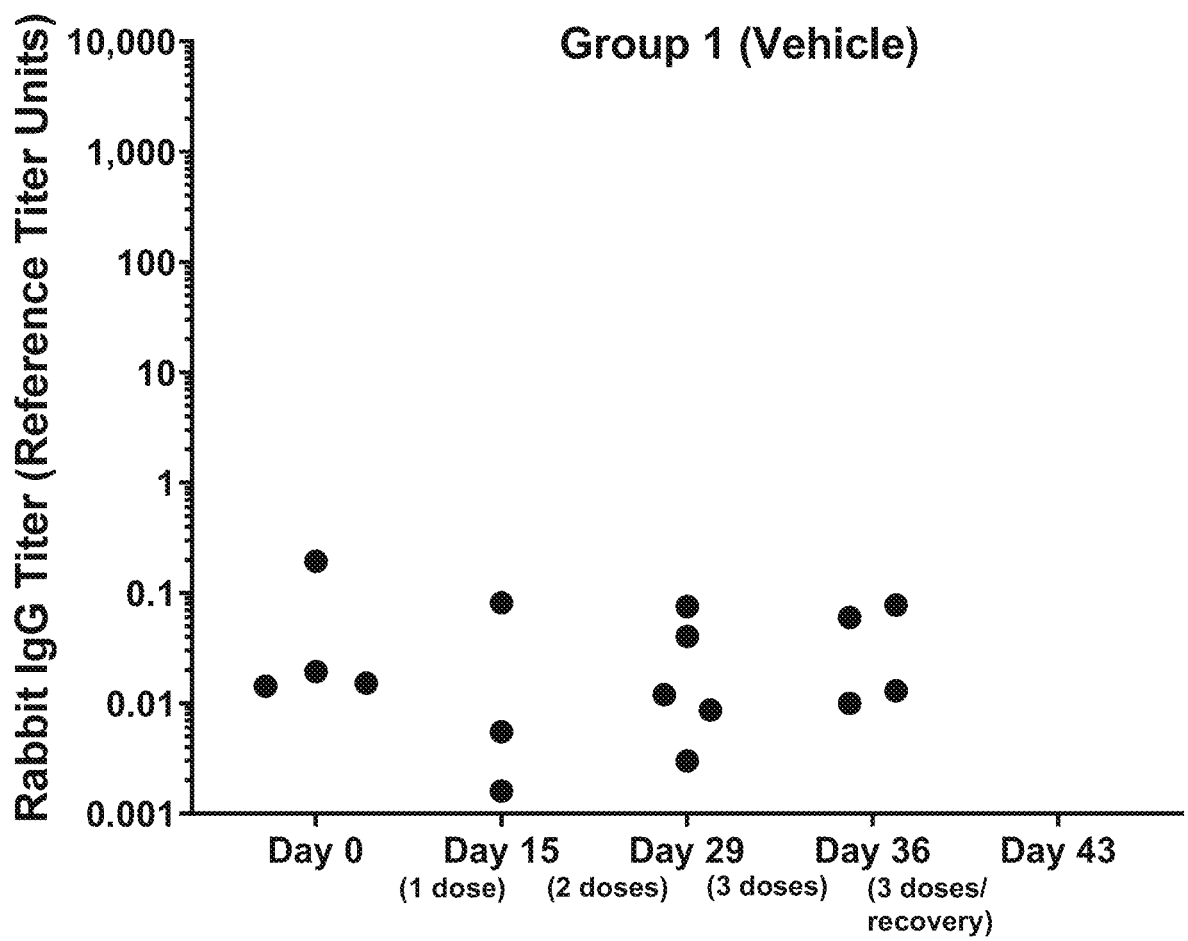
FIG. 67 illustrates the anti-SP/RBD IgG Ab titer in New Zealand White Rabbits subcutaneously administered a vehicle control with Montanide™ ISA 720 adjuvant on Day 1, Day 15, and Day 29 measured before the first dose, second dose and third dose and after the third dose.
Figure 68:
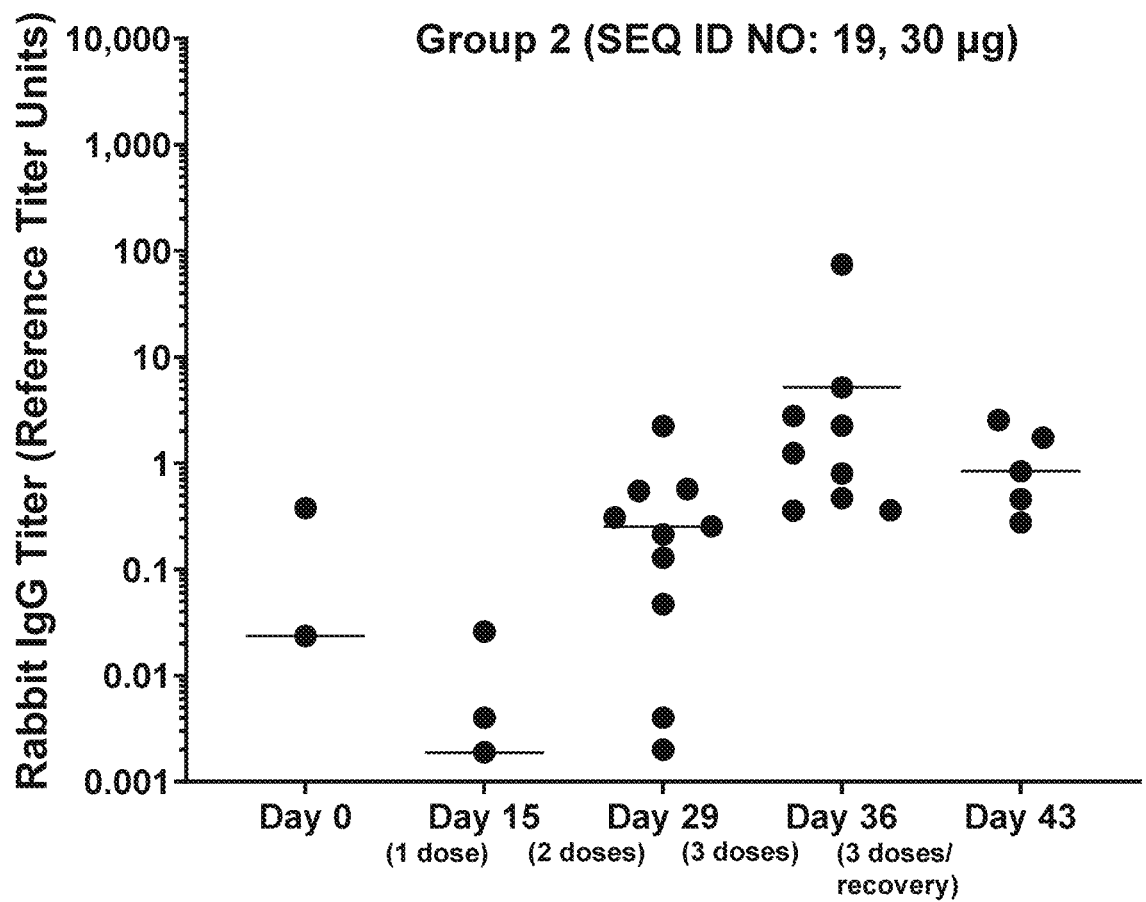
FIG. 68 illustrates the substantial anti-SP/RBD IgG Ab titer in New Zealand White Rabbits administered a 30 µg dose level of the SARS-CoV-2-RBD-hIgG-Fc fusion protein of SEQ ID NO: 19 without adjuvant on Day 1, Day 15, and Day 29 measured before the first dose, second dose and third dose and after the third dose.

The serum samples were added to plastic-bound recombinant RBD wild-type (Lake Pharma, Worcester, Mass.) or mutants N501Y (UK variant, provided by Sino Biological, Wayne, Pa.) or E484K (South Africa variant, provided by AcroBiosystems, Newark, Del.). Bound RBD-specific IgG was detected with labelled anti-mouse IgG secondary antibodies and IgG µg/mL titer values determined via a mouse ELISA reference serum standard curve. The results shown in FIG. 65 illustrate that such immune sera from mice bound recombinant RBD mutants, N501Y and E484K, as well as, or greater than, the wild-type RBD molecule, indicating that the UK (N501Y) and South African (E484K) viral variants are not likely to escape SEQ ID NO: 19 induced immunity.

Primary SARS-CoV-2-RBD-hIgG-Fc Fusion Vaccines Evaluated in Non-Human Primates

Figure 60:
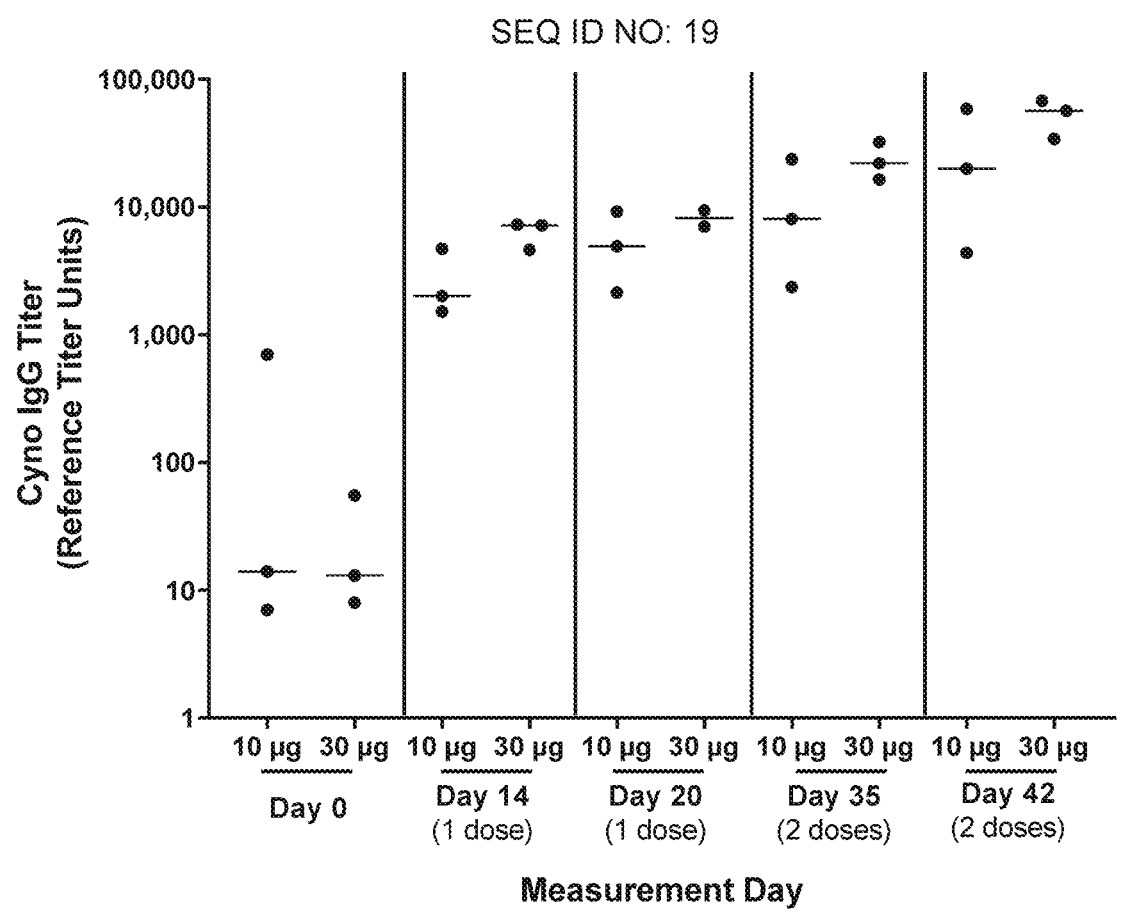
FIG. 60 illustrates the anti-SP/RBD IgG Ab titer response in male and female Cynomolgus monkeys administered either a 10 µg or 30 µg dose level of the SARS-CoV-2-RBD-hIgG-Fc fusion protein of SEQ ID NO: 19 formulated with the Montanide™ ISA 720 adjuvant at 30%/70% (v/v) on Day 0, Day 14, Day 21, Day 35 and Day 42 after an injection on Day 0 and Day 21.

To translate the SARS-CoV-2-RBD-hIgG-Fc fusion protein immunogenicity results from mice to human clinical studies, the SARS-CoV-2-RBD-hIgG-Fc fusion protein of SEQ ID NO: 19 formulated in Montanide™ ISA 720 was tested in the more genetically-relevant NHP species, Cynomolgus monkeys, according to Example 27 and Example 28. The SARS-CoV-2-RBD-hIgG-Fc fusion protein of SEQ ID NO: 19 at 10 µg and 30 µg dose levels formulated with Montanide™ ISA 720 potently induced IgG titers as measured according to Example 11 in which the 30 µg dose level showed greater immunogenicity than the 10 µg dose level at all timepoints after the first and second doses (FIG. 60). Furthermore, this IgG titer immunogenicity profile was consistent with the potency of inhibiting ACE2-SP/RBD binding that was well above the potency of human convalescent serum (FIG. 61) for both the 10 µg and 30 µg dose levels as measured according to Example 13. In furthering such translational research, this inhibitory potency of disrupting the biochemical interaction of recombinant ACE2 and SP/RBD was confirmed with the neutralization of live SARS-CoV-2 virus from infecting live VERO-E6 cells in the Plaque Reduction Neutralization Test (PRNT) according to the procedure of Example 28 and shown in FIG. 62. These results demonstrate the value of testing vaccination in NHPs and provide valuable guidance for translation to humans.

Figure 64:
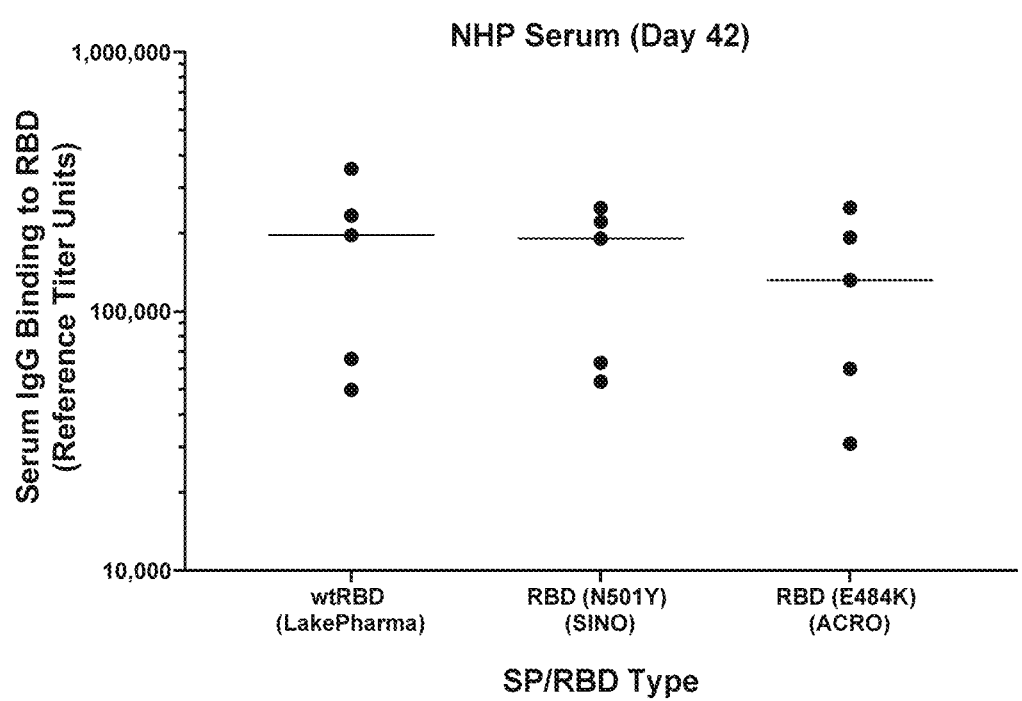
FIG. 64 illustrates that immune sera from NHP treated with SEQ ID NO: 19 bound the recombinant N501Y and E484K SP/RBD mutants as well as, or greater than, the wild-type SP/RBD molecule.

To further confirm that the SARS-CoV-2-RBD-hIgG-Fc Fusion Protein Vaccine of SEQ ID NO: 19 with the adjuvant, Montanide™ ISA 720 was effective against variants of the SARS-CoV-2 virus, serum samples from five NHPs immunized with 2 doses of the SARS-CoV-2-RBD-hIgG-Fc Fusion Protein Vaccine of SEQ ID NO: 19 with the adjuvant, Montanide™ ISA according to Example 27 were extracted on Day 42 and the serum samples were added to plastic-bound recombinant RBD wild-type or mutants N501Y or E484K. The results shown in FIG. 64 illustrate that such, similar to the mouse study, immune sera from NHP and mice bound recombinant RBD mutants, N501Y and E484K, as well as, or greater than, the wild-type RBD molecule.

Efficacy of the SEQ ID NO: 19 vaccine was evaluated in the immunized NHP of Example 27 using the rhesus macaque challenge model of SARS-CoV-2. Two groups of NHP (one vaccinated and administered a booster injection according to Example 27, the other naïve) were challenged with SARS-CoV-2 virus on Day 0. Blood was collected prior to the challenge and on Day 7. Nasal swabs, oral swabs, and collection of BAL fluid was performed prior to the challenge and on Days 2, 4, and 7. Necroscopy post termination was performed on Day 7.

Figure 78:
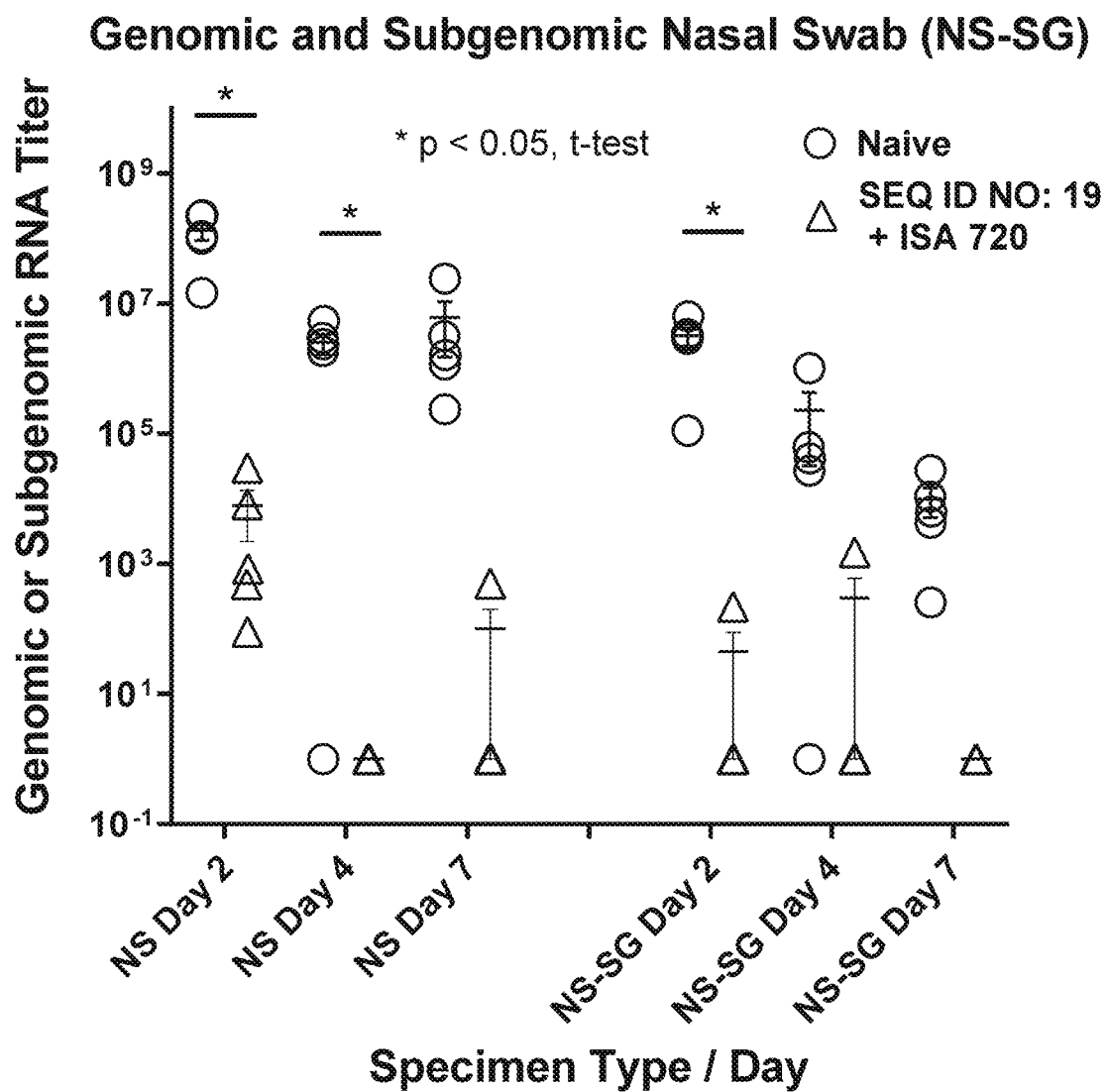
FIG. 78 illustrates the genomic or subgenomic SARS-CoV-2 viral RNA copies per mL of nasal swabs taken from naïve NHP and NHP that have been immunized with the SARS-CoV-2-RBD-hIgG-Fc fusion protein of SEQ ID NO: 19 with Montanide™ ISA 720 according to Example 36.
Figure 79:
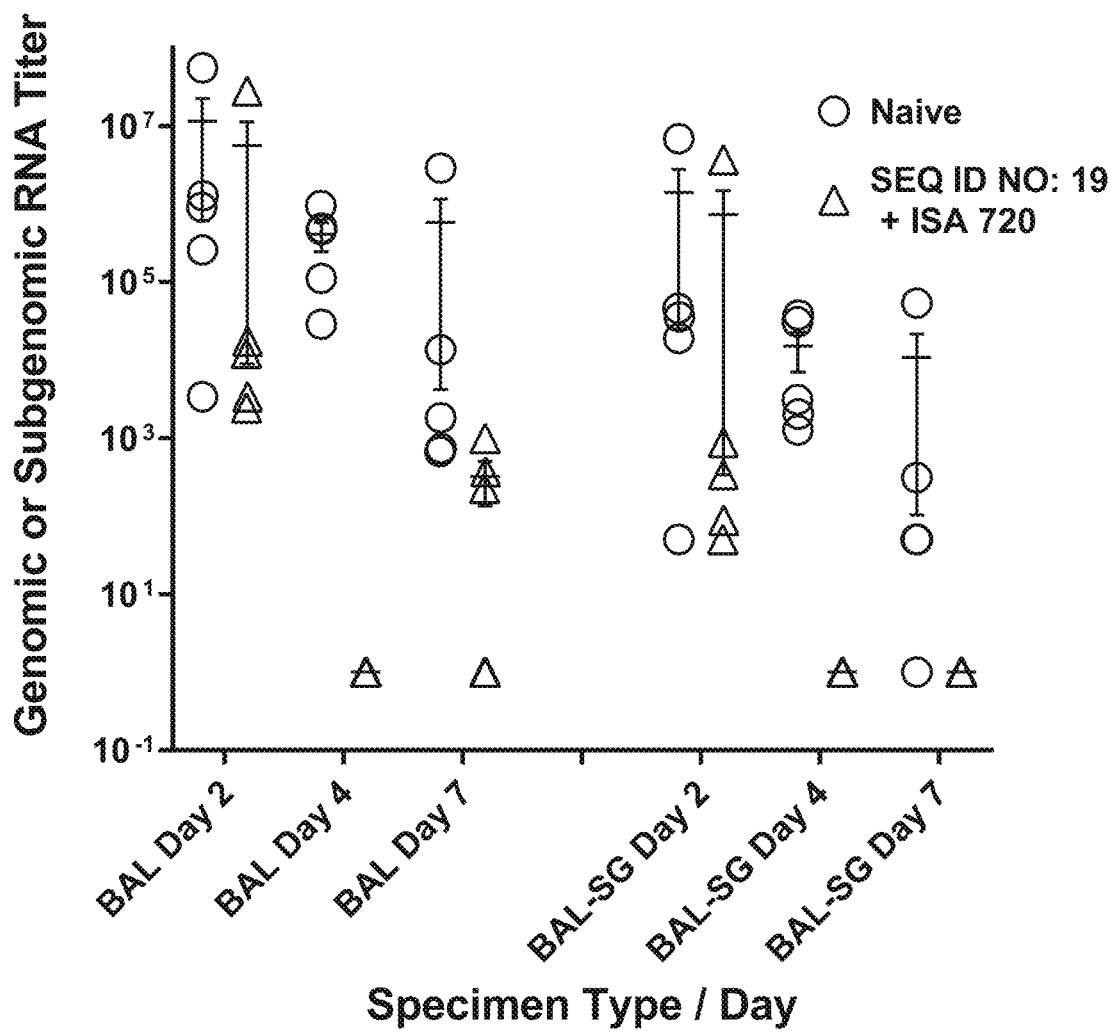
FIG. 79 illustrates the genomic or subgenomic SARS-CoV-2 viral RNA copies per mL of bronchoalveolar lavage (BAL) fluids collected from naïve NHP and NHP that have been immunized with the SARS-CoV-2-RBD-hIgG-Fc fusion protein of SEQ ID NO: 19 with Montanide™ ISA 720 according to Example 36.

The NHPs immunized with SEQ ID NO: 19 with Montanide™ ISA-720 demonstrated significant anti-SP/RBD IgG titers and ACE2 inhibition ID50 values just prior to the viral challenge as compared to the naïve control NHPs with negligible or undetectable levels for both assays. The post-challenge negligible levels of SARS-CoV-2 virus genomic (Example 39) and subgenomic RNA titer (Example 40) in nasal swabs (FIG. 78) and BAL samples (FIG. 79) demonstrate the efficacy of the vaccine in protecting against COVID-19. The low subgenomic RNA (sgRNA) counts are particularly encouraging since these are replicative intermediates, and therefore, their abundance is related to viral replication activity and severity of host infection. Taken together, the data conclusively demonstrate that SEQ ID NO: 19 with Montanide™ ISA-720 protects against COVID-19 and that there is no risk of aggravation of COVID-19 disease in the NHPs.

Primary SARS-CoV-2-RBD-hIgG-Fc Fusion Vaccines Evaluated in Rabbits

A preclinical GLP toxicology IND-enabling study using New Zealand White Rabbits was performed by Sinclair Research, LLC (Auxvasse, Mo.) as described in more detail in Example 30, Example 31, Example 32, Example 33, and Example 34. Rabbits were used because this species has been extensively used for preclinical studies of vaccine-induced immunogenicity that results in robust Ab responses. In addition, rabbits express the SARS-CoV-2 viral receptor, ACE2, that allows the virus to bind and infect the animal causing disease symptoms similar to those of human COVID-19 disease.

Figure 70:
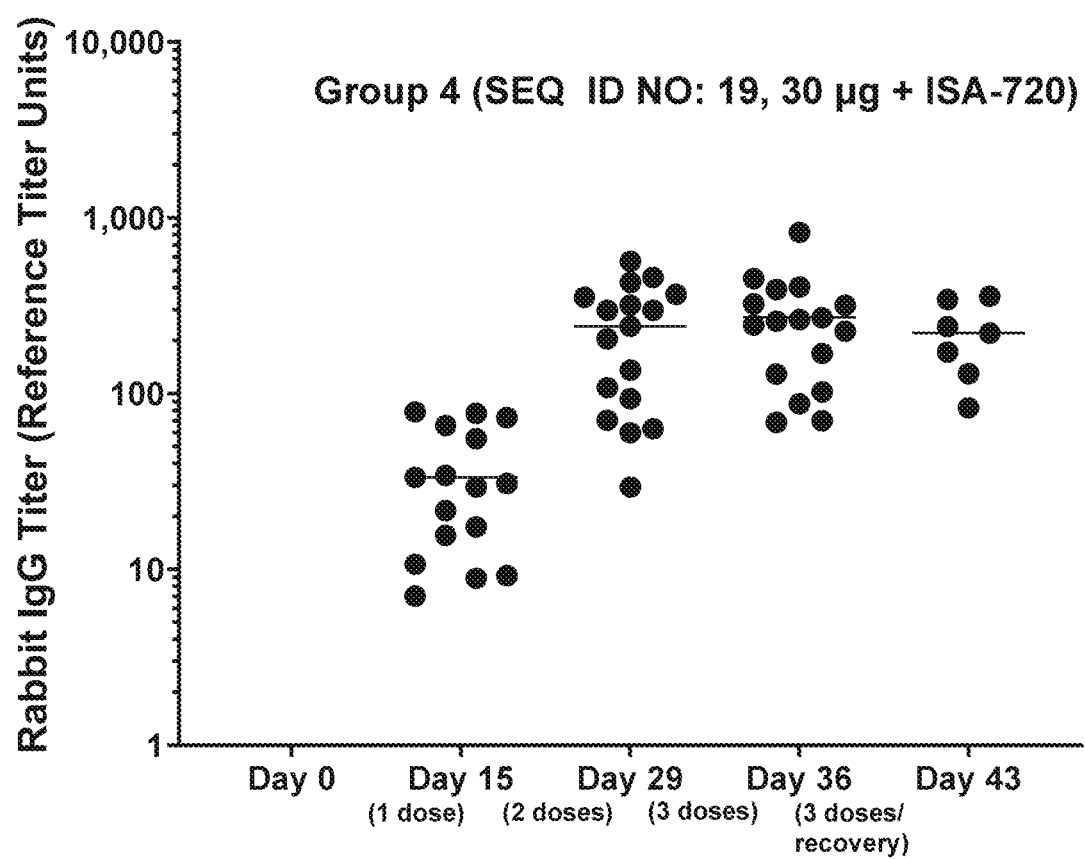
FIG. 70 illustrates the substantial anti-SP/RBD IgG Ab titer in New Zealand White Rabbits administered a 30 µg dose level of the SARS-CoV-2-RBD-hIgG-Fc fusion protein of SEQ ID NO: 19 with Montanide™ ISA 720 adjuvant on Day 1, Day 15, and Day 29 measured before the first dose, second dose and third dose and after the third dose.
Figure 71:
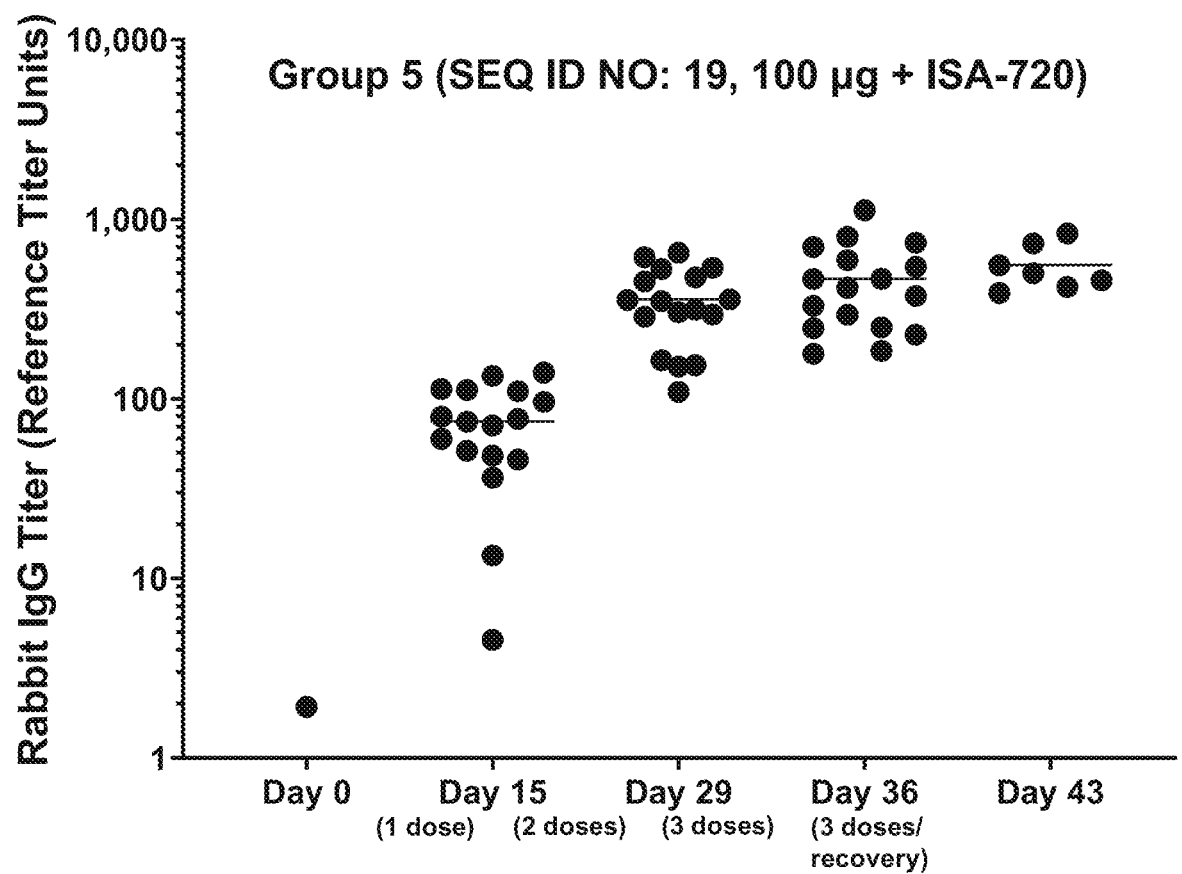
FIG. 71 illustrates the substantial anti-SP/RBD IgG Ab titer in New Zealand White Rabbits administered a 100 µg dose level of the SARS-CoV-2-RBD-hIgG-Fc fusion protein of SEQ ID NO: 19 with Montanide™ ISA 720 adjuvant on Day 1, Day 15, and Day 29 measured before the first dose, second dose and third dose and after the third dose.
Figure 72:
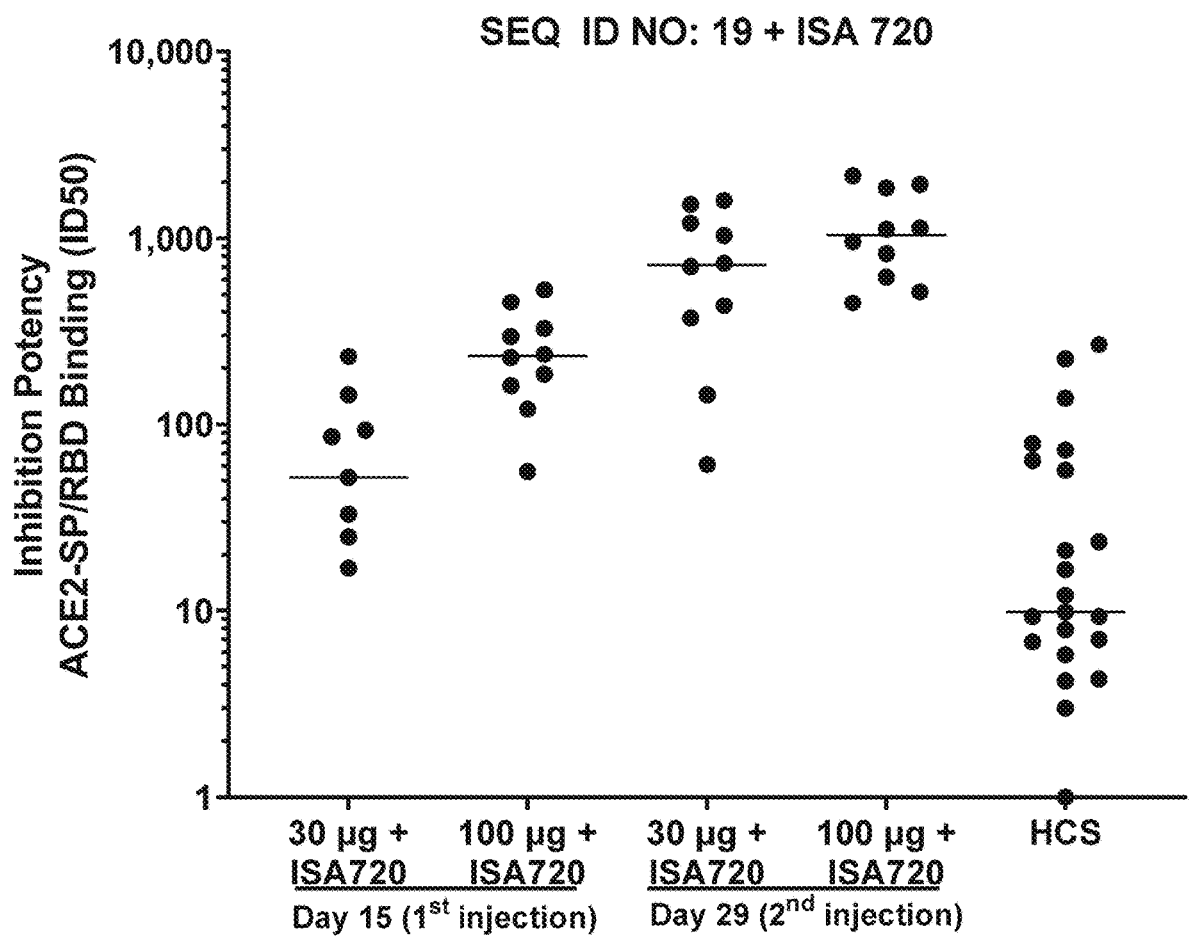
FIG. 72 illustrates the induced ACE2-SP/RBD binding inhibition potency (ID50) in New Zealand White Rabbits administered a 30 µg or 100 µg dose level of the SARS-CoV-2-RBD-hIgG-Fc fusion protein of SEQ ID NO: 19 with Montanide™ ISA measured on Day 15 and Day 29 after an injection on Day 0 and Day 21.
Figure 73:
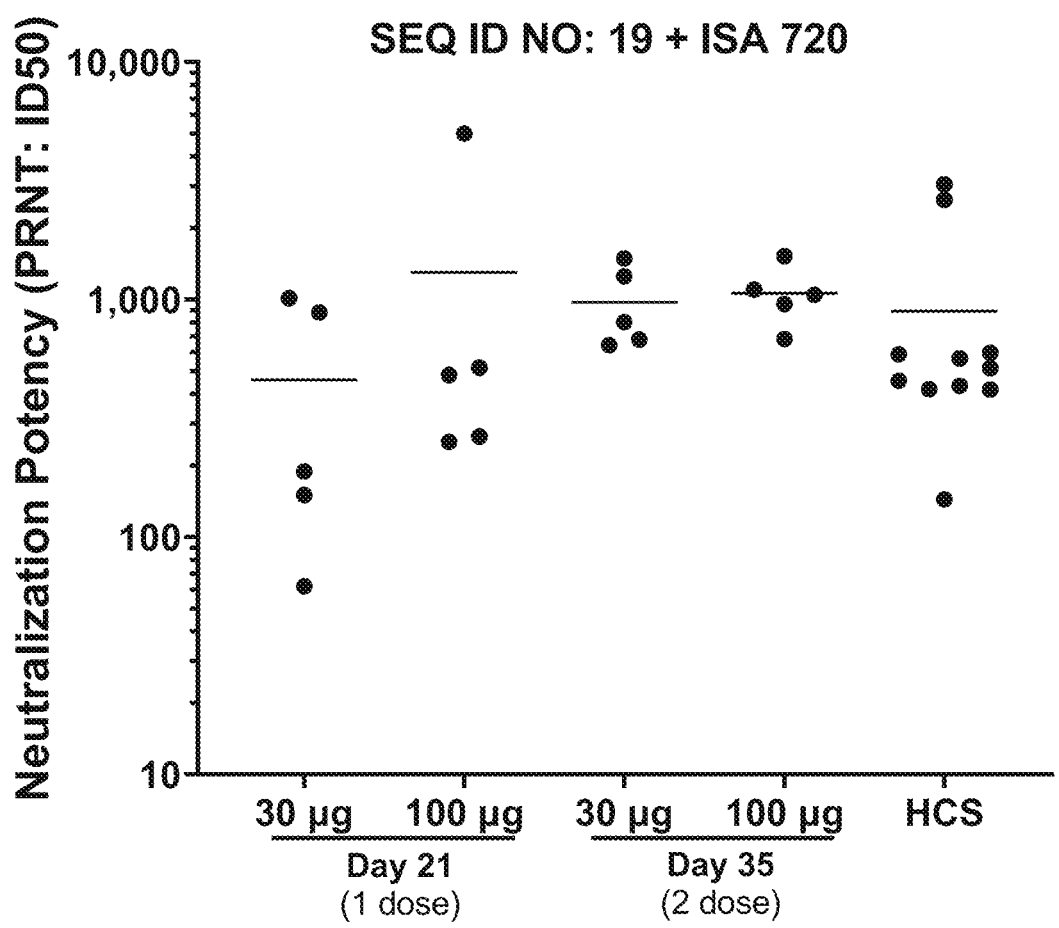
FIG. 73 illustrates the SARS-CoV-2-RBD-hIgG-Fc fusion protein of SEQ ID NO: 19 induced SARS-CoV-2 virus neutralization potency in New Zealand White Rabbit serum samples measured on Day 21, and Day 35, where SEQ ID NO: 19 was emulsified with Montanide™ ISA 720 adjuvant and administered on Days 0 and 21, compared to human convalescent serum.

As described in Example 31, substantial specific IgG titers were induced in the rabbits injected at a dose levels of 30 µg and 100 µg of the SARS-CoV-2-RBD-hIgG-Fc fusion protein of SEQ ID NO: 19 with the Montanide™ ISA 720 adjuvant after the first, second, and third injections (FIG. 70 and FIG. 71). The serum samples were also evaluated for functional inhibitory potency as described in Example 13. In this ACE2 inhibition assay, there was a clear dose response in inhibitory potency between the 30 µg and 100 µg dose levels of the adjuvanted SARS-CoV-2-RBD-hIgG-Fc fusion protein of SEQ ID NO: 19 that were elevated and became similar 14 days after the second dose (FIG. 72). The potency values at both timepoints were substantially above those obtained for human convalescent serum. This inhibitory potency was further confirmed with the neutralization of live SARS-CoV-2 virus from infecting live VERO-E6 cells in the Plaque Reduction Neutralization Test (PRNT) according to the procedure of Example 15 and shown in FIG. 73.

The results obtained in rabbits demonstrate that the SARS-CoV-2-RBD-hIgG-Fc fusion protein of SEQ ID NO: 19 emulsified in ISA 720 induces functional immunogenicity at levels found in humans that recovered from COVID-19 infection and disease, which puts these toxicology results into a clinical context favoring the expectation of a clean safety profile. No test article-related mortality or organ weight changes were observed at the main study termination. Mild effects, such as increases in fibrinogen, were most likely due to the Montanide™ ISA 720 adjuvant during the Dosing Phase and subsided during the recovery phase. The expected macroscopic and microscopic transient injection site AEs were also likely due to the adjuvant. Considering the relevant clinical levels of immunogenicity in this toxicology study, it was concluded that there were no safety issues that would raise concerns for moving into clinical trials.

Figure 74:
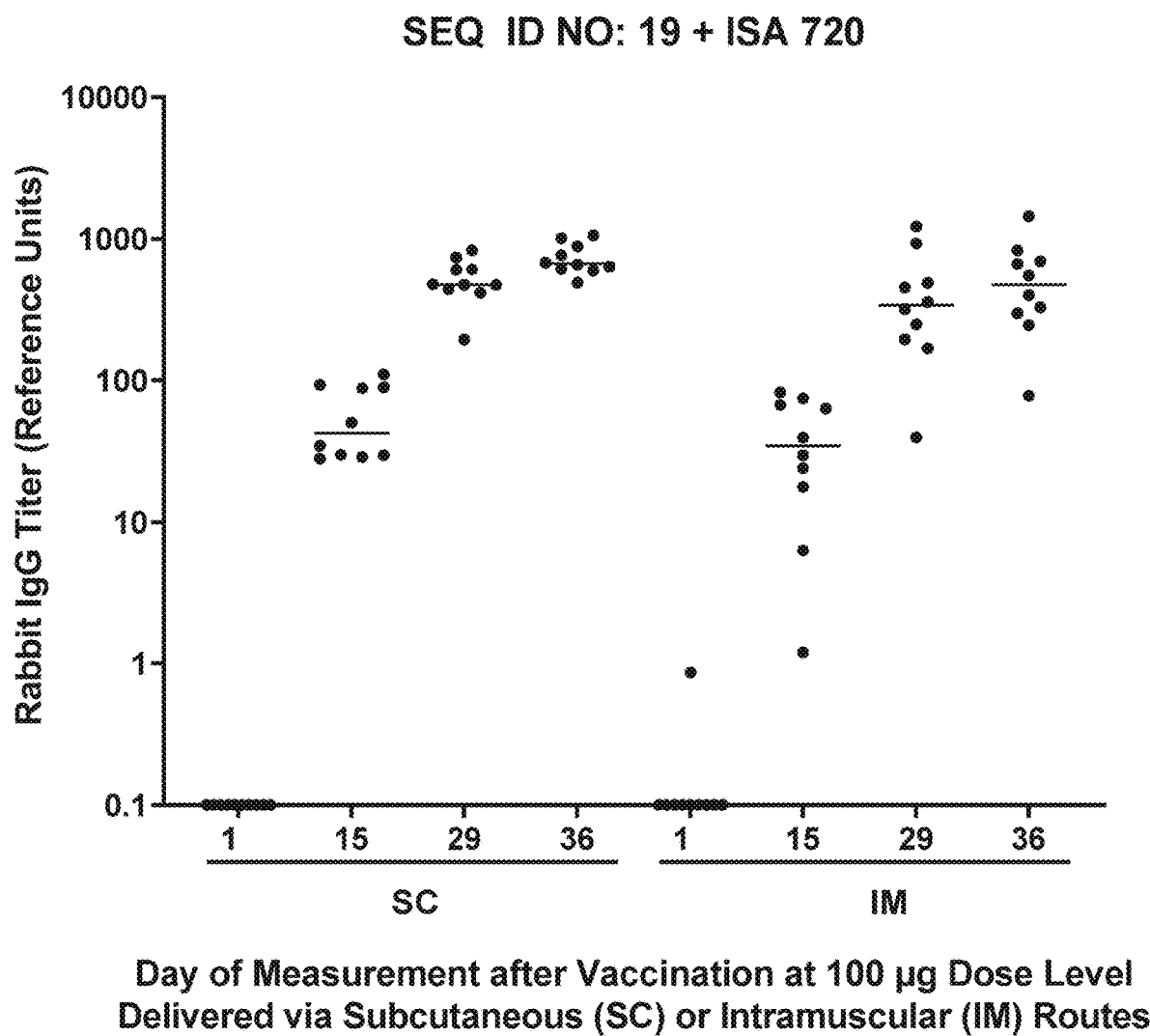
FIG. 74 illustrates the anti-SP/RBD IgG Ab titer in New Zealand White Rabbits administered a 100 μg dose level of the SARS-CoV-2-RBD-hIgG-Fc fusion protein of SEQ ID NO: 19 with Montanide™ ISA 720 adjuvant via subcutaneous (SC) injection or intramuscular injection (IM), measured on Day 15, Day 29, and Day 36 after an injection on Day 0 and Day 21.
Figure 75:
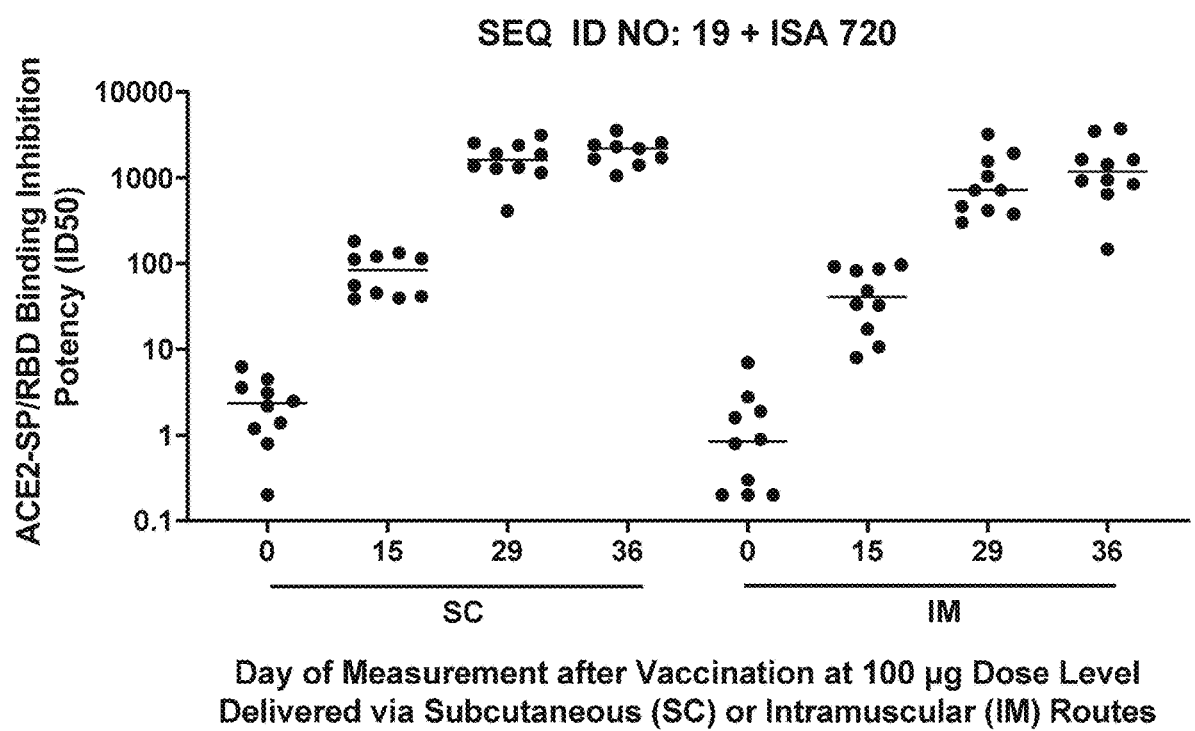
FIG. 75 illustrates the induced ACE2-SP/RBD binding inhibition potency (ID50) in New Zealand White Rabbits administered a 100 μg dose level of the SARS-CoV-2-RBD-hIgG-Fc fusion protein of SEQ ID NO: 19 with Montanide™ ISA 720 adjuvant via subcutaneous (SC) injection or intramuscular injection (IM), measured on Day 15, Day 29, and Day 36 after an injection on Day 0 and Day 21.

Intramuscular (i.m.) as compared to subcutaneous (s.c.) delivery routes were evaluated according to Example 33 with a bridging study. Analysis at Day 15, Day 29 and Day 36 demonstrated no statistically significant differences in anti-RBD Ab titer (FIG. 74) or ACE2-inhibition potency (FIG. 75) between the s.c. and i.m. administrations of the SARS-CoV-2-RBD-hIgG-Fc fusion protein of SEQ ID NO: 19 (100 µg dose level) in Montanide™ ISA 720 as measured according to Example 13, supporting the evaluation of either route of administration in clinical trials.

Figure 76:
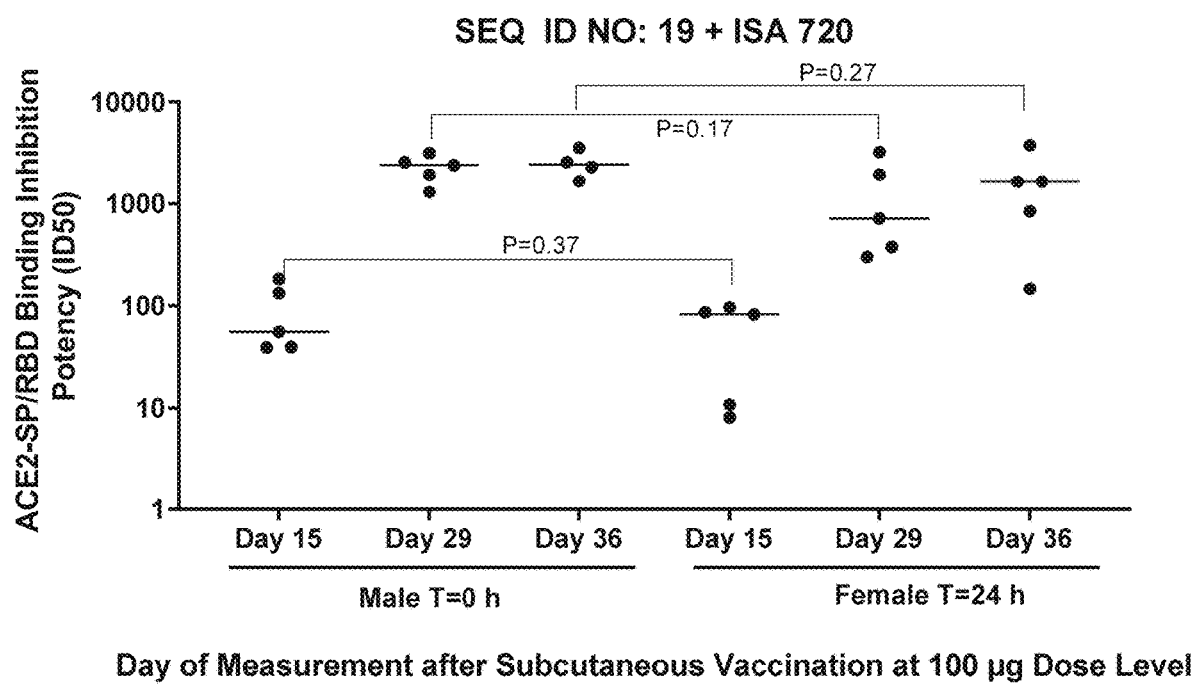
FIG. 76 illustrates the anti-SP/RBD IgG Ab titer in New Zealand White Rabbits administered a fresh emulsion and an emulsion stored for 24 hours at 2-8° C. of 100 μg dose level of the SARS-CoV-2-RBD-hIgG-Fc fusion protein of SEQ ID NO: 19 with Montanide™ ISA 720 adjuvant via subcutaneous (SC) injection measured on Day 15, Day 29, and Day 36 after an injection on Day 0 and Day 21.
Figure 77:
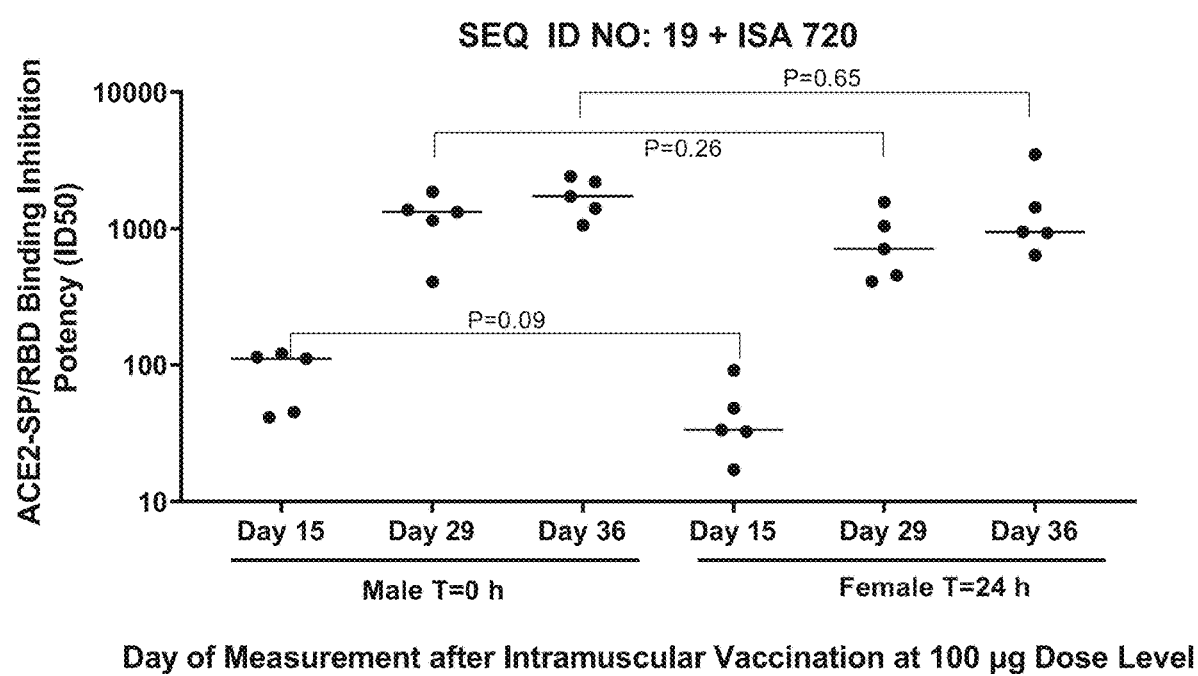
FIG. 77 illustrates the anti-SP/RBD IgG Ab titer in New Zealand White Rabbits administered a fresh emulsion and an emulsion stored for 24 hours at 2-8° C. of 100 μg dose level of the SARS-CoV-2-RBD-hIgG-Fc fusion protein of SEQ ID NO: 19 with Montanide™ ISA 720 adjuvant via intramuscular (IM) injection measured on Day 15, Day 29, and Day 36 after an injection on Day 0 and Day 21.

Differences between freshly made emulsion and the same emulsion after being stored at refrigeration temperatures for 24 hours were analyzed using a sub-group study on the ACE2-SP/RBD binding inhibition potency (IC50) results (measured according to Example 13) measured on Day 15 (after one dose), Day 29 (after 2 doses) and Day 36 (after three doses). Again, as described above for the mouse immunogenicity studies (Example 26), there was no statistical difference in inhibitory potency between the fresh and stored emulsion indicating that the adjuvanted SEQ ID NO: 19 formulation performance is stable for at least 24 hours after preparation as shown in FIG. 76 (for subcutaneous administration) and FIG. 77 (for intramuscular administration).

SARS-CoV-2-RBD-hIgG-Fc Fusion Proteins for Use as a Booster Vaccine

In examples, a SARS-CoV-2-RBD-hIgG-Fc fusion protein may be used as a booster vaccine. Administration of the fusion protein to subjects that already have low but measurable antibody levels to the SARS-CoV-2 antigen to amplify their antibody titers increases their antiviral protection. SP/RBD fragment variants are synthesized to maximize antigenicity while the Fc region prolongs antigen residence time as compared to the native SARS-CoV-2 SP/RBD of SEQ ID NO: 2. Without wishing to be bound to any particular theory of mechanism, it is believed that during the longer in vivo residence time, the naturally glycosylated human Fc fragment will present the SARS-CoV-2 RBD analog antigen to antigen producing cells (APCs), which is expected to produce a strong immune response to the SARS-CoV-2 RBD antigen. Specifically, the APCs internalize the SARS-CoV-2 RBD antigen via Fc(gamma) receptors, and then process and present RBD fragments (FIG. 12) to CD4+Th cells that in turn promote ("help") B cell activation and anti-SARS-CoV-2 RBD IgG (i.e., Ab) production (FIG. 12).

Describing FIG. 12 in detail, antigen-presenting cells may be, for example, dendritic cells (DCs), monocytes or macrophages that can internalize the molecules of the SARS-CoV-2-RBD-hIgG-Fc fusion protein of SEQ ID NO: 19 via Fc-receptor mediated phagocytosis (e.g., through the Fc region of the SARS-CoV-2-RBD-hIgG-Fc fusion protein binding to the Fc(gamma) receptors in immune cells). Fc-mediated uptake of the SARS-CoV-2-RBD-hIgG-Fc fusion protein by, for example, a subset of DCs (e.g., $cDC_{25}$) promotes the development of anti-SARS-CoV-2 T helper 2 (Th2) cells through secretion of IL-10 and IL-33. Anti-SARS-CoV-2 Th2 cells activate anti-SARS-CoV-2 B-cells, for example by cross linking their antigen receptors to allow the B-cells to attract the Th2 cells. B-cell antigen receptor (BCR) mediated uptake binds the SARS-CoV-2 RBD fragment of the SARS-CoV-2-RBD-hIgG-Fc fusion protein molecules, then delivers the SARS-CoV-2 antigen to intracellular sites where it is degraded and returned to the B-cell surface as peptides bound to MHC class II molecules. The peptide MCH class II complex can be recognized by the SARS-CoV-2-specific helper T cells simulating them to make proteins that in turn cause the B-cell to proliferate and its progeny to differentiate into B cells that secrete anti-SARS-CoV-2 antibodies. The SARS-CoV-2-RBD-hIgG-Fc fusion protein of SEQ ID NO: 19 may directly expose the SARS-CoV-2 SP/RBD fragment to antigen producing cells for a protracted period of time due to the presence of the Fc fragment. Furthermore, and as previously described, the glycosylated Fc fragment in the SARS-CoV-2-RBD-hIgG-Fc fusion protein according to SEQ ID NO: 19 is expected to induce a very strong immune response directed to the therapeutic or antigen portion of the fusion protein. These properties in combination significantly increase the amount of anti-viral antibodies while also decreasing the amount of antigen necessary to produce the required immune response.

In examples, a therapy comprising treatment of a patient with the SARS-CoV-2-RBD-hIgG-Fc fusion protein of SEQ ID NO: 19, SEQ ID NO: 16, SEQ ID NO: 18, SEQ ID NO: 20, or SEQ ID NO: 21 or a pharmaceutical composition thereof, may be administered as a booster vaccine to recovered patients of COVID-19 that are already antibody-positive to SARS-CoV-2, as a means to amplify their antibody titers and affinity so that when these treated patients are subsequently confronted with the virus, they will have sufficient immunity to prevent infection and/or serious symptoms related to infection with the SARS-CoV-2 virus. Furthermore, a therapy comprising a treatment of a patient with the SARS-CoV-2-RBD-hIgG-Fc fusion protein of SEQ ID NO: 19, SEQ ID NO: 16, SEQ ID NO: 18, SEQ ID NO: 20, or SEQ ID NO: 21 or a pharmaceutical composition thereof, may be administered as a booster vaccine to subjects that have been previously immunized with a vaccine against the SARS-CoV-2 virus as a means to amplify their antibody titers and affinity specifically against the SP/RBD. Such a therapy is critical in cases where vaccines are not 100% effective and/or the where induced antibody titers wane over time. In examples, a SARS-CoV-2-RBD-hIgG-Fc fusion protein of SEQ ID NO: 19, SEQ ID NO: 16, SEQ ID NO: 18, SEQ ID NO: 20, or SEQ ID NO: 21 or a pharmaceutical composition thereof may be administered to a patient by subcutaneous injection (s.c.) or intramuscularly (i.m.), as the s.c. or i.m. injection sites are more likely to induce a strong antibody response due to there being more dendritic cells (DCs) in the subcutaneous and intramuscular spaces.

Booster SARS-CoV-2-hIgG-Fc Fusion Vaccines Evaluated in Mice and NHP

The efficacy of the booster vaccine use was evaluated in mice as described in more detail in Example 12. BALB/c mice were injected up to three times at predetermined intervals (e.g., every three weeks) with several SARS-CoV-2-RBD-hIgG-Fc fusion proteins or pharmaceutical compositions thereof, and serum was collected at regular intervals. The serum SARS-CoV-2 SP/RBD IgG antibody titers were measured according to the procedures in Example 10 or Example 11 and their neutralizing capacities were assessed according to Example 13. Experimental variables included the SARS-CoV-2-RBD-hIgG-Fc fusion protein composition and dose level, number of injections, and type of adjuvant. It is expected that the immunized mice may be left untreated for an additional 30-60 days until their antibody levels wane down to baseline/minimum levels and then given an additional series of injections of SARS-CoV-2-RBD-hIgG-Fc fusion proteins or pharmaceutical compositions thereof to evaluate the recall (memory) immune response.

Figure 63:
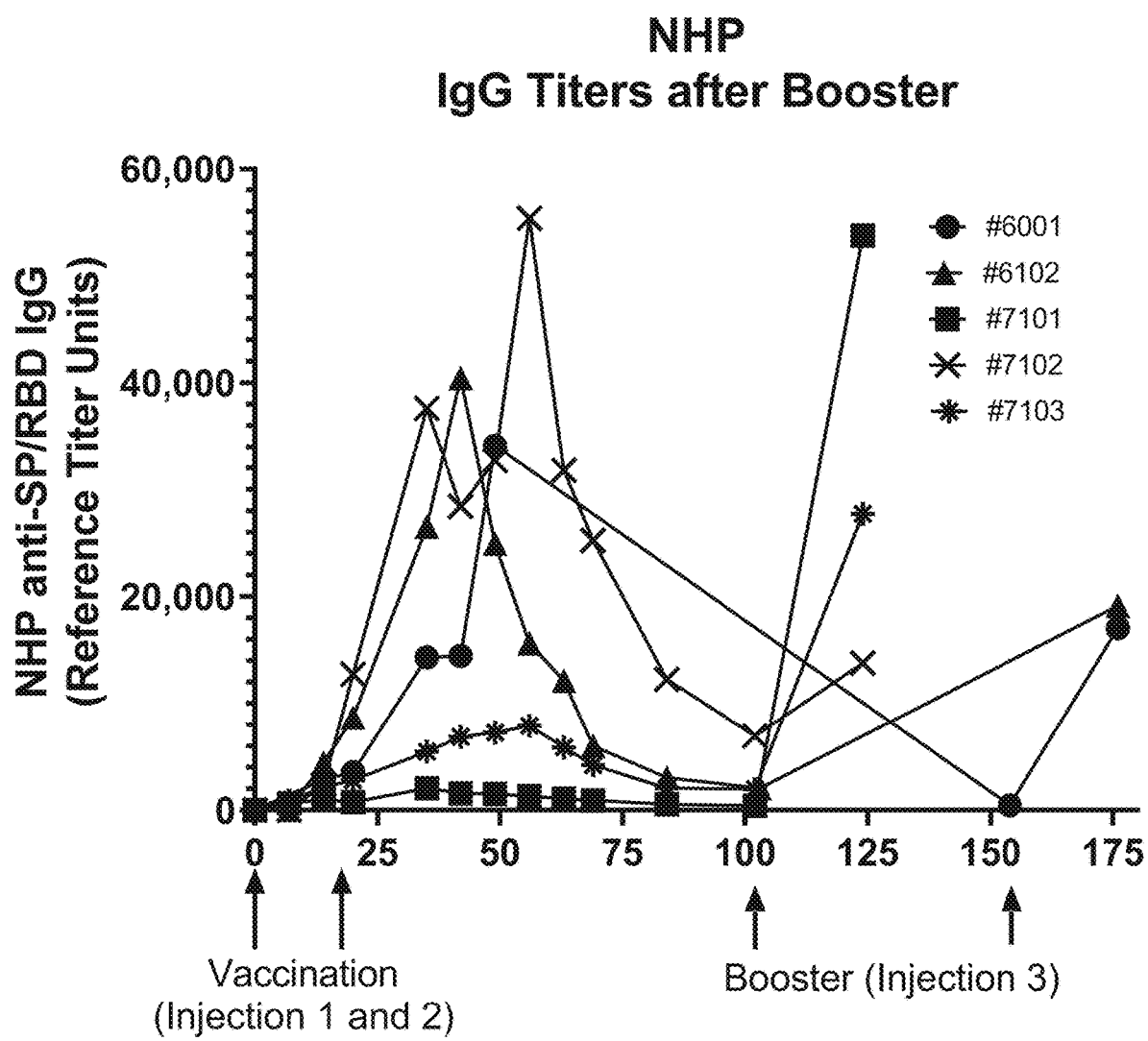
FIG. 63 illustrates the anti-SP/RBD response in inoculated NHP after receiving a booster injection.

In an analysis of the use of the SARS-CoV-2-RBD-hIgG-Fc fusion protein of SEQ ID NO: 19 with Montanide™ ISA 720 as a booster, NHP were first injected with a 10 µg or 30 µg dose of the fusion proteins and serum was collected at regular intervals as described in Example 27. After between three and four and a half months when their antibody levels had waned, the NHPs were injected with a booster vaccine (third injection) at the 30 µg dose level. As shown in FIG. 63, in all cases the booster vaccine triggered a strong memory immune response.

Fc Fusion Protein Production

In embodiments, a fusion protein can be expressed by a cell as described in more detail in the Examples section.

Expression and Purification

An Fc fusion protein can be expressed recombinantly, e.g., in a eukaryotic cell, e.g., mammalian cell or non-mammalian cell. Exemplary mammalian cells used for expression include HEK cells (e.g., HEK293 cells) or CHO cells. CHO cells can be subdivided into various strains or subclasses, (e.g., CHO DG44, CHO-M, CHO-SE™ and CHO-K1), and some of these cell strains may be genetically engineered for optimal use with a particular type of nucleic acid molecule (e.g., a vector comprising DNA) or a particular cell growth media composition as described in the Examples section. Cells may be transfected with a nucleic acid molecule (e.g., vector) encoding the Fc fusion protein (e.g., where the entire Fc fusion protein is encoded by a single nucleic acid molecule). HEK293 cells may be transfected with a vector that encodes for the Fc fusion protein, but this process only results in temporary expression of the Fc fusion protein for a period of time (e.g., 3 days, 4 days, 5, days, 7 days, 10 days, 12 days, 14 days, or more) before the host cell stops expressing appreciable levels of the Fc fusion protein (i.e., transient transfection). HEK293 cells that are transiently transfected with nucleic acid sequences encoding for Fc fusion proteins often allow for more rapid production of recombinant proteins which facilitates making and screening multiple Fc fusion protein candidates. In examples, CHOSE™ (LakePharma, Belmont, Calif.) cells are transfected with a vector that encodes for the Fc fusion protein, but this process only results in temporary expression of the Fc fusion protein for a period of time (e.g., 3 days, 4 days, 5, days, 7 days, 10 days, 12 days, 14 days, or more) before the host cell stops expressing appreciable levels of the Fc fusion protein (i.e., transient transfection). CHO-SE™ (LakePharma, Belmont, Calif.) cells that are transiently transfected with nucleic acid sequences encoding for Fc fusion proteins often allow for more rapid production of recombinant proteins which facilitates making and screening multiple Fc fusion protein candidates. CHO cells may be transfected with a vector that is permanently incorporated into the host cell DNA and leads to consistent and permanent expression (i.e., stable transfection) of the Fc fusion protein as long as the cells are cultured appropriately. CHO cells and CHO cell lines that are stably transfected with nucleic acids encoding for Fc fusion proteins often take longer to develop, but they often produce higher protein yields and are more amenable to manufacturing low cost products (e.g., products for use in the veterinary pharmaceutical market). Cells and cell lines can be cultured using standard methods in the art.

In examples, the Fc fusion protein may be purified or isolated from the cells (e.g., by lysis of the cells). The Fc fusion protein is secreted by the cells and may be purified or isolated from the cell culture media in which the cells were grown. Purification of the Fc fusion protein can include using column chromatography (e.g., affinity chromatography) or using other separation methods based on differences in size, charge, and/or affinity for certain molecules. Purification of the Fc fusion protein involves selecting or enriching for proteins containing an Fc fragment, e.g., by using Protein A beads or a Protein A column that cause proteins containing an Fc fragment to become bound with high affinity at neutral solution pH to the Protein A covalently conjugated to the Protein A beads. The bound Fc fusion protein may then be eluted from the Protein A beads by a change in a solution variable (e.g., a decrease in the solution pH). Other separation methods such as ion exchange chromatography and/or gel filtration chromatography can also be employed alternatively or additionally. Purification of the Fc fusion protein may further comprise filtering or centrifuging the protein preparation, diafiltration, ultrafiltration, and filtration through porous membranes of various sizes, as well as final formulation with excipients.

The purified Fc fusion protein can be characterized, e.g., for purity, protein yield, structure, and/or activity, using a variety of methods, e.g., absorbance at 280 nm (e.g., to determine protein yield), size exclusion or capillary electrophoresis (e.g., to determine the molecular weight, percent aggregation, and/or purity), mass spectrometry (MS) and/or liquid chromatography (LC-MS) (e.g., to determine purity and/or glycosylation), and/or ELISA (e.g., to determine extent of binding, e.g., affinity, to a SARS-CoV-2 antibody or ACE2). Exemplary methods of characterization are also described in the Examples section.

The protein yield of an Fc fusion protein after production in transiently transfected HEK cells and protein A purification may be greater than 5 mg/L, 10 mg/L, or 20 mg/L, or more preferably greater than 50 mg/L (e.g., greater than 60 mg/L, greater than 70 mg/L, greater than 80 mg/L, greater than 90 mg/L, greater than 100 mg/L). The % homodimer of an Fc fusion protein after production in transiently transfected HEK cells and protein A purification is greater than 70% (e.g., greater than 80%, greater than 85%, greater than 90%, greater than 95%, greater than 96%, greater than 97%, greater than 98%, greater than 99%). The homodimer titer of an Fc fusion protein after production in transiently transfected HEK cells and protein A purification, calculated as the product between the Fc fusion protein yield and the % homodimer, may be greater than 50 mg/L (e.g., greater than 60 mg/L, greater than 70 mg/L, greater than 80 mg/L, greater than 90 mg/L, greater than 100 mg/L).

In examples, the protein yield of an Fc fusion protein after production in transiently transfected CHOSE™ (LakePharma, Belmont, Calif.) cells and protein A purification is greater than 5 mg/L or 10 mg/L. In preferred embodiments, the protein yield of an Fc fusion protein after production in transiently transfected CHOSE™ (LakePharma, Belmont, Calif.) cells and protein A purification is greater than 20 mg/L (e.g., greater than 30 mg/L, greater than 40 mg/L, greater than 50 mg/L, greater than 60 mg/L, greater than 70 mg/L, greater than 80 mg/L, greater than 90 mg/L, greater than 100 mg/L). The % homodimer of an Fc fusion protein after production in transiently transfected CHOSE™ (LakePharma, Belmont, Calif.) cells and protein A purification may be greater than 70% (e.g., greater than 80%, greater than 85%, greater than 90%, greater than 95%, greater than 96%, greater than 97%, greater than 98%, greater than 99%). In embodiments, the homodimer titer of an Fc fusion protein after production in transiently transfected CHOSE™ (LakePharma, Belmont, Calif.) cells and protein A purification, calculated as the product between the Fc fusion protein yield and the % homodimer is greater than 20 mg/L (e.g., greater than 30 mg/L, greater than 40 mg/L, greater than 50 mg/L, greater than 60 mg/L, greater than 70 mg/L, greater than 80 mg/L, greater than 90 mg/L, greater than 100 mg/L).

The protein yield of an Fc fusion protein after production in stably transfected CHO cells (e.g., CHO cell lines or CHO cell clones) and protein A purification may be greater than 100 mg of Fc fusion protein per L (e.g., mg/L of culture media). In embodiments, the protein yield of an Fc fusion protein after production in stably transfected CHO cells (e.g., CHO cell lines or CHO cell clones) and protein A purification is greater than 50 mg Fc fusion protein/L of culture media (e.g., greater than 100 mg/L, greater than 200 mg/L, greater than 300 mg/L, greater than 400 mg/L, greater than 500 mg/L, greater than 600 mg/L or more). The % homodimer of an Fc fusion protein after production in stably transfected CHO cells (e.g., CHO cell lines or CHO cell clones) and protein A purification may be greater than 70% (e.g., greater than 80%, greater than 85%, greater than 90%, greater than 95%, greater than 96%, greater than 97%, greater than 98%, greater than 99%). In embodiments, the homodimer titer of an Fc fusion protein after production in stably transfected CHO cells (e.g., CHO cell lines or CHO cell clones) and protein A purification, calculated as the product between the Fc fusion protein yield and the % homodimer is greater than 150 mg/L (e.g., greater than 200 mg/L, greater than 300 mg/L, greater than 400 mg/L, greater than 500 mg/L, greater than 600 mg/L or more).

Pharmaceutical Compositions and Routes of Administration

The amount and concentration of the Fc fusion protein in the pharmaceutical compositions, as well as the quantity of the pharmaceutical composition administered to a subject, can be selected based on clinically relevant factors, such as medically relevant characteristics of the subject (e.g., age, weight, gender, other medical conditions, and the like), the solubility of compounds in the pharmaceutical compositions, the potency and activity of the compounds, and the manner of administration of the pharmaceutical compositions.

Formulations of the present disclosure include those suitable for parenteral administration. The phrases "parenteral administration" and "administered parenterally" as used herein means modes of administration other than enteral and topical administration, usually by intravenous, intramuscular, or subcutaneous injection.

Examples of suitable aqueous and non-aqueous carriers that may be employed in the pharmaceutical compositions of the disclosure include water, saline, ethanol, salts, polyols (such as glycerol, propylene glycol, polyethylene glycol, and the like), and suitable mixtures thereof, vegetable oils, such as olive oil, and injectable organic esters, such as ethyl oleate, buffering agents, such as potassium and/or sodium phosphates, pH buffers, such as hydrochloric acid and/or sodium hydroxide, and the like. Proper fluidity can be maintained, for example, by the use of coating or emulsifier materials, such as lecithin, by the maintenance of the required particle size in the case of dispersions, and by the use of surfactants, e.g., Tween-like surfactants. In some examples, the pharmaceutical composition (e.g., as described herein) comprises a Tween-like surfactant, e.g., polysorbate-20, Tween-20 or Tween-80. In some examples, the pharmaceutical composition (e.g., as described herein) comprises a Tween-like surfactant, e.g., Tween-80, at a concentration between about 0.001% and about 2%, or between about 0.005% and about 0.1%, or between about 0.01% and about 0.5%.

The Fc fusion protein may be administered as a bolus, infusion, or an intravenous push, or administered through syringe injection, pump, pen, needle, or indwelling catheter. The Fc fusion protein may be administered by a subcutaneous bolus injection. In examples, the Fc fusion protein or a pharmaceutical composition thereof is administered to a patient by subcutaneous injection (s.c.) or intramuscularly (i.m.), as the s.c. or i.m. injection sites are more likely to induce a strong antibody response due to there being more dendritic cells (DCs) in the subcutaneous and intramuscular spaces. Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site. Additional pharmaceutically-acceptable ingredients for use in the compositions include buffering agents, salts, stabilizing agents, diluents, preservatives, antibiotics, isotonic agents, and the like.

Dosages

In use, a therapeutically-effective amount of the Fc fusion protein is administered to a subject in need thereof. Administration of the Fc fusion protein elicits an immune response in the subject, and more specifically an immune response against coronavirus infection, more specifically SARS-CoV-2 or variants. The immune response will be demonstrated by a lack of observable clinical symptoms, or reduction of clinical symptoms normally displayed by an infected subject, reduced viral shedding, faster recovery times from infection, and/or reduced duration of infection. In another embodiment, a method of activating an immune cell at a site of infection or disease is provided comprising administering a therapeutically-effective amount of the Fc fusion protein to a mammal. In another aspect, a method of increasing antibody production in a subject is provided comprising administering a therapeutically-effective amount of the Fc fusion protein to a mammal.

It will be appreciated that therapeutic and prophylactic methods described herein are applicable to humans as well as any suitable warm-blooded animal, including, without limitation, dogs, cats, and other companion animals, as well as, rodents, primates, horses, cattle, sheep, pigs, etc. The methods can be also applied for clinical research and/or study.

As used herein, the phrase "effective amount" or "therapeutically effective amount" is meant to refer to a therapeutic or prophylactic amount of the Fc fusion protein that would be appropriate for an embodiment of the present disclosure, that will elicit the desired therapeutic or prophylactic effect or response, including alleviating some or all of such symptoms of infection or reducing the predisposition to the infection, when administered in accordance with the desired treatment regimen. One of skill in the art recognizes that an amount may be considered therapeutically "effective" even if the condition is not totally eradicated or prevented, but it or its symptoms and/or effects are improved or alleviated partially in the subject. The therapeutically effective dosage of Fc fusion peptide may vary depending on the size and species of the subject, and according to the mode of administration.

Actual dosage levels of the Fc fusion protein can be varied so as to obtain an amount of the active ingredient that is effective to achieve the desired therapeutic response for a particular subject. The selected dosage level will depend upon a variety of factors including the activity of the particular fusion protein employed, or the ester, salt or amide thereof, the route of administration, the time of administration, the rate of excretion of the particular compound being employed, the duration of the treatment, other drugs, compounds and/or materials used in combination with the particular fusion protein employed, the age, sex, weight, condition, general health and prior medical history of the subject being treated, and like factors well known in the medical arts. In general, a suitable dose of an Fc fusion protein will be the amount that is the lowest dose effective to produce a therapeutic effect. Such an effective dose will generally depend upon the factors described above.

The immunogenic formulation is provided, in various aspects, in unit dosage form for ease of administration and uniformity of dosage. "Unit dosage form" as used herein refers to physically discrete units suited as unitary dosages for the subject to be treated, each unit containing a predetermined quantity of the SARS-CoV-2-RBD-hIgG-Fc fusion protein calculated to produce the desired therapeutic effect in association with the required pharmaceutical carrier. The specification for the dosage unit forms are dictated by and are directly dependent on the unique characteristics of the excipient(s) and therapeutic agent(s) and the particular biological effect to be achieved. In one or more embodiments, the formulation is provided in a kit of components for administration of the SARS-CoV-2-RBD-hIgG-Fc fusion protein to the subject. In one or more embodiments, a pharmaceutical composition comprising the SARS-CoV-2-RBD-hIgG-Fc fusion protein dispersed in a suitable carrier is provided in a unit dosage form (e.g., vial). In one or more embodiments, the kit further comprises a discrete unit dosage form (e.g., vial) containing an adjuvant and/or other carrier system for onsite mixing of the SARS-CoV-2-RBD-hIgG-Fc fusion protein for administration. In one or more embodiments, the kit comprises one or more emulsifying needles and syringes for onsite mixing of the immunogenic formulation for administration. In one or more embodiments, the kit comprises one or more dosing syringes for administering the prepared immunological composition to the subject. In one or more embodiments, the kit further comprises instructions for preparing the immunogenic composition and/or administering the immunogenic composition.

Figure 69:
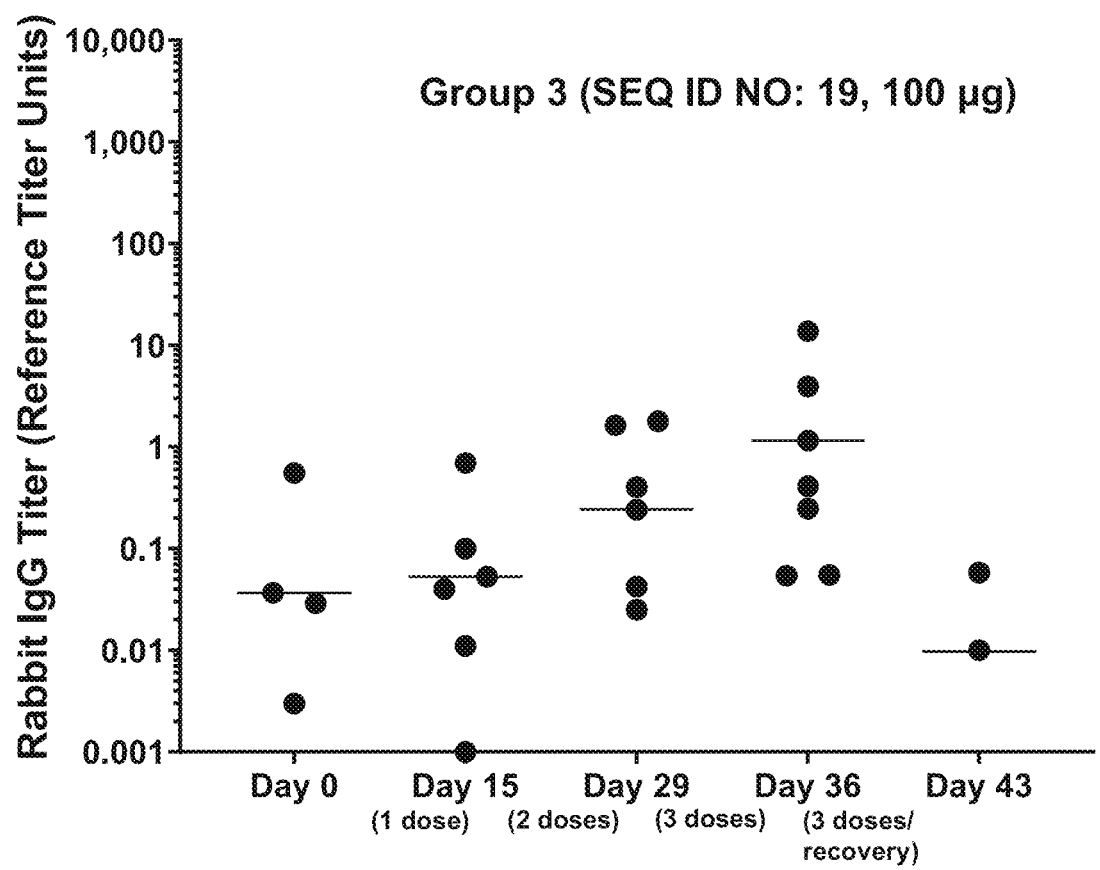
FIG. 69 illustrates the substantial anti-SP/RBD IgG Ab titer in New Zealand White Rabbits administered a 100 µg dose level of the SARS-CoV-2-RBD-hIgG-Fc fusion protein of SEQ ID NO: 19 without adjuvant on Day 1, Day 15, and Day 29 measured before the first dose, second dose and third dose and after the third dose.

In examples following the procedures described above and in the Examples that follow, it was shown that dose levels between 1 µg and 100 µg of SARS-CoV-2-RBD-hIgG-Fc fusion protein induced significant anti-SP/RBD Ab titers 21 days after a single injection in mice and rabbits. In examples, dose levels of 10 µg and 30 µg were effective in non-human primates (see FIG. 60, FIG. 61, and FIG. 62). The kinetics of the response in rabbits demonstrated that a dose level of 100 µg induced the highest immunogenicity (as in IgG Ab titers) after the $1^{st}$ $2^{nd}$ and $3^{rd}$ doses (both without adjuvant—see FIG. 69, and with Montanide™ ISA-720 adjuvant—see FIG. 71).

An initial evaluation of SEQ ID NO: 17 immunogenicity was performed according to Example 17 in 6- to 8-week old female BALB/c mice administered 0.05, 0.1, 0.3, 1, 3, 10, 30, or 100 µg of SEQ ID NO: 17 without adjuvant or 3 µg or 10 µg SEQ ID NO: 17 with adjuvants as indicated in Table 1 (all SARS-CoV-2-RBD-hIgG-Fc fusion protein:adjuvant mixtures were 50%:50% v/v, except for SARS-CoV-2-RBD-hIgG-Fc fusion protein:Montanide™ ISA 720 which was mixed at 30%/70% v/v). In addition, SEQ ID NO: 2 lacking an Fc fusion moiety was evaluated to investigate the immunogenic contribution of the Fc fragment.

TABLE 1

Test Parameters for Dose Level Finding Investigations Based on Immunogenicity Study in BALB/c Mice According to Example 13 With the SP/RBD of SEQ ID NO: 2 and With the SARS-CoV-2 SP/RBD-Fc Fusion Protein of SEQ ID NO: 17 With or Without Adjuvants.

| Cohort # | SARS-CoV-2 SP/RBD-Fc fusion protein SEQ ID NO: | Test Article | |
|---|---|---|---|
| | | Dose Level (µg/Dose) | Adjuvant |
| 1 | Saline Control | | |
| 2 | SEQ ID NO: 17 | 0.05 | |
| 3 | SEQ ID NO: 17 | 0.1 | |
| 4 | SEQ ID NO: 17 | 0.3 | |
| 5 | SEQ ID NO: 17 | 1 | |
| 6 | SEQ ID NO: 17 | 3 | |
| 7 | SEQ ID NO: 17 | 10 | |
| 8 | SEQ ID NO: 17 | 30 | |
| 9 | SEQ ID NO: 17 | 100 | |
| 10 | SEQ ID NO: 17 | 3 | Advax-1 |
| 11 | SEQ ID NO: 17 | 10 | Advax-1 |
| 12 | SEQ ID NO: 17 | 3 | Montanide ™ ISA 51 |
| 13 | SEQ ID NO: 17 | 10 | Montanide ™ ISA 51 |
| 14 | SEQ ID NO: 17 | 10 | Advax-2 |
| 15 | SEQ ID NO: 17 | 10 | Advax -3 |
| 16 | SEQ ID NO: 17 | 10 | vac-adx-10 |
| 17 | SEQ ID NO: 17 | 10 | Montanide ™ ISA 720 |
| 18 | SP/RBD | 5 | |

TABLE 1-continued

Test Parameters for Dose Level Finding Investigations Based on Immunogenicity Study in BALB/c Mice According to Example 13 With the SP/RBD of SEQ ID NO: 2 and With the SARS-CoV-2 SP/RBD-Fc Fusion Protein of SEQ ID NO: 17 With or Without Adjuvants.

| Cohort # | SARS-CoV-2 SP/RBD-Fc fusion protein SEQ ID NO: | Test Article | |
|---|---|---|---|
| | | Dose Level (µg/Dose) | Adjuvant |
| 19 | SP/RBD | 15 | |
| 20 | SP/RBD | 40 | |

The present disclosure contemplates formulation of the Fc fusion protein in any of the aforementioned pharmaceutical compositions and preparations. Furthermore, the present disclosure contemplates administration via any of the foregoing routes of administration. One of skill in the art can select the appropriate formulation, dose level and route of administration based on the condition being treated and the overall health, age, and size of the patient being treated.

EXAMPLES

The present technology is further illustrated by the following Examples. It is to be understood, however, that these examples are provided by way of illustration and nothing therein should be taken as a limitation upon the overall scope of the technology.

General Examples for Synthesis, Purification and Validation of SARS-CoV-2-RBD-hIgG-Fc Fusion Proteins

Example 1: Synthesis and Methods of Making of a SARS-CoV-2-RBD-hIgG-Fc Fusion Protein in HEK293 Cells SARS-CoV-2-RBD-hIgG-Fc fusion proteins were synthesized as follows. A gene sequence of interest was constructed using proprietary software (LakePharma, Belmont, Calif.) and was cloned into a high expression mammalian vector. HEK293 cells were seeded in a shake flask 24 hours before transfection and were grown using serum-free chemically defined media. A DNA expression construct that encodes the SARS-CoV-2-RBD-hIgG-Fc fusion protein of interest was transiently transfected into a suspension of HEK293 cells using the (LakePharma, Belmont, Calif.) standard operating procedure for transient transfection. After 20 hours, the cells were counted to determine the viability and viable cell count, and the titer was measured by FortéBio® Octet® (Pall FortéBio LLC, Fremont, Calif.). Additional readings were taken throughout the transient transfection production run. The culture was harvested on or after Day 5.

Example 2: Synthesis and Methods of Making of a SARS-CoV-2-RBD-hIgG-Fc Fusion Protein in Transiently Transfected CHO Cells SARS-CoV-2-RBD-hIgG-Fc fusion proteins were synthesized as follows. A gene sequence of interest was constructed using proprietary software (LakePharma, Belmont, Calif.) and was cloned into a human Fc fusion protein-specific high expression vector. CHOSE™ (LakePharma, Belmont, Calif.) cells were seeded in a shake flask 24 hours before transfection and were grown using serum-free chemically defined media (MEDNA Bio). A DNA expression construct that encodes the SARS-CoV-2-RBD-hIgG-Fc fusion protein of interest was transiently transfected into a suspension of CHO-SE cells using standard operating procedures for transient transfection (LakePharma, Belmont, Calif.). After nearly 24 hours, the cells were counted to determine the viability and viable cell count, and the titer was measured by FortéBio® Octet® (Pall FortéLLC, Fremont, Calif.). Additional readings were taken throughout the transient transfection production run. The culture was harvested on or after Day 7.

Example 3: Synthesis and Methods of Making a SARS-CoV-2-RBD-hIgG-Fc Fusion Protein in Stably Transfected CHO Cells A CHO cell line was originally derived from CHO-K1 (LakePharma, Belmont, Calif.), and the endogenous glutamine synthetase (GS) genes were knocked out by recombinant technology using methods known in the art. Stable expression DNA vectors were designed and optimized for CHO expression and GS selection and incorporated into a high expression mammalian vector (LakePharma, Belmont, Calif.). The sequence of each completed construct was confirmed prior to initiating scale up experiments. The suspension-adapted CHO cells were cultured in a humidified 5% $CO_2$ incubator at 37° C. in a chemically defined media (CD OptiCHO; Invitrogen, Carlsbad, Calif.). No serum or other animal-derived products were used in culturing the CHO cells.

Approximately 80 million suspension-adapted CHO cells, growing in CD OptiCHO media during the exponential growth phase, were transfected by electroporation using MaxCyte® STX® system (MaxCyte, Inc., Gaithersburg, Md.) with 80 μg DNA to a create a stable CHO cell line for each SARS-CoV-2-RBD-hIgG-Fc fusion protein (DNA construct contains the full-length sequence of the SARS-CoV-2-RBD-hIgG-Fc fusion protein). After twenty-four hours, the transfected cells were counted and placed under selection for stable integration of the SARS-CoV-2-RBD-hIgG-Fc fusion genes. The transfected cells were seeded into CD OptiCHO selection media containing between 0-100 μM methionine sulfoximine (MSX) at a cell density of $0.5\times10^6$ cells/mL in a shaker flask and incubated at 37° C. with 5% $CO_2$. During a selection process, the cells were spun down and resuspended in fresh selection media every 2-3 days until the CHO stable pool recovered its growth rate and viability. The cell culture was monitored for growth and titer.

The cells were grown to $2.5\times10^6$ cells per mL. At the time of harvest for cell banking, the viability was above 95%. The cells were then centrifuged, and the cell pellet was resuspended in the CD OptiCHO media with 7.5% dimethyl sulfoxide (DMSO) to a cell count of $15\times10^6$ cells per mL per vial. Vials were cryopreserved for storage in liquid nitrogen.

A small-scale-up production was performed using the CHO cells as follows. The cells were scaled up for production in CD OptiCHO growth medium containing 100 μM MSX at 37° C. and fed every 2-4 days as needed, with CD OptiCHO growth medium supplemented with glucose and additional amino acids as necessary for approximately 14-21 days. The conditioned media supernatant harvested from the stable pool production run was clarified by centrifuge spinning. The protein was run over a Protein A (MabS elect, GE Healthcare, Little Chalfont, United Kingdom) column pre-equilibrated with binding buffer. Washing buffer was then passed through the column until the OD280 value (Nano- Drop, Thermo Scientific) was measured to be at or near background levels. The SARS-CoV-2-RBD-hIgG-Fc fusion protein was eluted using a low pH buffer, elution fractions were collected, and the OD280 value of each fraction was recorded. Fractions containing the target SARS-CoV-2-RBD-hIgG-Fc fusion protein were pooled and optionally further filtered using a 0.2 μM membrane filter.

The cell line may be optionally further subcloned to monoclonality and optionally further selected for high titer SARS-CoV-2-RBD-hIgG-Fc-fusion protein-expressing clones using the method of limiting dilution, a method known to those skilled in the art. After obtaining a high titer, monoclonal SARS-CoV-2-RBD-hIgG-Fc fusion protein-expressing cell line, production of the SARS-CoV-2-RBD-hIgG-Fc fusion protein was accomplished as described above in growth medium without MSX, or optionally in growth medium containing MSX, to obtain a cell culture supernatant containing the recombinant, CHO-made, SARS-CoV-2-RBD-hIgG-Fc fusion protein. The MSX concentration may be optionally increased over time to exert additional selectivity for clones capable of yielding higher product titers.

Example 4: Purification of a SARS-CoV-2-RBD-hIgG-Fc Fusion Protein Manufactured in HEK293 Cells Purification of a SARS-CoV-2-RBD-hIgG-Fc fusion protein was performed as follows. Conditioned media supernatants containing the secreted SARS-CoV-2-RBD-hIgG-Fc fusion protein were harvested from the transiently transfected HEK293 production runs and were clarified by centrifugation. The supernatant containing the desired SARS-CoV-2-RBD-hIgG-Fc fusion protein was run over a Protein A column, washed and eluted using a low pH gradient. Afterwards, the eluted fractions containing the desired protein were pooled and buffer exchanged into 200 mM HEPES, 100 mM NaCl, 50 mM NaOAc, pH 7.0 buffer. A final filtration step was performed using a 0.2 μm membrane filter. The final protein concentration was calculated from the solution optical density at 280 nm. Further optional purification by ion-exchange chromatography (e.g., using an anion exchange bead resin or a cation exchange bead resin), gel filtration chromatography, or other methods was performed as necessary.

Example 5: Purification of a SARS-CoV-2-RBD-hIgG-Fc Fusion Protein Manufactured in CHO Cells Purification of a SARS-CoV-2-RBD-hIgG-Fc fusion protein was performed as follows. Conditioned media supernatants containing the secreted SARS-CoV-2-RBD-hIgG-Fc fusion protein were harvested from the transiently transfected CHO or stably transfected CHO production runs and were clarified by centrifugation. The supernatant containing the desired SARS-CoV-2-RBD-hIgG-Fc fusion protein was run over a Protein A column, washed and eluted using a low pH gradient. Afterwards, the eluted fractions containing the desired protein were pooled and buffer exchanged into 200 mM HEPES, 100 mM NaCl, 50 mM NaOAc, pH 7.0 buffer. A final filtration step was performed using a 0.2 μm membrane filter. The final protein concentration was calculated from the solution optical density at 280 nm. Further optional purification by ion-exchange chromatography (e.g., using an anion exchange bead resin or a cation exchange bead resin), gel filtration chromatography, or other methods was performed as necessary.

Example 6: SARS-CoV-2-RBD-hIgG-Fc Fusion Protein Structure Confirmation by Non-Reducing and Reducing CE-SDS Capillary electrophoresis sodium dodecyl sulfate (CE-SDS) analysis is performed in a LabChip® GXII (Perkin Elmer, Waltham, Mass.) on a solution of a purified SARS-CoV-2-RBD-hIgG-Fc fusion protein dissolved in 200 mM HEPES, 100 mM NaCl, 50 mM NaOAc, pH 7.0 buffer, and the electropherogram is plotted. Under non-reducing conditions, the sample is run against known molecular weight (MW) protein standards, and the eluting peak represents the 'apparent' MW of the SARS-CoV-2-RBD-hIgG-Fc fusion protein homodimer.

Under reducing conditions (e.g., using beta-mercaptoethanol to break disulfide bonds of the SARS-CoV-2-RBD-hIgG-Fc fusion protein homodimer), the apparent MW of the resulting SARS-CoV-2-RBD-hIgG-Fc fusion protein monomer is compared against half the molecular weight of the SARS-CoV-2-RBD-hIgG-Fc fusion protein homodimer as a way of determining that the structural purity of the SARS-CoV-2-RBD-hIgG-Fc fusion protein is likely to be correct.

Example 7: SARS-CoV-2-RBD-hIgG-Fc Fusion Protein Sequence Identification by LC-MS with Glycan Removal To obtain an accurate estimate of the SARS-CoV-2-RBD-hIgG-Fc fusion protein mass via mass spectroscopy (MS), the sample is first treated to remove naturally occurring glycan that might interfere with the MS analysis. 100 μL of a 2.5 mg/mL SARS-CoV-2-RBD-hIgG-Fc fusion protein dissolved in 200 mM HEPES, 100 mM NaCl, 50 mM NaOAc, pH 7.0 buffer solution is first buffer exchanged into 0.1 M Tris, pH 8.0 buffer containing 5 mM EDTA using a Zeba desalting column (Pierce, ThermoFisher Scientific, Waltham, Mass.). 1.67 μL of PNGase F enzyme (Prozyme N-glycanase) is added to this solution to remove N-linked glycan present in the fusion protein (e.g., glycan linked to the side chain of the asparagine located at the cNg-N site), and the mixture is incubated at 37° C. overnight in an incubator. The sample is then analyzed via LC-MS (NovaBioassays, Woburn, Mass.) resulting in a molecular mass of the molecule which corresponds to the desired homodimer without the glycan. This mass is then further corrected since the enzymatic process used to cleave the glycan from the cNg-asparagine also deaminates the asparagine side chain to form an aspartic acid, and in doing so the enzymatically treated homodimer gains 2 Da overall, corresponding to a mass of 1 Da for each chain present in the homodimer. Therefore, the actual molecular mass is the measured mass minus 2 Da to correct for each of the enzymatic modifications of the SARS-CoV-2-RBD-hIgG-Fc fusion protein structure in the analytical sample.

Example 8: % Homodimer by Size-Exclusion Chromatography for a SARS-CoV-2-RBD-hIgG-Fc Fusion Protein Size-exclusion chromatography (SEC-HPLC) of SARS-CoV-2-RBD-hIgG-Fc fusion proteins was carried out using a Waters 2795HT HPLC (Waters Corporation, Milford, Mass.) connected to a 2998 Photodiode array at a wavelength of 280 nm. 100 µL or less of a sample containing a SARS-CoV-2-RBD-hIgG-Fc fusion protein of interest was injected into a MAbPac SEC-1, 5 µm, 4×300 mm column (ThermoFisher Scientific, Waltham, Mass.) operating at a flow rate of 0.2 mL/min and with a mobile phase comprising 50 mM sodium phosphate, 300 mM NaCl, and 0.05% w/v sodium azide, pH 6.2. The MAbPac SEC-1 column operates on the principle of molecular size separation. Therefore, larger soluble SARS-CoV-2-RBD-hIgG-Fc aggregates (e.g., multimers of SARS-CoV-2-RBD-hIgG-Fc fusion protein homodimers) eluted at earlier retention times, and the non-aggregated homodimers eluted at later retention times. In separating the mixture of homodimers from aggregated multimeric homodimers via analytical SEC-HPLC, the purity of the SARS-CoV-2-RBD-hIgG-Fc fusion protein solution in terms of the percentage of non-aggregated homodimer was ascertained.

Example 9: In Vitro Fc(Gamma), FcRn, and ACE2 Receptors Binding Affinity for a SARS-CoV-2-RBD-hIgG-Fc Fusion Protein The binding of a SARS-CoV-2-RBD-hIgG-Fc fusion protein to Fc(gamma) receptors at pH 7.4 is conducted using an ELISA assay as follows. Human Fc(gamma) receptors I, IIa, IIb, III and the FcRn receptor are used as mammalian receptors. A SARS-CoV-2-RBD-hIgG-Fc fusion protein is diluted to 10 μg/mL in sodium bicarbonate buffer at pH 9.6 and coated on Maxisorp (Nunc) microtiter plates overnight at 4° C., after which the microplate strips are washed 5 times with PBST (PBS/0.05% Tween-20) buffer and blocked with Superblock blocking reagent (ThermoFisher). Serial dilutions of biotinylated rhFc(gamma) receptors (recombinant human Fc(gamma)RI, Fc(gamma)RIIa, Fc(gamma)RIIb, Fc(gamma)RIII, FcRn; R&D Systems) are prepared in PBST/10% Superblock buffer from 6000 ng/mL to 8.2 ng/mL and loaded at 100 μL/well onto the microplate strips coated with the SARS-CoV-2-RBD-hIgG-Fc fusion protein. Recombinant human ACE2 receptor is purchased from R&D systems and biotinylated using known conjugation procedures and then prepared in PBST/10% Superblock buffer from 6000 ng/mL to 8.2 ng/mL and loaded at 100 μL/well onto the microplate strips coated with the SARS-CoV-2-RBD-hIgG-Fc fusion protein. The microtiter plate is incubated for 1 hour at room temperature after which the microplate strips are washed 5 times with PBST and then loaded with 100 μL/well of streptavidin-HRP diluted 1:10000 in PBST/10% Superblock buffer. After incubating for 45 min, the microplate strips are washed again 5 times with PBST. TMB is added to reveal the bound Fc(gamma), FcRn, or ACE2 receptors proteins and stopped with ELISA stop reagent (Boston Bioproducts). The plate is read in an ELISA plate reader at 450 nm, and the OD values (proportional to the binding of each rhFc(gamma), FcRn, or ACE2 receptor to the SARS-CoV-2-RBD-hIgG-Fc fusion protein) are plotted against log concentrations of each rhFc(gamma) receptor or FcRn or ACE2 receptor added to each well to generate binding curves using GraphPad Prism software.

General Examples for In Vivo Serology Assays for Evaluating SARS-CoV-2 RBD-hIgG-Fc Fusion Protein Action in Serum

Example 10: In Vivo Quantitative ELISA for Evaluating SARS-CoV-2 RBD IgG Antibody Titer in Human or Mouse Serum A quantitative SARS-CoV-2 SP/RBD-specific IgG ELISA is used to measure anti-SP/RBD IgG Ab titers in human or mouse serum and plasma samples, including heat-inactivated serum or heat-inactivated plasma. The ELISA method uses a recombinant SP/RBD immobilized on plastic wells of a 96-well microtiter ELISA plate (as is shown in FIG. 81) as the capture antigen that binds anti-SP/RBD-specific antibodies (IgG) in serum samples when incubated in the microplate wells. A wash step removes all unbound proteins leaving the anti-SP/RBD IgG bound to the plate. Anti-SP/RBD antibodies are detected via addition of anti-human or anti-mouse IgG antibody (not cross-reactive to IgM) that is conjugated to horseradish peroxidase (HRP), depending on the species origin of the serum sample. After a second wash to remove the unbound HRP-antibody conjugate, 3,3',5,5'-trimethylbenzidine (TMB) is added to each well that is catalyzed by the HRP enzyme causing a colorimetric change that is proportional to the amount of bound HRP-antibody conjugate. The color development is stopped by adding acid and the color density of each well is measured using a spectrophotometric microplate reader, and SoftMax Pro or Gen 5 software are used for acquiring absorbance data and for analyzing titer values for each sample using the standard curve. The standard curve is generated using serial dilutions of a purified human or mouse IgG sample of known quantity i.e., μg/mL) bound directly to the plastic well (i.e., the well does not contain bound-SP/RBD or any serum sample) and developed the same as described above for serum samples. The quantity of SP/RBD-specific antibodies (i.e., titer value) for each serum sample is expressed as μg/mL units derived from the standard curve using a 4-parameter curve fit model via an appropriate software (e.g., SoftMaxPro or Gen 5).

Example 11: Improved In Vivo Quantitative ELISA for Evaluating SARS-CoV-2 RBD IgG Antibody Titer in Mouse and NHP Serum A quantitative SARS-CoV-2 SP/RBD-specific IgG ELISA is used to measure anti-SP/RBD IgG Ab titers in mouse or NHP serum and plasma samples, including heat-inactivated serum or heat-inactivated plasma. The ELISA method uses a recombinant SP/RBD (Lake Pharma) immobilized on plastic wells of a 96-well microtiter ELISA plate (as is shown in FIG. 81) as the capture antigen that binds anti-SP/RBD-specific antibodies (IgG) in serum samples when incubated in the microplate wells.

SPD/RBD protein (Lake Pharma, Belmont Calif.) is diluted to 2.5 μg/mL in Carb/Bicarb coating buffer pH 9.6, vortexing to mix. 100 μL/well of coating solution is added to all wells of a Maxisorb ELISA plate using a multichannel pipette. The plate is covered with a plate sealer and incubated overnight at 2-8° C. Plates are washed 5× with PBST using a plate washer (300 μL/well/wash) to remove all unbound protein. 300 μL of Superblock blocking solution is added to each well and the plate is incubated for greater than 1 hour at room temperature.

Standard mouse serum or NHP serum is diluted to create a standard curve depending on the species-specific assay format. To create the first standard, a mouse serum or NHP serum sample known to be positive with high anti-SP/RBD titers is diluted 1:10 (20 μL of each sample plus 180 μL of Sample Dilution Buffer) and mixed thoroughly by vortexing. The remaining standards are created by 2-fold serial dilutions of the 1:10 sample Each dilution of standard mouse or NHP sample is run in duplicate at 100 μL/well on each plate.

Serum or plasma samples are diluted 1:100 (4 μL of each sample plus 396 μL of Sample Dilution Buffer) and mixed thoroughly by vortexing Blocking solution is decanted from plate wells and the plates are washed 5 times with PBST using a plate washer (100 μL PBST/well/w ash). 100 μL of diluted standard samples are loaded to each well in columns 1 and 2 of each plate. 100 μL of diluted test serum sample is added to the remaining wells. Test plates are covered with sealing tape and incubated for 1 hour at room temperature.

10 μL of anti-mouse or anti-NHP IgG-Fc HRP plus 9.99 mL of 1×HRP Conjugate Stock Stabilizer are mixed well by vortexing to create a 1:1000 stock solution. The stock solution is further diluted by vortexing 300 μL of 1:1000 solution with 11.7 mL of PBST/SB to create a 1:40,000 dilution. The plates are washed 5 times with 300 μL PBST/well/wash with a plate washer and the plates are patted dry with paper towel.

100 μL are added per well of 1:40,000 diluted anti-mouse or anti-NHP IgG-Fc HRP and the plates are incubated for 1 hour at room temperature in the dark. The plates are then washed five times with 300 μL PBST/well/wash with a plate washer and one time with dH$_2$O (300 μL dH$_2$O/well/wash) manually. The plates are then patted dry on paper towel. The TMB solution is added at 100 μL/well one column at a time in an orderly fashion starting from column 1 towards column 12 at equal time intervals followed by incubation for 10-20 minutes in the dark with monitoring of color development. The color development is stopped by adding 100 μL/well stop reagent in the same order starting from column 1 towards column 12 and at the same equal time intervals as done before for the TMB substrate solution. The color density of each well is measured within 30 minutes using a spectrophotometric microplate reader at 450 nM, and Soft-Max Pro or Gen 5 software is used for acquiring absorbance data and for analyzing titer values for each sample using the standard curve.

A standard curve is generated using the concentration (log of 1/dilution of standard mouse or NHP samples) versus OD values. Antibody titers in the samples are analyzed by linear regression through 10-12 points on the standard curve that resulted in the highest $R^2$ value. Values are reported as RBD-specific IgG titer (Reference (Ref) Titer Units).

Example 12: In Vivo General Preclinical Evaluation of the Effectiveness of SARS-CoV-2-RBD-hIgG-Fc Formulations in Inducing an Anti-SP/RBD IgG Ab Titer Response in Mice In vivo studies to evaluate the effectiveness of different SARS-CoV-2-RBD-hIgG-Fc fusion protein formulations are carried out in mice as follows.

6- to 8-week old female BALB/c mice or 8- to 10-month old female BALB/c mice (Jackson Laboratories, Bar Harbor, Me.) are acclimatized for at least 7 days before being weighed and then assigned into study groups for dosing. The older mice are used to model the effectiveness of the SARS-CoV-2-RBD-hIgG-Fc fusion protein formulations in older people (e.g., greater than 70 years old). N=5 mice are used per 6- to 8-week old group and N=15 mice are used per 8- to 10-month old group, and mice are randomly assigned into each study group. The mice are kept 5 animals per cage in automatically ventilated racks and are given standard irradiated feed and filtered water ad libitum. Mice are ear tagged individually for identification and the study cages are labeled with animal IDs, study name, and study group identification, and the study records including individual and group dosing sheets, blood/serum collection sheets, weight measurement, and health observation records per standard operating procedures (SOPs) and specific study protocols.

Mice are administered up to three doses of a SARS-CoV-2-RBD-hIgG-Fc fusion protein synthesized in transiently transfected HEK293 cells according to Example 1, transiently transfected CHO cells according to Example 2, or stably transfected CHO cells according to Example 3, or a SARS-CoV-2 Spike Protein RBD obtained from a commercial source. Doses are given three weeks apart (Day 0, Day 21, and Day 42) via subcutaneous (s.c.), intramuscular (i.m.), or intradermal (i.d.) injection. Mice are observed for one to three hours after dose administration for any immediate reactions and then daily for general health. All mice are non-terminally bled via submandibular venipuncture 7 to 14 days prior to the first immunization and then 12 to 14 days after each dose administration to obtain serum samples for SARS-CoV-2 RBD IgG Ab titer assessment. The collected blood is allowed to clot, and the serum is separated by centrifuging micro-vacutainer tubes and aliquoted and frozen for antibody analysis by ELISA according to the methods described in Example 10 or Example 11.

After the last serum collection at 12 to 14 days after the third immunization (i.e., Days 54 to 56) groups of mice that showed substantial antibody responses and the unimmunized control group may be kept for further evaluation. For the kept mice, blood is collected at 30 days and 60 days after the third dose (Day 72 and Day 102 respectively) from each mouse by submandibular venipuncture method, allowed to clot, and the serum is separated by centrifuging micro-vacutainer tubes and aliquoted and frozen for antibody analysis by ELISA according to the methods described in Example 10, Example 11 and Example 13.

The mice that are kept because they showed substantial antibody responses are given a booster dose of the SARS-CoV-2-RBD-hIgG-Fc fusion protein on Day 102 via s.c., i.m., or i.d. injection. Mice are observed for one to three hours after administration for any immediate reactions and then daily for general health. Blood is collected 12 to 14 days after the final booster dose from each mouse by submandibular venipuncture method, allowed to clot, and the serum is separated by centrifuging micro-vacutainer tubes and aliquoted and frozen for antibody analysis by ELISA according to the methods described in Example 10, Example 11 and Example 13 to evaluate the recall (memory) immune response in those groups.

Different adjuvants (e.g., Advax-2, Advax-3, VacAdx, Montanide™ ISA-51, Montanide™ ISA-720 or substitute) may be tested in combination with the SARS-CoV-2-RBD-hIgG-Fc fusion proteins. Appropriate v/v ratios of SARS-CoV-2-RBD-hIgG-Fc fusion protein and adjuvants are mixed/emulsified immediately prior to being administered to the mice.

Example 13: In Vivo General Serology Assay for Evaluating the Efficacy of SARS-CoV-2 Antibodies in Serum in Neutralizing ACE2 Binding to the SARS-CoV-2-Spike Protein-RBD The ACE2 Inhibition Enzyme Linked Immunosorbent Assay (ELISA) is designed to measure the level of inhibitory anti-SP/RBD IgG titers present in serum that inhibit the binding of recombinant human ACE2 to recombinant SP/RBD. The serial dilution of a serum sample in the assay will yield the Inhibitory Dilution 50% (ID50), a potency value of that sample, which represents the dilution at which 50% of the total ACE2 binding signal occurred. The assay can be used to assess samples from multiple species, e.g., human, NHP, mouse, and rabbit, such that any sample ID50 value can be compared to any other sample's value allowing for such comparisons across species and between separate experiments.

The assay is a competitive inhibition ELISA in which serially diluted serum samples and biotinylated-human ACE2 (biotin-huACE2, R&D Systems, Minneapolis, Minn.) are added to recombinant SP/RBD protein bound to plastic wells of a 96-well plate for competitive binding to SP/RBD. The level of inhibitory (i.e., neutralizing) IgG (i.e., antibodies) present in the serum sample will correlate to the degree of inhibition of biotin-huACE2 binding to SP/RBD. After washing away serum and biotin-huACE2, streptavidin-HRP (Thermo Fisher, Waltham, Mass.) is added that binds to any biotin-huACE2 that bound to SP/RBD which is followed by washes and color development via addition of a TMB substrate. The HRP (enzyme)/TMB (substrate) reaction is stopped by the addition of Stop Reagent (1% H2SO4) and the color intensity (optical density, OD) is measured via a microplate reader at 450 nm wavelength. The ID50 potency value for each sample is calculated as the reciprocal dilution that corresponds to the OD450 value that exactly 50% of the total signal (i.e., maximum OD450 value, 100%) achieved by non-competed biotin-huACE2, using GraphPad Prism software via a 4-parameter curve fit (log-inhibitor vs. response, variable slope) algorithm.

Example 14: In Vivo General Quantitative ELISA for Evaluating the Effectiveness of a SARS-CoV-2 RBD Formulation in Inducing an Anti-SP/RBD IgG Ab Titer Response for GLP Toxicology Studies in Rabbits In vivo studies to evaluate the toxicology of a SARS-CoV-2-RBD-hIgG-Fc fusion protein formulation of SEQ ID NO: 19 are carried out in rabbits as follows.

The SEQ ID NO: 19 induced immunogenicity assay is an ELISA in which Anti-SP/RBD antibodies present in the rabbit nonclinical study serum samples are captured using SARS-CoV-2 SP/RBD coated on microtiter wells and then detected by a HRP-enzyme conjugated anti-rabbit IgG H+L-HRP secondary antibody, followed by TMB substrate system. A standard curve (1000 ng/mL to 1.37 ng/mL) is generated using SARS-CoV-2 (2019-nCoV) Spike RBD Antibody Rabbit pAb spiked into buffer containing a percentage of normal rabbit serum matching the sample dilution level. (For example, when testing samples diluted 1:100, 1% normal serum buffer is used to prepare the standard curve.) Anti SP/RBD antibodies concentrations in the serum samples are analyzed by interpolating on the 4-parameter standard curve fitting using SoftMax software. Three positive assay controls (High QC, Mid QC, Low QC) and a negative control (Negative QC) were prepared by spiking the Rabbit pAb into buffer and were stored frozen at −20° C. as single-thaw use aliquots. (These QCs were also used in the validation assays to evaluate Accuracy and Precision.) Additional samples for specific validation tests (e.g., short-term stability, freeze/thaw stability) were prepared by spiking rabbit polyclonal Anti-SP/RBD antibodies directly into rabbit serum. For the purposes of validation, a minimum required dilution (MRD) of 1:100 in Sample Dilution Buffer was used for serum samples used during validation to match the MRD used for the actual study serum samples. Although most validation work requiring serum samples, or serum containing buffer, were conducted using reconstituted normal rabbit serum, selected parameters such as linearity and limits of quantitation also tested using pooled normal rabbit serum (BioIVT) to better represent the actual study serum samples.

As determined during validation, intra- and inter-assay accuracy for this assay range from 88-117% across all three non-zero QC levels, with inter- and intra-assay precision ranging from 6-10% and 1-11% respectively across all QC levels. Using pooled serum, the LLOQ was determined to be 2 ng/mL, vs. 1 ng/mL in normal serum. ULOQ was found to be 500 ng/mL in pooled serum, versus 1000 ng/mL in normal serum. As the pooled serum more closely represented the study samples, the LLOQ and ULOQ were set at 2 ng/mL and 500 ng/mL, respectively. The assay was found to be linear between these limits of quantitation, although a significant hook effect was seen above ~1000 ng/mL. At very high spiked antibody concentrations, measured values were found to be as low as 192 ng/mL. (Based on this result, any sample measuring above 192 ng/mL during study sample analysis was re-tested at a higher dilution level.) Spike-recovery was accurate across 11 different serum samples, with recoveries ranging from 74-105% at a high spike level (400 ng/mL), 91-117% at a mid-spike level (80 ng/mL), and 86-98% at a low spike level (10 ng/mL). Spiked serum samples were found to be stable through at least 3× freeze-thaw cycles (93-118% recovery), up to 1 week at 4° C. (90-93% recovery), and 4 hours at room temperature (92-106% recovery). These validation results show that the SEQ ID NO: 19 immunogenicity ELISA is highly accurate and reproducible, and fit for purpose.

Example 15: Plaque Reduction Neutralization Test (PRNT)

Neutralization Ab (nAb) titers are determined by the Plaque Reduction Neutralization Test (PRNT). Briefly, serum is heat-inactivated for 30 min at 56 degrees Celsius, then serially diluted 2-fold in a microtiter plate. A diluted virus suspension is added to the diluted samples at a 1:1 (v/v) ratio and incubated at 37 degrees Celsius for 1 h to allow serum IgG binding to virus. This serum-virus mixture is then added over a monolayer of Vero E6 cells at 80% confluency on tissue-culture-treated plastic plates for 1 h to allow free virus to infect cells (these cells express high levels of SP target protein, huACE2). At this time, an overlay of complete DMEM medium, 2×MEM, and 1.5% agarose is added in a 1:1:1 (v/v/v) ratio. Cells are incubated for 48 hours before fixating with 10% neutral buffered formalin for at least 30 min. The agarose overlay plugs are removed and cells stained with 0.5% Crystal Violet. After washing the stain away, cells are dried overnight at ambient temperature and plaques are enumerated. Negative and -positive control nAbs (Sino Biological, Wayne, Pa.) are used to convert absorbance values of sample dilution curves into neutralization percentage values from which ID50 neutralization potency values are derived for each sample.

Examples Illustrating In Vitro and In Vivo Performance of SARS-CoV-2-RBD-hIgG-Fc Fusion Proteins Example 16: In Vitro Human Fc(Gamma) and ACE2 Receptors Binding Affinity for a SARS-CoV-2-RBD-hIgG-Fc Fusion Protein of SEQ ID NO: 19

The in vitro binding of the SARS-CoV-2-RBD-hIgG-Fc fusion protein of SEQ ID NO: 19 to the human Fc(gamma)

and ACE2 receptors at pH 7.4 was conducted according to the procedure of Example 9. The in vitro binding of the human IgG to the human FcRn at pH 7.4 was conducted according to the procedure of Example 9.

Plates were read in an ELISA plate reader at 450 nm, and the OD values (proportional to the binding of each rhFc (gamma) receptor to the SARS-CoV-2-RBD-hIgG-Fc fusion protein of SEQ ID NO: 19) were plotted against log concentrations of each rhFc(gamma) receptor added to each well to generate binding curves using GraphPad Prism software.

Figure 19:
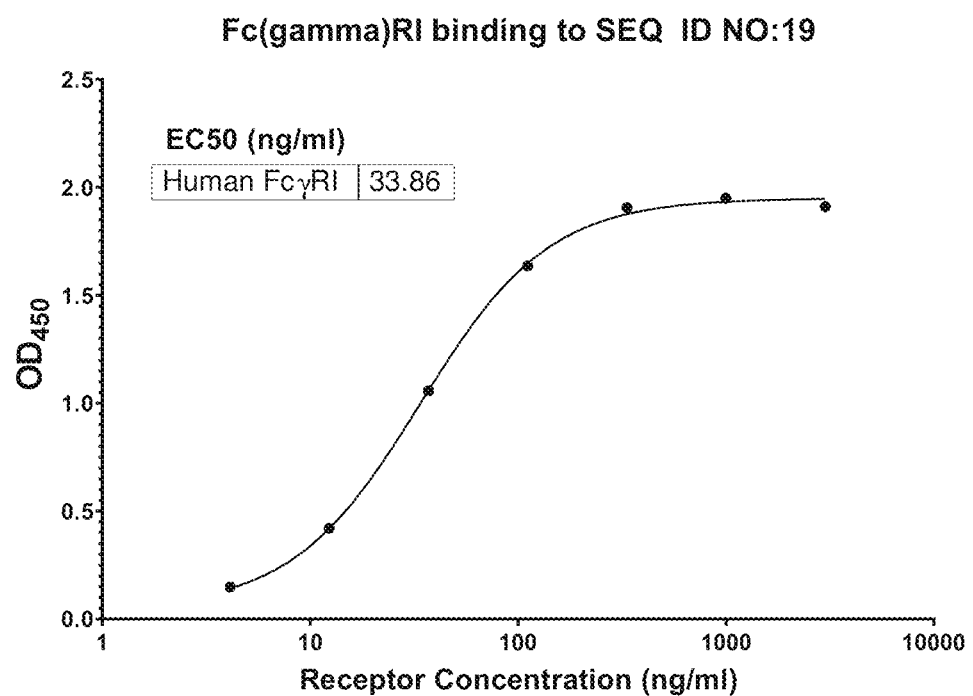
FIG. 19 illustrates the EC50 of human Fc(gamma)RI binding to the SARS-CoV-2-RBD-hIgG-Fc fusion protein of SEQ ID NO: 19.
Figure 20:
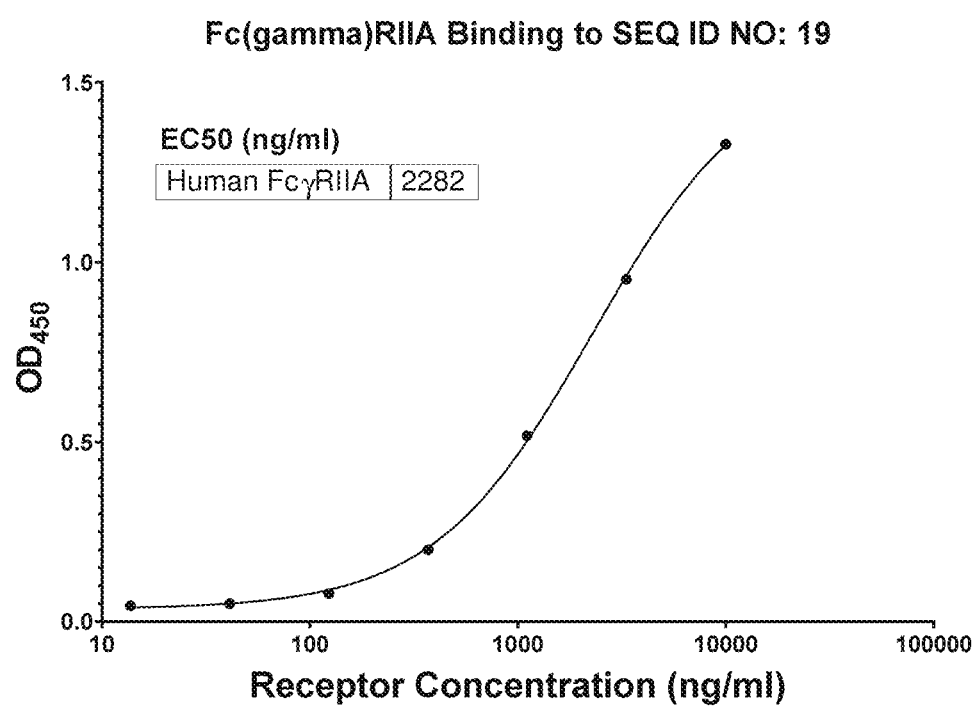
FIG. 20 illustrates the EC50 of human Fc(gamma)RIIa binding to the SARS-CoV-2-RBD-hIgG-Fc fusion protein of SEQ ID NO: 19.
Figure 21:
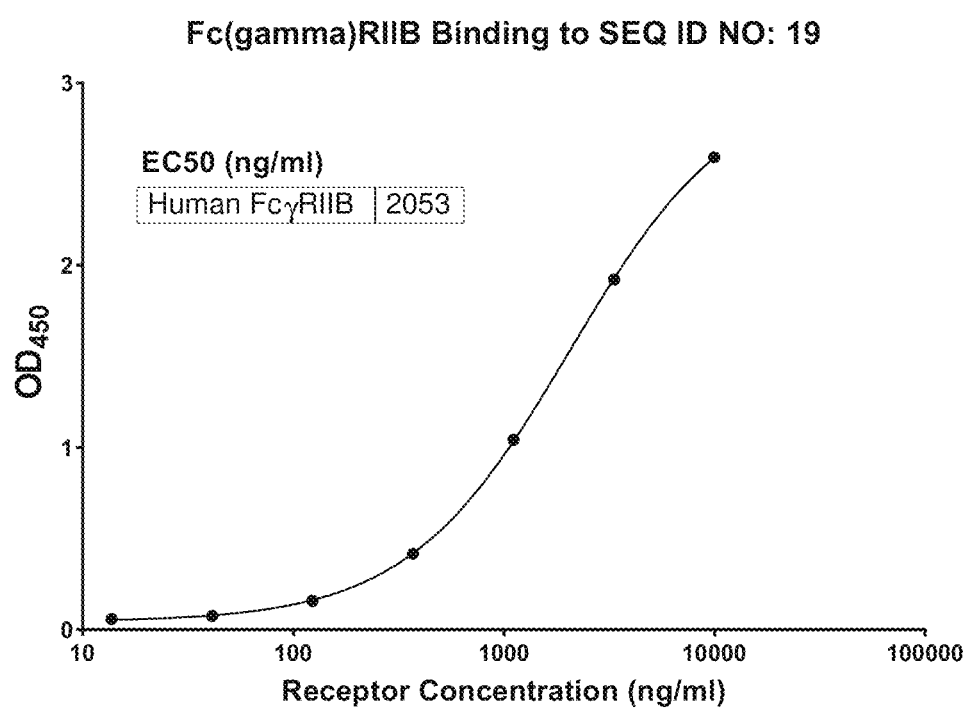
FIG. 21 illustrates the EC50 of human Fc(gamma)RIIb binding to the SARS-CoV-2-RBD-hIgG-Fc fusion protein of SEQ ID NO: 19.
Figure 22:
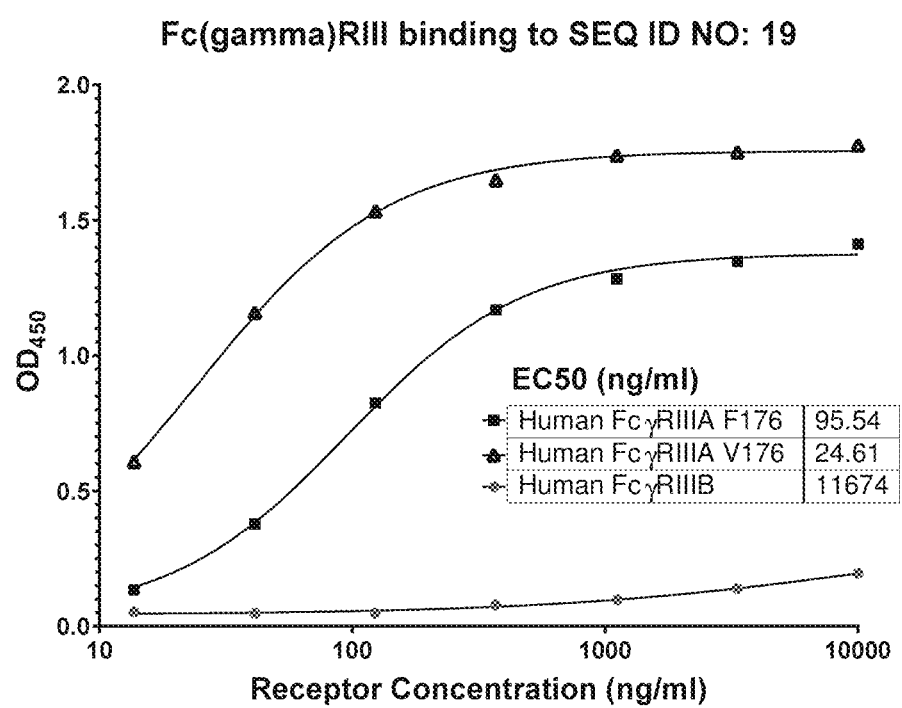
FIG. 22 illustrates the EC50 of human Fc(gamma)RIII binding to the SARS-CoV-2-RBD-hIgG-Fc fusion protein of SEQ ID NO: 19.
Figure 23:
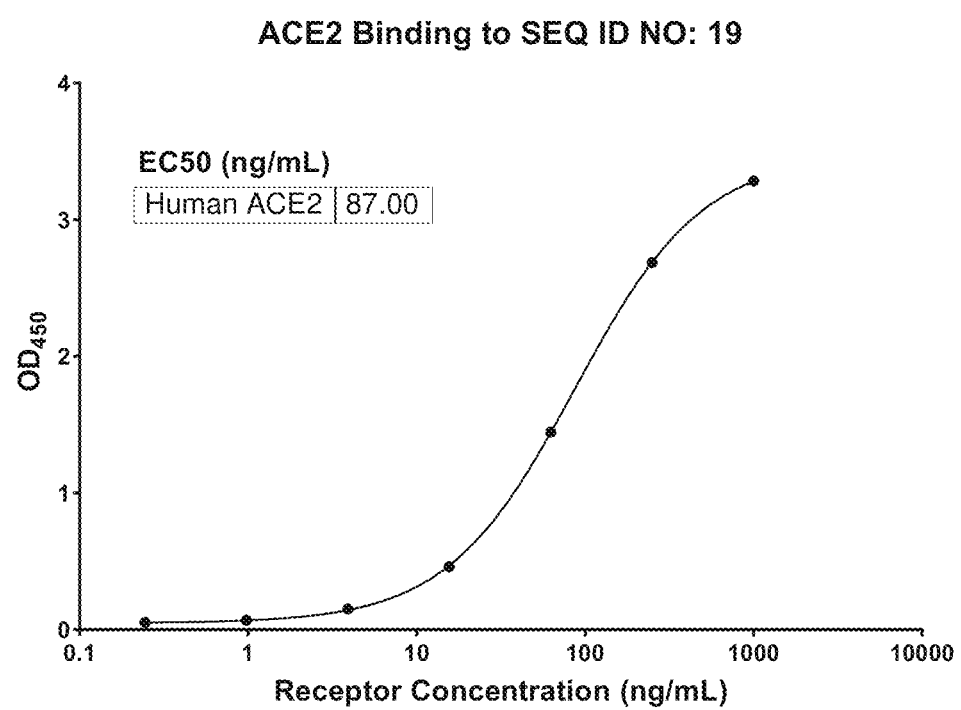
FIG. 23 illustrates the EC50 of human ACE2 binding to the SARS-CoV-2-RBD-hIgG-Fc fusion protein of SEQ ID NO: 19 and of human IgG.

As illustrated in FIG. 19, the EC50 of human Fc(gamma) RI binding to the SARS-CoV-2-RBD-hIgG-Fc fusion protein of SEQ ID NO: 19 is 33.86 ng/mL. As illustrated in FIG. 20, the EC50 of human Fc(gamma)RIIa binding to the SARS-CoV-2-RBD-hIgG-Fc fusion protein of SEQ ID NO: 19 is 2282 ng/mL. As illustrated in FIG. 21, the EC50 of human Fc(gamma)RIIb binding to the SARS-CoV-2-RBD-hIgG-Fc fusion protein of SEQ ID NO: 19 is 2053 ng/mL. As illustrated in FIG. 22, the EC50 of human Fc(gamma) RIIIa F176 binding to the SARS-CoV-2-RBD-hIgG-Fc fusion protein of SEQ ID NO: 19 is 95.54 ng/mL, the EC50 of human Fc(gamma)RIIIa V176 binding to the SARS-CoV-2-RBD-hIgG-Fc fusion protein of SEQ ID NO: 19 is 24.61 ng/mL, and the EC50 of human Fc(gamma)RIIIb binding to the SARS-CoV-2-RBD-hIgG-Fc fusion protein of SEQ ID NO: 19 is 11674 ng/mL. As illustrated in FIG. 23, the EC50 of human ACE2 binding to the SARS-CoV-2-RBD-hIgG-Fc fusion protein of SEQ ID NO: 19 is 87.00 ng/mL.

Figure 24:
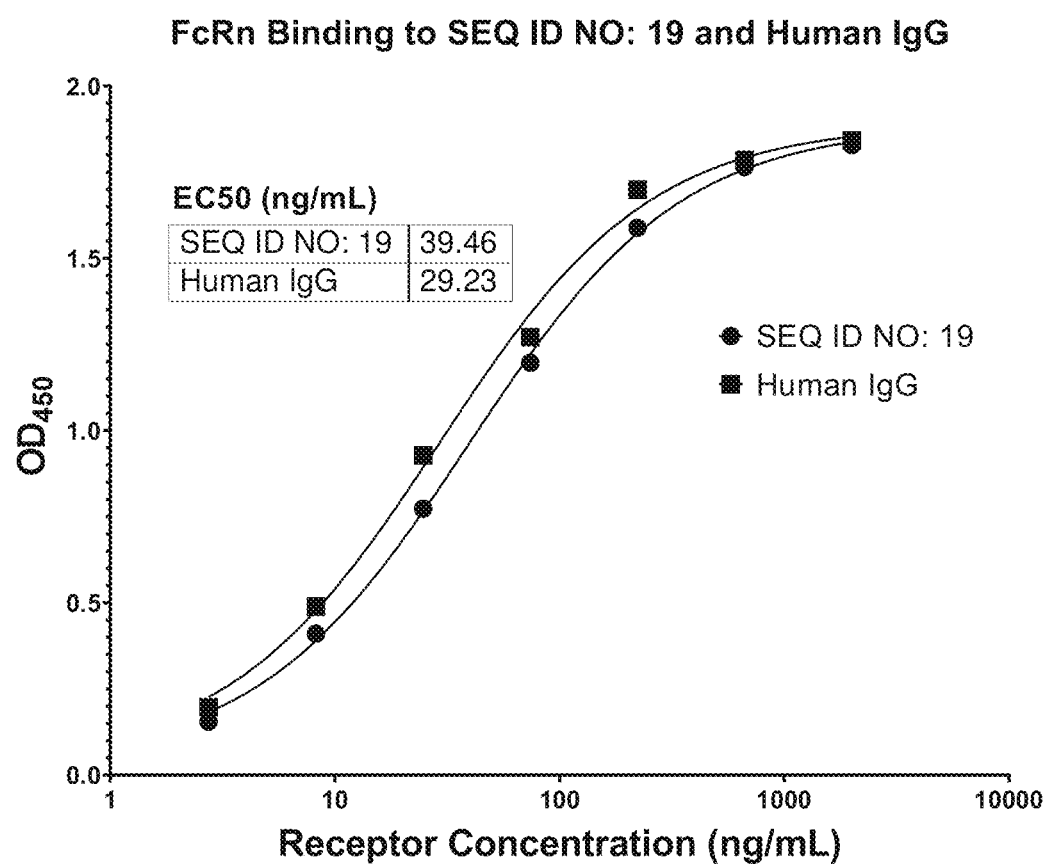
FIG. 24 illustrates the EC50 of human FcRn receptor binding to the SARS-CoV-2-RBD-hIgG-Fc fusion protein of SEQ ID NO: 19.

As illustrated in FIG. 24, the EC50 of human FcRn binding to the SARS-CoV-2-RBD-hIgG-Fc fusion protein of SEQ ID NO: 19 is 39.46 ng/mL, while the EC50 of human FcRn binding to human IgG (used as a control) is 29.23 ng/mL, indicating that the FcRn receptor binding is preserved using SEQ ID NO: 19 compared to a human IgG control.

Example 17: In Vivo Screening of the Effectiveness of the SARS-CoV-2-RBD-hIgG-Fc Fusion Protein of SEQ ID NO: 17 in Mice without Adjuvant The SARS-CoV-2-RBD-hIgG-Fc fusion protein of SEQ ID NO: 17 was synthesized according to Example 1 and purified according to Example 4. The fusion protein structure was confirmed by non-reducing and reducing CE-SDS according to Example 6 and the fusion protein sequence identification was confirmed by LC-MS with glycan removal according to Example 7.

According to the procedure of Example 12, eight groups of N=5, 6- to 8-week old female BALB/c mice were administered via subcutaneous injection the SARS-CoV-2-RBD-hIgG-Fc fusion protein of SEQ ID NO: 17 at dose levels varying from 0.05 μg/dose to 100 μg/dose on Day 0, Day 21 and Day 42 without adjuvant in a 100 μL volume according to Table 2. All mice were non-terminally bled via submandibular venipuncture at 14 and 21 days after each injection to obtain serum samples for anti-SP/RBD Ab titer assessment. The induced anti-SP/RBD IgG Ab titer response (mean IgG μg/mL via an IgG ELISA standards curve) after administration of the SARS-CoV-2-RBD-hIgG-Fc fusion protein of SEQ ID NO: 17 without adjuvant was measured according to Example 10 and plotted against the administered dose level in μg immediately before the second dose on Day 21 as illustrated in FIG. 25, and on Day 35 as illustrated in FIG. 26.

TABLE 2

Test Groups and Dose Levels of SEQ ID NO: 17.

| GROUP | SARS-CoV-2 SP/RBD-Fc fusion protein SEQ ID NO: | Dose Level (μg/Dose) |
|---|---|---|
| 1 | SEQ ID NO: 17 | 0.05 |
| 2 | SEQ ID NO: 17 | 0.1 |
| 3 | SEQ ID NO: 17 | 0.3 |
| 4 | SEQ ID NO: 17 | 1 |
| 5 | SEQ ID NO: 17 | 3 |
| 6 | SEQ ID NO: 17 | 10 |
| 7 | SEQ ID NO: 17 | 30 |
| 8 | SEQ ID NO: 17 | 100 |

The data show that dose levels between 1 μg and 100 μg resulted in noticeable increase in the induced anti-SP/RBD IgG Ab titer response, with the best responses at Day 35 occurring for 1 μg, 10 μg, and 100 μg dose levels. The kinetic response to dose levels of 1 μg, 3 μg, 10 μg, 30 μg and 100 μg of SEQ ID NO: 17 after 1, 2, and 3 doses is illustrated in FIG. 27, highlighting that measurable increase in anti-SP/RBD IgG Ab titer response can be seen 14 Days after each dose, and that the SP/RBD IgG Ab titer response continued to increase with each additional dose for all dose levels.

Example 18: In Vivo Screening of the Effectiveness of the SP-RBD of SEQ ID NO: 2 in Mice without Adjuvant The SARS-CoV-2 SP/RBD (without the Fc) of SEQ ID NO: 2 was obtained from a commercial source (item #46438; Lake Pharma, Inc., San Mateo, Calif.) and was used to compare the enhancement of Ab responses by an Fc containing SP/RBD-Fc protein, SEQ ID NO: 17, which was synthesized according to Example 1, purified according to Example 4, structurally confirmed by non-reducing and reducing CE-SDS according to Example 6 and with structure identification confirmed by LC-MS with glycan removal according to Example 7. The relative dose levels were standardized based on equal molar amounts of the SP/RBD Ag between the SARS-CoV-2-RBD-hIgG-Fc fusion protein of SEQ ID NO: 17 and SP/RBD of SEQ ID NO: 2.

According to the procedure of Example 12, groups of N=5, 6- to 8-week old female BALB/c mice were administered via subcutaneous injection the SP/RBD of SEQ ID NO: 2 at dose levels of 5 μg/dose, 15 μg/dose, and 40 μg/dose in a 100 μL volume or the SARS-CoV-2-RBD-hIgG-Fc fusion protein of SEQ ID NO: 17 without adjuvant at dose levels of 1 μg/dose, 3 μg/dose, 5 μg/dose, 30 μg/dose, and 100 μg/dose in a 100 μL volume on Day 0, Day 21 and Day 42, without adjuvant according to Table 3. One group of mice was administered a saline control. All mice were non-terminally bled via submandibular venipuncture at 14 and 21 days after each injection to obtain serum samples for anti-SP/RBD Ab titer assessment. The induced anti-SP/RBD IgG Ab titer response (mean IgG μg/mL via an IgG ELISA standards curve) after administration of the SP/RBD of SEQ ID NO: 2 or the SARS-CoV-2-RBD-hIgG-Fc fusion protein of SEQ ID NO: 17 without adjuvant at each of the dose levels was measured according to Example 10 on Day 14 and Day 21 and is illustrated in FIG. 28.

Importantly, there is a relative "epitope dose" difference of approximately 0.5 between the SP/RBD of SEQ ID NO: 2 (27 kDa monomer) and SEQ ID NO: 17 (104 kDa dimer) based on formula weight and consideration of SEQ ID NO:

17 bivalency; i.e., the bivalent SARS-CoV-2-RBD-hIgG-Fc fusion protein of SEQ ID NO: 17 contains two moieties of the SP/RBD epitope with a total formula weight that is approximately twice that of 2 SARS-CoV-2-RBD-hIgG-Fc fusion protein monomers (i.e., 104 kDa vs 54 kDa, respectively). For example, 10 µg of SEQ ID NO: 17 dimer is equivalent to ~5 µg of SEQ ID NO: 17 monomer.

TABLE 3

Test Cohorts and Dose Levels of SEQ ID NO: 17 and SEQ ID NO: 2.

| Cohort | SARS-CoV-2 SP/RBD-Fc fusion protein SEQ ID NO: | Dose Level (µg/Dose) |
|---|---|---|
| 1 | SEQ ID NO: 17 | 0.05 |
| 2 | SEQ ID NO: 17 | 0.1 |
| 3 | SEQ ID NO: 17 | 0.3 |
| 4 | SEQ ID NO: 17 | 1 |
| 5 | SEQ ID NO: 17 | 3 |
| 6 | SEQ ID NO: 17 | 10 |
| 7 | SEQ ID NO: 17 | 30 |
| 8 | SEQ ID NO: 17 | 100 |
| 9 | SEQ ID NO: 2 | 5 |
| 10 | SEQ ID NO: 2 | 15 |
| 11 | SEQ ID NO: 2 | 40 |
| 12 | PBS | — |

The effect of the Fc moiety is demonstrated at both Day 14 and Day 21. The induced anti-SP/RBD IgG Ab titer response of SEQ ID NO: 17 including the Fc fragment reached near maximum titers even at 14 days after the initial dose as shown in FIG. 28, whereas the SP/RBD with no Fc fragment induced virtually no anti-SP/RBD IgG Ab titer response even after 21 days. This difference in immunogenicity between these two non-adjuvanted materials demonstrates the significant "built-in adjuvant" capability of the Fc moiety of the fusion protein Ag.

Example 19: In Vivo Screening of the Effectiveness of the SARS-CoV-2-RBD-hIgG-Fc Fusion Protein of SEQ ID NO: 17 in Mice with Adjuvant The SARS-CoV-2-RBD-hIgG-Fc fusion protein of SEQ ID NO: 17 was synthesized according to Example 1 and purified according to Example 4. The fusion protein structure was confirmed by non-reducing and reducing CE-SDS according to Example 6 and the fusion protein sequence identification was confirmed by LC-MS with glycan removal according to Example 7. The SARS-CoV-2 SP/RBD (without the Fc) of SEQ ID NO: 2 was obtained from a commercial source (item #46438; Lake Pharma, Inc., San Mateo, Calif.).

According to the procedure of Example 12, groups of N=5, 6- to 8-week old female BALB/c mice were administered the SARS-CoV-2-RBD-hIgG-Fc fusion protein of SEQ ID NO: 17 at a dose levels and adjuvants as given in Table 4 and Table 5 and the SP/RBD of SEQ ID NO: 2 at a dose level of 5 µg/dose at Day 0, Day 21 and Day 42. The induced anti-SP/RBD IgG Ab titer response (mean IgG µg/mL via an IgG ELISA standards curve) after administration of the SARS-CoV-2-RBD-hIgG-Fc fusion protein of SEQ ID NO: 17 and the SP/RBD of SEQ ID NO: 2 was measured according to Example 10 at Day 21 (illustrated in FIG. 29), at Day 35 (illustrated in FIG. 30), Day 56 (illustrated in FIG. 31) and Day 88 (illustrated in FIG. 32).

TABLE 4

Description of Adjuvants Screened in Preliminary SP/RBD-Fc Immunization Studies in BALB/C Mice.

| Adjuvant | Manufacturer | Description |
|---|---|---|
| Advax-1 Advax-2 Advax -3 | Vaxine Pty Ltd (Bedford Park South, Australia) | Based on delta inulin that has been previously shown in animal models to enhance the immunogenicity of a broad range of viral and bacterial Ag's in addition to being safe and effective in preliminary human clinical trials. Notably, Advax ™ adjuvant was recently shown to enhance the immunogenicity and protection conferred by both inactivated and recombinant SARS vaccines, without the excess Th2 bias of alum adjuvants and hence without the risk of inducing significant eosinophilic immunopathology. |
| Vac-adx-10 | InvivoGen (San Diego, CA) | A squalene-based oil-in-water nano-emulsion with a formulation similar to that of MF59 ® that has been licensed in Europe for adjuvanted flu vaccines. |
| Montanide ™ ISA 51 | Seppic Inc. (Paris, France) | A water-in-oil (W/O) emulsion composed of a mineral oil and a surfactant from the mannide monooleate family that is used as an adjuvant carrier with immune stimulatory effect. When mixed with Ag's in a ratio of 50/50 v/v (1:1), ISA-51 enhances Ag-specific Ab titers and cytotoxic T-lymphocyte (CTL) responses. |
| Montanide ™ ISA 720 | Seppic Inc. (Paris, France) | An adjuvant which forms a stable water-in-oil emulsion. Its use with several recombinant malaria proteins has resulted in high Ab levels in mice, rabbits and sheep. Montanide ™ ISA 720 contains a natural metabolizable oil and a highly-refined emulsifier from the mannide monooleate family. |

TABLE 5

Test Cohorts, Dose Levels and Adjuvants
with SEQ ID NO: 17, SEQ ID NO: 2 and PBS.

| Cohort | SARS-CoV-2 SP/RBD-Fc fusion protein SEQ ID NO: | Dose Level (µg/Dose) | Adjuvant |
|---|---|---|---|
| 1 | SEQ ID NO: 17 | 3 | Advax-1 50%:50% v/v |
| 2 | SEQ ID NO: 17 | 10 | Advax-1 50%:50% v/v |
| 3 | SEQ ID NO: 17 | 3 | Montanide ™ ISA 51 50%:50% v/v |
| 4 | SEQ ID NO: 17 | 10 | Montanide ™ ISA 51 50%:50% v/v |
| 5 | SEQ ID NO: 17 | 10 | Advax-2 50%:50% v/v |
| 6 | SEQ ID NO: 17 | 10 | Advax -3 50%:50% v/v |
| 7 | SEQ ID NO: 17 | 10 | vac-adx-10 50%:50% v/v |
| 8 | SEQ ID NO: 17 | 10 | Montanide ™ ISA 720 30%/70% v/v |
| 9 | SEQ ID NO: 2 | 5 | |
| 10 | PBS | | |

Figure 32:
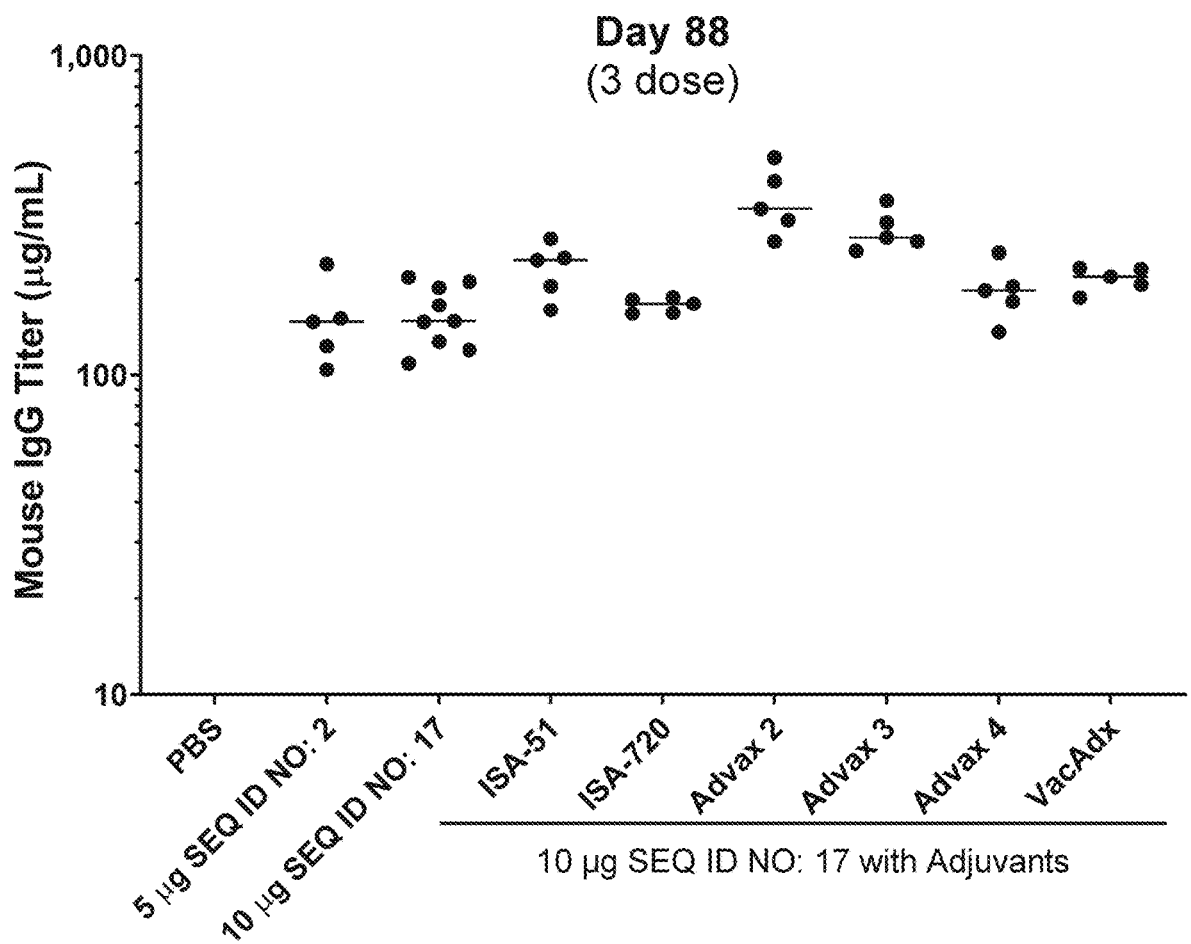
FIG. 32 illustrates the anti-SP/RBD IgG Ab titer response in 6- to 8-week old female BALB/c mice in various adjuvanted formulations containing a 10 μg dose level of the SARS-CoV-2-RBD-hIgG-Fc fusion protein of SEQ ID NO: 17 on Day 88 after an injection on Day 0, Day 21 and Day 42.

Some, but not all, adjuvanted formulations containing a 10 µg dose level enhanced immunogenicity after one (Day 21), two (Day 35), and three (Day 56) doses by approximately 3- to 5-fold, demonstrating a range of effectiveness among the adjuvants. Notably, 32 days after the third dose (i.e., Day 88), titers induced by all formulations remained significantly elevated, demonstrating the durability of responses to SEQ ID NO: 17 even at three months after the first injection (FIG. 32). Also, the Fc portion of the SARS-CoV-2-RBD-hIgG-Fc fusion protein of SEQ ID NO: 17 was necessary to induce significant anti-SP/RBD IgG Ab titers after the first 2 doses because the SEQ ID NO: 2 (that lacks an Fc fragment) was not effective at Day 21 and only modestly effective at Day 35 relative to SEQ ID NO: 17.

Example 20: In Vivo Evaluation of the Efficacy of the ACE2-Binding Inhibition Potency Induced by the SARS-CoV-2-RBD-hIgG-Fc Fusion Protein of SEQ ID NO: 17 in Mice with and without Adjuvant In vivo evaluation of the efficacy of the ACE2-binding inhibition potency was carried out to determine whether vaccine-induced IgG titers measured by an Ag-binding ELISA are relevant to the viral neutralization capacity of immune serum, especially with respect to inhibiting the binding of SP/RBD of the SARS-CoV-2 virus to the endogenous human target protein, ACE2. The potency of immune serum to inhibit the binding of recombinant SP/RBD to recombinant ACE2 in an ELISA format with SP/RBD bound to the plate and labelled-recombinant human ACE2 added with or without serial dilutions of immune serum was carried out.

In vivo studies to further evaluate the effectiveness of the SARS-CoV-2-RBD-hIgG-Fc fusion protein of SEQ ID NO: 17 were carried out in 6- to 8-week old Balb/c mice (Jackson Laboratories, Bar Harbor, Me.) according to the general methods described in Example 12. The SARS-CoV-2-RBD-hIgG-Fc fusion protein of SEQ ID NO: 17 was synthesized according to Example 1 and purified according to Example 4. The fusion protein structure was confirmed by non-reducing and reducing CE-SDS according to Example 6 and the fusion protein sequence identification was confirmed by LC-MS with glycan removal according to Example 7. The SARS-CoV-2-RBD-hIgG-Fc fusion protein of SEQ ID NO: 17 at a dose level of 10 µg/dose with no adjuvant and the SARS-CoV-2-RBD-hIgG-Fc fusion protein of SEQ ID NO: 17 at a dose level of 10 µg/dose with various adjuvants were administered subcutaneously on Day 0, Day 21, and Day 42 according to Table 6.

TABLE 6

Test Cohorts, Dose Levels and Adjuvants With SEQ ID NO: 17.

| Cohort | SARS-CoV-2 SP/RBD-Fc fusion protein SEQ ID NO: | Dose Level (µg/Dose) | Adjuvant |
|---|---|---|---|
| 1 | SEQ ID NO: 17 | 10 | |
| 2 | SEQ ID NO: 17 | 10 | Montanide ™ ISA 51 50%:50% v/v |
| 3 | SEQ ID NO: 17 | 10 | Advax -2 50%:50% v/v |
| 4 | SEQ ID NO: 17 | 10 | Advax -3 50%:50% v/v |
| 5 | SEQ ID NO: 17 | 10 | Vac-Adx-10 50%:50% v/v |
| 6 | SEQ ID NO: 17 | 10 | Montanide ™ ISA 720 30%/70% v/v |

Figure 33:
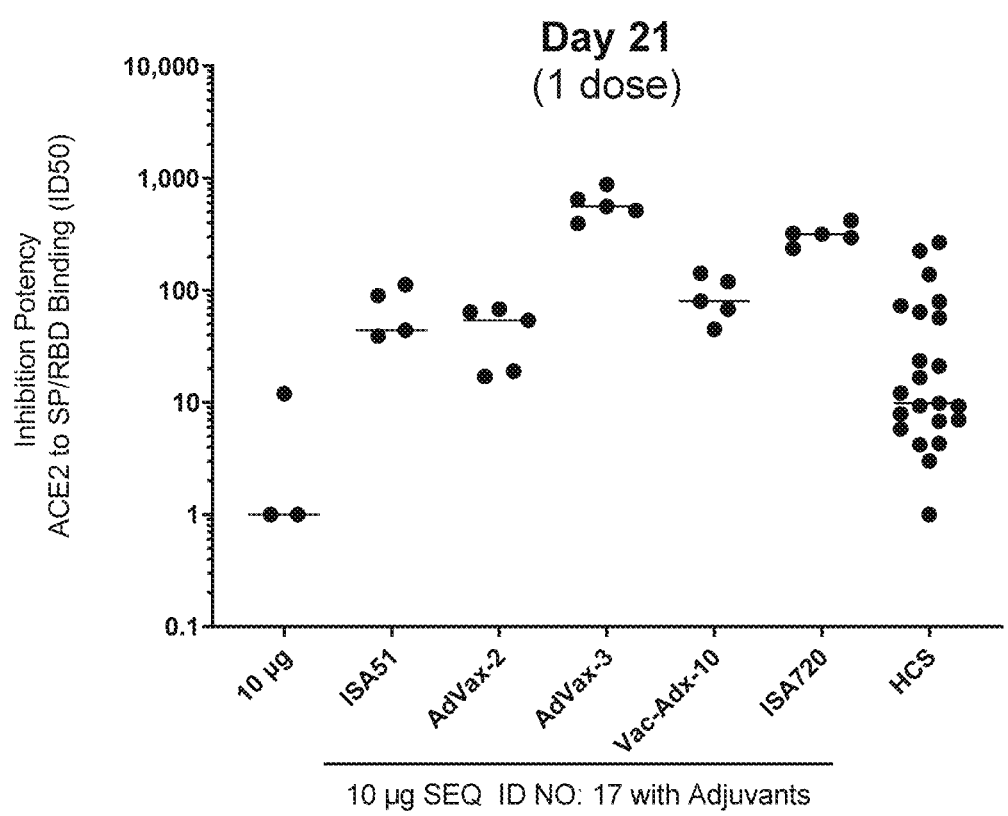
FIG. 33 illustrates the ACE2-SP/RBD binding inhibition potency (ID50) calculated at Day 21 after a single injection on Day 0 of the SARS-CoV-2-RBD-hIgG-Fc fusion protein of SEQ ID NO: 17 with and without adjuvants in 6- to 8-week old mice compared to human convalescent serum.
Figure 34:
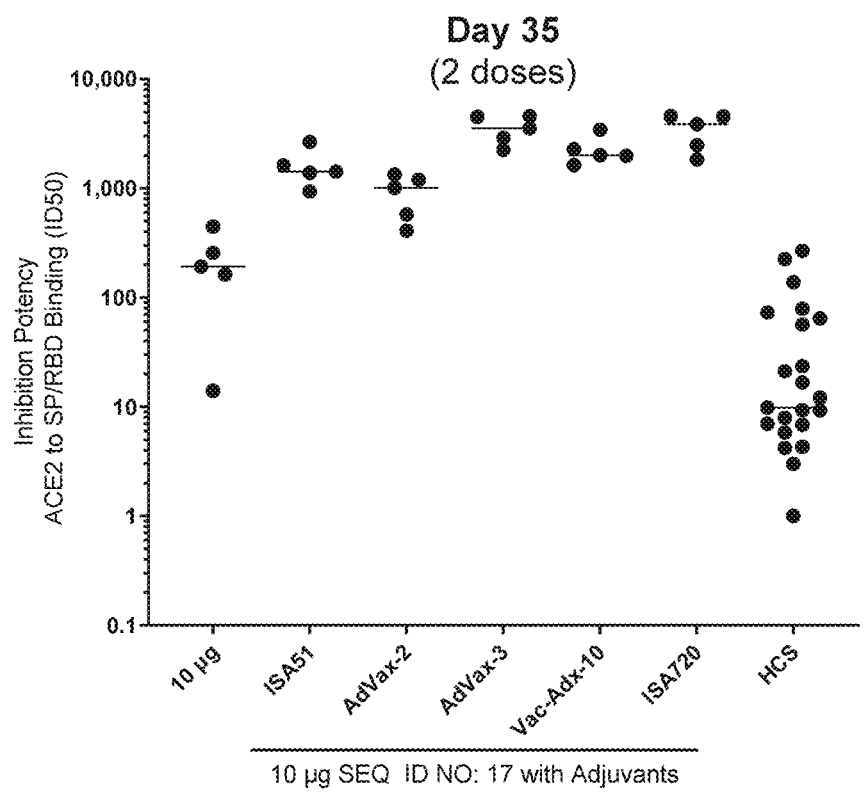
FIG. 34 illustrates the ACE2-SP/RBD binding inhibition potency (ID50) calculated at Day 35 after an injection on Day 0 and on Day 21 of the SARS-CoV-2-RBD-hIgG-Fc fusion protein of SEQ ID NO: 17 with and without adjuvants in 6- to 8-week old mice compared to human convalescent serum.
Figure 35:
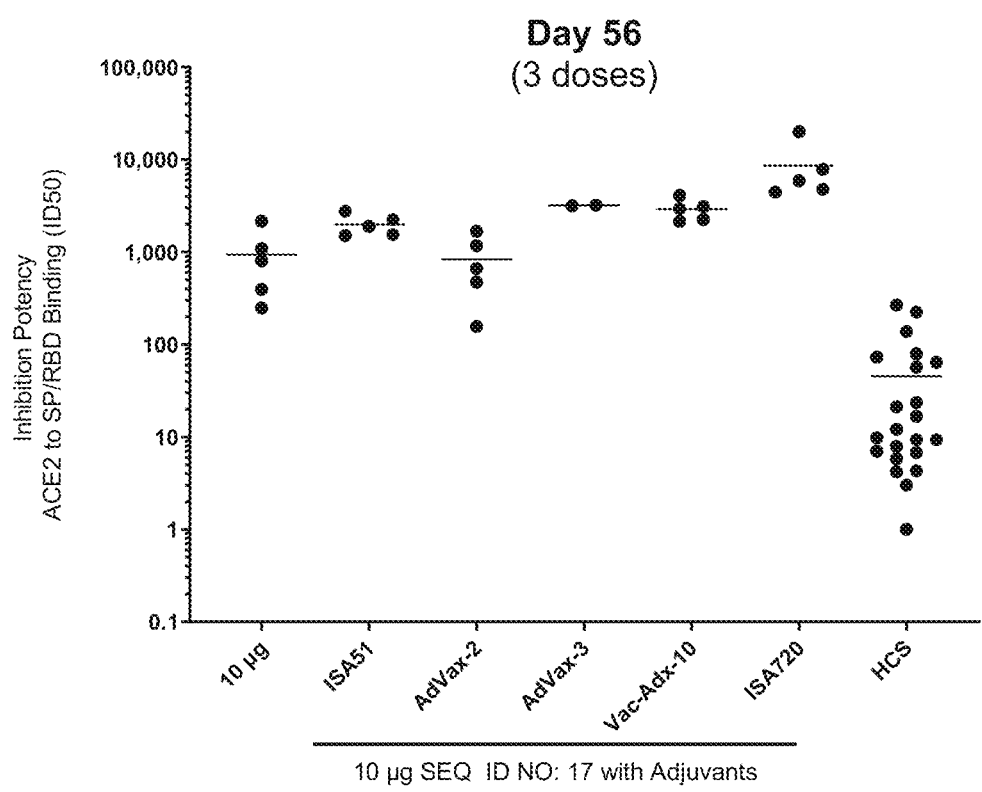
FIG. 35 illustrates the ACE2-SP/RBD binding inhibition potency (ID50) calculated at Day 56 after injections on Day 0, Day 21 and Day 42 of the SARS-CoV-2-RBD-hIgG-Fc fusion protein of SEQ ID NO: 17 with and without adjuvants in 6- to 8-week old mice compared to human convalescent serum.

Blood was collected 21 days after each dose from each mouse (and prior to the next dose) by submandibular venipuncture method, allowed to clot, and the serum was separated by centrifuging micro-vacutainer tubes and aliquoted and frozen for antibody analysis by ELISA according to the methods described in Example 10. The results from the serology assay described in Example 13 assessed the potency of inhibiting the binding of recombinant SP/RBD to bound recombinant human ACE2. Serial dilutions of pooled serum samples were performed from which inhibitory dilution 50% (ID50) values were derived using GraphPad Prism software (i.e., equal volumes of serum from each mouse in a particular group were mixed and this pooled sample was evaluated). An ID50 value represents the reciprocal of the dilution at which 50% of the ACE2 binding was achieved by a serum sample. The inhibition potency of ACE2 SP/RBD binding measured as the ID50 calculated at Day 21 after a single injection on Day 0 is illustrated in FIG. 33. The ID50 calculated at Day 42 after injections at Day 0 and Day 21 is illustrated in FIG. 34. The ID50 calculated at Day 56 after injections at Day 0, Day 21 and Day 42 is illustrated in FIG. 35, with a final ID50 calculated at Day 88 illustrated in FIG. 36.

Such ID50 values of immune serum from mice immunized with 3 doses of SEQ ID NO: 17 showed a response in which the inhibition potency was maintained to 32 days after the last injection (Day 88) (FIG. 36). Moreover, the Montanide™ ISA 720 adjuvant consistently induced the top potency at each timepoint. The Montanide™ ISA 720 result was particularly interesting and surprising given that the total IgG titers obtained with this adjuvant were not exceptionally potent relative to the other adjuvanted formulations, thus suggesting induction of greater intrinsic potency per IgG molecule with ISA 720. These data strongly supported the selection of Montanide™ ISA 720 as the lead adjuvant candidate for this vaccine development program.

Example 21: In Vivo Screening of the Effectiveness and the Efficacy of the Induced ACE2-Binding Inhibition Potency of the SARS-CoV-2-RBD-hIgG-Fc Fusion Protein of SEQ ID NO: 17 with and without Adjuvant in Older Mice During the current COVID-19 outbreak, individuals greater than 60 years of age were found to have a greater susceptibility to severe illness with a higher mortality rate. Therefore, it is important to evaluate the capacity of vaccine formulations to induce immune responses in older mice whose immune systems are a reliable model for the senescent immune systems of aging human adults. Because of the higher natural mortality in mice after 8 months of age, approximately 15 mice were allocated for each study group.

In vivo studies to evaluate the effectiveness of the SARS-CoV-2-RBD-hIgG-Fc fusion protein of SEQ ID NO: 17 with and without adjuvant were carried out in 8- to 10-month old female BALB/c mice (Jackson Laboratories, Bar Harbor, Me.) according to the general methods described in Example 12. The SARS-CoV-2-RBD-hIgG-Fc fusion protein of SEQ ID NO: 17 was synthesized according to Example 1 and purified according to Example 4. The fusion protein structure was confirmed by non-reducing and reducing CE-SDS according to Example 6 and the fusion protein sequence identification was confirmed by LC-MS with glycan removal according to Example 7.

Groups of N=15, 8- to 10-month old female BALB/c mice were subcutaneously administered the SARS-CoV-2-RBD-hIgG-Fc fusion protein of SEQ ID NO: 17 at a dose levels of 10 µg/dose with and without adjuvants according to Table 7 in a 100 µL volume, at Day 0, Day 21 and Day 42. Blood was collected 21 days after each dose from each mouse (and prior to the next dose) by submandibular venipuncture method, allowed to clot, and the serum was separated by centrifuging micro-vacutainer tubes and aliquoted and frozen for antibody analysis by ELISA according to the methods described in Example 10.

TABLE 7

Test Cohorts, Dose Levels and Adjuvants with SEQ ID NO: 17.

| Cohort | SARS-CoV-2 SP/RBD-Fc fusion protein SEQ ID NO: | Dose Level (µg/Dose) | Adjuvant |
|---|---|---|---|
| 1 | SEQ ID NO: 17 | 10 | |
| 2 | SEQ ID NO: 17 | 10 | Montanide ™ ISA 51 50%:50% v/v |
| 3 | SEQ ID NO: 17 | 10 | Montanide ™ ISA 720 30%/70% v/v |
| 4 | SEQ ID NO: 17 | 10 | Advax -2 50%:50% v/v |

Figure 37:
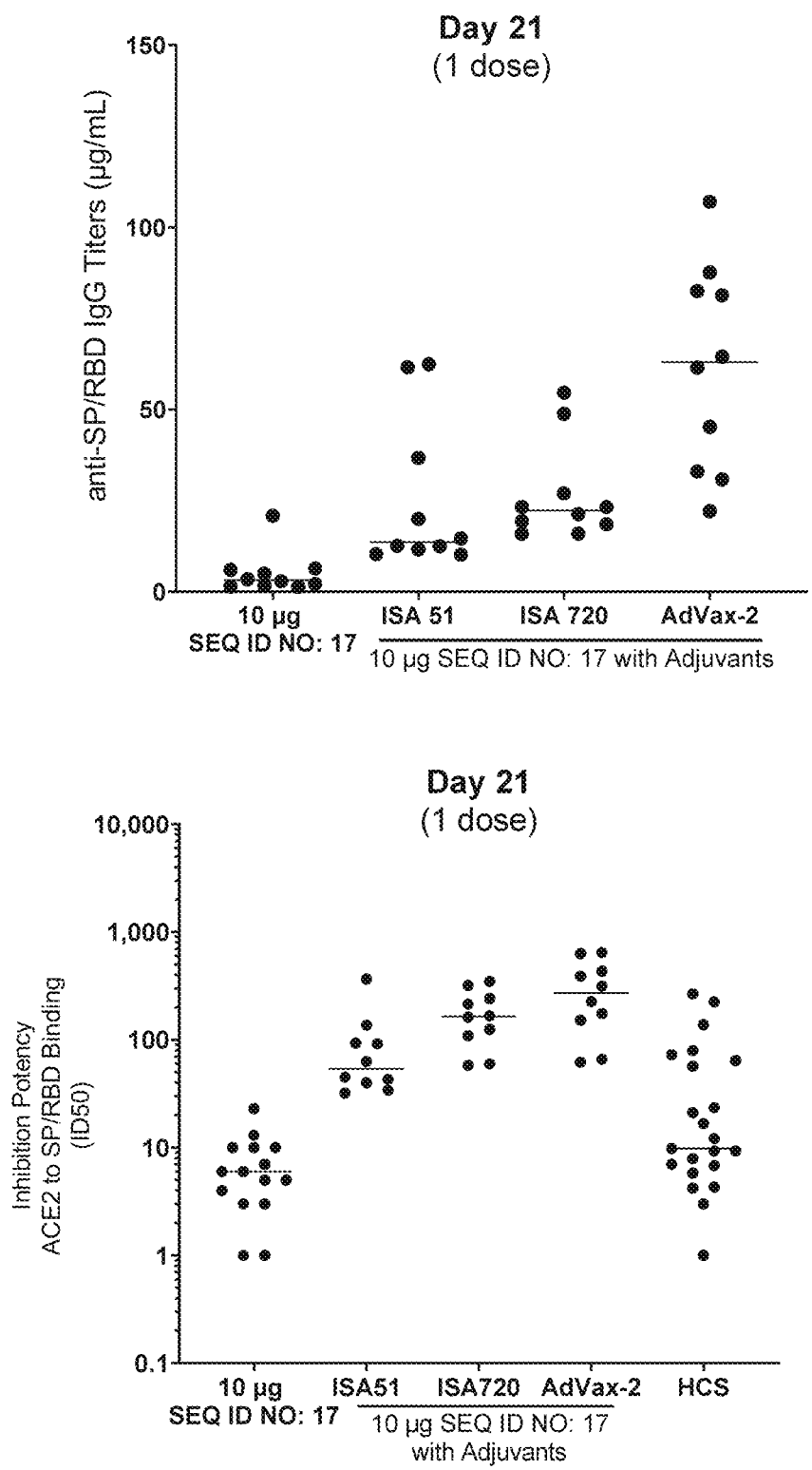
FIG. 37 illustrates the induced anti-SP/RBD IgG Ab response and the ACE2-SP/RBD binding inhibition potency (ID50) after administration of the SARS-CoV-2-RBD-hIgG-Fc fusion protein of SEQ ID NO: 17 to 8- to 10-month old mice with adjuvant at various dose levels as measured after one dose on Day 21.

The induced anti-SP/RBD IgG Ab titer responses (mean IgG µg/mL via an IgG ELISA standards curve) after administration of the SARS-CoV-2-RBD-hIgG-Fc fusion protein of SEQ ID NO: 17 according to Table 7 in a 100 µL volume was measured according to Example 10 and plotted. The measured SP/RBD IgG Ab titer responses at Day 21 are illustrated in FIG. 37. The measured SP/RBD IgG Ab titer responses at Day 35 are illustrated in FIG. 38. The measured SP/RBD IgG Ab titer responses at Day 56 are illustrated in FIG. 39.

The adjuvants strongly potentiated this immunogenicity in formulations with 10 µg/dose of SEQ ID NO: 17. Similar to the immunogenic profile in younger mice, Montanide™ ISA 720 dramatically enhanced the inhibition potency ID50 (as measured according to Example 13) of the SARS-CoV-2-RBD-hIgG-Fc fusion protein of SEQ ID NO: 17 by 17-fold relative to the level obtained without adjuvant at Day 56. Importantly, this inhibition potency induced by the SARS-CoV-2-RBD-hIgG-Fc fusion protein of SEQ ID NO: 17 with and without adjuvant was above that of human convalescent serum, demonstrating the promising effectiveness of such a SP/RBD-Fc vaccine. Thus, the SARS-CoV-2-RBD-hIgG-Fc fusion protein of SEQ ID NO: 17 maintains immunogenicity of anti-SP/RBD IgG titers with sufficient potency in an aged immune system in the presence and absence of adjuvant, thus providing a strong rationale for testing such a vaccine in elderly subjects.

Example 22: In Vivo Screening of the Effectiveness of the SARS-CoV-2-RBD-hIgG-Fc Fusion Protein of SEQ ID NO: 19 in Mice with and without Adjuvant In vivo studies to evaluate the effectiveness of the SARS-CoV-2-RBD-hIgG-Fc fusion protein of SEQ ID NO: 19 in generating SP/RBD IgG Ab titer responses were carried out. The SARS-CoV-2-RBD-hIgG-Fc fusion protein of SEQ ID NO: 19 was synthesized according to Example 3 and purified according to Example 5. The fusion protein structure was confirmed by non-reducing and reducing CE-SDS according to Example 6 and the fusion protein sequence identification was confirmed by LC-MS with glycan removal according to Example 7.

According to the procedure of Example 12, groups of N=5 6- to 8-week old female BALB/c mice (Jackson Laboratories) were administered via subcutaneous injection the SARS-CoV-2-RBD-hIgG-Fc fusion protein of SEQ ID NO: 19 at dose levels of 1 µg and 10 µg with and without adjuvants according to Table 8 in a 100 µL volume on Day 0, Day 21 and Day 42.

TABLE 8

Test Cohorts, Dose Levels and Adjuvants with SEQ ID NO: 19.

| Cohort | SARS-CoV-2 SP/RBD-Fc fusion protein SEQ ID NO: | Dose Level (µg/Dose) | Adjuvant |
|---|---|---|---|
| 1 | SEQ ID NO: 19 | 1 | |
| 2 | SEQ ID NO: 19 | 10 | |
| 3 | SEQ ID NO: 19 | 1 | Montanide ™ ISA 720 30%/70% v/v |
| 4 | SEQ ID NO: 19 | 10 | Montanide ™ ISA 720 30%/70% v/v |
| 5 | SEQ ID NO: 19 | 1 | Montanide ™ ISA 51 50%:50% v/v |
| 6 | SEQ ID NO: 19 | 10 | Montanide ™ ISA 51 50%:50% v/v |
| 7 | SEQ ID NO: 19 | 1 | Advax-2 50%:50% v/v |
| 8 | SEQ ID NO: 19 | 10 | Advax-2 50%:50% v/v |

Blood was collected 14 days after each dose (i.e., on Day 14, Day 35, and Day 56) from each mouse by submandibular venipuncture method, allowed to clot, and the serum was separated by centrifuging micro-vacutainer tubes and aliquoted and frozen for analysis by ELISA.

Figure 40:
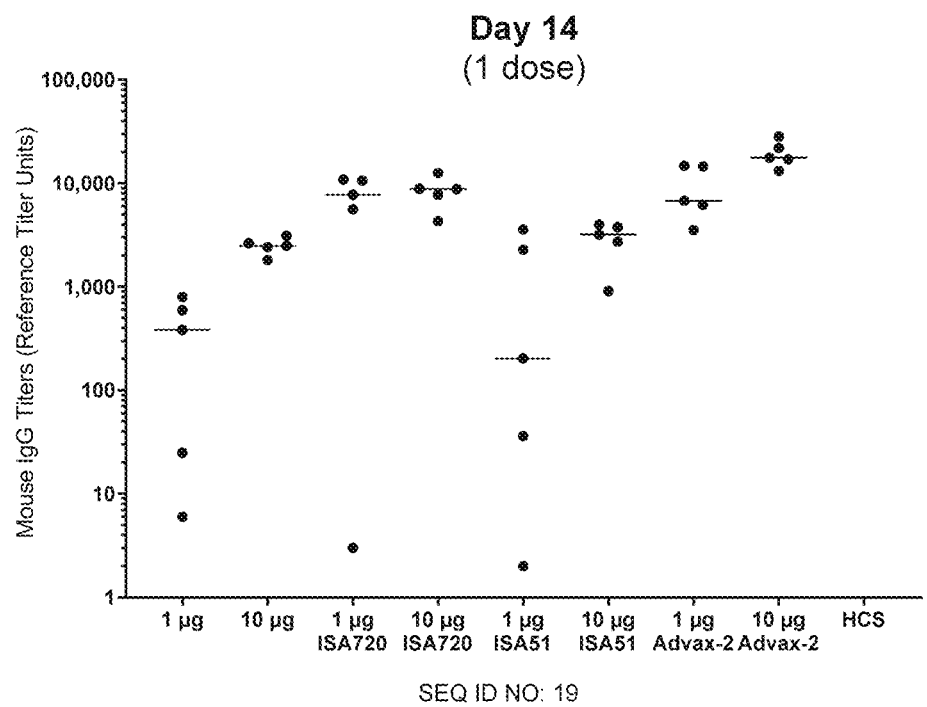
FIG. 40 illustrates the anti-SP/RBD IgG Ab titer response in 6- to 8-week old female BALB/c mice administered either a 1 μg or 10 μg dose level of the SARS-CoV-2-RBD-hIgG-Fc fusion protein of SEQ ID NO: 19 with and without various adjuvants on Day 14 after one dose.
Figure 41:
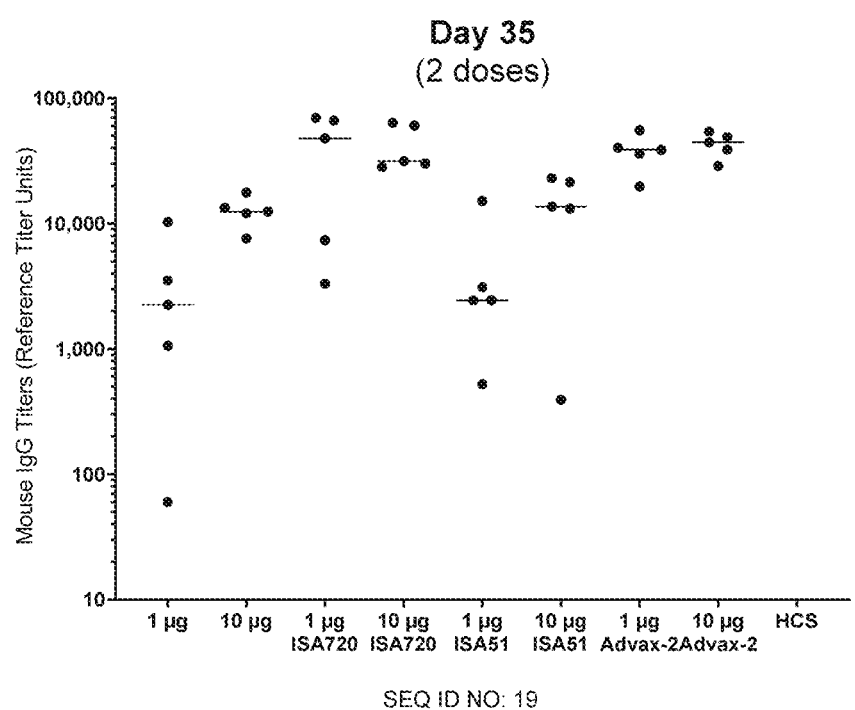
FIG. 41 illustrates the anti-SP/RBD IgG Ab titer response in 6- to 8-week old female BALB/c mice administered either a 1 μg or 10 μg dose level of the SARS-CoV-2-RBD-hIgG-Fc fusion protein of SEQ ID NO: 19 with and without various adjuvants on Day 35 after an injection on Day 0 and Day 21.
Figure 42:
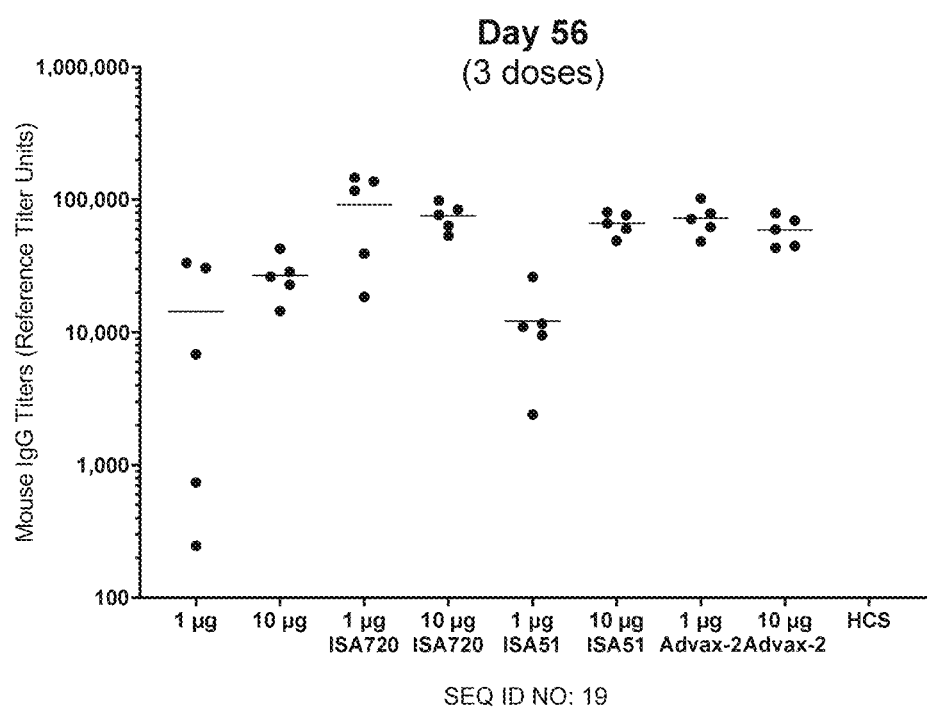
FIG. 42 illustrates the anti-SP/RBD IgG Ab titer response in 6- to 8-week old female BALB/c mice administered either a 1 μg or 10 μg dose level of the SARS-CoV-2-RBD-hIgG-Fc fusion protein of SEQ ID NO: 19 with and without various adjuvants on Day 56 after an injection on Day 0, Day 21 and Day 42.

The induced SP/RBD IgG Ab titer responses (mean IgG μg/mL via an IgG ELISA standards curve) were measured according to Example 11 on Day 14 (FIG. 40), Day 35 (FIG. 41), and Day 56 (FIG. 42).

The SARS-CoV-2-RBD-hIgG-Fc fusion protein of SEQ ID NO: 19 induced substantial IgG titers at 1 and 10 μg dose levels in the absence of adjuvant, consistent with the immunogenicity profile of SEQ ID NO: 17 in Example 17, showing a pronounced dose-response between the two dose levels after the $1^{st}$ (Day 14) and $2^{nd}$ (Day 35) doses. As expected, the SARS-CoV-2-RBD-hIgG-Fc fusion protein of SEQ ID NO: 19 formulated with different adjuvants induced substantially higher titers relative to those in the absence of adjuvant after each dose (~3- to 10-fold after the $1^{st}$ and $2^{nd}$ doses), and the adjuvant Montanide™ ISA 720 was similar in effectiveness to Ad-Vax-2 after each dose whereas Montanide™ ISA 51 was less effective.

Example 23: In Vivo Evaluation of the Efficacy of the ACE2-Binding Inhibition Potency and Plaque Reduction Neutralization Test (PRNT) Induced by the SARS-CoV-2-RBD-hIgG-Fc Fusion Protein of SEQ ID NO: 19 in Mice with and without Adjuvant In vivo studies to evaluate the efficacy of the ACE2-binding inhibition potency induced by the SARS-CoV-2-RBD-hIgG-Fc fusion protein of SEQ ID NO: 19 in mice with and without adjuvant were carried out.

The SARS-CoV-2-RBD-hIgG-Fc fusion protein of SEQ ID NO: 19 was synthesized according to Example 3 and purified according to Example 5. The fusion protein structure was confirmed by non-reducing and reducing CE-SDS according to Example 6 and the fusion protein sequence identification was confirmed by LC-MS with glycan removal according to Example 7.

According to the procedure of Example 12, groups of N=5 6- to 8-week old female BALB/c mice (Jackson Laboratories) were administered via subcutaneous injection the SARS-CoV-2-RBD-hIgG-Fc fusion protein of SEQ ID NO: 19 at dose levels of 1 μg and 10 μg with and without adjuvants according to Table 8 in a 100 μL volume on Day 0, Day 21 and Day 42.

Blood was collected 14 days after each dose (i.e., on Day 14, Day 35, and Day 56) from each mouse by submandibular venipuncture method, allowed to clot, and the serum was separated by centrifuging micro-vacutainer tubes and aliquoted and frozen for analysis by ELISA.

Figure 43:
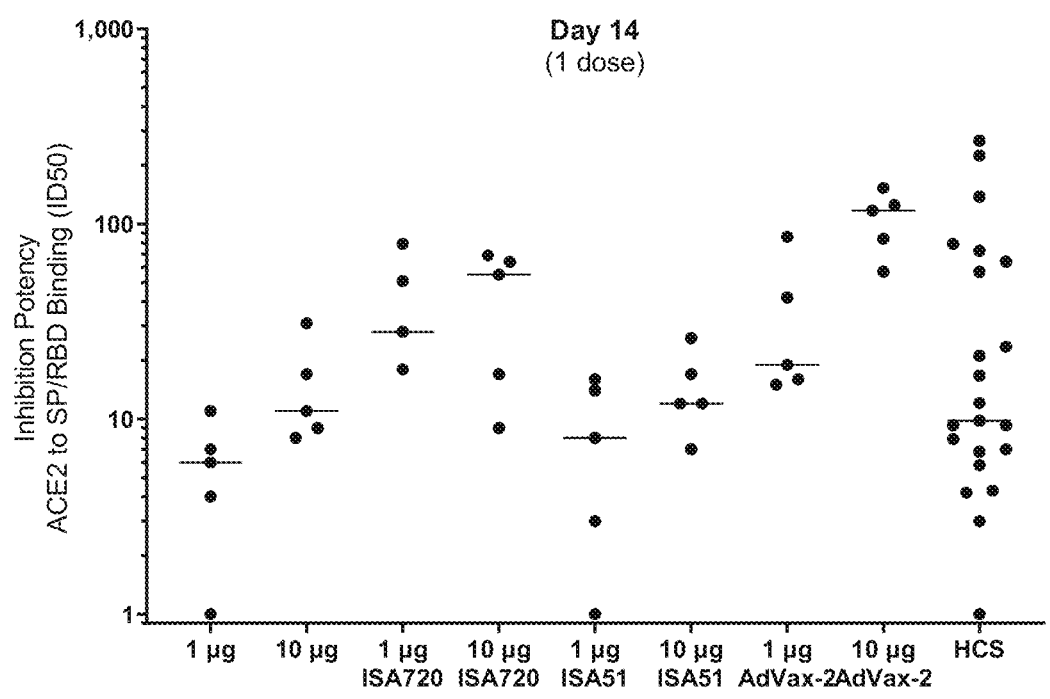
FIG. 43 illustrates the ACE2-SP/RBD binding inhibition potency (ID50) in 6- to 8-week old female BALB/c mice administered either a 1 μg or 10 μg dose level of the SARS-CoV-2-RBD-hIgG-Fc fusion protein of SEQ ID NO: 19 with and without various adjuvants on Day 14 after one injection.
Figure 44:
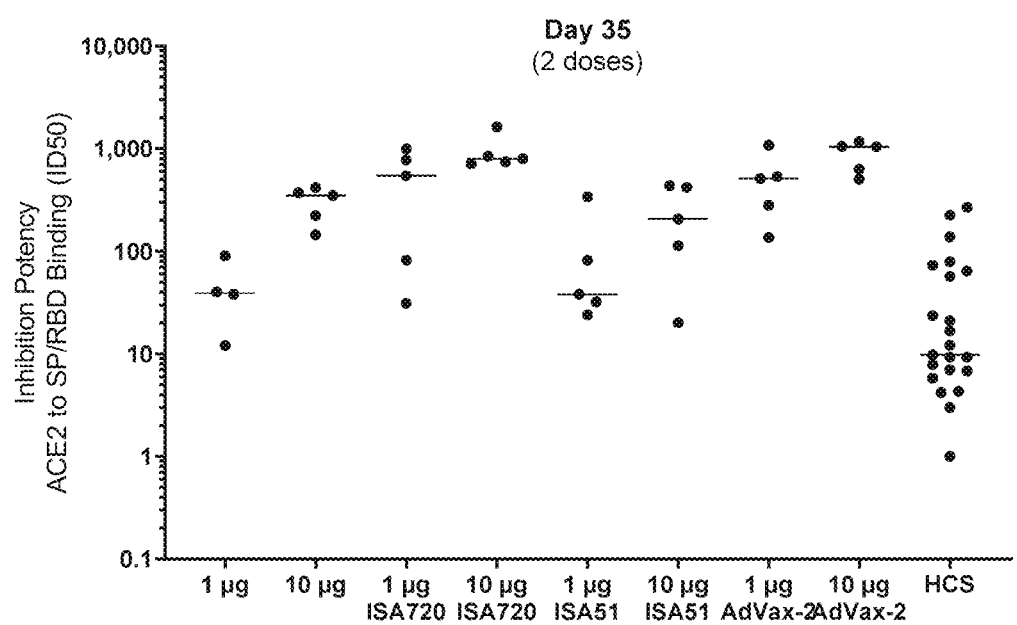
FIG. 44 illustrates the ACE2-SP/RBD binding inhibition potency (ID50) in 6- to 8-week old female BALB/c mice administered either a 1 μg or 10 μg dose level of the SARS-CoV-2-RBD-hIgG-Fc fusion protein of SEQ ID NO: 19 with and without various adjuvants on Day 35 after an injection on Day 0 and Day 21, compared to human convalescent serum.

The results from the serology assay described in Example 13 assessed the potency of inhibiting the binding of recombinant SP/RBD to bound recombinant human ACE2. Serial dilutions of pooled serum samples were performed from which inhibitory dilution 50% (ID50) values were derived using GraphPad Prism software (i.e., equal volumes of serum from each mouse in a particular group were mixed and this pooled sample was evaluated). An ID50 value represents the reciprocal of the dilution at which 50% of the ACE2 binding was achieved by a serum sample. The inhibition potency of ACE2 SP/RBD binding measured as the ID50 calculated at Day 14 after a single injection on Day 0 is illustrated in FIG. 43. The ID50 calculated at Day 35 after injections at Day 0 and Day 21 is illustrated in FIG. 44. The ID50 calculated at Day 56 after injections at Day 0, Day 21 and Day 42 is illustrated in FIG. 45.

Figure 45:
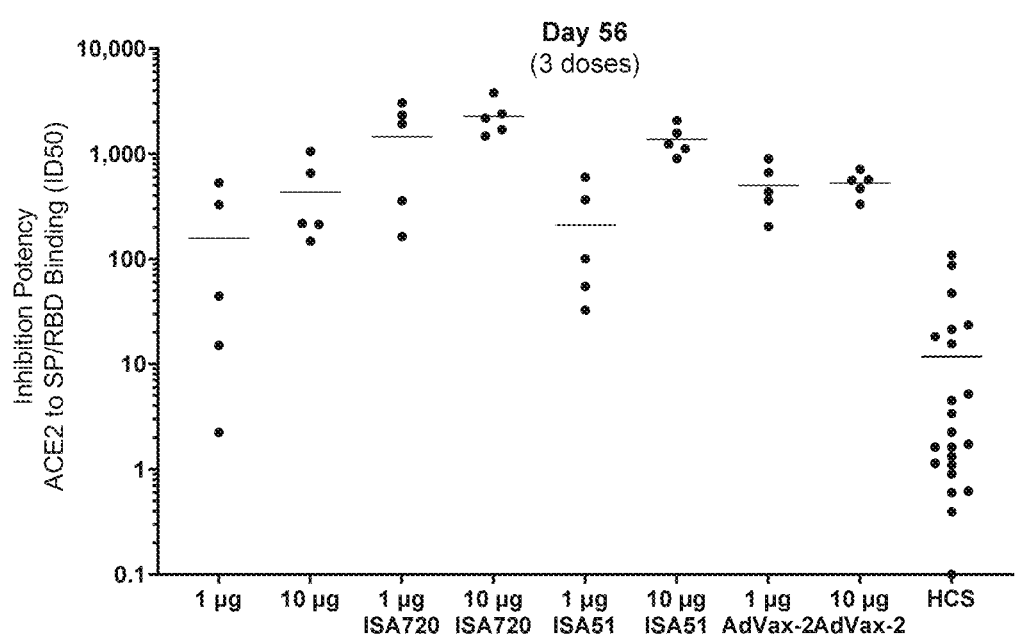
FIG. 45 illustrates the ACE2-SP/RBD binding inhibition potency (ID50) in 6- to 8-week old Female BALB/c mice administered either a 1 μg or 10 μg dose level of the SARS-CoV-2-RBD-hIgG-Fc fusion protein of SEQ ID NO: 19 with and without various adjuvants on Day 56 after an injection on Day 0, Day 21 and Day 42, compared to human convalescent serum.

The SARS-CoV-2-RBD-hIgG-Fc fusion protein of SEQ ID NO: 19 induced strong ACE2-SP/RBD inhibitory potencies (ID50 values) that were significantly above those of human convalescent serum at after each dose (FIG. 43, FIG. 44, and FIG. 45). Note that the SARS-CoV-2-RBD-hIgG-Fc fusion protein of SEQ ID NO: 19 in formulation with the Montanide™ ISA720 adjuvant achieved the highest potencies after the 3rd dose. In all cases the higher doses of the SARS-CoV-2-RBD-hIgG-Fc fusion protein of SEQ ID NO: 19 produce higher affinity antibodies which are more likely to inhibit the entry of SARS-CoV-2 virus into a patient's cells. Contrary to expectations, the results from the ACE2 binding inhibition assay described in Example 13 demonstrated that the SARS-CoV-2-RBD-hIgG-Fc fusion protein of SEQ ID NO: 19 in formulation with the Montanide™ ISA 720 adjuvant produces the most inhibitory antibodies of all the adjuvant formulations despite inducing one of the lowest levels of anti-RBD IgG antibody titers when measured as described in Example 11. The Montanide™ ISA 720 adjuvant may be highly advantageous to increase the subcutaneous residence time and antigen presentation potential of the SARS-CoV-2-RBD-hIgG-Fc fusion protein of SEQ ID NO: 19 to produce the highest affinity virus neutralizing antibodies.

Plaque Reduction Neutralization Test (PRNT) was conducted according to Example 15 using Cohort 3 and Cohort 4 as described in Table 8 (administered the SARS-CoV-2-RBD-hIgG-Fc fusion protein of SEQ ID NO: 19 with Montanide™ ISA 720 adjuvant at dose levels of 1 μg and 10 μg). The induced SARS-CoV-2 virus neutralization potency in mouse serum samples is shown in FIG. 46. Interestingly, immunization of mice with the SARS-CoV-2-RBD-hIgG-Fc fusion protein of SEQ ID NO: 19 with Montanide™ ISA 720 adjuvant according to the procedure of Example 12 also showed strong PRNT neutralization potencies that followed an expected progressive elevation from one dose to two doses, such that potencies after the first dose were below those of human serum but those derived from serum after the second dose were much greater (~10-fold) than those of human convalescent serum. This is illustrated in FIG. 46. The neutralization potencies showed a similar profile as that of the ACE2-inhibition potencies.

Example 24: In Vivo Screening of the Effectiveness of the SARS-CoV-2-RBD-hIgG-Fc Fusion Protein of SEQ ID NO: 19 with and without Adjuvant to Induce Anti-SP/RBD IgG2a, IgG2b and IgG3 Isotype Titers in Mice In vivo studies to compare the effectiveness of generating anti-SP/RBD IgG2a, IgG2b and IgG3 isotype titers in mice of the SARS-CoV-2-RBD-hIgG-Fc fusion protein of SEQ ID NO: 19 with or without adjuvants were carried out. The SARS-CoV-2-RBD-hIgG-Fc fusion protein of SEQ ID NO: 19 was synthesized according to Example 3 and purified according to Example 5. The fusion protein structure was confirmed by non-reducing and reducing CE-SDS according to Example 6 and the fusion protein sequence identification was confirmed by LC-MS with glycan removal according to Example 7.

According to the procedure of Example 12, groups of N=5 6- to 8-week old female BALB/c mice (Jackson Laboratories) were administered via subcutaneous injection the SARS-CoV-2-RBD-hIgG-Fc fusion protein of SEQ ID NO: 19 with or without adjuvant according to

TABLE 9

Test Cohorts, Dose Levels and Adjuvants with SEQ ID NO: 19.

| Cohort | SARS-CoV-2 SP/RBD-Fc fusion protein SEQ ID NO: | Dose Level (μg/Dose) | Adjuvant |
|---|---|---|---|
| 1 | SEQ ID NO: 19 | 10 | |
| 2 | SEQ ID NO: 19 | 10 | Montanide ™ ISA 51 50%:50% v/v |
| 3 | SEQ ID NO: 19 | 10 | Montanide ™ ISA 720 30%/70% v/v |
| 4 | SEQ ID NO: 19 | 10 | Advax -2 50%:50% v/v |

Figure 47:
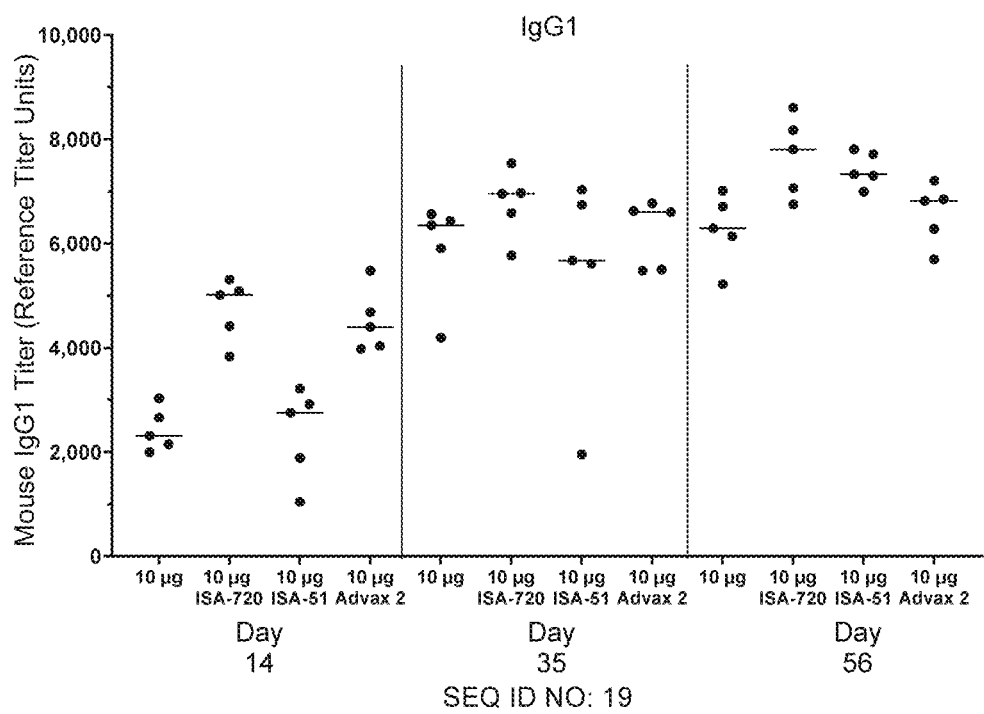
FIG. 47 illustrates the anti-SP/RBD IgG1 titer in 6-8 week old BALB/C mice administered a 10 μg dose level of the SARS-CoV-2-RBD-hIgG-Fc fusion protein of SEQ ID NO: 19 with or without adjuvants (including Montanide™ ISA 720) as measured on Day 14, Day 35, and Day 56 after an injection on Day 0, Day 21 and Day 42.
Figure 48:
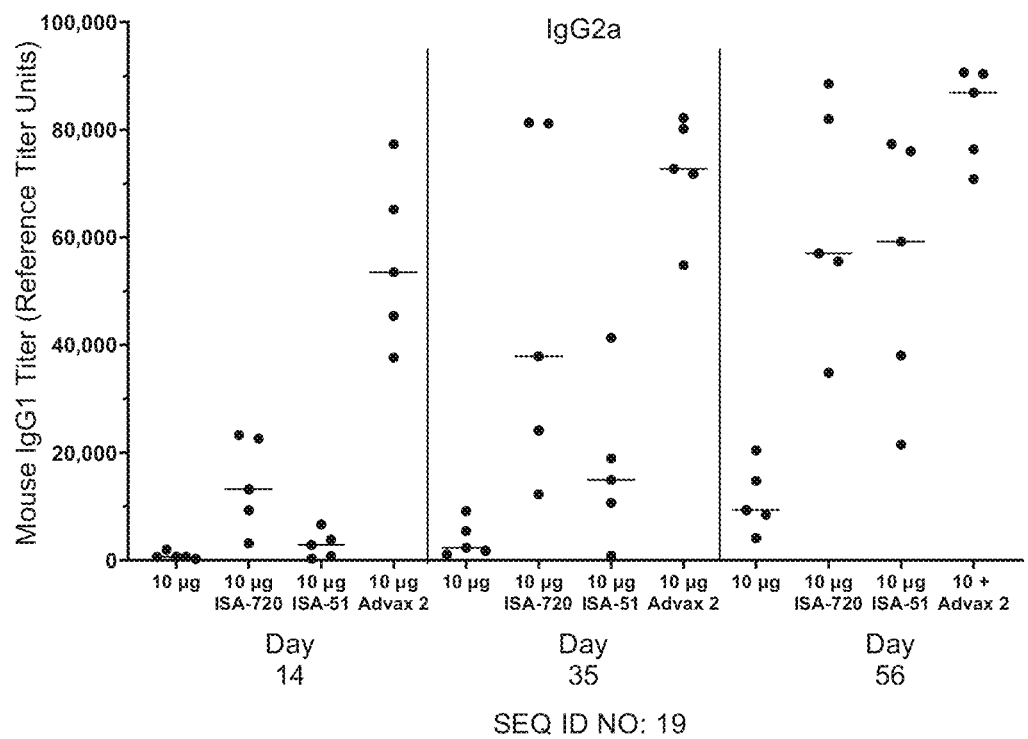
FIG. 48 illustrates the anti-SP/RBD IgG2a titer in 6-8 week old BALB/C mice administered a 10 µg dose level of the SARS-CoV-2-RBD-hIgG-Fc fusion protein of SEQ ID NO: 19 with or without adjuvants (including Montanide™ ISA 720) as measured on Day 14, Day 35, and Day 56 after an injection on Day 0, Day 21 and Day 42.
Figure 49:
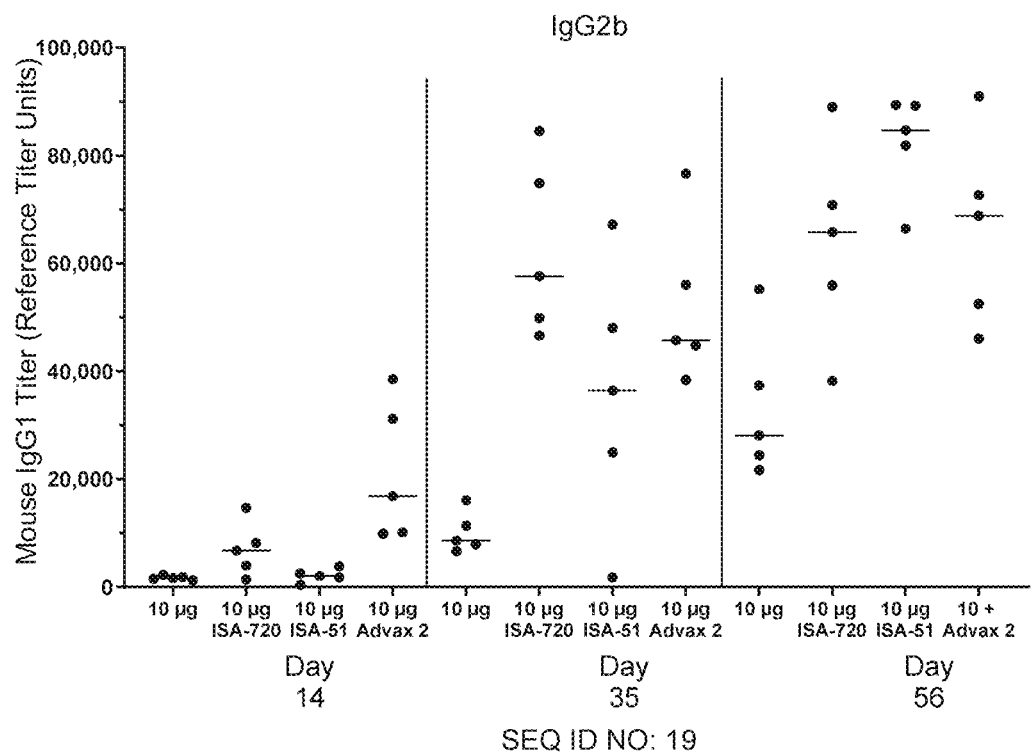
FIG. 49 illustrates the anti-SP/RBD IgG2b titer in 6-8 week old BALB/C administered a 10 µg dose level of the SARS-CoV-2-RBD-hIgG-Fc fusion protein of SEQ ID NO: 19 with or without adjuvants (including Montanide™ ISA 720) as measured on Day 14, Day 35, and Day 56 after an injection on Day 0, Day 21 and Day 42.
Figure 50:
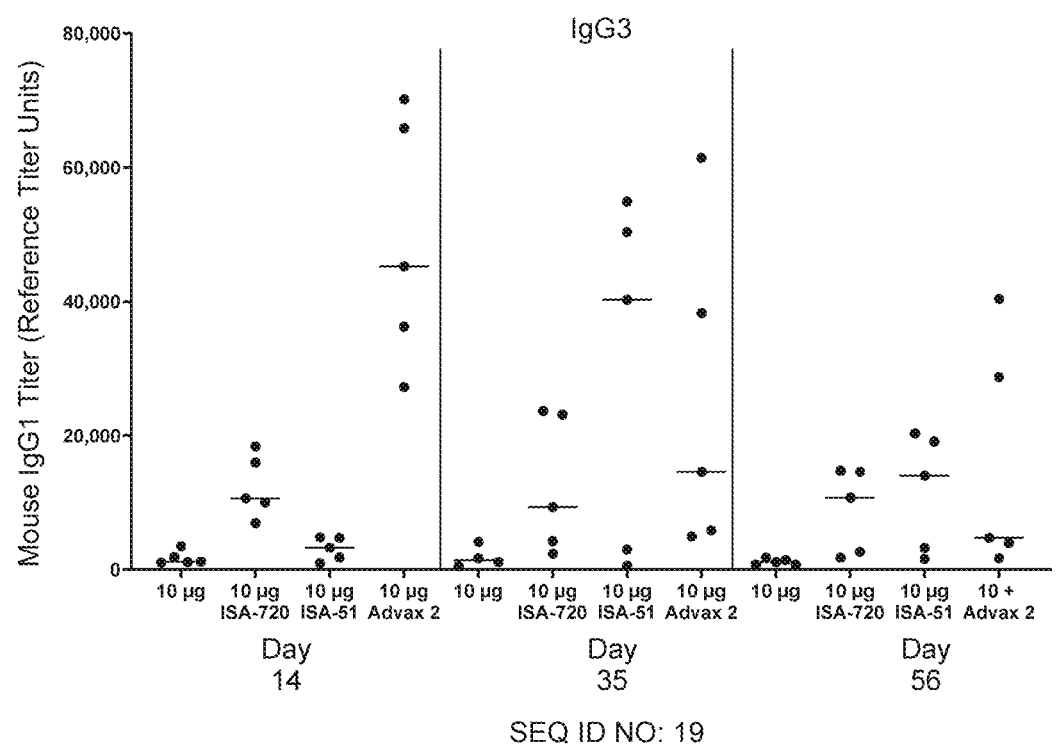
FIG. 50 illustrates the anti-SP/RBD IgG3 titer in 6-8 week old BALB/C mice administered a 10 µg dose level of the SARS-CoV-2-RBD-hIgG-Fc fusion protein of SEQ ID NO: 19 with or without adjuvants (including Montanide™ ISA 720) as measured on Day 14, Day 35, and Day 56 after an injection on Day 0, Day 21 and Day 42.

Blood was collected 14 days after each injection from each mouse by submandibular venipuncture method, allowed to clot, and the serum was separated by centrifuging micro-vacutainer tubes and aliquoted and frozen for antibody analysis by ELISA according to the methods described in Example 11. The SARS-CoV-2-RBD-hIgG-Fc fusion protein of SEQ ID NO: 19 with all adjuvants induced significant Th1-promoted IgG2a, IgG2b and IgG3 isotype titers in which Montanide™ ISA 720 consistently showed a strong enhancement at all timepoints (see FIG. 48, FIG. 49 and FIG. 50). In addition, Th2-promoted isotype, IgG1 titers were approximately 10-fold less than those of the Th1-associated isotype (FIG. 47). These results demonstrate that the Montanide™ ISA 720 adjuvant maintained a strong enhancing effect when delivered with SEQ ID NO: 19, especially by promoting the desired shift towards a Th1 response, supporting its dose-sparing characteristics and selection as the clinical lead adjuvant.

Example 25: In Vivo Screening of the Effectiveness of the SARS-CoV-2-RBD-hIgG-Fc Fusion Protein of SEQ ID NO: 23 with and without Adjuvant to Induce Anti-SP/RBD IgG Isotype Titers in Mice The role of the Fc fragment in its contribution to the immunogenicity of the SP/RBD-Fc fusion protein vaccine was further investigated in mice by attempting to understand how the use of a human IgG Fc construct in mice may affect the efficacy. Mouse IgG2a (SEQ ID NO: 22) is the functional analog to human IgG1.

(SEQ ID NO: 22)
EPRGPTIKPCPPCKCPAPNLLGGPSVFIFPPKIKDVLMISLSPIVTCVVVD

VSEDDPDVQISWFVNNVEVHTAQTQTHREDYNSTLRVVSALPIQHQDWMSG

KEFKCKVNNKDLPAPIERTISKPKGSVRAPQVYVLPPPEEEMTKKQVTLTC

MVTDFMPEDIYVEWTNNGKTELNYKNTEPVLDSDGSVFMYSKLRVEKKNWV

ERNSYSCSVVHEGLHNHHTTKSFSRTPGK

The experiments were aimed at determining i) whether the Fc species mismatch might be the cause of the underlying immunogenicity of the SP/RBD-Fc fusion protein and ii) whether results from human IgG Fc constructs in animal models are appropriate for predicting performance in humans.

The SARS-CoV-2-RBD-hIgG-Fc fusion protein of SEQ ID NO: 23 was therefore constructed comprising the SP/RBD of SEQ ID NO: 14 with the linker of SEQ ID NO: 5 and the mouse IgG2a Fc fragment of SEQ ID NO: 22.

(SEQ ID NO: 23)
RVQPTESIVRFPNITNLCPFGEVFNATRFASVYAWNRKRISNCVADYSVLY

NSASFSTFKCYGVSPTKLNDLCFTNVYADSFVIRGDEVRQIAPGQTGKIAD

YNYKLPDDFTGCVIAWNSNNLDSKVGGNYNYLYRLFRKSNLKPFERDISTE

IYQAGSTPCNGVEGFNCYFPLQSYGFQPTNGVGYQPYRVVVLSFELLHAPA

TVCGPKKSTNLVKNKCVNFGGGSGGGSEPRGPTIKPCPPCKCPAPNLLGGP

SVFIFPPKIKDVLMISLSPIVTCVVVDVSEDDPDVQISWFVNNVEVHTAQT

QTHREDYNSTLRVVSALPIQHQDWMSGKEFKCKVNNKDLPAPIERTISKPK

GSVRAPQVYVLPPPEEEMTKKQVTLTCMVTDFMPEDIYVEWTNNGKTELNY

KNTEPVLDSDGSYFMYSKLRVEKKNWVERNSYSCSVVHEGLHNHHTTKSFS

RTPGK

In vivo studies to compare the effectiveness of generating SP/RBD IgG isotype titer responses of the SARS-CoV-2-RBD-hIgG-Fc fusion protein of SEQ ID NO: 23 with the effectiveness of generating SP/RBD IgG isotype titer responses of the SARS-CoV-2-RBD-hIgG-Fc fusion protein of SEQ ID NO: 19 and of the SP/RBD of SEQ ID NO: 2 were carried out.

The SARS-CoV-2-RBD-hIgG-Fc fusion protein of SEQ ID NO: 19 was synthesized according to Example 2 and purified according to Example 5. The fusion protein structure was confirmed by non-reducing and reducing CE-SDS according to Example 6 and the fusion protein sequence identification was confirmed by LC-MS with glycan removal according to Example 7. The SARS-CoV-2-RBD-hIgG-Fc fusion protein of SEQ ID NO: 23 was obtained from a commercial source (catalog #SPD-05259, ACRO Biosystems, Newark, Del.). The SARS-CoV-2 Spike Protein Receptor Binding Domain (SP/RBD) (without the Fc) of SEQ ID NO: 2 was obtained from a commercial source (item #46438; Lake Pharma, Inc., San Mateo, Calif.).

According to the procedure of Example 12, groups of N=5 6- to 8-week old female BALB/c mice (Jackson Laboratories, Bar Harbor, Me.) were administered via subcutaneous injection the SARS-CoV-2-RBD-hIgG-Fc fusion protein of SEQ ID NO: 19, the SARS-CoV-2-RBD-hIgG-Fc fusion protein of SEQ ID NO: 23 or the SP/RBD of SEQ ID NO: 2 according to the dose levels given in Table 10 on Day 0 and Day 21.

TABLE 10

Test Cohorts and Dose Levels of SEQ ID NO: 19, SEQ ID NO: 23 and SEQ ID NO: 2.

| Cohort | SARS-CoV-2 SP/RBD-Fc fusion protein SEQ ID NO: | Dose level (µg/Dose) | Adjuvant |
|---|---|---|---|
| 1 | SEQ ID NO: 19 | 1 | |
| 2 | SEQ ID NO: 19 | 10 | |
| 3 | SEQ ID NO: 19 | 1 | Montanide ™ ISA 720 30%/70% v/v |
| 4 | SEQ ID NO: 19 | 10 | Montanide ™ ISA 720 30%/70% v/v |
| 5 | SEQ ID NO: 23 | 1 | |
| 6 | SEQ ID NO: 23 | 10 | |
| 7 | SEQ ID NO: 23 | 1 | Montanide ™ ISA 720 30%/70% v/v |
| 8 | SEQ ID NO: 23 | 10 | Montanide ™ ISA 720 30%/70% v/v |
| 9 | SEQ ID NO: 2 | 0.5 | |
| 10 | SEQ ID NO: 2 | 5 | |

Blood was collected 14 days after each injection from each mouse by submandibular venipuncture method, allowed to clot, and the serum was separated by centrifuging micro-vacutainer tubes and aliquoted and frozen for antibody analysis by ELISA according to the methods described in Example 11 and ACE2-SP/RBD binding inhibition potency according to the methods described in Example 13.

Figure 51:
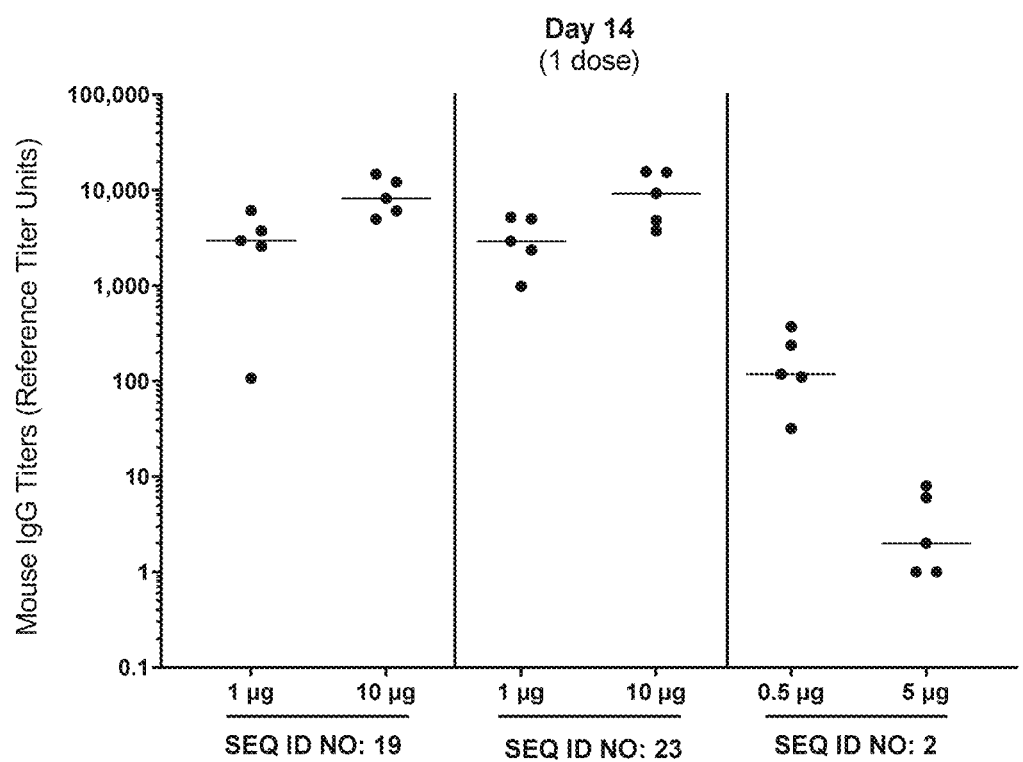
FIG. 51 illustrates the anti-SP/RBD IgG titers in 6- to 8-week old female BALB/c mice administered a single dose on Day 0 of either a 1 µg or 10 µg dose level of SEQ ID NO: 19 or SEQ ID NO: 23 (with mouse IgG2a-Fc) or a 0.5 µg or 5 µg dose level of SEQ ID NO: 2 as measured on Day 14.
Figure 52:
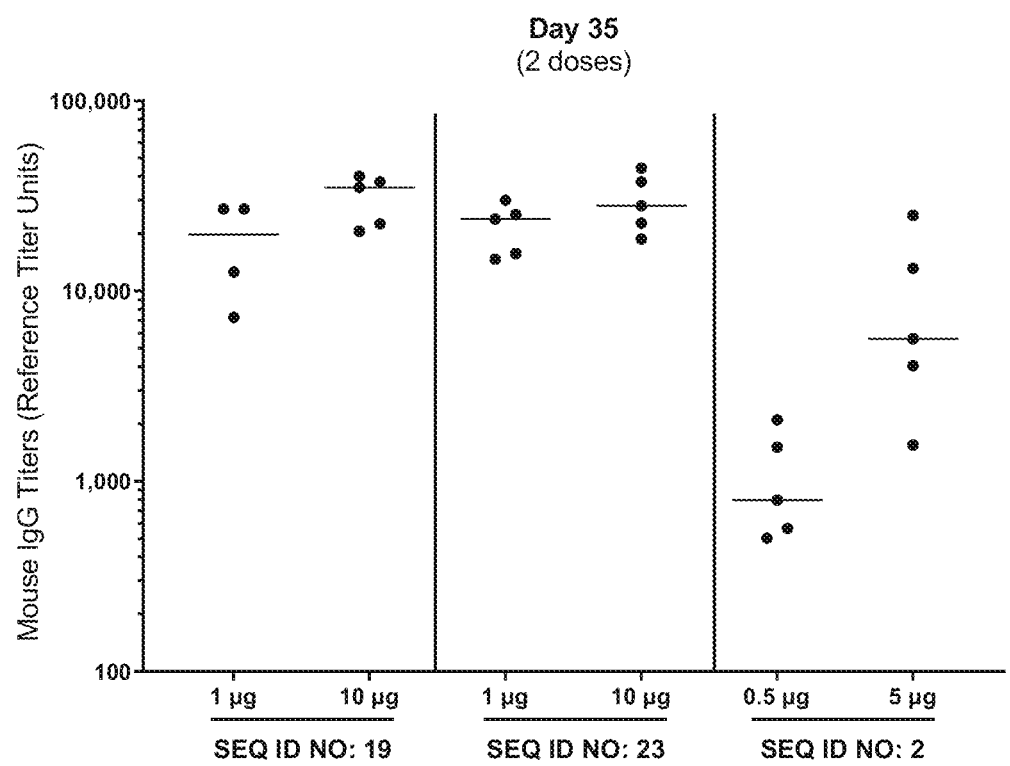
FIG. 52 illustrates the anti-SP/RBD IgG titers in 6- to 8-week old female BALB/c mice administered either a 1 µg or 10 µg dose level of SEQ ID NO: 19 or SEQ ID NO: 23 (with mouse IgG2a-Fc) or 0.5 µg or 5 µg dose level of SEQ ID NO: 2 as measured on Day 35 after an injection on Day 0 and Day 21.

Immunizations with SEQ ID NO: 19 and SEQ ID NO: 23 containing the murine Fc comprising mouse IgG2a without adjuvant (Cohorts 1, 2, 5, and 6 from Table 10) showed no significant differences in induction of IgG titer 14 days after the first or second doses (i.e., Day 14 as shown in FIG. 51 and Day 35 as shown in FIG. 52), demonstrating that human Fc antigenic sequences do not perform any differently than native mouse Fc sequences in the BALB/c mouse immunogenicity model. Similar to results obtained using SEQ ID NO: 17, SEQ ID NO: 2 without an Fc fragment (Cohorts 9 and 10 from Table 10) was not as immunogenic after the first and second doses relative to that of SEQ ID NO: 23 or SEQ ID NO: 19 in the absence of adjuvant. Given that the mouse version of the SARS-CoV-2-RBD-hIgG-Fc fusion protein (SEQ ID NO: 23) demonstrates enhanced immunogenicity in mice relative to the naked SP/RBD protein (SEQ ID NO: 2), it is highly likely that the human version will demonstrate enhanced immunogenicity in humans.

Figure 53:
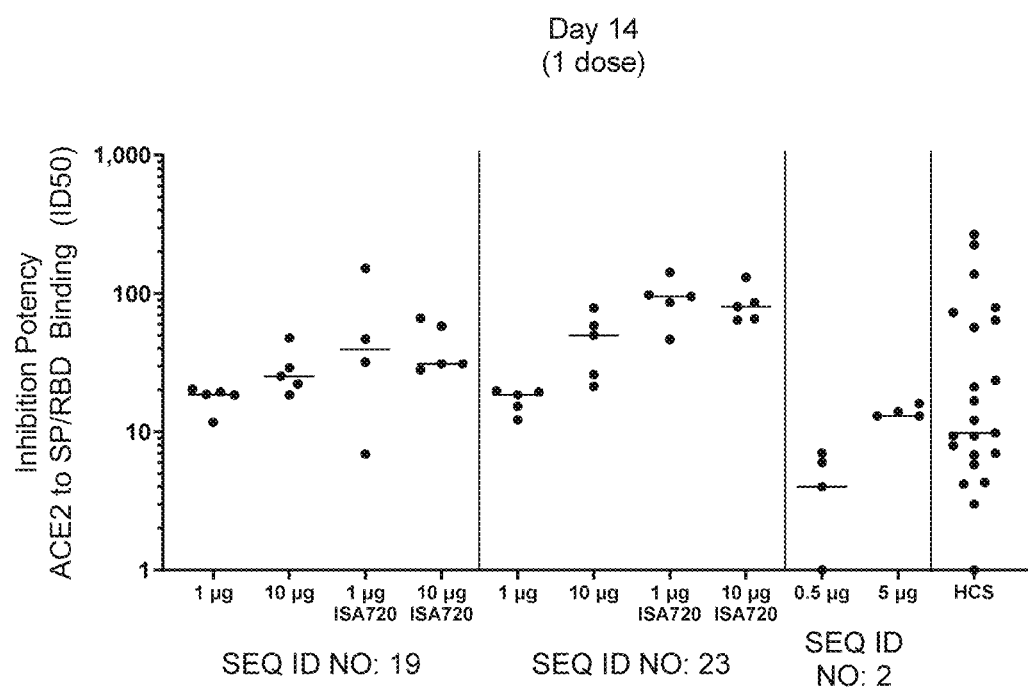
FIG. 53 illustrates the induced ACE2-SP/RBD binding inhibition potency (ID50) in 6- to 8-week old female BALB/c mice administered either a 1 µg or 10 µg dose level of SEQ ID NO: 19 or SEQ ID NO: 23 (with mouse IgG2a-Fc) or a 0.5 µg or 5 µg dose level of SEQ ID NO: 2 as measured on Day 14 compared to human convalescent serum.
Figure 54:
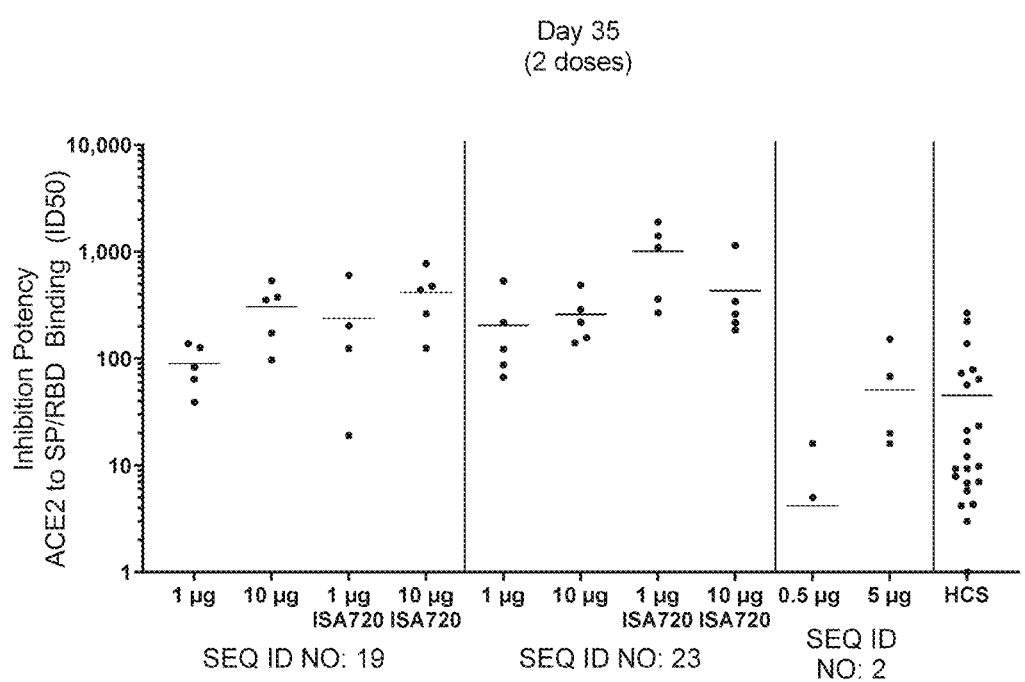
FIG. 54 illustrates the induced ACE2-SP/RBD binding inhibition potency (ID50) in 6- to 8-week old female BALB/c mice administered either a 1 µg or 10 µg dose level of SEQ ID NO: 19 or SEQ ID NO: 23 (with mouse IgG2a-Fc) or a 0.5 µg or 5 µg dose level of SEQ ID NO: 2 as measured on Day 35 after an injection on Day 0 and Day 21 compared to human convalescent serum.

Immunizations with SEQ ID NO: 19 and SEQ ID NO: 23 containing the murine Fc comprising mouse IgG2a with adjuvant (Cohort 3, 4, 7 and 8 from Table 10) showed no significant differences in ACE2-SP/RBD binding inhibition potency 14 days after the first or second doses (i.e., Day 14 as shown in FIG. 53 and Day 35 as shown in FIG. 54), demonstrating that human Fc antigenic sequences do not perform any differently than native mouse Fc sequences in the BALB/c mouse immunogenicity model. Both SEQ ID NO: 19 and SEQ ID NO: 23 exhibited ACE2-SP/RBD binding inhibition potency greater than human convalescent serum (HCS) even after just one dose. Similar to results obtained using SEQ ID NO: 17, SEQ ID NO: 2 without an Fc fragment was not as potent in terms of ACE2-SP/RBD binding inhibition after the first and second doses relative to SEQ ID NO: 23 or SEQ ID NO: 19 even in the absence of adjuvant. Given that the mouse version of the SARS-CoV-2-RBD-hIgG-Fc fusion protein (SEQ ID NO: 23) demonstrates enhanced immunogenicity in mice relative to the naked SP/RBD protein (SEQ ID NO: 2), it is highly likely that the human version will demonstrate enhanced immunogenicity in humans.

Example 26: In Vivo Screening of the Effectiveness of the SARS-CoV-2-RBD-hIgG-Fc Fusion Protein of SEQ ID NO: 19 in Mice with Montanide™ ISA-720 Adjuvant after Storage In vivo studies to compare the effectiveness of generating SP/RBD IgG Ab titer responses of freshly made SARS-CoV-2-RBD-hIgG-Fc fusion protein of SEQ ID NO: 19 with Montanide™ ISA 720 emulsion with the same emulsion stored at 4° C. and 25° C. for one day and seven days after preparation were carried out. The SARS-CoV-2-RBD-hIgG-Fc fusion protein of SEQ ID NO: 19 was synthesized according to Example 3 and purified according to Example 5. The fusion protein structure was confirmed by non-reducing and reducing CE-SDS according to Example 6 and the fusion protein sequence identification was confirmed by LC-MS with glycan removal according to Example 7.

According to the procedure of Example 12, groups of N=5 6- to 8-week old female BALB/c mice (Jackson Laboratories, Bar Harbor, Me.) were administered via subcutaneous injection the SARS-CoV-2-RBD-hIgG-Fc fusion protein of SEQ ID NO: 19 at a dose level of 10 µg mixed with Montanide™ ISA 720 adjuvant 30%/70% v/v fresh or after storage for 1 day or 7 days at 4° C. and 25° C.

Blood was collected at Day 14 after the injection from each mouse by submandibular venipuncture method, allowed to clot, and the serum was separated by centrifuging micro-vacutainer tubes and aliquoted and frozen for antibody analysis by ELISA according to the methods described in Example 13.

The results from the ACE2 binding inhibition assay described in Example 13 demonstrated that the SARS-CoV-2-RBD-hIgG-Fc fusion protein of SEQ ID NO: 19 induced similar inhibitory potency in serum (ID50 values) in mice after injection of freshly made emulsion versus the emulsion stored for 1 day and 7 days at 4° C. and 25° C. As shown in FIG. 55, there is no significant difference (p>0.05) in ID50 values between the animals injected with freshly made emulsion versus any of the aged emulsions.

Example 27: Preliminary Dosing Effectiveness and Efficacy of the ACE2-Binding Inhibition Potency Induced by SEQ ID NO: 19 with the Adjuvant, Montanide™ ISA 720, in Non-Human Primates (NHPs; i.e., Cynomolgus Monkeys)

To translate this human IgG1 Fc fusion protein immunogenicity knowledge from mice to human clinical studies, the SARS-CoV-2-RBD-hIgG-Fc fusion protein of SEQ ID NO: 19 formulated with or without adjuvant (Montanide™ ISA 720) was tested in the more genetically-relevant NHP species, Cynomolgus monkeys. The Cynomolgus monkey IgG1-Fc region sequence is highly similar to the human IgG1-Fc sequence and Cynomolgus IgG effector functions and human IgG1 was indeed active in Cynomolgus monkeys but with a somewhat reduced potency. Thus, efficacy results obtained in Cynomolgus monkeys with a human IgG1-Fc fusion protein are likely to slightly underpredict the performance of the human IgG1-Fc fusion protein in humans. Lastly, the translatability of Cynomolgus monkey results was confirmed by demonstrating that the human IgG Fc fragment of SEQ ID NO: 19 is able to bind to Cynomolgus FcR and FcRn homologs with similar potency as obtained for the human FcR and FcRn receptors. Different concentrations of His-Tagged human and Cynomolgus FcR homolog molecules were added to plastic-bound SEQ ID NO: 19. After washing away unbound molecules, bound molecules were detected with labelled anti-His secondary antibody and developed colorimetrically with absorbance (OD 450) determined via a spectrophotometer. As shown in FIG. 56, FIG. 57, FIG. 58 and FIG. 59, the translatability of Cynomolgus monkey results was confirmed by demonstrating that the human IgG Fc fragment of SEQ ID NO: 19 is able to bind to Cynomolgus FcR and FcRn homologs with similar potency as obtained for the human FcR and FcRn receptors, thus establishing clinical relevancy of the NHP model.

The SARS-CoV-2-RBD-hIgG-Fc fusion protein of SEQ ID NO: 19 was synthesized according to Example 2 or Example 3 and purified according to Example 5. The fusion protein structure was confirmed by non-reducing and reducing CE-SDS according to Example 6 and the fusion protein sequence identification was confirmed by LC-MS with glycan removal according to Example 7.

Groups of N=3 male and female Cynomolgus monkeys were subcutaneously administered the SARS-CoV-2-RBD-hIgG-Fc fusion protein of SEQ ID NO: 19 in Montanide™ ISA 720 adjuvant at 30%/70% (v/v) via a single subcutaneous injection on Day 0 and Day 21 according to Table 11. Five of the six monkeys were administered a booster injection of the SARS-CoV-2-RBD-hIgG-Fc fusion protein of SEQ ID NO: 19 in Montanide™ ISA 720 adjuvant at 30%/70% (v/v) between approximately 3 and 4½ months after the second injection.

TABLE 11

Cynomolgus Monkey Test Groups and Dose Levels for SEQ ID NO: 19 with Montanide ™ ISA 720 30%/70% v/v.

| Group | Animal | SARS-CoV-2 SP/RBD-Fc fusion protein SEQ ID NO: | Sex | Dose Level (µg/Dose) | Dosing Schedule |
|---|---|---|---|---|---|
| 1 | 6001 | SEQ ID NO: 19 + ISA 720 | M | 30 | 0, 21, 154 |
| 1 | 6101 | SEQ ID NO: 19 + ISA 720 | F | 30 | 0, 21 |
| 1 | 6102 | SEQ ID NO: 19 + ISA 720 | F | 30 | 0, 21, 104 |
| 2 | 7101 | SEQ ID NO: 19 + ISA 720 | F | 10 | 0, 21, 104 |
| 2 | 7102 | SEQ ID NO: 19 + ISA 720 | F | 10 | 0, 21, 104 |
| 2 | 7103 | SEQ ID NO: 19 + ISA 720 | F | 10 | 0, 21, 104 |

Blood was collected from each NHP, allowed to clot, and the serum was separated by centrifuging micro-vacutainer tubes and aliquoted and frozen for antibody analysis by ELISA according to the methods described in Example 11.

The induced anti-SP/RBD IgG Ab titer response (mean IgG µg/mL via an IgG ELISA reference serum standard curve) of the SARS-CoV-2-RBD-hIgG-Fc fusion protein of SEQ ID NO: 19 formulated with Montanide™ ISA 720 adjuvant at dose levels of 10 µg and 30 µg was measured on Day 0 after one dose, Day 14 after one dose, Day 20 after one dose, Day 35 after two doses and Day 42 after two doses according to Example 11, revealing potently induced IgG Ab titers, in which the higher dose level of 30 µg showed greater immunogenicity than the lower dose level of 10 µg at all timepoints after the Day 0 and Day 21 doses as shown in FIG. 60.

Figure 61:
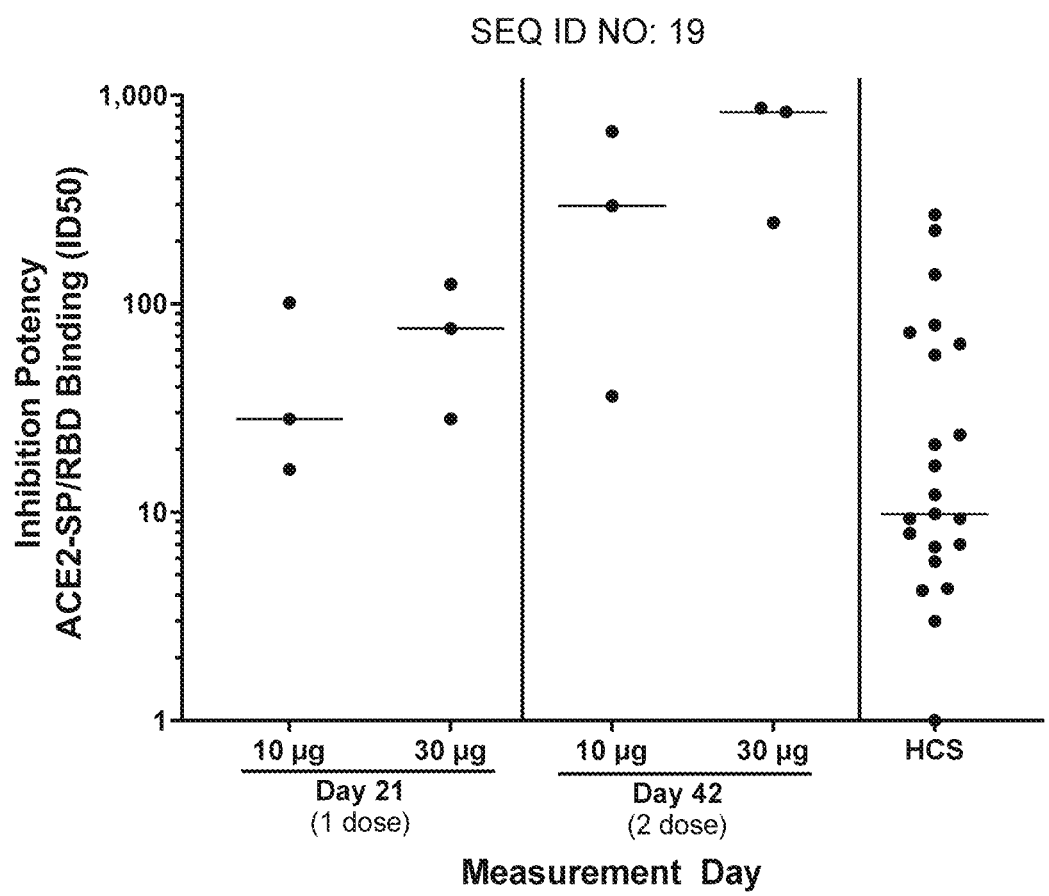
FIG. 61 illustrates the induced ACE2-SP/RBD binding inhibition potency (ID50) in male and female Cynomolgus monkeys administered either a 10 µg or 30 µg dose level of the SARS-CoV-2-RBD-hIgG-Fc fusion protein of SEQ ID NO: 19 formulated with the Montanide™ ISA 720 adjuvant at 30%/70% (v/v) on Day 21 and Day 42 after an injection on Day 0 and Day 21.

For the animals that received a booster (third) dose either at Day 102 or Day 154 after the anti-SP/RBD IgG Ab titer had dropped, the induced anti-SP/RBD IgG Ab titer response following a single booster dose was significant as shown in FIG. 61, indicating a strong memory recall.

Furthermore, these IgG Ab titer immunogenicity profiles were consistent the ACE2-binding inhibition potency (ID50) induced by the SARS-CoV-2-RBD-hIgG-Fc fusion protein of SEQ ID NO: 19 and measured according to Example 13, which was well above the potency of human convalescent serum (HCS) as shown in FIG. 61, where the ID50 value represents the reciprocal of the dilution at which 50% of the ACE2 binding was achieved by a serum sample, which was calculated on Day 21 after 1 dose and Day 42 after 2 doses for both the 10 µg and 100 µg dose level.

Example 28: Plaque Reduction Neutralization Test to Confirm the Inhibitory Potency of Disrupting the Biochemical Interaction of Recombinant ACE2 and SP/RBD of SEQ ID NO: 19 with the Adjuvant, Montanide™ ISA 720, in Non-Human Primates (NHPs; i.e., Cynomolgus Monkeys)

In furthering such translational research, this inhibitory potency of disrupting the biochemical interaction of recombinant ACE2 and SP/RBD was confirmed with the neutralization of live SARS-CoV-2 virus from infecting live VERO-E6 cells in the Plaque Reduction Neutralization Test (PRNT).

Groups of N=3 male and female Cynomolgus monkeys were subcutaneously administered the SARS-CoV-2-RBD-hIgG-Fc fusion protein of SEQ ID NO: 19 in Montanide™ ISA 720 adjuvant at 30%/70% (v/v) on Day 0 and Day 21 according to Table 11. Blood was collected from each NHP, allowed to clot, and the serum was separated by centrifuging micro-vacutainer tubes, aliquoted, and frozen for analysis.

Figure 62:
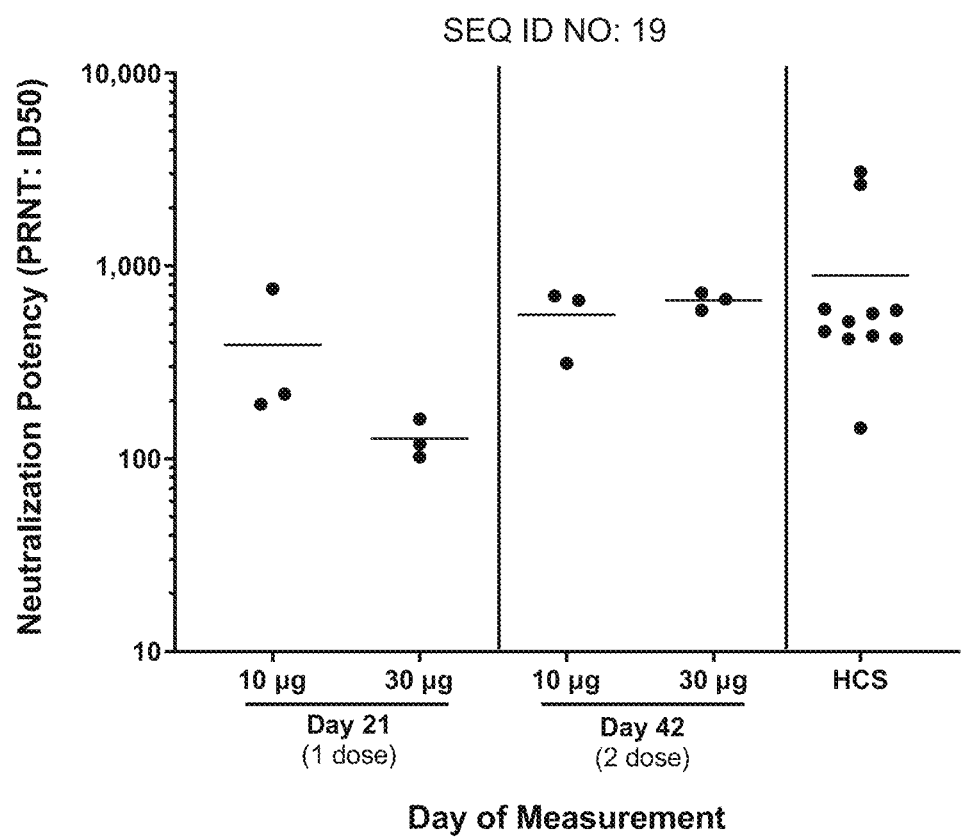
FIG. 62 illustrates the SARS-CoV-2-RBD-hIgG-Fc fusion protein of SEQ ID NO: 19 induced SARS-CoV-2 virus neutralization potency in NHP serum samples as measured on Day 21 and Day 42, where SEQ ID NO: 19 formulated with Montanide™ ISA 720 adjuvant at 30%/70% (v/v) after an injection on Day 0 and Day 21, compared to human convalescent serum.

The Plaque Reduction Neutralization Test was conducted according to Example 15. The SARS-CoV-2-RBD-hIgG-Fc fusion protein of SEQ ID NO: 19 induced SARS-CoV-2 virus neutralization potency in NHP serum samples is shown in FIG. 62. The neutralization potencies showed a similar profile as that of the ACE2-inhibition potencies, although such PRNT ID50 values were similar to those of human convalescent serum.

These results demonstrate the value of testing vaccination in NHPs and provide valuable guidance for designing the first-in-human clinical trials and set expectations for the translation to humans.

Example 29: Effectiveness of a SARS-CoV-2-RBD-hIgG-Fc Fusion Protein Vaccine of SEQ ID NO: 19 with the Adjuvant, Montanide™ ISA 720 Against the UK Variant (N501Y) and the South African Variant (E484K) of SARS-CoV-2 in Mice and Non-Human Primates (NHPs; i.e., Cynomolgus Monkeys)

Analysis was performed in an attempt to understand whether the SARS-CoV-2-RBD-hIgG-Fc fusion protein of SEQ ID NO: 19 with the adjuvant, Montanide™ ISA 720 was effective against variants of the SARS-CoV-2 virus, specifically a UK and South African viral variant.

FIG. 66 illustrates a side by side comparison of the SARS-CoV-2 native SP/RBD of SEQ ID NO: 2 and the analog SP/RBD fragment of the UK N501Y viral variant (SEQ ID NO: 24) and the South African E484K viral variant (SEQ ID NO: 25) performed using Clustal Omega where "*" represents complete homology across all sequences at a given sequence position. A ":" (colon) indicates conservation between groups of strongly similar properties with scoring greater than 0.5 in the Gonnet PAM 250 matrix. A "-" (dash) indicates a sequence gap, meaning that no local homology exists within a particular set of comparisons within a certain range of the sequences.

```
                                                      (SEQ ID NO: 24)
PNITNLCPFGEVFNATRFASVYAWNRKRISNCVADYSVLYNSASFSTFKCY

GVSPTKLNDLCFTNVYADSFVIRGDEVRQIAPGQTGKIADYNYKLPDDFTG

CVIAWNSNNLDSKVGGNYNYLYRLFRKSNLKPFERDISTEIYQAGSTPCNG

VEGFNCYFPLQSYGFQPTYGVGYQPYRVVVLSFELLHAPATVCGPKKSTNL

VKNKCVNFNFNGLTGTGVLTESNKKFLPFQQFGRDIADTTDAVRDPQTLE (SEQ ID NO: 25)
PNITNLCPFGEVFNATRFASVYAWNRKRISNCVADYSVLYNSASFSTFKCY

GVSPTKLNDLCFTNVYADSFVIRGDEVRQIAPGQTGKIADYNYKLPDDFTG

CVIAWNSNNLDSKVGGNYNYLYRLFRKSNLKPFERDISTEIYQAGSTPCNG

VKGFNCYFPLQSYGFQPTNGVGYQPYRVVVLSFELLHAPATVCGPKKSTNL

VKNKCVNFNFNGLTGTGVLTESNKKFLPFQQFGRDIADTTDAVRDPQTLE
```

Serum samples from NHPs dosed according to Example 27 were extracted on Day 42 from animals 1, 2, 3, 5 and 6. Serum samples from mice dosed according to Example 22 were extracted on Day 56. Both the NHPs and the mice had been immunized with 2 doses of the SARS-CoV-2-RBD-hIgG-Fc Fusion Protein Vaccine of SEQ ID NO: 19 with the adjuvant, Montanide™ ISA 720.

The serum samples were added to plastic-bound recombinant RBD wildtype (Lake Pharma, San Mateo, Calif.) or mutants N501Y (UK variant, provided by SINO Biological, Wayne Pa.) or E484K (South Africa variant, provided by AcroBiosystems, Newark, Del.). Bound RBD-specific IgG was detected with labelled anti-NHP or anti-mouse IgG secondary antibodies and developed colorimetrically (OD450 values). IgG μg/mL titer values were determined via a NHP or mouse ELISA reference serum standard curve and the Mean (N=4) was reported.

The results shown in FIG. 64 and FIG. 65 illustrate that such immune sera from NHP and mice bound recombinant RBD mutants, N501Y and E484K, as well as, or greater than, the wild-type RBD molecule, indicating that the UK (N501Y) and South African (E484K) viral variants are not likely to escape SEQ ID NO: 19 induced immunity.

Examples Illustrating Toxicity Study Results of the SARS-CoV-2-RBD-hIgG-Fc Fusion Protein of SEQ ID NO: 19

Example 30: Repeat Dose Toxicity Study of a SARS-CoV-2-RBD-hIgG-Fc Fusion Protein Vaccine of SEQ ID NO: 19 in New Zealand White Rabbits with a 2-Week Recovery Period A toxicology IND-enabling study using New Zealand White Rabbits was performed.

Rabbits were chosen because this species has been extensively used for preclinical studies of vaccine-induced immunogenicity that results in robust Ab responses. In addition, rabbits express the SARS-CoV-2 viral receptor, ACE2, that allows the virus to bind and infect the animal causing disease symptoms similar to those of human COVID-19. The vaccine antigenic subunit is the ACE2 receptor binding domain of the spike protein of SARS-CoV-2 virus fused to a human IgG1 Fc molecule that could potential directly bind ACE2 in rabbits (expressed on lung, epithelium, neurons) and cause pathology.

The safety, toxicity, toxicokinetic and immunogenicity profiles of the SARS-CoV-2-RBD-hIgG-Fc fusion protein of SEQ ID NO: 19 with or without Montanide™ ISA 720 adjuvant was evaluated using vaccine formulations injected subcutaneously every 14 days for a total of 3 injections, and to evaluate reversibility of any toxicity signs during a 14-day treatment-free recovery period. The aggressive 14-day injection schedule is to ensure that the intended less-aggressive 28-day injection schedule in human clinical studies is sufficiently supported by animal toxicology. Study endpoints include clinical observations, body weight gain/loss, food consumption, clinical pathology, and terminal gross necropsy, organ weights, and histopathology.

The SARS-CoV-2-RBD-hIgG-Fc fusion protein of SEQ ID NO: 19 was synthesized according to Example 3 and purified according to Example 5. The fusion protein structure was confirmed by non-reducing and reducing CE-SDS according to Example 6 and the fusion protein sequence identification was confirmed by LC-MS with glycan removal according to Example 7.

The subjects of the study are male and female New Zealand naïve, specific pathogen-free white rabbits of 3 to 4 months of age and weighing 2 to 4 kg. The rabbits are housed in stainless steel mobile caging alone or in groups and undergo a 14 day acclimation period prior to dosing.

5 male and 5 female rabbits per Main Study treatment groups and 3 male and 3 female rabbits per Recovery treatment groups received either a 30 μg or a 100 μg dose of the SARS-CoV-2-RBD-hIgG-Fc fusion protein of SEQ ID NO: 19 formulated with Montanide™ ISA 720 adjuvant or without adjuvant, or a vehicle negative control (saline). Recovery groups were included to investigate the reversibility of any adverse effects observed during the treatment period, and to screen for any possible delayed adverse effects. The specific details of the repeat-dosing toxicology study in rabbits are given in Table 12.

TABLE 12

SEQ ID NO: 19 Repeat-Dosing Toxicology Study in Rabbits.

| Group | Test article | Dose Level (µg) | Number of animals | | | | Dosing schedule (3 doses total) |
| | | | M Main Study | F | M Recovery | F | |
| --- | --- | --- | --- | --- | --- | --- | --- |
| 1 | Vehicle | — | 5 | 5 | 3 | 3 | Day 1, 15, 29 |
| 2 | SEQ ID NO: 19 | 30 | 5 | 5 | 3 | 3 | Day 1, 15, 29 |
| 3 | SEQ ID NO: 19 | 100 | 5 | 5 | 3 | 3 | Day 1, 15, 29 |
| 4 | SEQ ID NO: 19 with Montanide ™ ISA 720 | 30 | 5 | 5 | 3 | 3 | Day 1, 15, 29 |
| 5 | SEQ ID NO: 19 with Montanide ™ ISA 720 | 100 | 5 | 5 | 3 | 3 | Day 1, 15, 29 |

The target product profile of the SARS-CoV-2-RBD-hIgG-Fc fusion protein of SEQ ID NO: 19 includes no more than 2 immunization injections in humans, therefore a "clinical dosing+1" strategy was used wherein 3 vaccine doses were administered subcutaneously on Days 1, 15, and 29 (Day 15 and Day 29 toxicokinetic injections are designed to be in the presence of anti-SP/RBD titers induced from the Day 1 and Day 15 injections, respectively). Both s.c. and i.m. routes of administration were evaluated.

Example 31: Serum Levels of SARS-CoV-2-RBD-hIgG-Fc Fusion Protein, Serum Levels of Anti-SP/RBD IgG, and Observational and Quantitative Safety Assessments in GLP Toxicology Studies in Rabbits The PK/TK assay is an enzyme linked immunosorbent assay (ELISA) in which the SARS-CoV-2-RBD-hIgG-Fc fusion protein of SEQ ID NO: 19 present in the rabbit serum study samples is captured by goat anti-Human IgG (Fc) coated on microtiter wells and then is quantitated by an anti-human IgG-Fc biotin conjugate which is then reacted with high sensitivity Streptavidin-HRP detection antibody followed by TMB substrate system. Purified SEQ ID NO: 19 is used for preparing standard curves for the assay as well as for making assay controls. Four QCs (High QC, Mid QC, Low QC and Negative QC) were prepared at 10× by spiking purified SEQ ID NO: 19 stock solution into normal rabbit serum (Jackson Immuno), and tested in multiple runs to establish their nominal values and stored frozen at −20° C. as small-volume aliquots for single-thaw use. These QCs were used as the spiked validation samples in the validation assays to evaluate accuracy, precision, limit of quantitation, dilution linearity, spike recovery, and short-term stability.

During pre-validation, a minimum required dilution (MRD) of 1:10 was determined as optimal for this ELISA, and this dilution was used in the validation runs. Thus, 10% of normal rabbit serum (Jackson Immuno; lyophilized normal rabbit serum reconstituted in $H_2O$) was added in the dilution buffer used for making standard curves during primary validation runs. When spike recovery was tested with actual normal rabbit sera (BioIVT), significant under-recovery of spiked values was observed due to matrix effects not seen with the normal rabbit serum.

Based on these results, it was determined that pooled rabbit serum, rather than normal rabbit serum, should be used in preparation of the standard curve in order to better represent recovery of SEQ ID NO: 19 in non-clinical rabbit serum samples. Selected parameters such as accuracy and precision, linearity, and spike and recovery were re-tested using 10% pooled normal rabbit serum (BioIVT) in the standard curve buffer.

When using the pooled serum standard curve, intra- and inter-assay accuracy ranged from 93-105% at all three non-zero QC levels. The assay was found to be linear between 2 ng/mL and 100 ng/mL, and those values were found to be the lower limit of quantification (LLOQ) and upper limit of quantification (ULOQ) respectively. When using the pooled serum standard curve, spike-recovery was extremely accurate across 11 different serum samples, with recoveries ranging from 100-117% at a high spike level (70 ng/mL), 107-116% at a mid-spike level (40 ng/mL), and 108-123% at a low spike level (10 ng/mL). Spike serum samples were found to be stable through at least 3× freeze-thaw cycles (95-103% recovery), up to one week at 4° C. (97-100% recovery), and 4 hours at room temperature (91-98% recovery). Validation results show that the SEQ ID NO: 19 PK/TK ELISA was highly accurate and reproducible, and fit for purpose.

A 4-timepoint TK study was conducted in which the same animal was bled at pre-dose, 6 h, 24 h, and 48 h after the 1st, 2nd, and 3rd injections in which an appropriate volume of blood was obtained for each bleed for TK analyses in addition to immunogenicity analyses.

Systemic effects on the immune system were evaluated by draining lymph nodes and performing hematology and serum chemistry before the 1st dose and approximately 2-3 days following the administration of the 1st and last doses, at takedown for the Main Study, and at takedown of the Recovery groups, and included absolute and relative differential white blood cell (WBC) counts (lymphocytes, monocytes, granulocytes, abnormal cells), albumin/globulin ratio, enzymes, and electrolytes. Serum samples were evaluated for vaccine-specific Ab titers and TK levels.

Daily clinical observations included examination of local inflammatory reactions at the injection sites for up to three days after the injection and weekly thereafter (such observations included swelling, pain reaction to touch, impaired locomotion, and granulomatous nodules). Daily observation for health status (lethargic, lack of movement, difficulty in walking, not eating etc.) was also performed. Weekly body weights and food consumption (lack of appetite, anorexia) were monitored and assessed at study termination after an approximately 12 hour period of fasting.

At study termination, blood samples were collected for serum chemistry, hematology, and immunological investigations, and at which time a complete gross necropsy was conducted with examination of gross lesions and organ weights. Histopathological examinations of tissues were performed, and special attention paid to immune organs (both local and distant lymph nodes, spleen, bone marrow, and Peyer's patches), pivotal organs (lung, liver, kidneys, brain, and reproductive organs), and the site of vaccine administration. Local toxicity (at the site of vaccine administration) assessment included evaluation for inflammatory reactions (e.g., soft granulomatous nodules, hard fibrous nodules, ulceration, etc.) and sites excised, and histopathology examination performed. Eosinophilia in lung tissue was especially evaluated.

Doses were formulated and prepared according to Table 12. Dosing sites were rotated, clipped prior to dosing, and marked with indelible marker and rabbits were dosed subcutaneously on Days 1, 15 and 29, Rabbits were observed for detailed clinical observations prior to and 1-hour following each dose as well as twice daily, daily and weekly. Draize Scoring to assess injection site inflammation was performed at 24, 48, & 72-hours following each dose. If a non-zero score was given at 72-hours post-dose, the site was scored every seven days until the finding resolved or the animals were sacrificed.

Body temperature was measured prior to each dose, and 6 and 24-hours following each dose. If body temperature exceeded 40° C., additional measurements were taken every 24-hours until values returned to normal, or animals were sacrificed. Body weights were recorded prior to the first dose, at 24 and 48-hours following the first dose, weekly, and prior to each scheduled necropsy. The rabbits were exampled once in the acclimation period and then twice daily for mortality. Food consumption was quantitively measured daily. An ophthalmology exam was performed once prior to the first dose and prior to each scheduled necropsy.

Clinical chemistry and hematology were performed once prior to first dose, 48-hours following the first and last doses, on all animals at necropsy of the main study groups, and on the remaining animals at end of recovery period. Coagulation was examined once prior to the first dose, 3 days following each dose, on all animals at necropsy of the main study groups, and on the remaining animals at end of recovery period.

Blood was collected from all animals for C-Reactive Protein once prior to 1st dose, 3 days following each dose, on all animals at necropsy of the main study groups, and on remaining animals at end of recovery period. Blood was collected from all animals for ADA via ELISA prior to the first dose and 14-days following each dose (with the exception of the final dose), on all animals at necropsy of the main study groups, and on remaining animals at end of recovery period. 4-point Toxicokinetics (TK) blood sampling for each animal in the study were collected on 1st, 2nd, and 3rd doses; i.e., blood was taken at Day 1 pre-dose, and 6 h, 24 h, and 48 h after each dose, and then 1 additional sampling at the Day 36 takedown for the Main Study and at Day 43 for the Recovery animals; serum SEQ ID NO: 19 concentration analysis was performed via ELISA.

Full necropsy on Day 36 (main study) and Day 43 (recovery) was performed with full tissue collection and standard organ weights on all animals at each scheduled necropsy. Histopathology examination was performed via tissues processed to slides and was evaluated on all main study and recovery animals as well as any found dead and those euthanized in extremis.

There was no mortality as a result of the toxicology study. During the dosing phase, increases in fibrinogen in males given 100 µg SEQ ID NO: 19 with Montanide™ ISA 720 from dosing phase Day 4, and 30 or 100 µg SEQ ID NO: 19 with Montanide™ ISA 720 from dosing phase Day 32, and females given 100 µg 100 µg SEQ ID NO: 19 with Montanide™ ISA 720 from dosing phase Day 18, and 30 or 100 µg 100 µg SEQ ID NO: 19 with Montanide™ ISA 720 from dosing phase Day 32 were generally statistically significant and likely related to the test article and to the microscopic finding of chronic-active inflammation. During the Recovery Phase, differences in fibrinogen were considered recovered. Statistically significant differences in fibrinogen were present in females but were comparable to acclimation values and were considered likely unrelated to the test article and due to biological variation. There were no other test article-related clinical pathology changes at the scheduled collections.

Statistically significant differences in alanine aminotransferase, aspartate aminotransferase, calcium, lactate dehydrogenase, potassium, chloride, percent lymphocytes, activated partial thromboplastin time, in males only, and sodium in females only were considered due to biologic variation and unrelated to the test article. Statistically significant differences in glucose, globulin, or albumin/globulin ratio, heterophils and percent heterophils, prothrombin time in males and females were comparable to acclimation values or inconsistent between sessions. These differences were small, not present in males, or values were comparable to values at acclimation and considered unrelated to the test article and due to biological variation. There were no organ weight differences at the main or recovery terminations. Small differences were not statistically significant, independent of dose, or inconsistent between sexes and were considered unrelated to test article administration.

In Toxicokinetics (TK) studies, SEQ ID NO: 19 induced Anti-Drug Antibody (ADA) IgG titers specific for the SP/RBD Ag in rabbits were measured. The rabbits were divided into N=10 animals/group that received 3 doses at 14 days apart of PBS Vehicle (Group 1), 30 µg SEQ ID NO: 19 (Group 2), 100 µg SEQ ID NO: 19 (Group 3), 30 µg of SEQ ID NO: 19 with Montanide™ ISA 720 (Group 4), or 100 µg of SEQ ID NO: 19 with Montanide™ ISA 720 (Group 5). Serum samples were collected after designated times and evaluated for anti-SP/RBD IgG Ab titers (IgG μg/mL Mean via ELISA using a rabbit IgG standard curve) according to Example 14.

The SARS-CoV-2-RBD-hIgG-Fc fusion protein of SEQ ID NO: 19 without adjuvant (i.e., Groups 2 and 3 as shown in FIG. 68 and FIG. 69) showed negligible-to-weak anti-SP/RBD-specific IgG titers at all timepoints that were in the range of those of the vehicle control Group 1 (as shown in FIG. 67); i.e., below 10 μg/mL. However, substantial specific IgG titers were induced in the presence of Montanide™ ISA 720 adjuvant with SEQ ID NO: 19 doses of 30 μg and 100 μg (Groups 4 and 5, respectively) after the 1st (Day 15), 2nd (Day 29), and 3rd (Day 43) injections that were well above (~10-fold) those of human convalescent serum after the 2nd and 3rd doses, as shown in FIG. 70 and FIG. 71. There was a slight trend (not statistically significant) of a dose response between the 30 μg and 100 μg dose levels in Group 4 and 5 treated with SARS-CoV-2-RBD-hIgG-Fc fusion protein of SEQ ID NO: 19 with the adjuvant Montanide™ ISA 720.

Example 32: Functional Inhibitory Potency Results from Rabbit Serum Samples Collected from GLP Toxicology Studies in Rabbits The serum samples used for the primary endpoints of TK and ADA were collected after designated times and evaluated for potency (ID50 values) to inhibit ACE2-SP/RBD binding (according to the method of Example 13) and to inhibit live SARS-CoV-2 virus from infecting VERO-E6 cells in the Plaque Reduction Neutralization Test (PRNT)

according to the method of Example 15. As described in Example 31, N=10 animals/group received two doses at 14 days apart of 30 μg of SEQ ID NO: 19 with Montanide™ ISA 720 (Group 4) or 100 μg of SEQ ID NO: 19 with ISA 720 (Group 5). Because the desired SARS-CoV-2-RBD-hIgG-Fc fusion protein of SEQ ID NO: 19 vaccine includes formulation with the Montanide™ ISA 720 adjuvant, only Groups 4 and 5 were evaluated in the two functional assays. An ID50 value represents the reciprocal of the dilution at which 50% of the assay signal was achieved by a serum sample.

In the ACE2 inhibition assay of Example 13, there was a clear dose response in inhibitory potency between the 30 μg and 100 μg dose levels that were elevated and became similar 14 days after the 2nd dose as shown in FIG. 72. These potencies values at both timepoints were substantially above those obtained for human convalescent serum. Evaluation of the capacity to inhibit live virus from infecting cells demonstrated a strong potency at both 30 μg and 100 μg dose levels as illustrated in FIG. 73, showing a trend toward greater potency after the second dose (i.e., Day 35) and that this potency was similar to that of human convalescent serum. These results demonstrate that the SARS-CoV-2-RBD-hIgG-Fc fusion protein of SEQ ID NO: 19 emulsified in Montanide™ ISA 720 induces functional immunogenicity in this GLP toxicology study at levels found in humans that recovered from COVID-19 infection and disease, which puts these toxicology results into a clinical context favoring the expectation of a clean safety profile.

Example 33: Repeat Dose Toxicity Study of the SARS-CoV-2-RBD-hIgG-Fc Fusion Protein of SEQ ID NO: 19 in New Zealand White Rabbits to Bridge Toxicology Results of the Subcutaneous Route with Those of Intramuscular Route The majority of licensed vaccines are administered by intramuscular (i.m.) injection, but some are approved for subcutaneous (s.c.) or intradermal (i.d.) use, mainly because of the theoretical rationale that s.c. and i.d. are sites that contain greater numbers of APCs that can deliver vaccine Ag to draining lymph nodes in a more efficient manner than could an i.m. route. Intramuscular administration is often preferred because it is easy to perform and is generally well tolerated, with a low risk for adverse reactions at the site of injection. However, vaccine delivery to the skin as a highly immunocompetent site compared with the muscle has long been considered a strategy to amplify vaccine responses. In some cases, such as with yellow fever or influenza virus vaccines, s.c. was superior to i.m. injections resulting in enhanced immunogenicity in healthy individuals, especially in non- or low-responders. In some cases, vaccination in s.c. resulted in more efficient activation of APCs at the site of injection (compared with i.m.) that was accompanied by transiently higher levels of vaccine-specific T cell responses and Ab titers. However, in general, there appears to be little risk of differences in immunogenicity between s.c. and i.m. routes demonstrated in comparator clinical studies with several approved vaccines such as those for hepatitis B and A viruses, herpes zoster virus, influenza, diphtheria toxin, measles, mumps, rubella, and varicella, and tick-borne encephalitis virus. Nevertheless, there appears to be a slight elevation in the incidence of mild injection site adverse events via s.c. relative to i.m. immunized individuals, which has motivated i.m. vaccination as the desired route of delivery.

New Zealand White Rabbits are utilized for the study under the same study design and general protocol used in Example 32. The study design is described in Table 13 and Table 14. Induction of anti-SP/RBD IgG titers (measured according to Example 14) that inhibit ACE2-binding in male (N=5) and female (N=5) rabbits with a 100 μg dose of SEQ ID NO: 19 (100) emulsified in ISA 720 adjuvant administered either s.c. or i.m. on Day 1, Day 15, and Day 29 and serum was collected on Day 0, on Day 15 (before administration of dose 2), Day 29 (before administration of dose 3) and on Day 36 for binding inhibition analysis measured according to Example 13. An ID50 value represents the reciprocal of the dilution at which 50% of the ACE2 binding was achieved by a serum sample.

Analysis demonstrated no statistically significant differences in IgG titer or ACE2 inhibition potency titers between the s.c. and i.m. administrations of a 100 μg dose of SEQ ID NO: 19 in Montanide™ ISA 720 at any of the measurement days (FIG. 74 and FIG. 75), supporting the evaluation of either route of administration in clinical trials.

TABLE 13

Study Design for Repeat Dose Toxicity Study of SEQ ID NO: 19 in New Zealand White Rabbits Bridging Results Subcutaneous vs. Intramuscular routes.

| Group | Test article | Route of administration | SEQ ID NO: 19 Dose Level (μg) | Number of animals M | Number of animals F | Dosing schedule (3 doses total) |
|---|---|---|---|---|---|---|
| 1 | vehicle | s.c. | — | 5 | 5 | Day 1, 15, 29 |
| 2 | SEQ ID NO: 19 + Montanide ™ ISA 720 | s.c. | 100 | 5 | 5 | Day 1, 15, 29 |
| 3 | vehicle | i.m. | — | 5 | 5 | Day 1, 15, 29 |
| 4 | SEQ ID NO: 19 + Montanide ™ ISA 720 | i.m. | 100 | 5 | 5 | Day 1, 15, 29 |

TABLE 14

Blood/Tissue Sampling and all Analyses for SEQ
ID NO: 19 IM vs SC Bridging Study in Rabbits

| Test | Day of analysis and tissue sampling (5/sex/group) | | | | | | |
|---|---|---|---|---|---|---|---|
| | −7 | 1 | 4 | 15 | 18 | 29[b] | 32 | 36 |
| SEQ ID NO: 19 dosing[a] | | X | | X | | X | | |
| Hematology | X | | X | | | | X | X |
| Blood Chemistry | X | | X | | | | X | X |
| Injection site examination (Draze scoring) | | X | X | X | X | X | X | X |
| Coagulation Parameters (PT, PTT) | X | | X | | X | | X | X |
| Physical Exams | X | | | | | | | X |
| Necropsy/Histopathology on i.m. injection site muscle (Tissue collection) | | | | | | | | X |
| Standard endpoints with daily (food consumption, clinical observation, Mortality/Moribundity) and weekly (body weight) observations | X | X | X | X | X | X | X | X |
| Toxicokinetics (TK)[b] | | X | | X[c] | | X[c] | | X[c] |
| Immunogenicity-ADA | X | | | X[c] | | X[c] | | X[c] |
| Take-Down | | | | | | | | X |

[a] s.c. or i.m. injection dosing on Days 1, 15, and 29, a total of 3 injections; take-down of animals in main study on Day 36.
[b] 4-point TK sampling profile for each animal in the study on the 1st, 2nd, and 3rd doses (i.e., Day 1 pre-dose, 6, 24, 48 h around each dose), then 1 addition sampling at the Day 36 takedown; serum AKS-452 concentration analysis via ELISA by Sponsor
[c] The same blood samples will be used for both TK and Immunogenicity.

Example 34: Subgroup Analysis of the SARS-CoV-2-RBD-hIgG-Fc Fusion Protein of SEQ ID NO: 19 in New Zealand White Rabbits to Analyze the Effect of Freshly Made Vs. Aged Emulsion with Adjuvant Due to the logistics of having to dose so many animals in the GLP Repeat Dose Toxicity study in Rabbits (Example 30), half of the animals (male rabbits) were dosed on the day the SEQ ID NO: 19 with Montanide™ ISA 720 emulsion was prepared (T=0), and the other half of the animals (female rabbits) were dosed 24 hours (T=24) after storing the emulsion at 2-8° C. Therefore, it was possible to perform a sub-group analysis on the ACE2-SP/RBD Binding Inhibition Potency (IC50) results (measured according to Example 13) measured on Day 15 (after one dose), Day 29 (after 2 doses) and Day 36 (after three doses) to determine whether there was any difference in performance between the freshly made and stored emulsion. Again, as described above for the mouse immunogenicity studies (Example 26), there was no statistical difference in inhibitory potency between the fresh and stored emulsion indicating that the adjuvanted SEQ ID NO: 19 formulation performance is stable for at least 24 hours after preparation as shown in FIG. 76 (for subcutaneous administration) and FIG. 77 (for intramuscular administration).

Examples for Efficacy Testing in the NHP SARS-CoV-2 Viral Challenge Model for NHP Immunized with the SARS-CoV-2-RBD-hIgG-Fc Fusion Protein Vaccine of SEQ ID NO: 19 with the Adjuvant, Montanide™ ISA 720

Example 35: Group Assignment for SEQ ID NO: 19+ISA 720 Efficacy Testing in the NHP SARS-CoV-2 Viral Challenge Model Efficacy of the SEQ ID NO: 19 vaccine is evaluated in the immunized NHP of Example 27 using the rhesus macaque challenge model of SARS-CoV-2. After challenge, SARS-CoV-2 burden is monitored through the experiment through collection and analysis of bronchoalveolar lavage (BAL) fluid, nasal wash fluid, as well as nasal and oropharyngeal swabs. Viral loads are assessed in tissues after necropsy.

Two groups of N=5 Cynomolgus monkeys were challenged as shown below in Table 15. One group consisted of 5 of the 6 Cynomolgus monkeys that had been immunized SARS-CoV-2-RBD-hIgG-Fc Fusion Protein Vaccine of SEQ ID NO: 19 with the adjuvant, Montanide™ ISA 720 according to Example 27 and then injected with a booster vaccine (third injection) of SARS-CoV-2-RBD-hIgG-Fc Fusion Protein Vaccine of SEQ ID NO: 19 with the adjuvant, Montanide™ ISA 720 at the 30 μg dose level between three and four and a half months after their first injection. The second group consisted of 5 Cynomolgus monkeys that had not been treated

TABLE 15

Group Assignment for SARS-CoV-2 Viral Challenge

| Group No. | Treatment | | Animal ID | Sex | DOB | Body Weight (kg) |
|---|---|---|---|---|---|---|
| 1 | Untreated control | | 9071 | Male | Unknown | 11.62 |
| | | | 9067 | Male | Unknown | 8.10 |
| | | | 9068 | Male | Unknown | 8.30 |
| | | | 9084 | Male | Unknown | 6.50 |
| | | | 9029 | Male | Unknown | 6.10 |
| 2 | SEQ ID NO: 19 + ASA 720 | 30 μg 10 μg | L938 | Female | Jul. 3, 2018 | 2.54 |
| | | | M287 | Male | Oct. 15, 2018 | 3.13 |
| | | | K183 | Female | Jan. 26, 2017 | 3.60 |
| | | | K265 | Female | May 11, 2017 | 3.82 |
| | | | 1608006 | Female | Aug. 10, 2016 | 2.76 |

The two groups were challenged with SARS-CoV-2 virus on Day 0. Blood was collected prior to the challenge and on Day 7. Nasal swabs, oral swabs, and collection of BAL fluid was performed prior to the challenge and on Days 2, 4, and 7. Necroscopy post termination was performed on Day 7. The study schedule is given in Table 16.

TABLE 16

SARS-CoV-2 Viral Challenge Study Schedule

| Study Day | Event | Monitoring Clinical scores, body weights and temperatures | EDTA bleed | SST bleed | BAL qPCR/ sgRNA Assays | Nasal Swabs qPCR/ sgRNA Assays | Necropsy qPCR/ sgRNA Assays/ TCID50 |
|---|---|---|---|---|---|---|---|
| Day −6 | Pre-sampling | X | 2 mL | 8 mL | 5 mL | X | X |
| Day 0 | SARS-CoV-2 Challenge (IN/IT Route) | X | | | | | |

TABLE 16-continued

SARS-CoV-2 Viral Challenge Study Schedule

| Study Day | Event | Monitoring Clinical scores, body weights and temperatures | EDTA bleed | SST bleed | BAL qPCR/ sgRNA Assays | Nasal Swabs qPCR/ sgRNA Assays | Necropsy qPCR/ sgRNA Assays/ TCID50 |
|---|---|---|---|---|---|---|---|
| Day 1 | | X | | | | | |
| Day 2 | | X | 2 mL | | 2 mL | X | X |
| Day 3 | | X | | | | | |
| Day 4 | | X | 2 mL | | 2 mL | X | X |
| Day 5 | | X | | | | | |
| Day 6 | | X | | | | | |
| Day 7 | Termination | X | 2 mL | 16 mL | 16 mL | X | X | X |

Example 36: Viral Inoculation for SEQ ID NO: 19+ISA 720 Efficacy Testing in the NHP SARS-CoV-2 Viral Challenge Model Virus inoculum was prepared by serial dilution in PBS to reach the intended dose level of 1×105 TCID50 in 2 mL. Administration of virus was conducted under Ketamine sedation. Intranasal (IN) route administration was performed as follows. Using a calibrated P1000 pipettor, 0.5 mL of the viral inoculum was administered dropwise into each nostril, 1.0 mL per animal. The anesthetized NHP was held on its back on the procedure table. A technician tilted the animal's head back so that the nostrils are pointing towards the ceiling. The technician placed the tip of the syringe into the first nostril, slowly depressed the plunger, injected the inoculum into the nasal passage, and then removed the syringe. This was repeated for the second nostril. The animal's head was tilted back for about 20 seconds and then returned to its housing unit and monitored until fully recovered.

Intratracheal (IT) route administration was performed as follows. One (1) mL of diluted virus was delivered intratracheally using a French rubber catheter/feeding tube, size 10, sterile, (cut 4"-6" in length). The prescribed dose of inoculum was drawn into a syringe. Before inserting the syringe with the inoculum on the catheter, the technician pulled back the syringe allowing 1.5 cc of air into the syringe. This air pushes all the inoculum through the catheter. The anesthetized animal was positioned for the procedure and its mouth opened by an assistant. The syringe containing the inoculum was attached to a sterile French catheter or feeding tube. Once the epiglottis was visualized and the glottis is opened, the small end of the feeding tube was inserted into the glottis. Once in place, the technician injected the inoculum into the trachea and then removed the catheter from the trachea. New or sterilized equipment was used for each animal. The study animal was returned to its housing unit and monitored until fully recovered.

The challenge inoculum was back-titered via a plaque or TCID50 assay for verification of proper dose level. Remaining inoculum was also aliquoted into 2 mL cryovials and stored at temperatures below −70° C. for use as a positive control in the viral load assays.

Example 37: Sample Collection for SEQ ID NO: 19+ISA 720 Efficacy Testing in the NHP SARS-CoV-2 Viral Challenge Model Collection of mucosal secretions was performed on the sedated NHP using cotton swabs (COPAN flocked swab). The swabs were inserted into the nasal cavity and rotated gently. Following collection, the swabs were placed into a collection vial (2/specimen) containing 1 mL PBS for qPCR analysis. All vials were stored at temperatures below −70° C. until viral load testing.

The bronchoalveolar lavage (BAL) procedure was performed on the anesthetized animal by the "chair method". For this procedure one technician performed the actual BAL wash procedure, and another technician placed their hand on the animal's chest. This was to decrease or avoid any animal movement caused by possible coughing during the procedure to minimize any possible specimen contamination. The NHP was placed in dorsal recumbency in the chair channel. The handle at the chair base was slid up against the animal to keep the animal from sliding down the chair channel. Once the handle was into position supporting the animal's weight, the handle was then tightened into position. A red rubber feeding tube was premeasured and marked before placement. The animal's head was tilted back and down below the edge of the chair channel. A red rubber feeding tube was then inserted into the animal's trachea via a laryngoscope during inspiration. The tube was placed into correct positioning and the BAL wash procedure was executed. A total of 10 mL was flushed through the tube. Upon sample completion, the handle at the base of the chair was loosened and the animal was removed from the chair.

The volume instilled and recovered from each animal, as well as any presence of blood in the BAL samples, was recorded. The collected BAL samples were placed immediately onto wet ice and processed for isolation of fluid (e.g., for viral load analysis). For this procedure, the tube was centrifuged (8 min. 300-400×g) at 4° C., the supernatant removed. The following BAL aliquots were prepared and cryopreserved until viral load (VL) or other testing: 3×0.2 mL for VL testing; 3×1 mL for other assays and banking.

Example 38: Blood Collection for SEQ ID NO: 19+ISA 720 Efficacy Testing in the NHP SARS-CoV-2 Viral Challenge Model Blood was collected while under anesthesia in accordance with Table 16. The blood was withdrawn from anesthetized animals using femoral venipuncture using a Vacutainer 21 g×1" blood collection needle or Abbott Butterfly 23 g×¾" tubing attached to Vacutainer blood collection tubes. Blood was collected into BD Vacutainer® tubes containing EDTA anticoagulant and analyzed using an in-house IDEXX BioResearch analyzer. The following routine panels were analyzed: CBC: WBC, RBC, HGB, HCT, MCV, MCH, MCHC, NRBC, Neutrophils SEG, lymphocytes, monocytes, eosinophils, basophils, absolute neutrophils SEG, absolute lymphocytes, absolute eosinophils, absolute basophils.

Scheduled necropsies were carried out for lung tissue collection. The animal was weighed, and body temperature recorded and followed by the removal of the lungs from the chest cavity. Gross evaluations of the animal and lungs was captured and recorded along with digital images of the lungs. Tissues were sampled for viral load assays by collecting two small pieces (0.1-0.2 gram each) from the left and right caudal and cranial lobes (total of 8 pieces). Following tissue collection for viral analysis, the lungs were insufflated with and immersed in 10% neutral buffered formalin NBF. Collected lung and other issues will be preserved in NBF for histologic processing and analysis.

For viral load assays, tissues were weighed, placed into pre-labeled Sarstedt cryovials (2/sample), and snap-frozen on dry ice (time of snap-freezing was documented on the weight harts). Prior to testing in the viral load assay, the tissues were homogenized in 0.5 mL cold medium (DMEM/10% FBS/gentamicin) or RNA-Stat (for the PCR-based assay) for approximately 20 seconds using a hand-held tissue homogenizer (SOP BV-035; Omni International, Kennesaw, Ga.). The samples were then spun down to remove debris and supernatants isolated for viral load determination.

Example 39: Quantitative RT-PCR Assay for SARS-CoV-2 for SEQ ID NO: 19+ISA 720 Efficacy Testing in the NHP SARS-CoV-2 Viral Challenge Model The amounts of RNA copies per mL bodily fluid or per gram tissue was determined using a qRT-PCR assay. The qRT-PCR assay utilizes primers and a probe specifically designed to amplify and bind to a conserved region of Nucleocapsid gene of coronavirus. The signal was compared to a known standard curve and calculated to give copies per mL. For the qRT-PCR assay, viral RNA was first isolated from nasal wash using the Qiagen MinElute virus spin kit (cat. no. 57704). For tissues it was extracted with RNA-STAT 60 (Tel-test "B")/chloroform, precipitated and resuspended in RNAse-free water. To generate a control for the amplification reaction, RNA was isolated from the applicable virus stock using the same procedure. The amount of RNA was determined from an O.D. reading at 260, using the estimate that 1.0 OD at A260 equals 40 µg/mL of RNA. With the number of bases known and the average base of RNA weighing 340.5 g/mole, the number of copies was then calculated, and the control diluted accordingly. A final dilution of $10^8$ copies per 3 µL was then divided into single use aliquots of 10 µL. These were stored at −80° C. until needed. Several aliquots were chosen at random and compared to previous controls to verify consistency. For the master mix preparation, 2.5 mL of 2× buffer containing Taq-polymerase, obtained from the TaqMan RT-PCR kit (Bioline cat #BIO-78005), was added to a 15 mL tube. From the kit, 50 µL of the RT and 100 µL of RNAse inhibitor was also added. The primer pair at 2 µM concentration was then added in a volume of 1.5 mL. Lastly, 0.5 mL of water and 350 µL of the probe at a concentration of 2 µM were added and the tube vortexed. For the reactions, 45 µL of the master mix and 5 µL of the sample RNA were added to the wells of a 96-well plate. All samples were tested in triplicate. The plates were sealed with a plastic sheet.

For control curve preparation, samples of the control RNA were obtained from the −80° C. freezer. The control RNA was prepared to contain $10^6$ to $10^7$ copies per 3 µL. Eight (8) 10-fold serial dilutions of control RNA was prepared using RNAse-free water by adding 5 µL of the control to 45 µL of water and repeating this for 7 dilutions. This gives a standard curve with a range of 1 to $10^7$ copies/reaction. Duplicate samples of each dilution were prepared as described above. If the copy number exceeded the upper detection limit, the sample was diluted as needed. For amplification, the plate was placed in an Applied Biosystems 7500 Sequence detector and amplified using the following program: 48° C. for 30 minutes, 95° C. for 10 minutes followed by 40 cycles of 95° C. for 15 seconds, and 1 minute at 55° C. The number of copies of RNA per mL was calculated by extrapolation from the standard curve and multiplying by the reciprocal of 0.2 mL extraction volume. This gave a practical range of 50 to $5\times10^8$ RNA copies per mL for nasal washes, and for tissues the viral loads were given per gram.

Example 40: Subgenomic mRNA Assay for SARS-CoV-2 for SEQ ID NO: 19+ISA 720 Efficacy Testing in the NHP SARS-CoV-2 Viral Challenge Model The RT-PCR assay for the sgRNA utilizes primers and a probe specifically designed to amplify and bind to a region of the E gene messenger RNA from the Coronavirus. This was not packaged into the virion. The signal was compared to a known standard curve of plasmid containing the sequence of part of the messenger RNA including part that is not in the virus and calculated to give copies per mL for the qRT-PCR assay. To generate a control for the amplification reaction, a plasmid containing a portion of the E gene messenger RNA. A final dilution of $10^6$ copies per 3 µL was then divided into single use aliquots of 10 µL. These were stored at −80° C. until needed.

Several aliquots were chosen at random and compared to previous controls to verify consistency. The samples extracted for Viral RNA were then amplified to pick up sgRNA. The control DNA was prepared to contain $10^7$ copies per 3 µL. Seven (7) 10-fold serial dilutions of control RNA were prepared using AVE by adding 5 µL of the control to 45 µL of water and repeating this for 7 dilutions. This gives a standard curve with a range of 1 to $10^6$ copies/reaction. Duplicate samples of each dilution were prepared as described above. If the copy number exceeded the upper detection limit, the sample was diluted as needed. For amplification, the plate was placed in an Applied Biosystems 7500 Sequence detector and amplified using the following program: 48° C. for 30 minutes, 95° C. for 10 minutes followed by 40 cycles of 95° C. for 15 seconds, and 1 minute at 55° C. The number of copies of RNA per mL was calculated by extrapolation from the standard curve and multiplying by the reciprocal of 0.2 mL extraction volume. This gave a practical range of 50 to $5\times10^7$ RNA copies per mL for nasal washes, and for tissues the viral loads were given per gram.

Example 41: Antibody ELISA for SARS-CoV-2 Spike Protein for SARS-CoV-2 for SEQ ID NO: 19 with Montanide™ ISA 720 Efficacy Testing in the NHP SARS-CoV-2 Viral Challenge Model A standard indirect ELISA was performed to analyze serum samples for binding antibodies to the SARS-CoV-2 spike protein as pre-screening of the animals. The assay used the coating antigen and an IgG secondary antibody. For this assay, Nunc MaxiSorp 96-well plates (Thermo Scientific, Cat #439454) were coated with 50 µL of SARS-CoV-2 spike protein (Sino Biological, cat. no. 40589-V08B1) diluted to 2 µg/mL in 1× Carbonate-Bicarbonate Buffer (CBB, Sigma, Cat #C3041-50CAP). Plates were incubated statically overnight at 2-8° C. Unbound coating antigen in each well was removed by washing 5 times with 200 µL with PBS+0.05% Tween-20. Plates were blocked with 100 µL of PBS+1% BSA. Test and positive control samples were diluted in assay diluent (PBS-Tween20-1% BSA) to starting point dilution of 1:20 followed by four folds serial dilution using U bottom dilution plates.

Once blocking was completed, Blocking Buffer was removed by inversion and each sample was plated. Plates were incubated for 1 hour at room temperature statically, followed by washing 5 times with 200 µL PBS+0.05% Tween-20 to remove unbound sera. 50 µL of the secondary detection antibody (Goat anti-Monkey IgG (H+L) Secondary Antibody, HRP, Invitrogen, PA1-84631) was added at a dilution of 1:10,000 and plates were incubated for 60 minutes at room temperature. Unbound antibodies were subsequently removed by washing 5 times with 200 µL with PBS+0.05% Tween-20 and 1 time with 200 µL of PBS. To develop, 100 µL of 1-Step Ultra TMB substrate (SERA CARE, KPL Cat #5120-0075) was added to each well and the plate was developed. The reaction was stopped after ~10 min. with 50 µL of TMB stop solution (SERA CARE, Cat #5150-0020). The plates were read within 30 min. at 450 nm with a Thermo Labsystems Multiskan spectrophotometer.

Example 42: Plaque Reduction Neutralization Test (PRNT) for SARS-CoV-2 for SEQ ID NO: 19 with Montanide™ ISA 720 Efficacy Testing in the NHP SARS-CoV-2 Viral Challenge Model The PRNT assay was conducted on serum samples for pre-screening. For this assay, Vero E6 cells (ATCC, cat #CRL-1586) were plated in 24-well plates at 175,000 cells/well in DMEM+10% FBS+Gentamicin. The plates were incubated at 37° C., 5.0% $CO_2$ until cells reach 80-100% confluency the following day. On the assay day, the serum samples were heat inactivated at 56° C. for 30 minutes. The assay set-up was performed as follows: In a 96 deep well plate, 405 μL of diluent (DMEM+2% FBS+gentamicin) was added to column 1 and 300 μL of diluent was added to columns 3, 5, 7, 9 and 11. Forty-five (45) μL of heat inactivated serum sample was added in the first column (1:10 dilution). When all samples had been added, the contents of the wells were mix up and down ~5 times using a P200 pipettor, and 150 μL was transferred to column 3 for a 1:3-fold dilution. This was repeated for the next set of wells down the plate to column 11. For the virus positive control, 300 μL of diluent was added to columns 1, 3, 5, 7, 9 and 11 while 600 μL of diluent was added to 1 row, representing the negative control. A 30 pfu/well concentration of virus was prepared and kept on ice until use.

After the titration plate had been prepared as described above, 300 μL of 30 pfu/well virus dilution was added to all samples and positive control wells. This doubled the sample dilution factor (1st well begins at 1:20). The plate was then covered with a plate sealer and incubated at 37° C., 5.0% CO2 for 1 hour. After the incubation had been completed, the media from the 24-well plate was removed and 250 μL of titrated samples was added in duplicate from the titration plate using a multichannel pipette. Only one plate was prepared at a time to avoid drying out the cells. The 24-well plates were incubated at 37° C., 5.0% $CO_2$ for 1 hour for virus infection. During this time, the 0.5% methylcellulose media was heated in a 37° C. water bath. After one-hour incubation, 1 mL of the 0.5% methylcellulose media was added to each well and the plates are incubated at 37° C., 5% $CO_2$ for 3 days. The methylcellulose medium was removed, and the plates washed once with 1 mL PBS. The plates were fixed with 4004, ice cold methanol per well at −20° C. for 30 minutes. After fixation, the methanol was discarded, and the monolayers stained with 250 μL per well of 0.2% crystal violet (20% MeOH, 80% $dH_2O$) for 30 minutes at room temperature. The plates were finally washed once with PBS or $dH_2O$ and let dry for ~15 min. The plaques in each well were recorded and the IC50 and IC90 titers were calculated based on the average number of plaques detected in the virus control wells.

Example 43: Infectious Viral Load Assay (TCID50) for SARS-CoV-2 for SEQ ID NO: 19 with Montanide™ ISA 720 Efficacy Testing in the NHP SARS-CoV-2 Viral Challenge Model Vero E6 cells (ATCC cat. no. CRL-1586) were plated at 25,000 cells/well in DMEM+10% FBS+Gentamicin and the cultures were incubated at 37° C., 5.0% $CO_2$. Cells should be 80-100% confluent the following day. Medium was aspirated and replaced with 180 μL of DMEM+2% FBS+gentamicin. Twenty (20) μL of sample was added to top row in quadruplicate and mixed using a P200 pipettor 5 times. Using the pipettor, 20 μL was transferred to the next row, and repeated down the plate (columns A-H) representing 10-fold dilutions. The tips were disposed for each row and repeated until the last row. Positive (virus stock of known infectious titer in the assay) and negative (medium only) control wells were included in each assay set-up. The plates were incubated at 37° C., 5.0% $CO_2$ for 4 days. The cell monolayers were visually inspected for CPE. Non-infected wells have a clear confluent cell layer while infected cells have cell rounding. The presence of CPE was marked on the lab form as a + and absence of CPE as −. The TCID50 value was calculated using the Read-Muench formula.

Example 44: Results for SEQ ID NO: 19 with Montanide™ ISA 720 Efficacy Testing in the NHP SARS-CoV-2 Viral Challenge Model As shown in Table 17, the five NHPs immunized with SEQ ID NO: 19 with ISA-720 demonstrated significant anti-SP/RBD IgG titers and ACE2 inhibition ID50 values just prior to the viral challenge as compared to the five naïve control NHPs with negligible or undetectable levels for both assays. The post-challenge results shown in FIG. 78 are a stark demonstration of the efficacy of the SEQ ID NO: 19 with ISA-720 vaccine in protecting against COVID-19 infection as evidenced by the negligible or undetectable levels of SARS-CoV-2 virus genomic and virus subgenomic RNA titer (measured according to the procedure of Example 39) in nasal swabs obtained according to the procedure of Example 37. Similarly, FIG. 79 illustrates negligible or undetectable levels of SARS-CoV-2 virus genomic and virus subgenomic RNA titers (measured according to the procedure of Example 40) in BAL samples obtained according to the procedure of Example 37. The low subgenomic RNA (sgRNA) counts are particularly encouraging since these are replicative intermediates, and therefore, their abundance is related to viral replication activity and severity of host infection. Taken together, the data conclusively demonstrate that SEQ ID NO: 19 with ISA-720 protects against COVID-19 and that there is no risk of aggravation of COVID-19 disease in the NHPs.

TABLE 17

Summary of Anti-SP/RBD IgG Titers and ACE2 Inhibition ID50 Values Just Prior to the Viral Challenge for SEQ ID NO: 19 with ISA-720 Vaccinated NHPs Compared to the Naive Control NHPs.

| Animal ID | Status | IgG Titer (Reference Titer Units) | ACE2-Inhibition (ID50) |
|---|---|---|---|
| 9071 | Naïve | 0 | 0 |
| 9067 | Naïve | 0 | 0 |
| 9068 | Naïve | 0 | 0 |
| 9084 | Naïve | 0 | 0 |
| 9029 | Naïve | 310 | 0 |
| 6102 | Immunized | 19,140 | 419 |
| 6001 | Immunized | 17,056 | 625 |
| 7101 | Immunized | 53,745 | 745 |
| 7103 | Immunized | 27,701 | 1229 |
| 7102 | Immunized | 13,784 | 239 |

Histopathological examinations were performed on major organs/tissues, particularly liver, lungs, respiratory tract, spleen, kidneys, brain, and lymph nodes. SARS-CoV-2 has been shown to infect hepatocytes and cause hepatitis in humans, hence histopathological examinations were performed to assess the degree of hepatitis severity, and its reduction associated with the challenge in vaccinated and non-vaccinated controls. Lungs and the respiratory tract were examined for lesions associated with severe infection and pneumonia.

General Examples for Synthesis, Purification and Validation of Canine Insulin-Fc Fusion Proteins Example 45: Synthesis and Methods of Making an Insulin-Fc Fusion Protein in HEK293 Cells Insulin-Fc fusion proteins were synthesized as follows. A gene sequence of interest was constructed using proprietary software (LakePharma, Belmont, Calif.) and was cloned into a high expression mammalian vector. HEK293 cells were seeded in a shake flask 24 hours before transfection and were grown using serum-free chemically defined media. A DNA expression construct that encodes the insulin-Fc fusion protein of interest was transiently transfected into a suspension of HEK293 cells using the (LakePharma, Belmont, Calif.) standard operating procedure for transient transfection. After 20 hours, the cells were counted to determine the viability and viable cell count, and the titer was measured by Forté0 Octet® (Pall FortéLLC, Fremont, Calif.). Additional readings were taken throughout the transient transfection production run. The culture was harvested on or after Day 5.

Example 46: Synthesis and Methods of Making an Insulin-Fc Fusion Protein in CHO Cells A CHO cell line was originally derived from CHO-K1 (LakePharma, Belmont, Calif.), and the endogenous glutamine synthetase (GS) genes were knocked out by recombinant technology using methods known in the art. Stable expression DNA vectors were designed and optimized for CHO expression and GS selection and incorporated into a high expression mammalian vector (LakePharma, Belmont, Calif.). The sequence of each completed construct was confirmed prior to initiating scale up experiments. The suspension-adapted CHO cells were cultured in a humidified 5% CO2 incubator at 37° C. in a chemically defined media (CD OptiCHO; Invitrogen, Carlsbad, Calif.). No serum or other animal-derived products were used in culturing the CHO cells.

Approximately 80 million suspension-adapted CHO cells, growing in CD OptiCHO media during the exponential growth phase, were transfected by electroporation using MaxCyte® STX® system (MaxCyte, Inc., Gaithersburg, Md.) with 80 µg DNA to a create a stable CHO cell line for each insulin-Fc fusion protein (DNA construct contains the full-length sequence of the insulin-Fc fusion protein). After twenty-four hours, the transfected cells were counted and placed under selection for stable integration of the insulin-Fc fusion genes. The transfected cells were seeded into CD OptiCHO selection media containing between 0-100 µM methionine sulfoximine (MSX) at a cell density of 0.5×106 cells/mL in a shaker flask and incubated at 37° C. with 5% CO2. During a selection process, the cells were spun down and resuspended in fresh selection media every 2-3 days until the CHO stable pool recovered its growth rate and viability. The cell culture was monitored for growth and titer.

The cells were grown to 2.5×106 cells per mL. At the time of harvest for cell banking, the viability was above 95%. The cells were then centrifuged, and the cell pellet was resuspended in the CD OptiCHO media with 7.5% dimethyl sulfoxide (DMSO) to a cell count of 15×106 cells per mL per vial. Vials were cryopreserved for storage in liquid nitrogen.

A small-scale-up production was performed using the CHO cells as follows. The cells were scaled up for production in CD OptiCHO growth medium containing 100 µM MSX at 37° C. and fed every 2-4 days as needed, with CD OptiCHO growth medium supplemented with glucose and additional amino acids as necessary for approximately 14-21 days. The conditioned media supernatant harvested from the stable pool production run was clarified by centrifuge spinning. The protein was run over a Protein A (MabSelect, GE Healthcare, Little Chalfont, United Kingdom) column pre-equilibrated with binding buffer. Washing buffer was then passed through the column until the OD280 value (Nano-Drop, Thermo Scientific) was measured to be at or near background levels. The insulin-Fc fusion protein was eluted using a low pH buffer, elution fractions were collected, and the OD280 value of each fraction was recorded. Fractions containing the target insulin-Fc fusion protein were pooled and optionally further filtered using a 0.2 µM membrane filter.

The cell line was optionally further subcloned to monoclonality and optionally further selected for high titer insulin-Fc-fusion protein-expressing clones using the method of limiting dilution, a method known to those skilled in the art. After obtaining a high titer, monoclonal insulin-Fc fusion protein-expressing cell line, production of the insulin-Fc fusion protein was accomplished as described above in growth medium without MSX, or optionally in growth medium containing MSX, to obtain a cell culture supernatant containing the recombinant, CHO-made, insulin-Fc fusion protein. The MSX concentration was optionally increased over time to exert additional selectivity for clones capable of yielding higher product titers.

Example 47: Purification of an Insulin Fc Fusion Protein

Purification of an insulin-Fc fusion protein was performed as follows. Conditioned media supernatants containing the secreted insulin-Fc fusion protein were harvested from the transiently or stably transfected HEK production runs and were clarified by centrifugation. The supernatant containing the desired insulin-Fc fusion protein was run over a Protein A column and eluted using a low pH gradient. Afterwards, the eluted fractions containing the desired protein were pooled and buffer exchanged into 200 mM HEPES, 100 mM NaCl, 50 mM NaOAc, pH 7.0 buffer. A final filtration step was performed using a 0.2 µm membrane filter. The final protein concentration was calculated from the solution optical density at 280 nm. Further optional purification by ion-exchange chromatography (e.g., using an anion exchange bead resin or a cation exchange bead resin), gel filtration chromatography, or other methods was performed as necessary.

Example 48: Insulin-Fc Fusion Protein Structure Confirmation by Non-Reducing and Reducing CE-SDS Capillary electrophoresis sodium dodecyl sulfate (CE-SDS) analysis was performed in a LabChip® GXII (Perkin Elmer, Waltham, Mass.) on a solution of a purified insulin-Fc fusion protein dissolved in 200 mM HEPES, 100 mM NaCl, 50 mM NaOAc, pH 7.0 buffer, and the electropherogram was plotted. Under non-reducing conditions, the sample was run against known molecular weight (MW) protein standards, and the eluting peak represented the 'apparent' MW of the insulin-Fc fusion protein homodimer.

Under reducing conditions (e.g., using beta-mercaptoethanol to break disulfide bonds of the insulin-Fc fusion homodimer), the apparent MW of the resulting insulin-Fc fusion protein monomer is compared against half the molecular weight of the insulin-Fc fusion protein homodimer as a way of determining that the structural purity of the insulin-Fc fusion protein is likely to be correct.

Example 49: Insulin-Fc Fusion Protein Sequence Identification by LC-MS with Glycan Removal To obtain an accurate estimate of the insulin-Fc fusion protein mass via mass spectroscopy (MS), the sample was first treated to remove naturally occurring glycan that might interfere with the MS analysis. 100 µL of a 2.5 mg/mL insulin-Fc fusion protein dissolved in 200 mM HEPES, 100 mM NaCl, 50 mM NaOAc, pH 7.0 buffer solution was first buffer exchanged into 0.1 M Tris, pH 8.0 buffer containing 5 mM EDTA using a Zeba desalting column (Pierce, ThermoFisher Scientific, Waltham, Mass.). 1.67 µL of PNGase F enzyme (Prozyme N-glycanase) was added to this solution in order to remove N-linked glycan present in the insulin-Fc fusion protein (e.g., glycan linked to the side chain of the asparagine located at the cNg-N site), and the mixture was incubated at 37° C. overnight in an incubator. The sample was then analyzed via LC-MS (NovaBioassays, Woburn, Mass.) resulting in a molecular mass of the molecule which corresponds to the desired homodimer without the glycan. This mass was then further corrected since the enzymatic process used to cleave the glycan from the cNg-asparagine also deaminates the asparagine side chain to form an aspartic acid, and in doing so the enzymatically treated homodimer gains 2 Da overall, corresponding to a mass of 1 Da for each chain present in the homodimer. Therefore, the actual molecular mass was the measured mass minus 2 Da to correct for the enzymatic modification of the insulin-Fc fusion protein structure in the analytical sample.

Example 50: % Homodimer by Size-Exclusion Chromatography for an Insulin-Fc Fusion Protein Size-exclusion chromatography (SEC-HPLC) of insulin-Fc fusion proteins was carried out using a Waters 2795HT HPLC (Waters Corporation, Milford, Mass.) connected to a 2998 Photodiode array at a wavelength of 280 nm. 100 µL or less of a sample containing an insulin-Fc fusion protein of interest was injected into a MAbPac SEC-1, 5 µm, 4×300 mm column (ThermoFisher Scientific, Waltham, Mass.) operating at a flow rate of 0.2 mL/min and with a mobile phase comprising 50 mM sodium phosphate, 300 mM NaCl, and 0.05% w/v sodium azide, pH 6.2. The MAbPac SEC-1 column operates on the principle of molecular size separation. Therefore, larger soluble insulin-Fc aggregates (e.g., multimers of insulin-Fc fusion protein homodimers) eluted at earlier retention times, and the non-aggregated homodimers eluted at later retention times. In separating the mixture of homodimers from aggregated multimeric homodimers via analytical SEC-HPLC, the purity of the insulin-Fc fusion protein solution in terms of the percentage of non-aggregated homodimer was ascertained.

Example 51: In Vitro Fc(Gamma) Receptor I Binding Affinity Assay for an Insulin Fc Fusion Protein The binding of insulin-Fc fusion proteins to the Fc(gamma) receptor I at pH 7.4 was conducted using an ELISA assay as follows. Since canine Fc(gamma) receptor I was not commercially available, human Fc(gamma) receptor I (i.e., rhFc(gamma) receptor I) was used as a surrogate mammalian receptor. Insulin-Fc compounds were diluted to 10 µg/mL in sodium bicarbonate buffer at pH 9.6 and coated on Maxisorp (Nunc) microtiter plates overnight at 4° C., after which the microplate strips were washed 5 times with PBST (PBS/0.05% Tween-20) buffer and blocked with Superblock blocking reagent (ThermoFisher). Serial dilutions of biotinylated rhFc(gamma) receptor I (recombinant human Fc(gamma)R-I; R&D Systems) were prepared in PBST/10% Superblock buffer from 6000 ng/mL to 8.2 ng/mL and loaded at 100 µL/well onto the microplate strips coated with insulin-Fc fusion protein. The microtiter plate was incubated for 1 hour at room temperature after which the microplate strips were washed 5 times with PBST and then loaded with 100 µL/well of streptavidin-HRP diluted 1:10000 in PBST/10% Superblock buffer. After incubating for 45 min, the microplate strips were washed again 5 times with PBST. TMB was added to reveal the bound Fc(gamma) receptor I proteins and stopped with ELISA stop reagent (Boston Bioproducts). The plate was read in an ELISA plate reader at 450 nm, and the OD values (proportional to the binding of rhFc(gamma) receptor I to insulin-Fc protein were plotted against log concentrations of rhFc(gamma) receptor I added to each well to generate binding curves using GraphPad Prism software.

Example 52: In Vivo Pharmacodynamics (PD) after Periodic Administrations of an Insulin Fc-Fusion Protein in Client Owned Canines A bioactive insulin-Fc fusion homodimer construct was synthesized according to Example 45 or Example 46 and purified according to Example 47 was assessed for its effects on fasting blood glucose levels as follows.

Protocol 1 is an unmasked, self-controlled, single arm, pilot field efficacy study treating client-owned dogs, diagnosed with diabetes mellitus, with an insulin-Fc fusion protein. The effect of the drug is assessed by comparing glycemic control (based on clinical signs, fructosamine levels, and interstitial glucose concentrations using a continuous glucose monitoring unit (CGMS)) while on a standard insulin therapy (for one week) vs. treatment with an escalating dose of an insulin-Fc fusion protein over 8 weeks. Doses are administered subcutaneously starting at 0.1 mg/kg and then increased each successive week up to a maximum of 0.5 mg/kg based on CGMS results and clinical signs. The Protocol 1 Study Timeline used for some dogs is given in Table 18.

TABLE 18

Protocol 1 Study Timeline

| | |
|---|---|
| Visit 1 (Day −7) | Screening (CBC/Chem/UA/PLI/fructosamine [6 mL of blood, 3 mL of urine]/abdominal ultrasound/chest radiographs). Sedation might be required for imaging studies. |
| Visit 2 (Day 0) | Sensor placement (+/−sedation). Continue insulin treatment as previously prescribed at home for 6 days. Discontinue insulin on the night of Day 6 (do not administer PM insulin on Day 6 and AM insulin on Day 7) |
| Visit 3 (Day 7) | Blood sample (1 mL for PK), 0.1 mg/kg insulin-Fc fusion protein injection (after BG >300 mg/dL), hospitalize for 2-3 days for observation and treatment of hypoglycemia if BG <50 |
| Visit 4 (Day 14) | Sensor placement (+/−sedation). Blood sample (1 mL for PK), insulin-Fc fusion protein injection. Consider dose increase based on CGMS. |
| Visit 5 (Day 21) | Blood sample (1 mL for PK), insulin-Fc fusion protein injection. Consider dose increase based on CGMS. |
| Visit 6 (Day 28) | Sensor placement (+/−sedation). Blood sample (1 mL for PK), insulin-Fc fusion protein injection. Consider dose increase based on CGMS. |
| Visit 7 (Day 35) | Insulin-Fc fusion protein injection. Consider dose increase based on CGMS. Blood sample (fructosamine, CBC/Chem/UA, 6 mL of blood total) |
| Visit 8 (Day 42) | Sensor placement (+/−sedation). Blood sample (1 mL for PK), insulin-Fc fusion protein injection. Consider dose increase based on CGMS. |
| Visit 9 (Day 49) | Blood sample (1 mL for PK), insulin-Fc fusion protein injection. Consider dose increase based on CGMS. |
| Visit 10 (Day 56) | Sensor placement (+/−sedation). Blood sample (1 mL for PK), insulin-Fc fusion protein injection. Consider dose increase based on CGMS. |
| Visit 11 (Day 63) | Blood sample (fructosamine, CBC/Chem/UA, 6 mL of blood total), +/−sedation. At the night of visit 11, resume insulin therapy as before the study (with commercially available insulin that the dog was on prior to the study). |

Protocol 2 is an unmasked, self-controlled, single arm, pilot field efficacy study treating client-owned dogs, diagnosed with diabetes mellitus, with an insulin-Fc fusion protein. The effect of the drug is assessed by comparing glycemic control (based on clinical signs, fructosamine levels, and interstitial glucose concentrations using a continuous glucose monitoring unit (CGMS)) while on a standard insulin therapy (for one week) vs. treatment with an escalating dose of insulin-Fc fusion protein over 5 weeks. Doses are administered subcutaneously starting at 0.1 mg/kg and then increased each successive week up to a maximum of 0.5 mg/kg based on CGMS results and clinical signs. The Protocol 2 Study Timeline used for some dogs is given in Table 19.

After completion of either of the above protocols, there is an optional "home use" evaluation for up to one year. During this phase, the veterinarians treat each dog on a case-by-case basis as they would with any other patient on conventional insulin. Clinical signs and interstitial glucose concentrations using a continuous glucose monitoring unit (CGMS) are monitored throughout this phase of the study. In addition, blood samples are collected as frequently as possible to evaluate fructosamine levels, blood chemistry and blood cell counts, and test for the presence of anti-drug and anti-insulin antibodies.

TABLE 19

Protocol 2 Study Timeline

| | |
|---|---|
| Visit 1 (Day −7) | Health Screening (physical exam/thorough review of diabetes history/CBC/Chem/UA/PLI/fructosamine [6 mL of blood, 3 mL of urine] |
| Visit 2 (Day 0) | Sensor placement (+/−sedation). Baseline serum sample and BG from blood sample. Continue insulin treatment as previously prescribed at home for 6 days. Discontinue insulin on the night of Day 6 (do not administer PM insulin on Day 6 or AM insulin on Day 7) |
| Visit 3 (Day 7) | Blood sample (1 mL for PK), 0.1 mg/kg insulin-Fc fusion protein injection, hospitalize for 1-2 days for observation and treatment of hypoglycemia (if BG <50 mg/dL) |
| Visit 4 (Day 14) | Sensor placement (+/−sedation). Blood sample (1 mL for PK), insulin-Fc fusion protein injection. Consider dose increase based on FGMS. |
| Visit 5 (Day 21) | Sensor placement (+/−sedation). Blood sample (1 mL for PK), insulin-Fc fusion protein injection. Consider dose increase based on FGMS. |
| Visit 6 (Day 28) | Sensor placement (+/−sedation). Blood sample (PK), insulin-Fc fusion protein injection. Consider dose increase based on FGMS. |
| Visit 7 (Day 35) | insulin-Fc fusion protein injection. Consider dose increase based on FGMS. Blood sample (fructosamine, CBC/Chem/UA, 6 mL of blood total) |

Example 53: In Vivo Anti-Insulin Antibody (AIA) Titer Measurement after Periodic Administrations of an Insulin Fc Fusion Protein in Canines—Protocol 1

Maxisorp ELISA Plates (Nunc) were coated with purified RHI diluted in coating buffer (pH=9.6 Carbonate-Biocarbonate buffer) at 30 μg/mL overnight at 4° C. Plates were then washed 5× with PBST (PBS+0.05% Tween 20) and blocked for ≥1 hour (or overnight) with SuperBlock blocking solution (ThermoFisher). For calculating the AIA in dog IgG units, strips were directly coated with 1:2 serial dilutions of dog IgG (Jackson Immunoresearch) in pH=9.6 Carb-Biocarb coating buffer at concentrations between 300-4.69 ng/mL overnight at 4° C. and were used to create a 7 point pseudo-standard curve. The standards strip plates were also washed and blocked with SuperBlock blocking solution for ≥1 hour (or overnight).

Test serum samples were diluted to ≥1:100 (typically tested as 1:200) in PBST/SB/20% HS sample dilution buffer (PBS+0.1% Tween 20+10% SuperBlock+20% horse serum) and added to RHI coated strips 100 μL/well in duplicates. Duplicate strips of dog IgG coated standard strips were also added to each plate and filled with PBST/SB (PBS+0.1% Tween 20+10% SuperBlock) buffer 100 μL/well. Plates were incubated for 1 hour at room temperature. Following incubation, plates were washed 5 times with PBST. For detection of AIAs, HRP conjugated Goat anti-Dog IgG F(ab')2 (Jackson Immunoresearch), which was cross-reacted to dog IgG, was diluted in PBST/SB to 1:10,000 and added 1004/well to both sample and standard wells and incubated for 45 minutes at room temperature in the dark. Plates were washed 5 times with PBST and developed by the adding 100 μL/well TMB substrate (Invitrogen) for 15-20 minutes at room temperature in the dark. Color development is then stopped by addition of 100 μL/well of ELISA Stop Solution (Boston Bioproducts) and absorbance is read at 450 nm using a SpectraMax plate reader within 30 minutes. Anti-drug antibody concentration was determined by interpolating the OD values in the 4-PL pseudo-standard curve using the SoftMax Pro software.

Example 54: In Vivo Anti-Insulin Antibody (AIA) Titer Measurement after Periodic Administrations of Insulin-Fc Fusion Protein in Canines—Protocol 2

The general procedure is as follows: The serum with labeled antigen is incubated with and without cold insulin overnight. Antibody-bound labeled antigens are precipitated with protein-A/G Sepharose in a 96-well plate format, with each serum tested in duplicate. The 96-well plates are washed to remove unbound labeled antigens. Each well is counted with a 96-well plate beta counter. The results are expressed as an index that adjusts the delta counts per minute (cpm) of the test serum for the delta cpm of positive and negative control sera in a particular assay.

The specific procedure involves the preparation of two buffers as follows: Buffer 1 (150 mM NaCl, 20 mM Tris-HCl, 1% BSA, 0.15% Tween-20, 0.1% Sodium Azide pH 7.4) and Buffer 2 (same as Buffer 1 except for 0.1% BSA instead of 1% BSA). Each serum sample is spun down to remove fibrin clots when necessary. Then the stock solution of radiolabeled insulin is prepared by dissolving 10 μCi of 1251-insulin powder in 1 mL of 5% BSA in PBS. The "hot" insulin antigen solution is prepared using 3040 μL of Buffer 1 and 160 μL of the stock radiolabeled insulin solution. The "cold inhibited" insulin antigen solution is prepared using 2784 μL of Buffer 1, 160 μL of the stock radiolabeled insulin solution, and 256 μL of Humulin® solution (Eli Lilly, Ind.). All solutions are kept on ice prior to use. 6 μL of each serum sample is mixed with 30 μL of the "hot" insulin antigen solution, and 6 μL of each serum sample is mixed with 30 μL of the "cold inhibited" insulin antigen solution in a PCR tube. The resulting mixtures are incubated overnight at 4° C. The plate is then coated with BSA by adding 150 μL of Buffer 1 to each well followed by overnight incubation at room temperature under an aluminum foil cover followed by washing and removal of the wash buffer. The Protein-A/G Sepharose mixture is prepared in two parts. The Protein-A Sepharose solution is prepared in Buffer 1 at a 62.5% concentration by volume. The Protein-G Sepharose solution is prepared in Buffer 1 at 40% concentration by volume. Finally, the Protein-A/G Sepharose mixture is prepared by mixing the Protein-A and Protein-G Sepharose solutions at a 4:1 ratio (final concentration: 50% Protein-A/8% Protein-G Sepharose). To perform the assay, 50 μL of the Protein A/G-Sepharose mixture and 30 μL of the overnight incubated serum solutions are added to each well in duplicate. The plate is mixed on a plate shaker for 45 minutes at 4° C. and then washed seven times using a Millipore plate washer device with 200 μL of wash buffer per well and then placed in a 37° C. incubator for 15 minutes to dry. 50 μL of scintillation cocktail (Microscint-20) is added to each well and the plate is counted using a 96-well plate counter to determine the cpm for each well.

EQUIVALENTS

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprise(s)," "comprising," "contain(s)," and "containing" are intended to be open and the use thereof permits the inclusion of additional elements or steps. Where ranges are given, endpoints are included.

Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

Additional advantages of the various embodiments of the technology will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

We claim:

1. A booster vaccine for increasing anti-SARS-COV-2 virus antibody titer in a patient previously immunized against SARS-COV-2 infection or who has previously had a SARS-COV-2 infection, said booster vaccine comprising an effective amount of a fusion protein that comprises the following sequence:

```
                                                (SEQ ID NO: 19)
RVQPTESIVRFPNITNLCPFGEVFNATRFASVYAWNRKRISNCVADYSVLY

NSASFSTFKCYGVSPTKLNDLCFTNVYADSFVIRGDEVRQIAPGQTGKIAD

YNYKLPDDFTGCVIAWNSNNLDSKVGGNYNYLYRLFRKSNLKPFERDISTE

IYQAGSTPCNGVEGFNCYFPLQSYGFQPTNGVGYQPYRVVVLSFELLHAPA

TVCGPKKSTNLVKNKCVNFNFNGLTGTGVLTESNKKFLPFQQFGRDIADTT

DAVRDPQTLEILDITPCSGGGSGGGSDKTHTCPPCPAPELLGGPSVFLFPP

KPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG.
```

2. The booster vaccine of claim 1, further comprising a pharmaceutically acceptable carrier.

3. The booster vaccine of claim 2, wherein said pharmaceutically acceptable carrier is selected from the group consisting of water, saline, ethanol, salts, polyols vegetable oils, ethyl oleate, potassium phosphate, sodium phosphate, hydrochloric acid, sodium hydroxide and mixtures thereof.

4. The booster vaccine of claim 2, consisting essentially of said fusion protein and said pharmaceutically acceptable carrier.

5. A method of increasing anti-SARS-COV-2 antibody titers in a patient previously immunized against SARS-COV-2 infection or who has previously had a SARS-CoV-2 infection, said method comprising administering a booster vaccine according to claim 1 to said patient, wherein anti-SARS-COV-2 antibodies increase in said patient after said administering.

6. The method of claim 5, wherein said patient is antibody-positive for SARS-COV-2 before said administering.

7. The method of claim 5, wherein said patient has initial measurable anti-SARS-COV-2 antibodies before said administering, and wherein said measurable anti-SARS-CoV-2 antibodies increase in said patient after said administering.

8. The method of claim 5, wherein said patient has recovered from said SARS-COV-2 infection.

9. The method of claim 8, wherein said booster vaccine is administered to said patient as an antibody amplification treatment (AAT), to increase said anti-SARS-COV-2 antibody titers before serum donation by said patient for convalescent serum treatment, thereby increasing the anti-SARS-COV-2 antibody titer of extracted patient sera.

10. The method of claim 5, wherein said patient previously immunized against SARS-COV-2 infection has measurable anti-SARS-CoV-2 antibodies that have waned since said previous immunization.

11. The method of claim 5, wherein said booster vaccine protects said patient from infection and/or serious symptoms related to infection with the SARS-COV-2 virus after increasing said anti-SARS-COV-2 antibody titers in said patient.

12. The method of claim 5, wherein said booster vaccine is administered to said patient by subcutaneous (s.c.) or intramuscular (i.m.) injection.

13. The method of claim 5, wherein said booster vaccine consists essentially of said fusion protein and a pharmaceutically acceptable carrier.

14. The method of claim 5, further comprising providing a unit dosage form of said booster vaccine and a dosing syringe for administering the booster vaccine to the patient.

15. The method of claim 14, wherein said unit dosage form of said booster vaccine consists essentially of said fusion protein and a pharmaceutically acceptable carrier in a vial.

16. A booster vaccine kit for increasing anti-SARS-COV-2 virus antibody titer in a patient previously immunized against SARS-COV-2 infection or who has previously had a SARS-COV-2 infection, said kit comprising:

a unit dosage form of a booster vaccine according to claim 1;

a dosing syringe for administering the booster vaccine to a patient; and instructions for administering said booster vaccine.

* * * * *

SEQUENCE LISTING

```
<160> NUMBER OF SEQ ID NOS: 33

<210> SEQ ID NO 1
<211> LENGTH: 1273
<212> TYPE: PRT
<213> ORGANISM: Human coronavirus SARS-CoV-2

<400> SEQUENCE: 1

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270
```

```
Arg Thr Phe Leu Leu Lys Tyr Asn Glu Asn Gly Thr Ile Thr Asp Ala
    275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
                340                 345                 350

Trp Asn Arg Lys Arg Ile Ser Asn Cys Val Ala Asp Tyr Ser Val Leu
                355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
                435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
    515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Arg Ala Arg Ser Val Ala
                675                 680                 685
```

```
Ser Gln Ser Ile Ile Ala Tyr Thr Met Ser Leu Gly Ala Glu Asn Ser
    690                 695                 700
Val Ala Tyr Ser Asn Asn Ser Ile Ala Ile Pro Thr Asn Phe Thr Ile
705                 710                 715                 720
Ser Val Thr Thr Glu Ile Leu Pro Val Ser Met Thr Lys Thr Ser Val
                725                 730                 735
Asp Cys Thr Met Tyr Ile Cys Gly Asp Ser Thr Glu Cys Ser Asn Leu
                740                 745                 750
Leu Leu Gln Tyr Gly Ser Phe Cys Thr Gln Leu Asn Arg Ala Leu Thr
                755                 760                 765
Gly Ile Ala Val Glu Gln Asp Lys Asn Thr Gln Glu Val Phe Ala Gln
770                 775                 780
Val Lys Gln Ile Tyr Lys Thr Pro Pro Ile Lys Asp Phe Gly Gly Phe
785                 790                 795                 800
Asn Phe Ser Gln Ile Leu Pro Asp Pro Ser Lys Pro Ser Lys Arg Ser
                805                 810                 815
Phe Ile Glu Asp Leu Leu Phe Asn Lys Val Thr Leu Ala Asp Ala Gly
                820                 825                 830
Phe Ile Lys Gln Tyr Gly Asp Cys Leu Gly Asp Ile Ala Ala Arg Asp
                835                 840                 845
Leu Ile Cys Ala Gln Lys Phe Asn Gly Leu Thr Val Leu Pro Pro Leu
850                 855                 860
Leu Thr Asp Glu Met Ile Ala Gln Tyr Thr Ser Ala Leu Leu Ala Gly
865                 870                 875                 880
Thr Ile Thr Ser Gly Trp Thr Phe Gly Ala Gly Ala Ala Leu Gln Ile
                885                 890                 895
Pro Phe Ala Met Gln Met Ala Tyr Arg Phe Asn Gly Ile Gly Val Thr
                900                 905                 910
Gln Asn Val Leu Tyr Glu Asn Gln Lys Leu Ile Ala Asn Gln Phe Asn
                915                 920                 925
Ser Ala Ile Gly Lys Ile Gln Asp Ser Leu Ser Ser Thr Ala Ser Ala
                930                 935                 940
Leu Gly Lys Leu Gln Asp Val Val Asn Gln Asn Ala Gln Ala Leu Asn
945                 950                 955                 960
Thr Leu Val Lys Gln Leu Ser Ser Asn Phe Gly Ala Ile Ser Ser Val
                965                 970                 975
Leu Asn Asp Ile Leu Ser Arg Leu Asp Lys Val Glu Ala Glu Val Gln
                980                 985                 990
Ile Asp Arg Leu Ile Thr Gly Arg  Leu Gln Ser Leu Gln  Thr Tyr Val
                995                 1000                1005
Thr Gln  Gln Leu Ile Arg Ala  Ala Glu Ile Arg Ala  Ser Ala Asn
    1010                1015                1020
Leu Ala  Ala Thr Lys Met  Ser Glu Cys Val Leu Gly  Gln Ser Lys
    1025                1030                1035
Arg Val  Asp Phe Cys Gly  Lys Gly Tyr His Leu Met  Ser Phe Pro
    1040                1045                1050
Gln Ser  Ala Pro His Gly  Val Phe Leu His Val  Thr Tyr Val
    1055                1060                1065
Pro Ala  Gln Glu Lys Asn Phe  Thr Thr Ala Pro Ala  Ile Cys His
    1070                1075                1080
Asp Gly  Lys Ala His Phe Pro  Arg Glu Gly Val Phe  Val Ser Asn
    1085                1090                1095
Gly Thr  His Trp Phe Val Thr  Gln Arg Asn Phe Tyr  Glu Pro Gln
```

```
                1100                1105                1110
Ile Ile Thr Thr Asp Asn Thr Phe Val Ser Gly Asn Cys Asp Val
        1115                1120                1125

Val Ile Gly Ile Val Asn Asn Thr Val Tyr Asp Pro Leu Gln Pro
        1130                1135                1140

Glu Leu Asp Ser Phe Lys Glu Glu Leu Asp Lys Tyr Phe Lys Asn
        1145                1150                1155

His Thr Ser Pro Asp Val Asp Leu Gly Asp Ile Ser Gly Ile Asn
        1160                1165                1170

Ala Ser Val Val Asn Ile Gln Lys Glu Ile Asp Arg Leu Asn Glu
        1175                1180                1185

Val Ala Lys Asn Leu Asn Glu Ser Leu Ile Asp Leu Gln Glu Leu
        1190                1195                1200

Gly Lys Tyr Glu Gln Tyr Ile Lys Trp Pro Trp Tyr Ile Trp Leu
        1205                1210                1215

Gly Phe Ile Ala Gly Leu Ile Ala Ile Val Met Val Thr Ile Met
        1220                1225                1230

Leu Cys Cys Met Thr Ser Cys Cys Ser Cys Leu Lys Gly Cys Cys
        1235                1240                1245

Ser Cys Gly Ser Cys Cys Lys Phe Asp Glu Asp Asp Ser Glu Pro
        1250                1255                1260

Val Leu Lys Gly Val Lys Leu His Tyr Thr
        1265                1270

<210> SEQ ID NO 2
<211> LENGTH: 254
<212> TYPE: PRT
<213> ORGANISM: Human coronavirus SARS-CoV-2

<400> SEQUENCE: 2

Pro Asn Ile Thr Asn Leu Cys Pro Phe Gly Glu Val Phe Asn Ala Thr
1               5                   10                  15

Arg Phe Ala Ser Val Tyr Ala Trp Asn Arg Lys Arg Ile Ser Asn Cys
            20                  25                  30

Val Ala Asp Tyr Ser Val Leu Tyr Asn Ser Ala Ser Phe Ser Thr Phe
        35                  40                  45

Lys Cys Tyr Gly Val Ser Pro Thr Lys Leu Asn Asp Leu Cys Phe Thr
    50                  55                  60

Asn Val Tyr Ala Asp Ser Phe Val Ile Arg Gly Asp Glu Val Arg Gln
65                  70                  75                  80

Ile Ala Pro Gly Gln Thr Gly Lys Ile Ala Asp Tyr Asn Tyr Lys Leu
                85                  90                  95

Pro Asp Asp Phe Thr Gly Cys Val Ile Ala Trp Asn Ser Asn Asn Leu
            100                 105                 110

Asp Ser Lys Val Gly Gly Asn Tyr Asn Tyr Leu Tyr Arg Leu Phe Arg
        115                 120                 125

Lys Ser Asn Leu Lys Pro Phe Glu Arg Asp Ile Ser Thr Glu Ile Tyr
    130                 135                 140

Gln Ala Gly Ser Thr Pro Cys Asn Gly Val Glu Gly Phe Asn Cys Tyr
145                 150                 155                 160

Phe Pro Leu Gln Ser Tyr Gly Phe Gln Pro Thr Asn Gly Val Gly Tyr
                165                 170                 175

Gln Pro Tyr Arg Val Val Val Leu Ser Phe Glu Leu Leu His Ala Pro
            180                 185                 190
```

-continued

```
Ala Thr Val Cys Gly Pro Lys Lys Ser Thr Asn Leu Val Lys Asn Lys
            195                 200                 205

Cys Val Asn Phe Asn Phe Asn Gly Leu Thr Gly Thr Gly Val Leu Thr
        210                 215                 220

Glu Ser Asn Lys Lys Phe Leu Pro Phe Gln Gln Phe Gly Arg Asp Ile
225                 230                 235                 240

Ala Asp Thr Thr Asp Ala Val Arg Asp Pro Gln Thr Leu Glu
                245                 250

<210> SEQ ID NO 3
<211> LENGTH: 7
<212> TYPE: PRT
<213> ORGANISM: Artificial Sequence
<220> FEATURE:
<223> OTHER INFORMATION: Synthetic Linker

<400> SEQUENCE: 3

Gly Gly Gly Ser Gly Gly Gly
1               5

<210> SEQ ID NO 4
<211> LENGTH: 21
<212> TYPE: PRT
<213> ORGANISM: Artificial Sequence
<220> FEATURE:
<223> OTHER INFORMATION: Synthetic Linker

<400> SEQUENCE: 4

Gly Gly Gly Gly Gly Gln Gly Gly Gly Gln Gly Gly Gly Gly Gln
1               5                   10                  15

Gly Gly Gly Gly Gly
            20

<210> SEQ ID NO 5
<211> LENGTH: 8
<212> TYPE: PRT
<213> ORGANISM: Artificial Sequence
<220> FEATURE:
<223> OTHER INFORMATION: Synthetic Linker

<400> SEQUENCE: 5

Gly Gly Gly Ser Gly Gly Gly Ser
1               5

<210> SEQ ID NO 6
<211> LENGTH: 226
<212> TYPE: PRT
<213> ORGANISM: Artificial Sequence
<220> FEATURE:
<223> OTHER INFORMATION: Synthetic Fc Fragment

<400> SEQUENCE: 6

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80
```

```
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly
225

<210> SEQ ID NO 7
<211> LENGTH: 232
<212> TYPE: PRT
<213> ORGANISM: Artificial Sequence
<220> FEATURE:
<223> OTHER INFORMATION: Synthetic Fc Fragment

<400> SEQUENCE: 7

Ser Pro Lys Ser Ser Asp Lys Thr His Thr Cys Pro Pro Cys Pro Ala
1               5                   10                  15
Pro Glu Leu Leu Gly Gly Pro Ser Val Phe Leu Phe Pro Pro Lys Pro
            20                  25                  30
Lys Asp Thr Leu Met Ile Ser Arg Thr Pro Glu Val Thr Cys Val Val
        35                  40                  45
Val Asp Val Ser His Glu Asp Pro Glu Val Lys Phe Asn Trp Tyr Val
    50                  55                  60
Asp Gly Val Glu Val His Asn Ala Lys Thr Lys Pro Arg Glu Glu Gln
65                  70                  75                  80
Tyr Asn Ser Thr Tyr Arg Val Val Ser Val Leu Thr Val Leu His Gln
                85                  90                  95
Asp Trp Leu Asn Gly Lys Glu Tyr Lys Cys Lys Val Ser Asn Lys Ala
            100                 105                 110
Leu Pro Ala Pro Ile Glu Lys Thr Ile Ser Lys Ala Lys Gly Gln Pro
        115                 120                 125
Arg Glu Pro Gln Val Tyr Thr Leu Pro Pro Ser Arg Asp Glu Leu Thr
    130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
            180                 185                 190
Ser Lys Leu Thr Val Asp Lys Ser Arg Trp Gln Gln Gly Asn Val Phe
        195                 200                 205
```

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 8
<211> LENGTH: 194
<212> TYPE: PRT
<213> ORGANISM: Artificial Sequence
<220> FEATURE:
<223> OTHER INFORMATION: Synthetic SARS-Cov-2 RBD Analog

<400> SEQUENCE: 8

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val

<210> SEQ ID NO 9
<211> LENGTH: 194
<212> TYPE: PRT
<213> ORGANISM: Artificial Sequence
<220> FEATURE:
<223> OTHER INFORMATION: Synthetic SARS-Cov-2 RBD Analog

<400> SEQUENCE: 9

Gln Ile Thr Asn Leu Cys Pro Phe Gly Glu Val Phe Gln Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Met Phe Thr Asn
50                  55                  60

Val Tyr Ala Asp Ser Phe Val Ile Arg Gly Asp Glu Val Arg Gln Ile
65                  70                  75                  80

```
Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val

<210> SEQ ID NO 10
<211> LENGTH: 92
<212> TYPE: PRT
<213> ORGANISM: Artificial Sequence
<220> FEATURE:
<223> OTHER INFORMATION: Synthetic SARS-Cov-2 RBD Analog

<400> SEQUENCE: 10

Val Ile Ala Trp Asn Ser Asn Asn Leu Asp Ser Lys Val Gly Gly Asn
1               5                   10                  15

Tyr Asn Tyr Leu Tyr Arg Leu Phe Arg Lys Ser Asn Leu Lys Pro Phe
                20                  25                  30

Glu Arg Asp Ile Ser Thr Glu Ile Tyr Gln Ala Gly Ser Thr Pro Cys
            35                  40                  45

Asn Gly Val Glu Gly Phe Asn Cys Tyr Phe Pro Leu Gln Ser Tyr Gly
        50                  55                  60

Phe Gln Pro Thr Asn Gly Val Gly Tyr Gln Pro Tyr Arg Val Val Val
65                  70                  75                  80

Leu Ser Phe Glu Leu Leu His Ala Pro Ala Thr Val
                85                  90

<210> SEQ ID NO 11
<211> LENGTH: 441
<212> TYPE: PRT
<213> ORGANISM: Artificial Sequence
<220> FEATURE:
<223> OTHER INFORMATION: Synthetic SARS-CoV-2-RBD-hIgG-Fc Fusion Protein

<400> SEQUENCE: 11

Gln Ile Thr Asn Leu Cys Pro Phe Gly Glu Val Phe Gln Ala Thr Arg
1               5                   10                  15

Phe Ala Ser Val Tyr Ala Trp Asn Arg Lys Arg Ile Ser Asn Cys Val
                20                  25                  30

Ala Asp Tyr Ser Val Leu Tyr Asn Ser Ala Ser Phe Ser Thr Phe Lys
            35                  40                  45

Cys Tyr Gly Val Ser Pro Thr Lys Leu Asn Asp Leu Met Phe Thr Asn
        50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95
```

Asp Asp Phe Thr Gly Cys Val Ile Ala Trp Asn Ser Asn Asn Leu Asp
                100                 105                 110

Ser Lys Val Gly Gly Asn Tyr Asn Tyr Leu Tyr Arg Leu Phe Arg Lys
            115                 120                 125

Ser Asn Leu Lys Pro Phe Glu Arg Asp Ile Ser Thr Glu Ile Tyr Gln
        130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Gly Gly Gly Gly Gln Gly Gly Gly Gln Gly Gly
        195                 200                 205

Gly Gln Gly Gly Gly Gly Asp Lys Thr His Thr Cys Pro Pro Cys
        210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
        290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly
        435                 440

<210> SEQ ID NO 12
<211> LENGTH: 339
<212> TYPE: PRT
<213> ORGANISM: Artificial Sequence
<220> FEATURE:
<223> OTHER INFORMATION: Synthetic SARS-CoV-2-RBD-hIgG-Fc Fusion Protein

<400> SEQUENCE: 12

Val Ile Ala Trp Asn Ser Asn Asn Leu Asp Ser Lys Val Gly Gly Asn
1               5                   10                  15

```
Tyr Asn Tyr Leu Tyr Arg Leu Phe Arg Lys Ser Asn Leu Lys Pro Phe
             20                  25                  30

Glu Arg Asp Ile Ser Thr Glu Ile Tyr Gln Ala Gly Ser Thr Pro Cys
         35                  40                  45

Asn Gly Val Glu Gly Phe Asn Cys Tyr Phe Pro Leu Gln Ser Tyr Gly
     50                  55                  60

Phe Gln Pro Thr Asn Gly Val Gly Tyr Gln Pro Tyr Arg Val Val Val
65                  70                  75                  80

Leu Ser Phe Glu Leu Leu His Ala Pro Ala Thr Val Gly Gly Gly Gly
                 85                  90                  95

Gly Gln Gly Gly Gly Gly Gln Gly Gly Gly Gly Gln Gly Gly Gly Gly
            100                 105                 110

Gly Asp Lys Thr His Thr Cys Pro Pro Cys Pro Ala Pro Glu Leu Leu
            115                 120                 125

Gly Gly Pro Ser Val Phe Leu Phe Pro Pro Lys Pro Lys Asp Thr Leu
            130                 135                 140

Met Ile Ser Arg Thr Pro Glu Val Thr Cys Val Val Val Asp Val Ser
145                 150                 155                 160

His Glu Asp Pro Glu Val Lys Phe Asn Trp Tyr Val Asp Gly Val Glu
                165                 170                 175

Val His Asn Ala Lys Thr Lys Pro Arg Glu Glu Gln Tyr Asn Ser Thr
            180                 185                 190

Tyr Arg Val Val Ser Val Leu Thr Val Leu His Gln Asp Trp Leu Asn
            195                 200                 205

Gly Lys Glu Tyr Lys Cys Lys Val Ser Asn Lys Ala Leu Pro Ala Pro
210                 215                 220

Ile Glu Lys Thr Ile Ser Lys Ala Lys Gly Gln Pro Arg Glu Pro Gln
225                 230                 235                 240

Val Tyr Thr Leu Pro Pro Ser Arg Asp Glu Leu Thr Lys Asn Gln Val
                245                 250                 255

Ser Leu Thr Cys Leu Val Lys Gly Phe Tyr Pro Ser Asp Ile Ala Val
            260                 265                 270

Glu Trp Glu Ser Asn Gly Gln Pro Glu Asn Asn Tyr Lys Thr Thr Pro
            275                 280                 285

Pro Val Leu Asp Ser Asp Gly Ser Phe Phe Leu Tyr Ser Lys Leu Thr
290                 295                 300

Val Asp Lys Ser Arg Trp Gln Gln Gly Asn Val Phe Ser Cys Ser Val
305                 310                 315                 320

Met His Glu Ala Leu His Asn His Tyr Thr Gln Lys Ser Leu Ser Leu
                325                 330                 335

Ser Pro Gly

<210> SEQ ID NO 13
<211> LENGTH: 273
<212> TYPE: PRT
<213> ORGANISM: Artificial Sequence
<220> FEATURE:
<223> OTHER INFORMATION: Synthetic SARS-Cov-2 RBD Analog

<400> SEQUENCE: 13

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
```

```
                35                  40                  45
Val Leu Tyr Asn Ser Ala Ser Phe Ser Thr Phe Lys Cys Tyr Gly Val
 50                  55                  60
Ser Pro Thr Lys Leu Asn Asp Leu Cys Phe Thr Asn Val Tyr Ala Asp
 65                  70                  75                  80
Ser Phe Val Ile Arg Gly Asp Glu Val Arg Gln Ile Ala Pro Gly Gln
                 85                  90                  95
Thr Gly Lys Ile Ala Asp Tyr Asn Tyr Lys Leu Pro Asp Asp Phe Thr
            100                 105                 110
Gly Cys Val Ile Ala Trp Asn Ser Asn Asn Leu Asp Ser Lys Val Gly
            115                 120                 125
Gly Asn Tyr Asn Tyr Leu Tyr Arg Leu Phe Arg Lys Ser Asn Leu Lys
            130                 135                 140
Pro Phe Glu Arg Asp Ile Ser Thr Glu Ile Tyr Gln Ala Gly Ser Thr
145                 150                 155                 160
Pro Cys Asn Gly Val Glu Gly Phe Asn Cys Tyr Phe Pro Leu Gln Ser
                165                 170                 175
Tyr Gly Phe Gln Pro Thr Asn Gly Val Gly Tyr Gln Pro Tyr Arg Val
            180                 185                 190
Val Val Leu Ser Phe Glu Leu Leu His Ala Pro Ala Thr Val Cys Gly
            195                 200                 205
Pro Lys Lys Ser Thr Asn Leu Val Lys Asn Lys Cys Val Asn Phe Asn
210                 215                 220
Phe Asn Gly Leu Thr Gly Thr Gly Val Leu Thr Glu Ser Asn Lys Lys
225                 230                 235                 240
Phe Leu Pro Phe Gln Gln Phe Gly Arg Asp Ile Ala Asp Thr Thr Asp
                245                 250                 255
Ala Val Arg Asp Pro Gln Thr Leu Glu Ile Leu Asp Ile Thr Pro Cys
            260                 265                 270
Ser

<210> SEQ ID NO 14
<211> LENGTH: 223
<212> TYPE: PRT
<213> ORGANISM: Artificial Sequence
<220> FEATURE:
<223> OTHER INFORMATION: Synthetic SARS-Cov-2 RBD Analog

<400> SEQUENCE: 14

Arg Val Gln Pro Thr Glu Ser Ile Val Arg Phe Pro Asn Ile Thr Asn
 1               5                  10                  15
Leu Cys Pro Phe Gly Glu Val Phe Asn Ala Thr Arg Phe Ala Ser Val
                20                  25                  30
Tyr Ala Trp Asn Arg Lys Arg Ile Ser Asn Cys Val Ala Asp Tyr Ser
            35                  40                  45
Val Leu Tyr Asn Ser Ala Ser Phe Ser Thr Phe Lys Cys Tyr Gly Val
 50                  55                  60
Ser Pro Thr Lys Leu Asn Asp Leu Cys Phe Thr Asn Val Tyr Ala Asp
 65                  70                  75                  80
Ser Phe Val Ile Arg Gly Asp Glu Val Arg Gln Ile Ala Pro Gly Gln
                 85                  90                  95
Thr Gly Lys Ile Ala Asp Tyr Asn Tyr Lys Leu Pro Asp Asp Phe Thr
            100                 105                 110
Gly Cys Val Ile Ala Trp Asn Ser Asn Asn Leu Asp Ser Lys Val Gly
            115                 120                 125
```

```
Gly Asn Tyr Asn Tyr Leu Tyr Arg Leu Phe Arg Lys Ser Asn Leu Lys
        130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220
```

<210> SEQ ID NO 15
<211> LENGTH: 217
<212> TYPE: PRT
<213> ORGANISM: Artificial Sequence
<220> FEATURE:
<223> OTHER INFORMATION: Synthetic SARS-CoV-2 RBD Analog

<400> SEQUENCE: 15

```
Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
                20                  25                  30

Tyr Ala Trp Asn Arg Lys Arg Ile Ser Asn Cys Val Ala Asp Tyr Ser
            35                  40                  45

Val Leu Tyr Asn Ser Ala Ser Phe Ser Thr Phe Lys Cys Tyr Gly Val
        50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys
    210                 215
```

<210> SEQ ID NO 16
<211> LENGTH: 461
<212> TYPE: PRT
<213> ORGANISM: Artificial Sequence
<220> FEATURE:
<223> OTHER INFORMATION: Synthetic SARS-CoV-2-RBD-hIgG-Fc Fusion Protein

<400> SEQUENCE: 16

```
Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe Gly
    210                 215                 220

Gly Gly Ser Gly Gly Ser Pro Lys Ser Ser Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415
```

```
Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
                435                 440                 445

Asn His Tyr Thr Gln Lys Ser Leu Ser Leu Ser Pro Gly
                450                 455                 460

<210> SEQ ID NO 17
<211> LENGTH: 462
<212> TYPE: PRT
<213> ORGANISM: Artificial Sequence
<220> FEATURE:
<223> OTHER INFORMATION: Synthetic SARS-CoV-2-RBD-hIgG-Fc Fusion Protein

<400> SEQUENCE: 17

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
                20                  25                  30

Tyr Ala Trp Asn Arg Lys Arg Ile Ser Asn Cys Val Ala Asp Tyr Ser
                35                  40                  45

Val Leu Tyr Asn Ser Ala Ser Phe Ser Thr Phe Lys Cys Tyr Gly Val
            50                  55                  60

Ser Pro Thr Lys Leu Asn Asp Leu Cys Phe Thr Asn Val Tyr Ala Asp
65              70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
                100                 105                 110

Gly Cys Val Ile Ala Trp Asn Ser Asn Asn Leu Asp Ser Lys Val Gly
                115                 120                 125

Gly Asn Tyr Asn Tyr Leu Tyr Arg Leu Phe Arg Lys Ser Asn Leu Lys
            130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
                180                 185                 190

Val Val Leu Ser Phe Glu Leu Leu His Ala Pro Ala Thr Val Cys Gly
                195                 200                 205

Pro Lys Lys Ser Thr Asn Leu Val Lys Asn Lys Cys Val Asn Phe Gly
            210                 215                 220

Gly Gly Ser Gly Gly Gly Ser Pro Lys Ser Ser Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
                275                 280                 285

Lys Phe Asn Trp Tyr Val Asp Gly Val Glu Val His Asn Ala Lys Thr
            290                 295                 300

Lys Pro Arg Glu Glu Gln Tyr Asn Ser Thr Tyr Arg Val Val Ser Val
305                 310                 315                 320
```

```
Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
            450                 455                 460

<210> SEQ ID NO 18
<211> LENGTH: 470
<212> TYPE: PRT
<213> ORGANISM: Artificial Sequence
<220> FEATURE:
<223> OTHER INFORMATION: Synthetic SARS-CoV-2-RBD-hIgG-Fc Fusion Protein

<400> SEQUENCE: 18

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe Gly
    210                 215                 220
```

Gly Gly Gly Gly Gln Gly Gly Gly Gln Gly Gly Gly Gln Gly
225                 230                 235                 240

Gly Gly Gly Gly Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
        290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly
465                 470

<210> SEQ ID NO 19
<211> LENGTH: 507
<212> TYPE: PRT
<213> ORGANISM: Artificial Sequence
<220> FEATURE:
<223> OTHER INFORMATION: Synthetic SARS-CoV-2-RBD-hIgG-Fc Fusion Protein

<400> SEQUENCE: 19

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Leu Asp Ser Lys Val Gly
115                 120                 125

Gly Asn Tyr Asn Tyr Leu Tyr Arg Leu Phe Arg Lys Ser Asn Leu Lys
130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
                180                 185                 190

Val Val Leu Ser Phe Glu Leu Leu His Ala Pro Ala Thr Val Cys Gly
                195                 200                 205

Pro Lys Lys Ser Thr Asn Leu Val Lys Asn Lys Cys Val Asn Phe Asn
210                 215                 220

Phe Asn Gly Leu Thr Gly Thr Gly Val Leu Thr Glu Ser Asn Lys Lys
225                 230                 235                 240

Phe Leu Pro Phe Gln Gln Phe Gly Arg Asp Ile Ala Asp Thr Thr Asp
                245                 250                 255

Ala Val Arg Asp Pro Gln Thr Leu Glu Ile Leu Asp Ile Thr Pro Cys
                260                 265                 270

Ser Gly Gly Gly Ser Gly Gly Gly Ser Asp Lys Thr His Thr Cys Pro
                275                 280                 285

Pro Cys Pro Ala Pro Glu Leu Leu Gly Gly Pro Ser Val Phe Leu Phe
                290                 295                 300

Pro Pro Lys Pro Lys Asp Thr Leu Met Ile Ser Arg Thr Pro Glu Val
305                 310                 315                 320

Thr Cys Val Val Val Asp Val Ser His Glu Asp Pro Glu Val Lys Phe
                325                 330                 335

Asn Trp Tyr Val Asp Gly Val Glu Val His Asn Ala Lys Thr Lys Pro
                340                 345                 350

Arg Glu Glu Gln Tyr Asn Ser Thr Tyr Arg Val Val Ser Val Leu Thr
                355                 360                 365

Val Leu His Gln Asp Trp Leu Asn Gly Lys Glu Tyr Lys Cys Lys Val
                370                 375                 380

Ser Asn Lys Ala Leu Pro Ala Pro Ile Glu Lys Thr Ile Ser Lys Ala
385                 390                 395                 400

Lys Gly Gln Pro Arg Glu Pro Gln Val Tyr Thr Leu Pro Pro Ser Arg
                405                 410                 415

Asp Glu Leu Thr Lys Asn Gln Val Ser Leu Thr Cys Leu Val Lys Gly
                420                 425                 430

Phe Tyr Pro Ser Asp Ile Ala Val Glu Trp Glu Ser Asn Gly Gln Pro
                435                 440                 445

Glu Asn Asn Tyr Lys Thr Thr Pro Pro Val Leu Asp Ser Asp Gly Ser
450                 455                 460

Phe Phe Leu Tyr Ser Lys Leu Thr Val Asp Lys Ser Arg Trp Gln Gln
465                 470                 475                 480

Gly Asn Val Phe Ser Cys Ser Val Met His Glu Ala Leu His Asn His
                485                 490                 495

Tyr Thr Gln Lys Ser Leu Ser Leu Ser Pro Gly
                500                 505

<210> SEQ ID NO 20
<211> LENGTH: 451

<212> TYPE: PRT
<213> ORGANISM: Artificial Sequence
<220> FEATURE:
<223> OTHER INFORMATION: Synthetic SARS-CoV-2-RBD-hIgG-Fc Fusion Protein

<400> SEQUENCE: 20

```
Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Gly Gly Ser Gly Gly Gly
210                 215                 220

Ser Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
370                 375                 380
```

```
Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly
    450

<210> SEQ ID NO 21
<211> LENGTH: 443
<212> TYPE: PRT
<213> ORGANISM: Artificial Sequence
<220> FEATURE:
<223> OTHER INFORMATION: Synthetic SARS-CoV-2-RBD-hIgG-Fc Fusion Protein

<400> SEQUENCE: 21

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285
```

Arg Glu Glu Gln Tyr Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
            325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
            435                 440

<210> SEQ ID NO 22
<211> LENGTH: 233
<212> TYPE: PRT
<213> ORGANISM: Mus musculus

<400> SEQUENCE: 22

Glu Pro Arg Gly Pro Thr Ile Lys Pro Cys Pro Pro Cys Lys Cys Pro
1               5                   10                  15

Ala Pro Asn Leu Leu Gly Gly Pro Ser Val Phe Ile Phe Pro Pro Lys
            20                  25                  30

Ile Lys Asp Val Leu Met Ile Ser Leu Ser Pro Ile Val Thr Cys Val
            35                  40                  45

Val Val Asp Val Ser Glu Asp Asp Pro Asp Val Gln Ile Ser Trp Phe
50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
            85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Ser
            115                 120                 125

Val Arg Ala Pro Gln Val Tyr Val Leu Pro Pro Pro Glu Glu Glu Met
            130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
            165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
            195                 200                 205

Tyr Ser Cys Ser Val Val His Glu Gly Leu His Asn His His Thr Thr
            210                 215                 220

```
Lys Ser Phe Ser Arg Thr Pro Gly Lys
225                 230
```

<210> SEQ ID NO 23
<211> LENGTH: 464
<212> TYPE: PRT
<213> ORGANISM: Artificial Sequence
<220> FEATURE:
<223> OTHER INFORMATION: Synthetic SARS-CoV-2-RBD-Mouse-IgG2a-Fc Fusion
      Protein

<400> SEQUENCE: 23

```
Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
                20                  25                  30

Tyr Ala Trp Asn Arg Lys Arg Ile Ser Asn Cys Val Ala Asp Tyr Ser
            35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe Gly
    210                 215                 220

Gly Gly Ser Gly Gly Ser Glu Pro Arg Gly Pro Thr Ile Lys Pro
225                 230                 235                 240

Cys Pro Pro Cys Lys Cys Pro Ala Pro Asn Leu Leu Gly Gly Pro Ser
                245                 250                 255

Val Phe Ile Phe Pro Pro Lys Ile Lys Asp Val Leu Met Ile Ser Leu
            260                 265                 270

Ser Pro Ile Val Thr Cys Val Val Val Asp Val Ser Glu Asp Asp Pro
        275                 280                 285

Asp Val Gln Ile Ser Trp Phe Val Asn Asn Val Glu Val His Thr Ala
    290                 295                 300

Gln Thr Gln Thr His Arg Glu Asp Tyr Asn Ser Thr Leu Arg Val Val
305                 310                 315                 320

Ser Ala Leu Pro Ile Gln His Gln Asp Trp Met Ser Gly Lys Glu Phe
                325                 330                 335

Lys Cys Lys Val Asn Asn Lys Asp Leu Pro Ala Pro Ile Glu Arg Thr
```

```
                  340             345             350
Ile Ser Lys Pro Lys Gly Ser Val Arg Ala Pro Gln Val Tyr Val Leu
        355                 360                 365

Pro Pro Pro Glu Glu Glu Met Thr Lys Lys Gln Val Thr Leu Thr Cys
        370                 375                 380

Met Val Thr Asp Phe Met Pro Glu Asp Ile Tyr Val Glu Trp Thr Asn
385                 390                 395                 400

Asn Gly Lys Thr Glu Leu Asn Tyr Lys Asn Thr Glu Pro Val Leu Asp
                405                 410                 415

Ser Asp Gly Ser Tyr Phe Met Tyr Ser Lys Leu Arg Val Glu Lys Lys
                420                 425                 430

Asn Trp Val Glu Arg Asn Ser Tyr Ser Cys Ser Val Val His Glu Gly
                435                 440                 445

Leu His Asn His His Thr Thr Lys Ser Phe Ser Arg Thr Pro Gly Lys
                450                 455                 460

<210> SEQ ID NO 24
<211> LENGTH: 254
<212> TYPE: PRT
<213> ORGANISM: Human coronavirus SARS-CoV-2

<400> SEQUENCE: 24

Pro Asn Ile Thr Asn Leu Cys Pro Phe Gly Glu Val Phe Asn Ala Thr
1               5                   10                  15

Arg Phe Ala Ser Val Tyr Ala Trp Asn Arg Lys Arg Ile Ser Asn Cys
                20                  25                  30

Val Ala Asp Tyr Ser Val Leu Tyr Asn Ser Ala Ser Phe Ser Thr Phe
            35                  40                  45

Lys Cys Tyr Gly Val Ser Pro Thr Lys Leu Asn Asp Leu Cys Phe Thr
        50                  55                  60

Asn Val Tyr Ala Asp Ser Phe Val Ile Arg Gly Asp Glu Val Arg Gln
65                  70                  75                  80

Ile Ala Pro Gly Gln Thr Gly Lys Ile Ala Asp Tyr Asn Tyr Lys Leu
                85                  90                  95

Pro Asp Asp Phe Thr Gly Cys Val Ile Ala Trp Asn Ser Asn Asn Leu
                100                 105                 110

Asp Ser Lys Val Gly Gly Asn Tyr Asn Tyr Leu Tyr Arg Leu Phe Arg
            115                 120                 125

Lys Ser Asn Leu Lys Pro Phe Glu Arg Asp Ile Ser Thr Glu Ile Tyr
130                 135                 140

Gln Ala Gly Ser Thr Pro Cys Asn Gly Val Glu Gly Phe Asn Cys Tyr
145                 150                 155                 160

Phe Pro Leu Gln Ser Tyr Gly Phe Gln Pro Thr Tyr Gly Val Gly Tyr
                165                 170                 175

Gln Pro Tyr Arg Val Val Val Leu Ser Phe Glu Leu Leu His Ala Pro
                180                 185                 190

Ala Thr Val Cys Gly Pro Lys Lys Ser Thr Asn Leu Val Lys Asn Lys
            195                 200                 205

Cys Val Asn Phe Asn Phe Asn Gly Leu Thr Gly Thr Gly Val Leu Thr
        210                 215                 220

Glu Ser Asn Lys Lys Phe Leu Pro Phe Gln Gln Phe Gly Arg Asp Ile
225                 230                 235                 240

Ala Asp Thr Thr Asp Ala Val Arg Asp Pro Gln Thr Leu Glu
                245                 250
```

<210> SEQ ID NO 25
<211> LENGTH: 254
<212> TYPE: PRT
<213> ORGANISM: Human coronavirus SARS-CoV-2

<400> SEQUENCE: 25

Pro Asn Ile Thr Asn Leu Cys Pro Phe Gly Glu Val Phe Asn Ala Thr
1               5                   10                  15

Arg Phe Ala Ser Val Tyr Ala Trp Asn Arg Lys Arg Ile Ser Asn Cys
            20                  25                  30

Val Ala Asp Tyr Ser Val Leu Tyr Asn Ser Ala Ser Phe Ser Thr Phe
        35                  40                  45

Lys Cys Tyr Gly Val Ser Pro Thr Lys Leu Asn Asp Leu Cys Phe Thr
    50                  55                  60

Asn Val Tyr Ala Asp Ser Phe Val Ile Arg Gly Asp Glu Val Arg Gln
65                  70                  75                  80

Ile Ala Pro Gly Gln Thr Gly Lys Ile Ala Asp Tyr Asn Tyr Lys Leu
                85                  90                  95

Pro Asp Asp Phe Thr Gly Cys Val Ile Ala Trp Asn Ser Asn Asn Leu
            100                 105                 110

Asp Ser Lys Val Gly Gly Asn Tyr Asn Tyr Leu Tyr Arg Leu Phe Arg
        115                 120                 125

Lys Ser Asn Leu Lys Pro Phe Glu Arg Asp Ile Ser Thr Glu Ile Tyr
130                 135                 140

Gln Ala Gly Ser Thr Pro Cys Asn Gly Val Lys Gly Phe Asn Cys Tyr
145                 150                 155                 160

Phe Pro Leu Gln Ser Tyr Gly Phe Gln Pro Thr Asn Gly Val Gly Tyr
                165                 170                 175

Gln Pro Tyr Arg Val Val Val Leu Ser Phe Glu Leu Leu His Ala Pro
            180                 185                 190

Ala Thr Val Cys Gly Pro Lys Lys Ser Thr Asn Leu Val Lys Asn Lys
        195                 200                 205

Cys Val Asn Phe Asn Phe Asn Gly Leu Thr Gly Thr Gly Val Leu Thr
    210                 215                 220

Glu Ser Asn Lys Lys Phe Leu Pro Phe Gln Gln Phe Gly Arg Asp Ile
225                 230                 235                 240

Ala Asp Thr Thr Asp Ala Val Arg Asp Pro Gln Thr Leu Glu
                245                 250

<210> SEQ ID NO 26
<211> LENGTH: 224
<212> TYPE: PRT
<213> ORGANISM: Canis familiaris

<400> SEQUENCE: 26

Asp Cys Pro Lys Cys Pro Ala Pro Glu Met Leu Gly Gly Pro Ser Val
1               5                   10                  15

Phe Ile Phe Pro Pro Lys Pro Lys Asp Thr Leu Leu Ile Ala Arg Thr
            20                  25                  30

Pro Glu Val Thr Cys Val Val Asp Leu Asp Pro Glu Asp Pro Glu
        35                  40                  45

Val Gln Ile Ser Trp Phe Val Asp Gly Lys Gln Met Gln Thr Ala Lys
    50                  55                  60

Thr Gln Pro Arg Glu Glu Gln Phe Asn Gly Thr Tyr Arg Val Val Ser
65                  70                  75                  80

```
Val Leu Pro Ile Gly His Gln Asp Trp Leu Lys Gly Lys Gln Phe Thr
                85                  90                  95

Cys Lys Val Asn Asn Lys Ala Leu Pro Ser Pro Ile Glu Arg Thr Ile
           100                 105                 110

Ser Lys Ala Arg Gly Gln Ala His Gln Pro Ser Val Tyr Val Leu Pro
           115                 120                 125

Pro Ser Arg Glu Glu Leu Ser Lys Asn Thr Val Ser Leu Thr Cys Leu
       130                 135                 140

Ile Lys Asp Phe Phe Pro Asp Ile Asp Val Glu Trp Gln Ser Asn
145                 150                 155                 160

Gly Gln Gln Glu Pro Glu Ser Lys Tyr Arg Thr Thr Pro Pro Gln Leu
               165                 170                 175

Asp Glu Asp Gly Ser Tyr Phe Leu Tyr Ser Lys Leu Ser Val Asp Lys
           180                 185                 190

Ser Arg Trp Gln Arg Gly Asp Thr Phe Ile Cys Ala Val Met His Glu
           195                 200                 205

Ala Leu His Asn His Tyr Thr Gln Glu Ser Leu Ser His Ser Pro Gly
       210                 215                 220

<210> SEQ ID NO 27
<211> LENGTH: 21
<212> TYPE: PRT
<213> ORGANISM: Artificial Sequence
<220> FEATURE:
<223> OTHER INFORMATION: Synthetic Linker

<400> SEQUENCE: 27

Gly Gly Gly Gly Gly Gln Gly Gly Gly Gln Gly Gly Gly Gly Gln
1               5                   10                  15

Gly Gly Gly Gly Gly
            20

<210> SEQ ID NO 28
<211> LENGTH: 57
<212> TYPE: PRT
<213> ORGANISM: Artificial Sequence
<220> FEATURE:
<223> OTHER INFORMATION: Synthetic Insulin Analog (B-C-A)

<400> SEQUENCE: 28

Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys
    50                  55

<210> SEQ ID NO 29
<211> LENGTH: 302
<212> TYPE: PRT
<213> ORGANISM: Artificial Sequence
<220> FEATURE:
<223> OTHER INFORMATION: Synthetic Canine Insulin-Fc Fusion Protein

<400> SEQUENCE: 29

Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly Gly
```

```
                20                  25                  30
Ser Gly Gly Gly Gly Ile Val Glu Gln Cys Cys Thr Ser Thr Cys
                35                  40                  45
Ser Leu Asp Gln Leu Glu Asn Tyr Cys Gly Gly Gly Gly Gln Gly
        50                  55                  60
Gly Gly Gln Gly Gly Gly Gln Gly Gly Gly Gly Asp Cys
65                  70                  75                  80
Pro Lys Cys Pro Ala Pro Glu Met Leu Gly Gly Pro Ser Val Phe Ile
                85                  90                  95
Phe Pro Pro Lys Pro Lys Asp Thr Leu Leu Ile Ala Arg Thr Pro Glu
            100                 105                 110
Val Thr Cys Val Val Val Asp Leu Asp Pro Glu Asp Pro Glu Val Gln
            115                 120                 125
Ile Ser Trp Phe Val Asp Gly Lys Gln Met Gln Thr Ala Lys Thr Gln
            130                 135                 140
Pro Arg Glu Glu Gln Phe Asn Gly Thr Tyr Arg Val Val Ser Val Leu
145                 150                 155                 160
Pro Ile Gly His Gln Asp Trp Leu Lys Gly Lys Gln Phe Thr Cys Lys
            165                 170                 175
Val Asn Asn Lys Ala Leu Pro Ser Pro Ile Glu Arg Thr Ile Ser Lys
            180                 185                 190
Ala Arg Gly Gln Ala His Gln Pro Ser Val Tyr Val Leu Pro Pro Ser
            195                 200                 205
Arg Glu Glu Leu Ser Lys Asn Thr Val Ser Leu Thr Cys Leu Ile Lys
            210                 215                 220
Asp Phe Phe Pro Pro Asp Ile Asp Val Glu Trp Gln Ser Asn Gly Gln
225                 230                 235                 240
Gln Glu Pro Glu Ser Lys Tyr Arg Thr Thr Pro Pro Gln Leu Asp Glu
                245                 250                 255
Asp Gly Ser Tyr Phe Leu Tyr Ser Lys Leu Ser Val Asp Lys Ser Arg
            260                 265                 270
Trp Gln Arg Gly Asp Thr Phe Ile Cys Ala Val Met His Glu Ala Leu
            275                 280                 285
His Asn His Tyr Thr Gln Glu Ser Leu Ser His Ser Pro Gly
            290                 295                 300

<210> SEQ ID NO 30
<211> LENGTH: 224
<212> TYPE: PRT
<213> ORGANISM: Artificial Sequence
<220> FEATURE:
<223> OTHER INFORMATION: Synthetic Fc Fragment
<220> FEATURE:
<221> NAME/KEY: MISC_FEATURE
<222> LOCATION: (73)..(73)
<223> OTHER INFORMATION: Xaa = S, Q, D, K, A

<400> SEQUENCE: 30

Asp Cys Pro Lys Cys Pro Ala Pro Glu Met Leu Gly Gly Pro Ser Val
1               5                   10                  15
Phe Ile Phe Pro Pro Lys Pro Lys Asp Thr Leu Leu Ile Ala Arg Thr
                20                  25                  30
Pro Glu Val Thr Cys Val Val Val Asp Leu Asp Pro Glu Asp Pro Glu
            35                  40                  45
Val Gln Ile Ser Trp Phe Val Asp Gly Lys Gln Met Gln Thr Ala Lys
        50                  55                  60
```

```
Thr Gln Pro Arg Glu Glu Gln Phe Xaa Gly Thr Tyr Arg Val Val Ser
 65                  70                  75                  80

Val Leu Pro Ile Gly His Gln Asp Trp Leu Lys Gly Lys Gln Phe Thr
                 85                  90                  95

Cys Lys Val Asn Asn Lys Ala Leu Pro Ser Pro Ile Glu Arg Thr Ile
            100                 105                 110

Ser Lys Ala Arg Gly Gln Ala His Gln Pro Ser Val Tyr Val Leu Pro
            115                 120                 125

Pro Ser Arg Glu Glu Leu Ser Lys Asn Thr Val Ser Leu Thr Cys Leu
        130                 135                 140

Ile Lys Asp Phe Phe Pro Pro Asp Ile Asp Val Glu Trp Gln Ser Asn
145                 150                 155                 160

Gly Gln Gln Glu Pro Glu Ser Lys Tyr Arg Thr Thr Pro Pro Gln Leu
                165                 170                 175

Asp Glu Asp Gly Ser Tyr Phe Leu Tyr Ser Lys Leu Ser Val Asp Lys
            180                 185                 190

Ser Arg Trp Gln Arg Gly Asp Thr Phe Ile Cys Ala Val Met His Glu
        195                 200                 205

Ala Leu His Asn His Tyr Thr Gln Glu Ser Leu Ser His Ser Pro Gly
210                 215                 220

<210> SEQ ID NO 31
<211> LENGTH: 57
<212> TYPE: PRT
<213> ORGANISM: Artificial Sequence
<220> FEATURE:
<223> OTHER INFORMATION: Synthetic Insulin Analog (B-C-A)

<400> SEQUENCE: 31

Phe Val Asn Gln His Leu Cys Gly Ser His Leu Val Glu Ala Leu Ala
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys
    50                  55

<210> SEQ ID NO 32
<211> LENGTH: 302
<212> TYPE: PRT
<213> ORGANISM: Artificial Sequence
<220> FEATURE:
<223> OTHER INFORMATION: Synthetic Canine Insulin-Fc Fusion Protein

<400> SEQUENCE: 32

Phe Val Asn Gln His Leu Cys Gly Ser His Leu Val Glu Ala Leu Ala
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Gln Gly
    50                  55                  60

Gly Gly Gln Gly Gly Gly Gln Gly Gly Gly Gly Asp Cys
65                  70                  75                  80

Pro Lys Cys Pro Ala Pro Glu Met Leu Gly Gly Pro Ser Val Phe Ile
                85                  90                  95
```

-continued

```
Phe Pro Pro Lys Pro Lys Asp Thr Leu Leu Ile Ala Arg Thr Pro Glu
            100                 105                 110

Val Thr Cys Val Val Val Asp Leu Asp Pro Glu Asp Pro Glu Val Gln
        115                 120                 125

Ile Ser Trp Phe Val Asp Gly Lys Gln Met Gln Thr Ala Lys Thr Gln
130                 135                 140

Pro Arg Glu Glu Gln Phe Ser Gly Thr Tyr Arg Val Val Ser Val Leu
145                 150                 155                 160

Pro Ile Gly His Gln Asp Trp Leu Lys Gly Lys Gln Phe Thr Cys Lys
                165                 170                 175

Val Asn Asn Lys Ala Leu Pro Ser Pro Ile Glu Arg Thr Ile Ser Lys
            180                 185                 190

Ala Arg Gly Gln Ala His Gln Pro Ser Val Tyr Val Leu Pro Pro Ser
        195                 200                 205

Arg Glu Glu Leu Ser Lys Asn Thr Val Ser Leu Thr Cys Leu Ile Lys
    210                 215                 220

Asp Phe Phe Pro Pro Asp Ile Asp Val Glu Trp Gln Ser Asn Gly Gln
225                 230                 235                 240

Gln Glu Pro Glu Ser Lys Tyr Arg Thr Thr Pro Pro Gln Leu Asp Glu
                245                 250                 255

Asp Gly Ser Tyr Phe Leu Tyr Ser Lys Leu Ser Val Asp Lys Ser Arg
            260                 265                 270

Trp Gln Arg Gly Asp Thr Phe Ile Cys Ala Val Met His Glu Ala Leu
        275                 280                 285

His Asn His Tyr Thr Gln Glu Ser Leu Ser His Ser Pro Gly
    290                 295                 300

<210> SEQ ID NO 33
<211> LENGTH: 231
<212> TYPE: PRT
<213> ORGANISM: Artificial Sequence
<220> FEATURE:
<223> OTHER INFORMATION: Synthetic Fc Fragment

<400> SEQUENCE: 33

Ser Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160
```

-continued

```
Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230
```